United States Patent
Zhan

(10) Patent No.: US 9,334,291 B2
(45) Date of Patent: May 10, 2016

(54) ANTIVIRAL COMPOUNDS HIGHLY EFFECTIVE AS HCV-NS5A INHIBITOR

(71) Applicant: Zheng-Yun James Zhan, Minhan (CN)

(72) Inventor: Zheng-Yun James Zhan, Minhan (CN)

(73) Assignee: AB PHARMA LTD., Shanghai (CN)

( * ) Notice: Subject to any disclaimer, the term of this patent is extended or adjusted under 35 U.S.C. 154(b) by 0 days.

(21) Appl. No.: 14/298,188

(22) Filed: Jun. 6, 2014

(65) Prior Publication Data

US 2014/0364429 A1 Dec. 11, 2014

(30) Foreign Application Priority Data

Jun. 6, 2013 (CN) .......................... 2013 1 0224756

(51) Int. Cl.

| | |
|---|---|
| *C07D 403/14* | (2006.01) |
| *C07D 409/14* | (2006.01) |
| *C07D 401/14* | (2006.01) |
| *A61K 45/06* | (2006.01) |
| *C07D 519/00* | (2006.01) |
| *C07D 491/056* | (2006.01) |
| *C07D 498/06* | (2006.01) |
| *C07D 491/113* | (2006.01) |

(52) U.S. Cl.
CPC .............. *C07D 519/00* (2013.01); *A61K 45/06* (2013.01); *C07D 401/14* (2013.01); *C07D 403/14* (2013.01); *C07D 409/14* (2013.01); *C07D 491/056* (2013.01); *C07D 491/113* (2013.01); *C07D 498/06* (2013.01)

(58) Field of Classification Search
None
See application file for complete search history.

(56) References Cited

U.S. PATENT DOCUMENTS 8,088,368 B2 * 1/2012 Guo et al. .................... 424/85.4

* cited by examiner

*Primary Examiner* — Samantha Shterengarts
(74) *Attorney, Agent, or Firm* — Oblon, McClelland, Maier & Neustadt, L.L.P.

(57) ABSTRACT

Provided are compounds antiviral compounds represented by formula Ia and Ib:

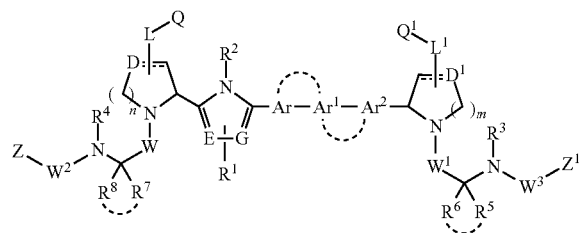

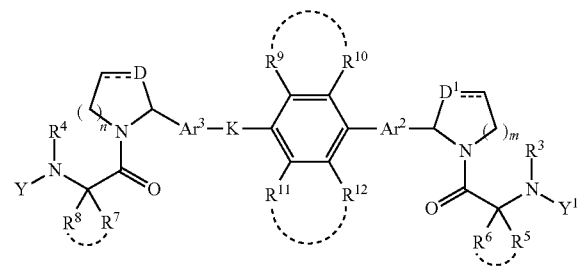

that are highly potent as HCV NS5A inhibitors, where the structural variables are as defined herein. These compounds are useful in, for example, inhibiting Hepatitis C virus and treating Hepatitis C virus infections.

30 Claims, No Drawings

ANTIVIRAL COMPOUNDS HIGHLY EFFECTIVE AS HCV-NS5A INHIBITOR

DESCRIPTION OF THE BACKGROUND

The present application claims benefit of the filing date of Chinese patent application No. CN201310224756.X, filed on Jun. 6, 2013, incorporated herein by reference.

FIELD OF THE INVENTION

The present invention relates to two classes of novel antiviral compounds, pharmaceutical compositions and their uses thereof as an effective HCV-NS5A inhibitor.

BACKGROUND OF THE INVENTION

Hepatitis C virus (HCV) infection leads to chronic liver disease such as cirrhosis and hepatocellular carcinoma. Hepatitis C virus (HCV) is a single-stranded positive RNA virus in the Flaviviridae family. HCV includes a nucleocapsid protein (C), envelope proteins (E1 and E2), and several non-structural proteins (NS1, NS2, NS3, NS4a, NS5a, and NS5b), and it is known that the NS3 and NS5 (NS5A and NS5B) proteins are essential for viral replication. So far, HCV infection is one of the major infection diseases, and about 3-5% of the world's population was infected with HCV.

Currently, there were several new HCV NS5A inhibitors such as BMS-790052, IDX791 and GS-5885 reported in Phase I-III clinical trials in USA and Europe [Ref: WO2008/021927 A2, WO2010/132601 A1, WO2011/075615 A1]. The present invention is based on the discovery of two classes of novel antiviral compounds highly effective as HCV-NS5A inhibitor with excellent potency and safety.

SUMMARY OF THE INVENTION

The present inventor relates to two classes of novel antiviral compounds of the following formulas Ia-Ib with the polyaryl and heteroaryl core based structure, which has been evaluated to be highly potent and effective for inhibiting the NS5A replication of hepatitis C virus (HCV). This invention further relates to pharmaceutical compositions comprising one or more new developed compounds (in a pure form or mixture of stereoisomers, solvates, hydrates, tautomers, prodrugs, or pharmaceutically acceptable salts thereof) and another agent(s) developed as therapeutic drugs for HCV treatment.

In the first aspect, the present invention provides a compound represented by the formula Ia or Ib, or a stereoisomer, tautomer, esterification or amidation prodrug or pharmaceutically acceptable salt thereof:

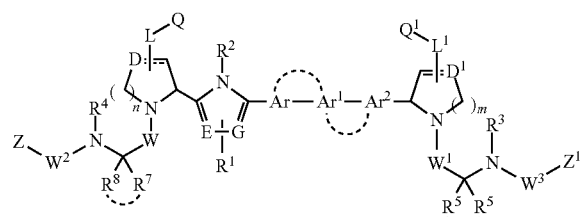

Ia

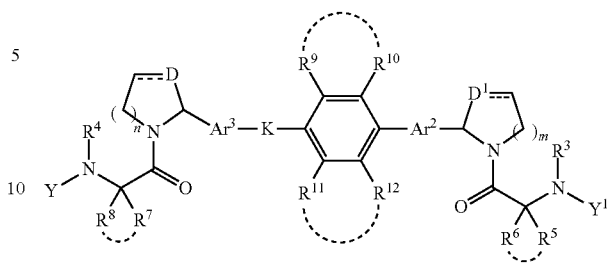

Ib wherein:

m=1, 2 or 3;

n=1, 2 or 3;

each dashed line "┅" is, independently, a single bond or double bond; when "┅" is a single bond, D and $D^1$ are each, independently, selected from the group consisting of O, S, N(Ra), $CH_2$, CH(OH), or C(Rb)(Rc);

Ra is H, $C_1$-$C_{20}$ hydroxy, alkyl, $C_1$-$C_{20}$ cycloalkyl, $C_6$-$C_{20}$ aryl, $C_2$-$C_{20}$ heteroaryl, $C_1$-$C_{20}$ alkoxycarbonyl, $C_3$-$C_{20}$ cycloalkyloxycarbonyl, $C_6$-$C_{20}$ aryloxycarbonyl, $C_2$-$C_{20}$ heterocycloalkyl-oxycarbonyl, $C_1$-$C_{20}$ alkylaminocarbonyl, $C_3$-$C_{20}$ cycloalkylaminocarbonyl, $C_1$-$C_{20}$ alkylamino sulfonamido, $C_2$-$C_{20}$ heterocycloalkyl-aminosulfonyl, or $C_6$-$C_{20}$ arylaminosulfonyl;

Rb and Rc are each, independently, selected from the group consisting of H, halogen, hydroxy, cyano, $C_1$-$C_{20}$ alkyl, $C_3$-$C_{20}$ cycloalkyl, $C_2$-$C_{20}$ heterocycloalkyl, $C_6$-$C_{20}$ aryl, $C_1$-$C_{20}$ alkoxy, alkylthio, $C_1$-$C_{20}$ alkoxycarbonyl, $C_6$-$C_{20}$ aryloxy, $C_6$-$C_{20}$ heteroaryloxy, $C_6$-$C_{20}$ fused aryloxy, $C_6$-$C_{20}$ fused heterocycloalkyl-oxy, $C_6$-$C_{20}$ aryloxycarbonyl, $C_2$-$C_{20}$ heterocycloalkyl oxycarbonyl, $C_2$-$C_{20}$ heteroaryl, $C_1$-$C_{20}$ alkylamino, $C_2$-$C_{20}$ heterocycloalkylamino, $C_6$-$C_{20}$ arylamino, $C_1$-$C_{20}$ alkylaminocarbonyl, $C_1$-$C_{20}$ alkylcarbonylamino, $C_1$-$C_{20}$ alkylsulfonamido, $C_2$-$C_{20}$ heterocycloalkyl-sulfonamido, $C_6$-$C_{20}$ arylsulfonamido, and $C_1$-$C_{20}$ alkylaminosulfonamido;

or Rb and Rc may be linked to form a $C_2$-$C_{20}$ cycloalkyl, $C_2$-$C_{20}$ cycloalkenyl, or $C_1$-$C_{20}$ cycloethereal group;

when "┅" is a double bond, D and/or $D^1$ are each, independently, selected from the group consisting of N, CH, and C(Rb), wherein the definition of Rb is the same as the Rb in D and $D^1$ above;

Ar, $Ar^1$, $Ar^2$ and $Ar^3$ are each, independently, selected from the group consisting of $C_6$-$C_{20}$ aryl, $C_2$-$C_{20}$ heteroaryl, $C_8$-$C_{20}$ fused aryl, and $C_4$-$C_{20}$ fused heteroaryl, or Ar and $Ar^1$ or $Ar^1$ and $Ar^2$ may be linked each other to form $C_{10}$-$C_{20}$ fused alkylaryl or $C_8$-$C_{20}$ aryl group, or $Ar^1$ or $Ar^2$ does not exist and the groups bonded to $Ar^1$ or $Ar^2$ are directly linked;

E and G are each, independently, selected from the group consisting of N, CH and C(Rb); wherein the definition of Rb is the same as the Rb in D and $D^1$ above;

K is $C_2$-$C_{20}$ mono-heteroaryl, $C_2$-$C_{20}$ poly-heteroaryl, or $C_2$-$C_{20}$ fused-heteroaryl represented by one of the following structures:

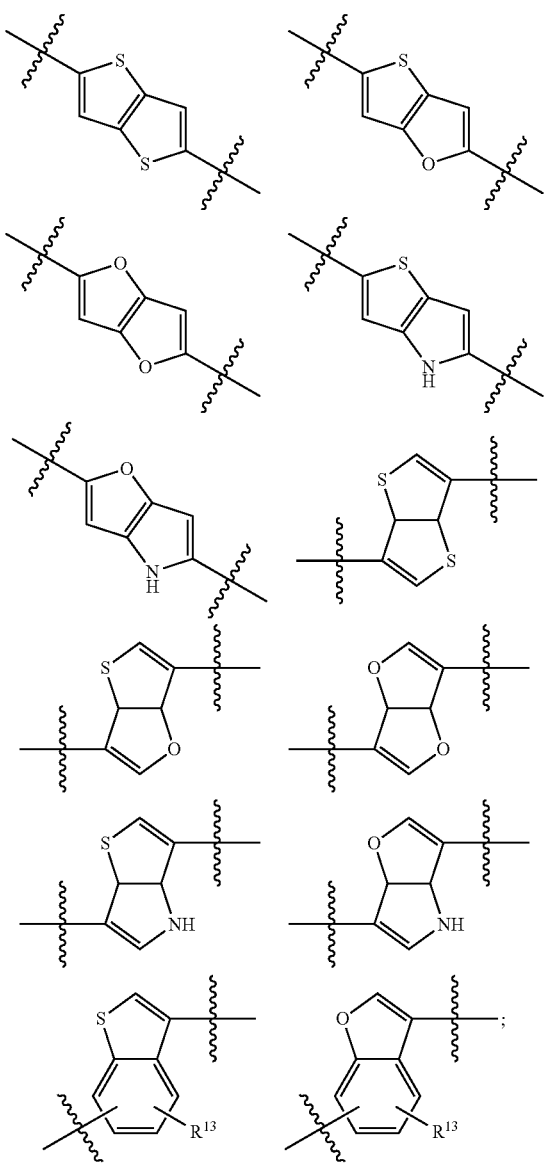

L and $L^1$ are each, independently linked with D and/or $D^1$, selected from the group consisting of O, S, N(Ra), C(=O), C(=O)O, C(=S)O, and C(=O)N(Ra), wherein the definition of Ra is the same as the Ra in D and $D^1$ above;

or L and/or $L^1$ are not present;

Q and $Q^1$ are each, independently, selected from the group consisting of $C_1$-$C_{20}$ alkyl, $C_1$-$C_{20}$ alkoxy, $C_1$-$C_{20}$ alkylamino, $C_3$-$C_{20}$ cycloalkylamino, $C_6$-$C_{20}$ aryl, $C_3$-$C_{20}$ heteroaryl, $C_3$-$C_{20}$ poly-heteroaryl, $C_3$-$C_{20}$ fused aryl, and $C_3$-$C_{20}$ heteroaryl group, wherein when L and/or $L^1$ is not present, Q and/or $Q^1$ is not present;

W and $W^1$ are each, independently, selected from the group consisting of carbonyl, thiocarbonyl, $C_1$-$C_{20}$ alkyl, $C_6$-$C_{20}$ aryl, and $C_2$-$C_{20}$ heteroaryl group;

$W^2$ and $W^3$ are each, independently, selected from the group consisting of carbonyl, thiocarbonyl, sulfonyl, $C_1$-$C_{20}$ alkyl, $C_2$-$C_{20}$ heterocycloalkyl, $C_6$-$C_{20}$ aryl, and $C_2$-$C_{20}$ heteroaryl group;

Y and $Y^1$ are each, independently, selected from the group consisting of H, $C_1$-$C_{20}$ alkyl, $C_3$-$C_{20}$ cycloalkyl, $C_6$-$C_{20}$ aryl, $C_1$-$C_{20}$ alkylcarbonyl, $C_6$-$C_{20}$ arylcarbonyl, $C_2$-$C_{20}$ heterocycloalkylcarbonyl, $C_1$-$C_{20}$ alkoxycarbonyl, $C_1$-$C_{20}$ cycloalkyl-oxy-carbonyl, $C_6$-$C_{20}$ aryloxycarbonyl, $C_2$-$C_{20}$ heteroaryloxycarbonyl, $C_1$-$C_{20}$ alkylaminocarbonyl, $C_1$-$C_{20}$ alkylsulfonyl, $C_3$-$C_{20}$ cycloalkylsulfonyl, $C_6$-$C_{20}$ arylsulfonyl, $C_1$-$C_{20}$ alkylamino sulfonyl, $C_3$-$C_{20}$ cycloalkylaminosulfonyl, and $C_6$-$C_{20}$ arylaminosulfonyl group;

Z and $Z^1$ are each, independently, selected from the group consisting of H, hydroxy, amino, $C_1$-$C_{20}$ alkyl, $C_3$-$C_{20}$ cycloalkyl, $C_1$-$C_{20}$ alkoxy, $C_3$-$C_{20}$ cycloalkyl-oxy, $C_1$-$C_{20}$ alkylamino, $C_3$-$C_{20}$ cycloalkylamino, $C_2$-$C_{20}$ heterocycloalkyl, $C_2$-$C_{20}$ heterocycloalkylamino, $C_6$-$C_{20}$ aryl, $C_6$-$C_{20}$ aryloxy, $C_6$-$C_{20}$ arylamino, $C_3$-$C_{20}$ heteroaryloxy, $C_3$-$C_{20}$ heteroarylamino, $C_1$-$C_{20}$ alkylsulfonamido, $C_3$-$C_{20}$ cycloalkylsulfonamido, $C_6$-$C_{20}$ arylsulfonamido, $C_1$-$C_{20}$ alkoxysulfonamido, $C_3$-$C_{20}$ cycloalkyl-oxy-sulfonamido, $C_6$-$C_{20}$ aryloxysulfonamido, $C_1$-$C_{20}$ alkylaminosulfonamido, $C_3$-$C_{20}$ cycloalkylaminosulfonamido, and $C_6$-$C_{20}$ arylaminosulfonamido group;

$R^1$, $R^2$, $R^3$ and $R^4$ are each, independently, selected from the group consisting of H, $C_1$-$C_{20}$ alkyl, $C_3$-$C_{20}$ cycloalkyl, $C_2$-$C_{20}$ heterocycloalkyl, $C_6$-$C_{20}$ aryl, $C_2$-$C_{20}$ heteroaryl, $C_1$-$C_{20}$ alkoxycarbonyl, $C_6$-$C_{20}$ aryloxycarbonyl, $C_2$-$C_{20}$ heterocycloalkyl-oxy carbonyl, $C_1$-$C_{20}$ alkylaminocarbonyl, $C_1$-$C_{20}$ alkylaminosulfonamido, $C_2$-$C_{20}$ heterocycloalkylamino sulfonyl, and $C_6$-$C_{20}$ arylaminosulfonyl group;

$R^5$, $R^6$, $R^7$ and $R^8$ are each, independently, selected from the group consisting of H, halogen, hydroxy, cyano, amino, $C_1$-$C_{20}$ alkyl, $C_3$-$C_{20}$ cycloalkyl, $C_2$-$C_{20}$ heterocycloalkyl, $C_1$-$C_{20}$ alkoxy, $C_1$-$C_{20}$ alkylamino, $C_2$-$C_{20}$ heterocycloalkylamino, $C_6$-$C_{20}$ aryl, $C_3$-$C_{20}$ heteroaryl, $C_6$-$C_{20}$ arylamino, $C_1$-$C_{20}$ alkoxycarbonylamino, $C_1$-$C_{20}$ alkylaminocarbonylamino, $C_1$-$C_{20}$ alkylsulfonamido, $C_2$-$C_{20}$ heterocycloalkylsulfonamido, $C_6$-$C_{20}$ arylsulfonamido, and $C_1$-$C_{20}$ alkylaminosulfonamido, or $R^5$ and $R^6$ may be linked to each other to form a cyclo group, or $R^7$ and $R^8$ may be linked to each other to form a cyclo group; and $R^9$, $R^{10}$, $R^{11}$ and $R^{12}$ are each, independently, selected from the group consisting of H, halogen, hydroxy, cyano, amino, $C_1$-$C_{20}$ alkyl, $C_3$-$C_{20}$ cycloalkyl, $C_1$-$C_{20}$ alkoxy, $C_1$-$C_{20}$ alkylamino, $C_2$-$C_{20}$ heterocycloalkylamino, $C_6$-$C_{20}$ aryl, $C_3$-$C_{20}$ heteroaryl, $C_6$-$C_{20}$ arylamino, and $C_1$-$C_{20}$ alkoxycarbonylamino, or the $R^9$ and $R^{10}$ may be linked to each other to form a cyclo or spiro group, and the $R^{11}$ and $R^{12}$ may be linked to each other to form a cyclo or spiro group.

In a preferred embodiment of the invention, m=1 or 2 and n=1 or 2.

In another preferred embodiment of the invention, the dashed line "┅┅" is double bond and D and/or $D^1$ are CH.

In another preferred embodiment of the invention:

the dashed line "┅┅" is single bond;

D and $D^1$ are each, independently, selected from the group consisting of O, S, N(Ra), $CH_2$, CH(OH) and C(Rb)(Rc);

Ra is H, hydroxy, $C_1$-$C_{12}$ alkyl, $C_1$-$C_{12}$ cycloalkyl, $C_6$-$C_{12}$ aryl, $C_2$-$C_{12}$ heteroaryl, $C_1$-$C_{12}$ alkoxycarbonyl, $C_3$-$C_{12}$ cycloalkyloxycarbonyl, $C_6$-$C_{12}$ aryloxycarbonyl, $C_2$-$C_{12}$ heterocyclo-oxycarbonyl, $C_1$-$C_{12}$ alkylaminocarbonyl, $C_3$-$C_{12}$ cycloalkylaminocarbonyl, $C_1$-$C_{12}$ alkylaminosulfonamido, $C_2$-$C_{12}$ heterocycloaminosulfonyl, or $C_6$-$C_{12}$ arylaminosulfonyl; and the Rb and Rc are each, independently, selected from the group consisting of H, halogen, hydroxy, cyano, $C_1$-$C_{12}$ alkyl, $C_3$-$C_{12}$ cycloalkyl, $C_2$-$C_{12}$ heterocyclo, $C_6$-$C_{12}$ aryl, $C_1$-$C_{12}$ alkoxy, $C_1$-$C_{12}$ alkylthio, $C_1$-$C_{12}$ alkoxycarbonyl, $C_6$-$C_{12}$ aryloxy, $C_6$-$C_{12}$ heteroaryloxy, $C_6$-$C_{12}$ fused aryloxy, $C_6$-$C_{12}$ fused heterocyclo-oxy, $C_6$-$C_{12}$ aryloxycarbonyl, $C_2$-$C_{12}$ heterocyclo oxycarbonyl, $C_2$-$C_{12}$ heteroaryl, $C_1$-$C_{12}$ alkylamino, $C_2$-$C_{12}$ heterocycloamino, $C_6$-$C_{12}$ arylamino, $C_1$-$C_{12}$ alkylaminocarbonyl, $C_1$-$C_{12}$ alkylcarbonylamino, $C_1$-$C_{12}$ alkylsulfonamido, $C_2$-$C_{12}$ heterocyclosulfonamido, $C_6$-$C_{12}$ arylsulfonamido, $C_1$-$C_{12}$ alkylaminosulfonamido; or Rb and Rc could be linked to form $C_2$-$C_{12}$ cycloalkyl, $C_2$-$C_{12}$ cycloalkenyl, or $C_1$-$C_{12}$ cycloethereal group.

In another preferred embodiment of the invention:

the dashed line " ----- " is single bond;

the D and/or $D^1$ is each O, N(Ra), $CH_2$, CH(OH) or C(Rb)(Rc), wherein

Ra is H, hydroxy, $C_1$-$C_5$ alkoxycarbonyl, $C_3$-$C_6$ cycloalkyloxycarbonyl, $C_3$-$C_{10}$ cycloalkylaminocarbonyl, $C_1$-$C_4$ alkylaminosulfonamido, or $C_2$-$C_{10}$ heterocycloaminosulfonyl group; and the Rb and Rc could be linked to form $C_2$-$C_5$ cycloalkyl, or $C_1$-$C_2$ cycloethereal group.

In another preferred embodiment of the invention, the Ar, $Ar^1$, $Ar^2$ and $Ar^3$ are each, independently, selected from the group consisting of $C_6$-$C_{12}$ aryl, $C_2$-$C_{12}$ heteroaryl, $C_8$-$C_{12}$ fused aryl, and $C_4$-$C_{12}$ fused heteroaryl, or Ar and $Ar^1$ or $Ar^1$ and $Ar^2$ may, be linked each other to form $C_{10}$-$C_{12}$ fused alkylaryl or $C_8$-$C_{12}$ aryl group, or $Ar^1$ or $Ar^2$ does not exist and the groups bonded to $Ar^1$ or $Ar^2$ are directly linked.

In another preferred embodiment of the invention, the Ar and $Ar^1$ are each selected from

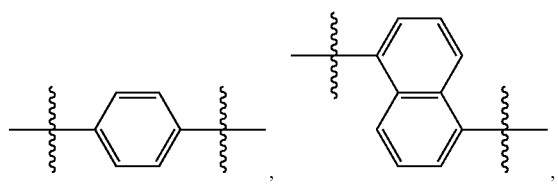 [SMILES: *c1ccc(*)cc1 ; *c1cccc2c(*)cccc12]

or the Ar and $Ar^1$ are linked each other as a fused aryl or heteroaryl group represented by the structure

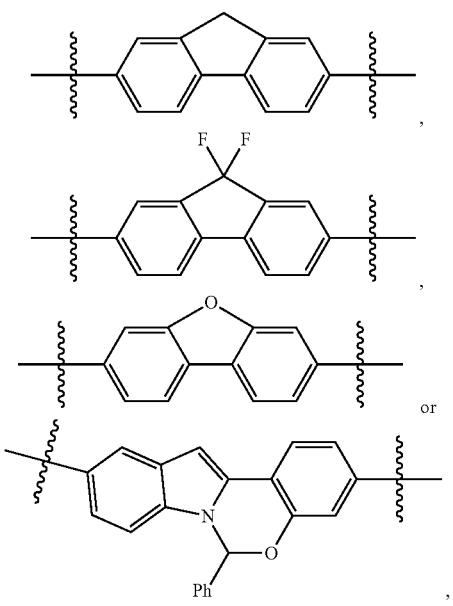

and the $Ar^2$ and $Ar^3$ are

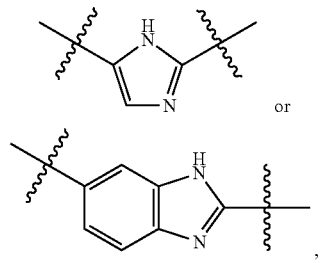

respectively.

In another preferred embodiment of the invention, E is N, and G is CH.

In another preferred embodiment of the invention, K is $C_2$-$C_{12}$ mono-heteroaryl, $C_2$-$C_{12}$ poly-heteroaryl, or $C_2$-$C_{12}$ fused-heteroaryl group.

In another preferred embodiment of the invention, K is represented by one of the following structures:

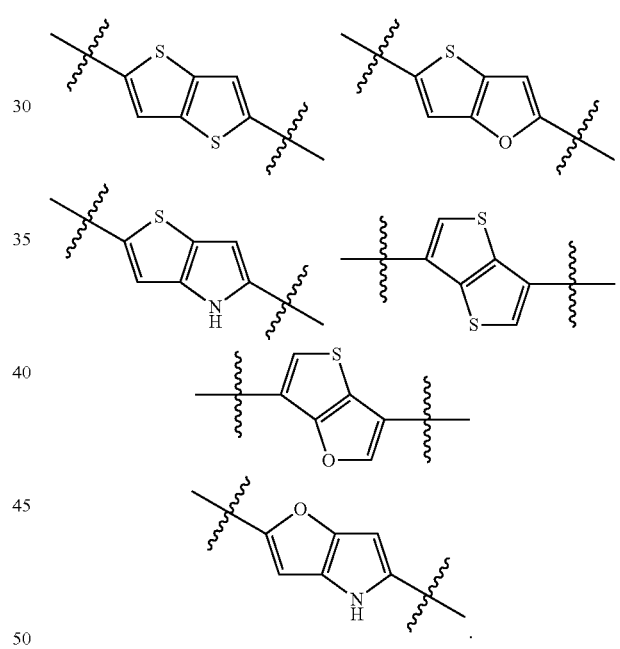

In another preferred embodiment of the invention, L and/or $L^1$ is selected from the group consisting of O, NH, or the L and/or $L^1$ does not exist.

In another preferred embodiment of the invention, Q and/or $Q^1$ are each, independently, selected from the group consisting of $C_1$-$C_{12}$ alkyl, $C_1$-$C_{12}$ alkoxy, $C_1$-$C_{12}$ alkylamino, $C_3$-$C_{12}$ cycloalkylamino, $C_6$-$C_{12}$ aryl, $C_3$-$C_{12}$ heteroaryl, $C_3$-$C_{12}$ poly-heteroaryl, $C_3$-$C_{12}$ fused aryl, and $C_3$-$C_{12}$ heteroaryl group, wherein when the L and/or $L^1$ does not exist, the Q and/or $Q^1$ does not exist.

In another preferred embodiment of the invention, Q and/or $Q^1$ is independently represented by one the following structures:

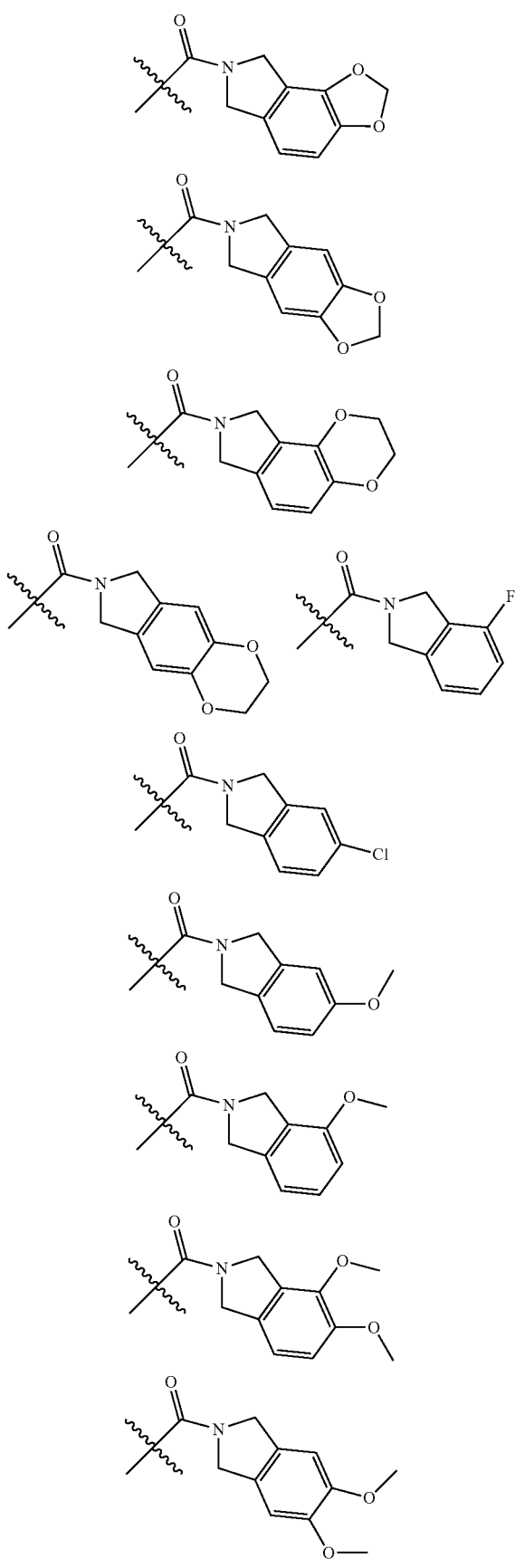

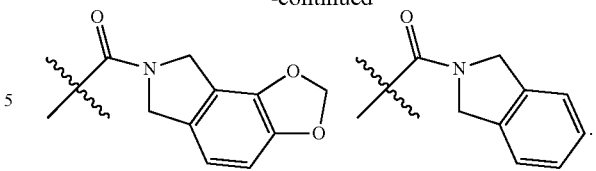

In another preferred embodiment of the invention, W and $W^1$ are each, independently, selected from the group consisting of carbonyl, thiocarbonyl, $C_1$-$C_{12}$ alkyl, $C_6$-$C_{12}$ aryl, and $C_2$-$C_{12}$ heteroaryl group.

In another preferred embodiment of the invention, W and $W^1$ are each a carbonyl group.

In another preferred embodiment of the invention, $W^2$ and $W^3$ are each, independently, selected from the group consisting of a carbonyl, thiocarbonyl, sulfonyl, $C_1$-$C_{12}$ alkyl, $C_2$-$C_{12}$ heterocyclo, $C_6$-$C_{12}$ aryl, and $C_2$-$C_{12}$ heteroaryl group.

In another preferred embodiment of the invention, $W^2$ and $W^3$ are each a carbonyl group.

In another preferred embodiment of the invention, Y and $Y^1$ are each, independently, selected from the group consisting of H, $C_1$-$C_{12}$ alkyl, $C_3$-$C_{12}$ cycloalkyl, $C_6$-$C_{12}$ aryl, $C_1$-$C_{12}$ alkylcarbonyl, $C_6$-$C_{12}$ arylcarbonyl, $C_2$-$C_{12}$ heterocyclocarbonyl, $C_1$-$C_{12}$ alkoxycarbonyl, $C_1$-$C_{12}$ cycloalkyl-oxy-carbonyl, $C_6$-$C_{12}$ aryloxycarbonyl, $C_2$-$C_{12}$ heteroaryloxycarbonyl, $C_1$-$C_{12}$ alkylaminocarbonyl, $C_1$-$C_{12}$ alkylsulfonyl, $C_3$-$C_{12}$ cycloalkylsulfonyl, $C_6$-$C_{12}$ arylsulfonyl, $C_1$-$C_{12}$ alkylamino sulfonyl, $C_3$-$C_{12}$ cycloalkylaminosulfonyl, and $C_6$-$C_{12}$ arylaminosulfonyl group.

In another preferred embodiment of the invention, Y and $Y^1$ are a $C_1$-$C_5$ alkoxycarbonyl, or $C_1$-$C_5$ alkylaminocarbonyl group.

In another preferred embodiment of the invention, Z and $Z^1$ are each, independently, selected from the group consisting of H, hydroxy, amino, $C_1$-$C_{12}$ alkyl, $C_3$-$C_{12}$ cycloalkyl, $C_1$-$C_{12}$ alkoxy, $C_3$-$C_{12}$ cycloalkyl-oxy, $C_1$-$C_{12}$ alkylamino, $C_3$-$C_{12}$ cycloalkylamino, $C_2$-$C_{12}$ heterocyclo, $C_2$-$C_{12}$ heterocycloamino, $C_6$-$C_{12}$ aryl, $C_6$-$C_{12}$ aryloxy, $C_6$-$C_{12}$ arylamino, $C_3$-$C_{12}$ heteroaryloxy, $C_3$-$C_{12}$ heteroarylamino, $C_1$-$C_{12}$ alkylsulfonamido, $C_3$-$C_{12}$ cycloalkylsulfonamido, $C_6$-$C_{12}$ arylsulfonamido, $C_1$-$C_{12}$ alkoxysulfonamido, $C_3$-$C_{12}$ cycloalkyl-oxy-sulfonamido, $C_6$-$C_{12}$ aryloxysulfonamido, $C_1$-$C_{12}$ alkylaminosulfonamido, $C_3$-$C_{12}$ cycloalkylaminosulfonamido, and $C_6$-$C_{12}$ arylaminosulfonamido group.

In another preferred embodiment of the invention, Z and $Z^1$ are $C_1$-$C_{12}$ alkoxy, or $C_1$-$C_{12}$ alkylamino group In another preferred embodiment of the invention, $R^1$, $R^2$, $R^3$ and $R^4$ are each, independently, selected from the group consisting of H, $C_1$-$C_{12}$ alkyl, $C_3$-$C_{12}$ cycloalkyl, $C_2$-$C_{12}$ heterocyclo, $C_6$-$C_{12}$ aryl, $C_2$-$C_{12}$ heteroaryl, $C_1$-$C_{12}$ alkoxycarbonyl, $C_6$-$C_{12}$ aryloxycarbonyl, $C_2$-$C_{12}$ heterocyclo-oxy carbonyl, $C_1$-$C_{12}$ alkylaminocarbonyl, $C_1$-$C_{12}$ alkylaminosulfonamido, $C_2$-$C_{12}$ heterocycloamino sulfonyl, and $C_6$-$C_{12}$ arylaminosulfonyl group.

In another preferred embodiment of the invention, $R^1$ does not exist, $R^2$ is H, $R^3$ is H, and $R^4$ is H.

In another preferred embodiment of the invention, $R^5$, $R^6$, $R^7$ and $R^8$ are each, independently, selected from the group consisting of H, halogen, hydroxy, cyano, amino, $C_1$-$C_{12}$ alkyl, $C_3$-$C_{12}$ cycloalkyl, $C_2$-$C_{12}$ heterocyclo, $C_1$-$C_{12}$ alkoxy, $C_1$-$C_{12}$ alkylamino, $C_2$-$C_{12}$ heterocycloamino, $C_6$-$C_{12}$ aryl, $C_6$-$C_{12}$ arylamino, $C_1$-$C_{12}$ alkoxycarbonylamino, $C_1$-$C_{12}$ alkylaminocarbonylamino, $C_1$-$C_{12}$ alkylsulfonamido, $C_2$-$C_{12}$ heterocyclosulfonamido, $C_6$-$C_{12}$ arylsulfonamido, and $C_1$-$C_{12}$ alkylaminosulfonamido, or $R^5$ and $R^6$ are linked to form a cyclo group, or $R^7$ and $R^8$ are linked to each other to form a cyclo group.

In another preferred embodiment of the invention:

$R^5$ and $R^7$ are H; and $R^6$ and $R^8$ are a $C_1$-$C_6$ alkyl, $C_2$-$C_6$ heterocyclo, $C_6$-$C_{10}$ aryl, or $C_3$-$C_8$ heteroaryl group.

In another preferred embodiment of the invention, $R^9$, $R^{10}$, $R^{11}$ and $R^{12}$ are each, independently, selected from the group consisting of H, halogen, hydroxy, cyano, amino, $C_1$-$C_{12}$ alkyl, $C_3$-$C_{12}$ cycloalkyl, $C_1$-$C_{12}$ alkoxy, $C_1$-$C_{12}$ alkylamino, $C_2$-$C_{12}$ heterocycloamino, $C_6$-$C_{12}$ aryl, $C_3$-$C_{12}$ heteroaryl, $C_6$-$C_{20}$ arylamino, and $C_1$-$C_{12}$ alkoxycarbonylamino, or $R^9$ and $R^{10}$ may be linked to each to form a cyclo or spiro group, and $R^{11}$ and $R^{12}$ may be linked to each other to form a cyclo or spiro group.

In another preferred embodiment of the invention, $R^9$, $R^{10}$, $R^{11}$ and $R^{12}$ are H.

In the second aspect, the present invention provides a pharmaceutical composition comprising one or more compounds selected from the structure Ia or Ib.

The third aspect of the present invention provides a pharmaceutical combination of any one or more compounds of the structure Ia or Ib in a therapeutically effective dose and/with a second or a third medicament in a therapeutically effective dose. Thus, the present invention provides a pharmaceutical composition, comprising at least one compound described above in a therapeutically effective dose and at least one additional medicament in a therapeutically effective dose.

The fourth aspect of the present invention provides a pharmaceutical combination of any compound of the structure Ia or Ib with any HIV inhibitors including but not limited to Indinavir or Ritonavir. Thus, the present invention provides a pharmaceutical composition, comprising at least one compound described above in a therapeutically effective dose and at least one HIV inhibitor in a therapeutically effective dose.

The fifth aspect of the present invention provides a pharmaceutical combination of at least one compound described above and any hepatitis B virus (HBV) inhibitor including but not limited to Lamivudine, Telbivudine, Adefovir, Entecavir, Tenofovir, or Clevudine.

The sixth aspect of the present invention provides a method for inhibiting HCV by using one or more compounds of the structure Ia or Ib in a therapeutically effective dose and a second or a third medicament in a therapeutically effective dose. Thus, the present invention provides a method of inhibiting HCV, comprising administering an effect amount of a compound or composition described above to a subject in need thereof.

The seventh aspect of the present invention provides a method for inhibiting HCV by using one or more compounds of the structure Ia or Ib and in combination with any or combined one or more of (1) Immune modulators including but not limited to Interferons, pegulated-interferons, or interferon derivatives, (2) HCV protease inhibitors, (3) HCV polymerase inhibitors, (4) nucleosides and its derivatives, (5) Cyclophilin inhibitors, (6) Glucosidase I inhibitors, (7) IMPDH inhibitors, (8) Caspase inhibitors, (9) TLR agonists, (10) HIV inhibitors, (11) anti-inflammatory drugs, (12) Cancer drugs, or (13) other compounds not covered from above (1)-(12).

Overall, all prepared new polyaryl and polyheteroaryl based antiviral compounds have been evaluated for their potency and toxicity. The present invention explores the relationship between the structures of new polyaryl and polyheteroaryl compounds and potency of HCV inhibition, and finally to provide valuable clue and potential effective and safe HCV inhibitors.

The present invention not only relates to design and synthesize the novel antiviral compounds as HCV-NS5A inhibitors, but also explores the relation between different novel polyaryl and fused heteroaryl compounds and their activity of HCV-NS5A inhibition, and finally to optimize and develop one of the best-in-class HCV-NS5A inhibitors.

Thus, the present invention also provides pharmaceutical composition comprising the compound described above and a pharmaceutically acceptable carrier.

The present invention also provides a composition comprising at least one compound as described above and at least one compound selected from the group consisting of an HIV inhibitor and a hepatitis B virus (HBV) inhibitor.

The present invention also provides a composition comprising at least one compound as described above and at least one compound selected from the group consisting of Lamivudine, Telbivudine, Adefovir, Entecavir, Tenofovir and Clevudine.

The present invention also provides a composition comprising at least one compound as described above and at least one compound selected from the group consisting of (1) Immune modulators, (2) HCV protease inhibitors, (3) HCV polymerase inhibitors, (4) nucleosides and derivatives thereof, (5) Cyclophilin inhibitors, (6) Glucosidase I inhibitors, (7) IMPDH inhibitors, (8) Caspase inhibitors, (9) TLR agonists, (10) HIV inhibitors, (11) anti-inflammatory drugs, and (12) anti-cancer drugs.

The present invention also provides a method of inhibiting Hepatitis C virus comprising contacting Hepatitis C virus with an effective amount of the compound as described above.

The present invention also provides a method of treating a subject infected with Hepatitis C virus comprising administering an effective amount of the compound as described above to the subject.

The present invention also provides a method of treating a subject infected with Hepatitis C virus comprising administering an effective amount of the composition as described above to the subject.

The present invention also provides a method of treating a subject infected with Hepatitis C virus comprising administering an effective amount of the composition as described above to the subject.

The present invention also provides a method of treating a subject infected with Hepatitis C virus comprising administering an effective amount of the composition as described above to the subject.

The present invention also provides a method of treating a subject infected with Hepatitis C virus comprising administering an effective amount of the composition described above to the subject.

DETAILED DESCRIPTION OF THE INVENTION

Details of the present invention are set forth in the following description for preparation and biological activity study of new HCV inhibitors Ia-Ib. The advantages of the present invention will be significantly observed from the following detailed description.

As used herein, the term "alkyl" refers to any linear or branched chain alkyl group having a number of carbon atoms and/or "alkylene" in the specified range, wherein one or more hydrogens could be replaced by one or more halogens.

The term "alkoxy" refers to an "alkyl-O—" group.

The term "cycloalkyl" refers to any cyclic ring of an alkane or alkene having a number of carbon atoms and/or "alkylene" in the specified range, wherein one or more hydrogens could be replaced by one or more halogens.

The term "cycloalkyl-oxy" refers to a "cycloalkyl-O—".

The term "cycloalkyl-amino" refers to a "cycloalkyl-N (Ra)—".

The term "halogen" (or "halo") refers to fluorine, chlorine, bromine and iodine atoms (or referred as fluoro, chloro, bromo, and iodo).

The term "carbonyl" refers to a "—C(O)—" group.

The term "alkylcarbonyl" refers to an "alkyl-C(O)—" group.

The term "alkoxy carbonyl" refers to an "alkyl-O—C(O)—" group.

The term "alkylamino carbonyl" refers to an "alkyl-NH—C(O)—" or "dialkyl-N—C(O)—" group.

The term "sulfonamido" refers to a "—S(O)$_2$NH—" or "—S(O)$_2$N(Ra)—" group, wherein Ra is alkyl or alkylcarbonyl group.

The term "alkyl sulfonamido" refers to an "alkyl-S(O)$_2$NH—" or "alkyl-S(O)$_2$N(Ra)—" group, wherein Ra is alkyl or alkylcarbonyl group.

The term "alkoxy sulfonamido" refers to an "alkyl-O—S(O)$_2$NH—" or "alkyl-O—S(O)$_2$N(Ra)—" group, wherein Ra is alkyl or alkylcarbonyl group.

The term "heteroaryl" refers to an aryl group with 1-3 hetero atoms including O, N, and/or S atoms.

The term "fused heteroaryl" refers to a bi-cyclic, tri-cyclic or tetra-cyclic heteroaryl group with 1-5 hetero atoms such as O, N, and/or S atoms.

The term "poly-heteroaryl" refers to a bi-, tri- or tetra-heteroaryl functional group with 1-5 hetero atoms (e.g., O, N, S, and P) in one or more fused rings.

The term "poly-heterocyclic" refers to a bi-cyclic, tri-cyclic or tetra-cyclic functional group with 1-5 hetero atoms (e.g., O, N, S, and P) in one or more fused rings.

The term "composition" is intended to encompass a product comprising the specified ingredients, as well as any product which results, directly or indirectly, from combining the specified ingredients.

The term "pharmaceutically acceptable" means that the ingredients of the pharmaceutical composition must be compatible with each other and not deleterious to the recipient thereof.

The term "effective amount" means that amount of active compound or pharmaceutical agent that elicits the biological or medicinal response in a tissue, system, animal or human that is being sought by a researcher, veterinarian, medical doctor or other clinician. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

The present invention provides two classes of novel antiviral compounds Ia-Ib, and pharmaceutically acceptable salts, and/or hydrates as HCV NS5A inhibitors with high potency. Moreover, toxicity study is determined to be non-toxic (LD$_{50}$>10,000) for most of highly potent HCV-NS5A inhibitors.

Synthesis of New Antiviral Compounds with General Structure Ia-Ib:

The reagents and raw materials used in the present invention are all commercially available.

Abbreviations of chemical materials, reagents, and solvents related to the synthesis of antiviral compounds in the present invention are listed in the parts of examples.

The compounds in the present invention could be synthesized by normal raw materials through several synthetic methods after designing the structure of different compounds in the present invention.

The present disclosure relates to the following key innovations:

First, compounds SM1 and SM2 with heterocyclic functional groups in structural figures 1 and 2 were subjected to the amidation coupling reaction to offer the intermediate 3 (IIa). Subsequently, the protecting groups (i.e., PG or/and PG1) in compound 3 were cleaved to offer the intermediate 4 or 5, respectively, followed by the coupling or amidation reaction to afford the novel compound 6 of formula Ia (see structural figure 3). The preparation method of these compounds were shown in the following schemes 1-3, respectively; wherein, the "X" group of SM1 and SM3 were selected from bromine (Br), and "Y" group of the SM2 and SM4 was selected from boric acid or boric acid ester in schemes 1 and 2.

The present invention also provides the preparation methods (1-3) of the compounds shown in Ia and Ib, as well as their stereoisomers, tautomers, esterification or amidation prodrugs and the pharmaceutically acceptable salts. These methods were described in the following sections:

Method 1:

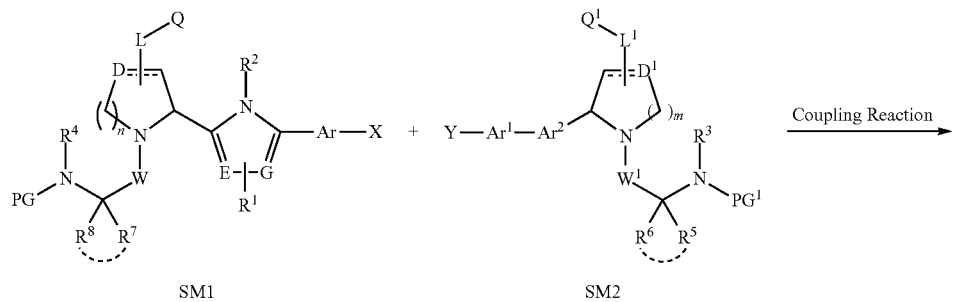

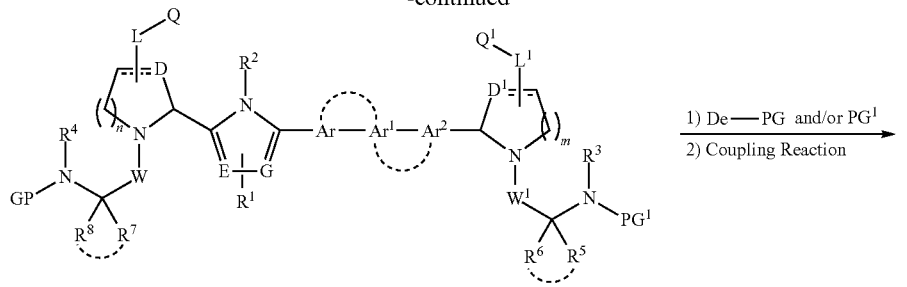
3 (IIa)
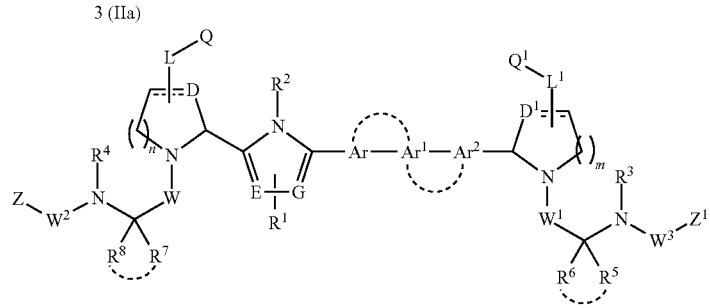
6 (Ia)
Method 2:
The Compound 6 (Ia) was also obtained by the coupling reaction of the compound SM3 with another compound SM4, respectively:
Method 3:
Another class of compounds 6fa-6fy (Ib) was also obtained by the coupling reaction of the compounds SM3 with other compounds SM4, respectively:
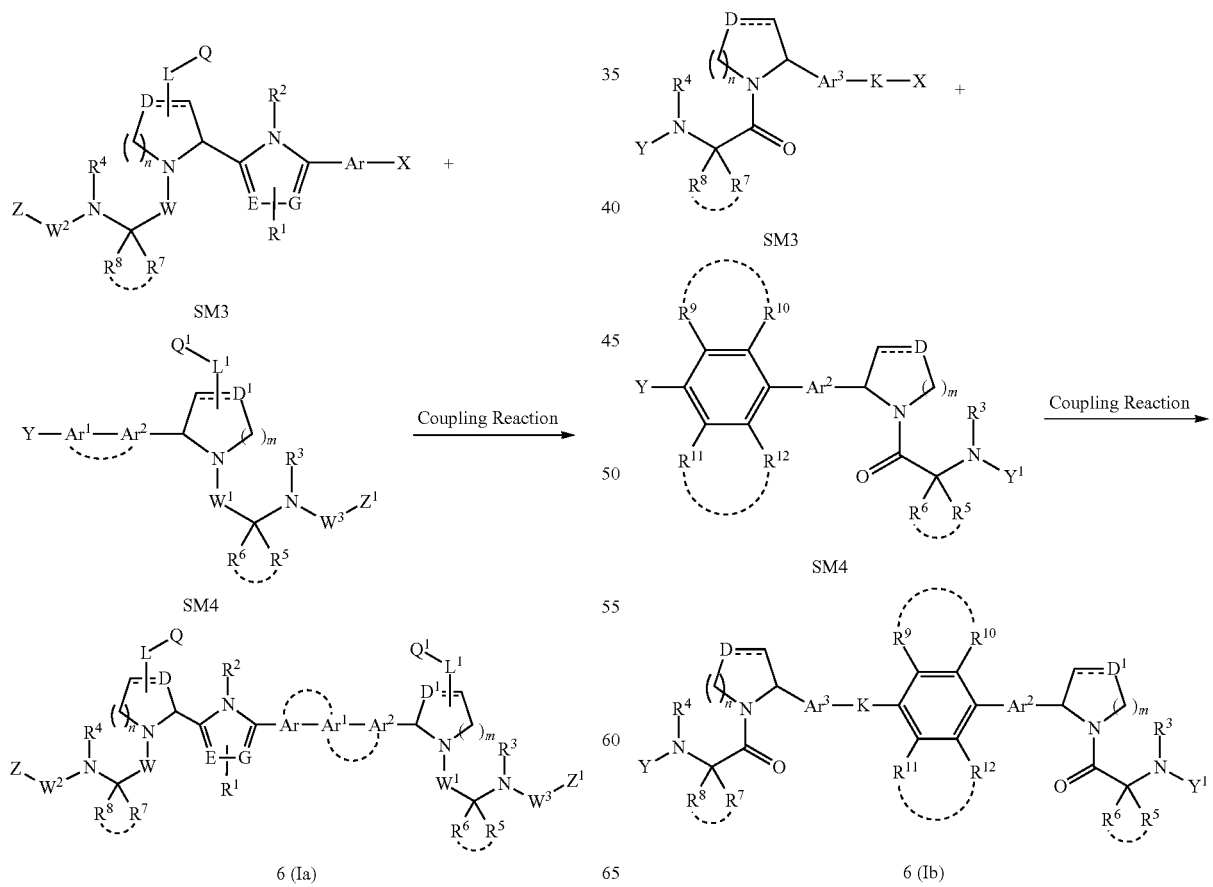

In the following example, the compounds SM3 (SM-3a to SM-3di) in structural figure 1 and heterocyclic compounds SM4 (SM-4a to SM-4bk) in structural figure 2 were subjected to the catalytic coupling reactions (Scheme 1) by Pd-based catalyst to prepare a series of novel compounds 6 of the formulas Ia and Ib (6a-6ep and 6fa-6fy in structural figure 3).
Scheme 1:
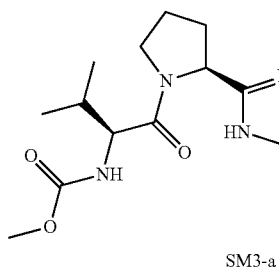
SM3-a
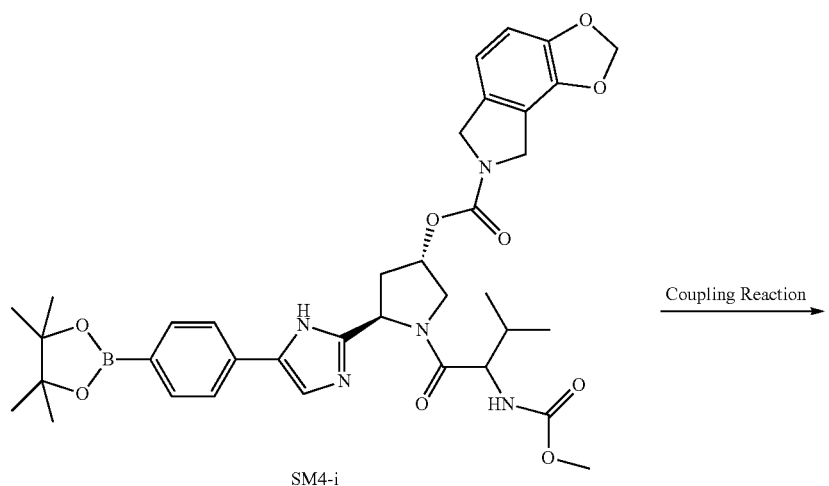
SM4-i
Coupling Reaction
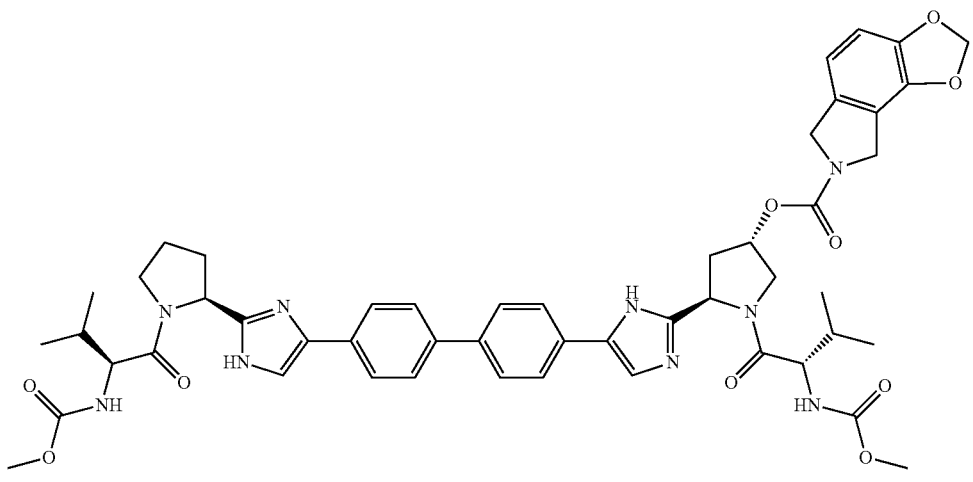
6a Starting materials SM3 and SM4 in structural figures 1 and 2 are critical materials required for the synthesis of target compounds Ia and Ib in present disclosure, the structures of them were shown as follows:
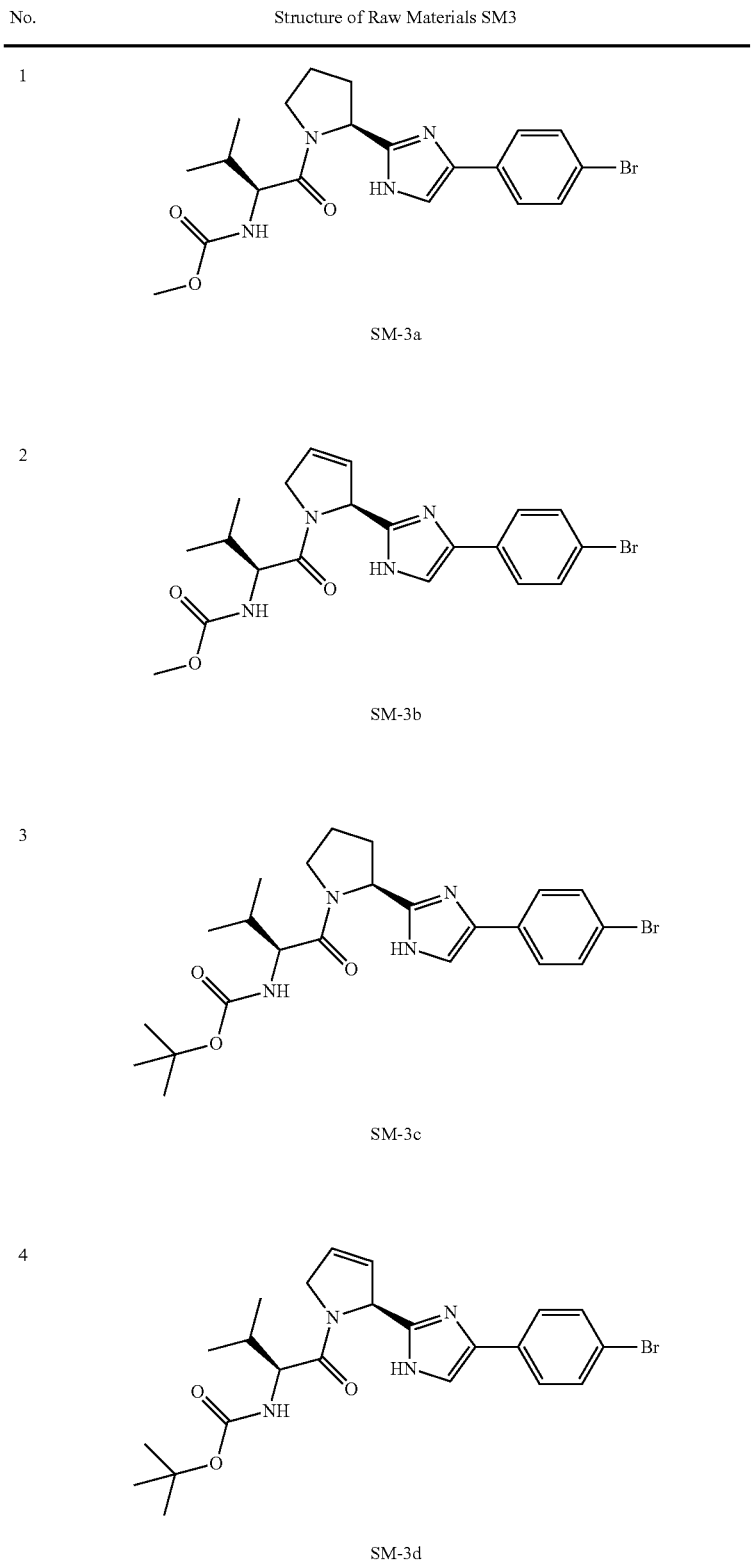
Structural FIG. 1: Chemical materials SM3 (SM-3a to SM-3cs)

Structural FIG. 1: Chemical materials SM3 (SM-3a to SM-3cs)
| No. | Structure of Raw Materials SM3 |
|-----|-------------------------------|
| 5 | 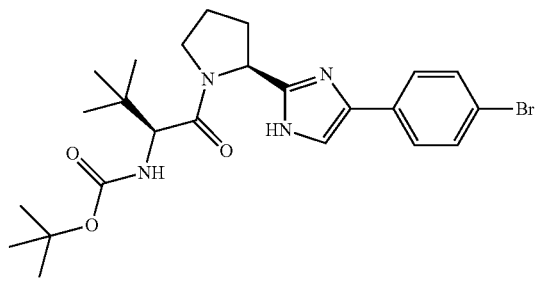 [SMILES: CC(C)(C)OC(=O)N[C@H](C(=O)N1CCC[C@H]1c1nc(-c2ccc(Br)cc2)c[nH]1)C(C)(C)C]<br>SM-3e |
| 6 | 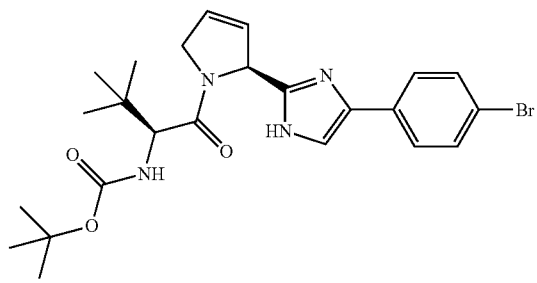 [SMILES: CC(C)(C)OC(=O)N[C@H](C(=O)N1CC=C[C@H]1c1nc(-c2ccc(Br)cc2)c[nH]1)C(C)(C)C]<br>SM-3f |
| 7 | 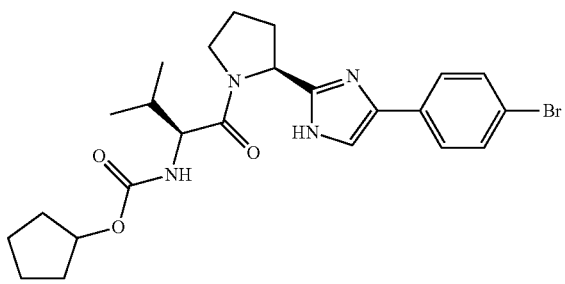 [SMILES: CC(C)[C@H](NC(=O)OC1CCCC1)C(=O)N1CCC[C@H]1c1nc(-c2ccc(Br)cc2)c[nH]1]<br>SM-3g |
| 8 | 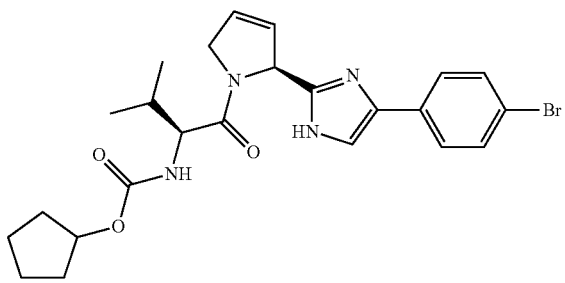 [SMILES: CC(C)[C@H](NC(=O)OC1CCCC1)C(=O)N1CC=C[C@H]1c1nc(-c2ccc(Br)cc2)c[nH]1]<br>SM-3h |

-continued
| Structural FIG. 1: Chemical materials SM3 (SM-3a to SM-3cs) | |
|---|---|
| No. | Structure of Raw Materials SM3 |
| 9 | 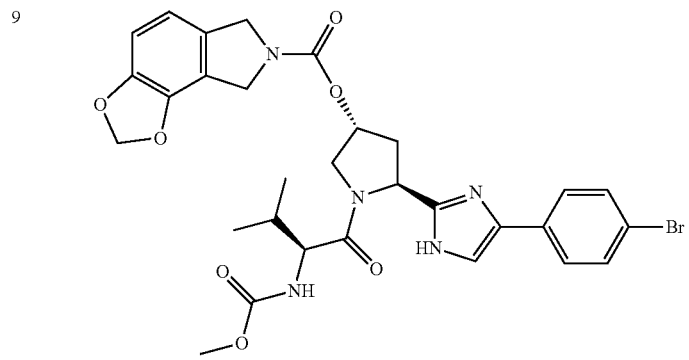\
SM-3i |
| 10 | 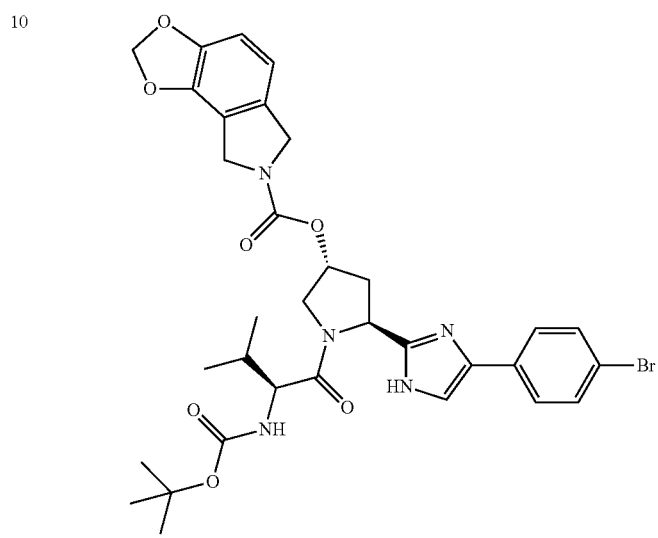\
SM-3j |
| 11 | 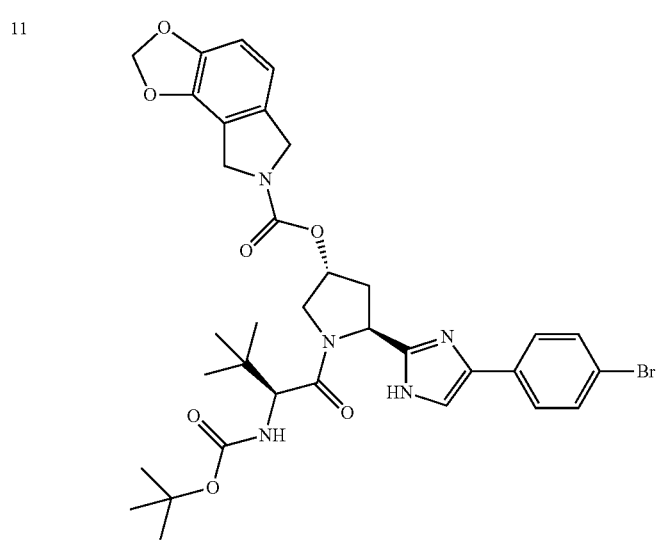\
SM-3k |

| Structural FIG. 1: Chemical materials SM3 (SM-3a to SM-3cs) | |
|---|---|
| No. | Structure of Raw Materials SM3 |
12
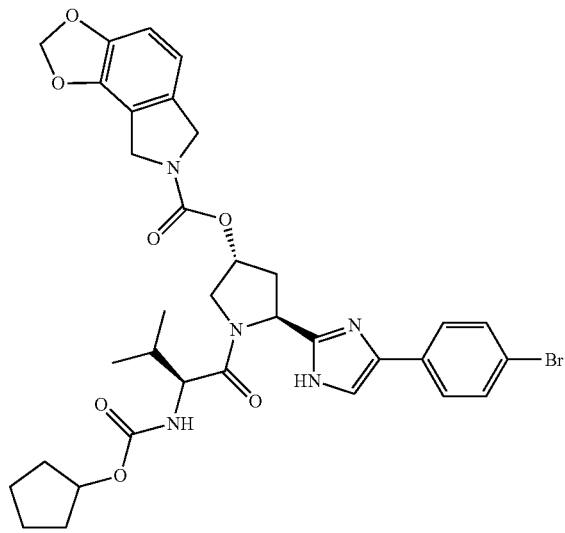 [SMILES: CC(C)[C@H](NC(=O)OC1CCCC1)C(=O)N1C[C@H](OC(=O)N2Cc3ccc4c(c3C2)OCO4)C[C@H]1c1nc(-c2ccc(Br)cc2)c[nH]1]
SM-3m
13
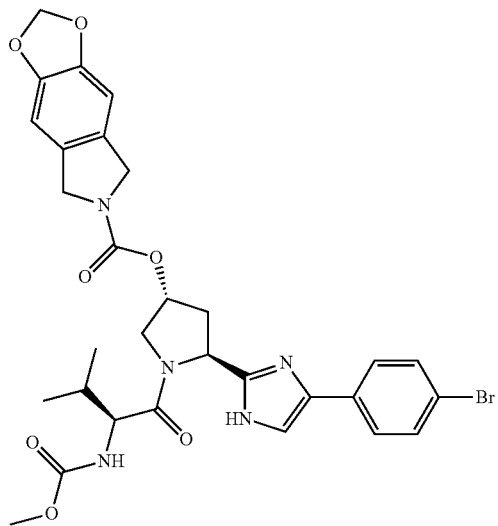 [SMILES: COC(=O)N[C@H](C(=O)N1C[C@H](OC(=O)N2Cc3cc4c(cc3C2)OCO4)C[C@H]1c1nc(-c2ccc(Br)cc2)c[nH]1)C(C)C]
SM-3n -continued
Structural FIG. 1: Chemical materials SM3 (SM-3a to SM-3cs)
| No. | Structure of Raw Materials SM3 |
|---|---|
14
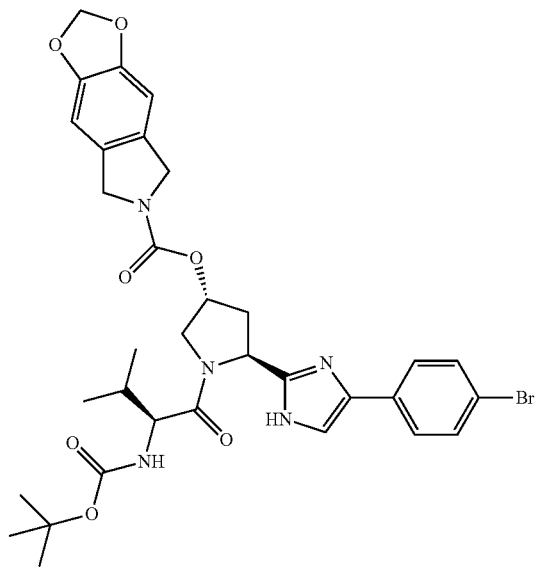 [SMILES: CC(C)[C@H](NC(=O)OC(C)(C)C)C(=O)N1C[C@H](OC(=O)N2Cc3cc4c(cc3C2)OCO4)C[C@H]1c1nc(-c2ccc(Br)cc2)c[nH]1]
SM-3p
15
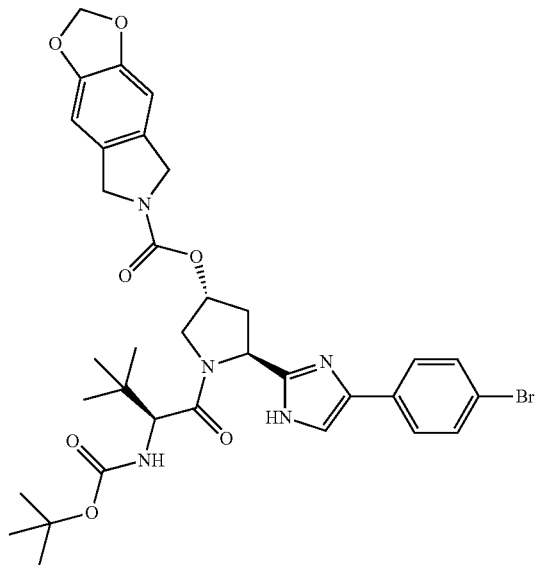 [SMILES: CC(C)(C)OC(=O)N[C@H](C(=O)N1C[C@H](OC(=O)N2Cc3cc4c(cc3C2)OCO4)C[C@H]1c1nc(-c2ccc(Br)cc2)c[nH]1)C(C)(C)C]
SM-3q Structural FIG. 1: Chemical materials SM3 (SM-3a to SM-3cs)
| No. | Structure of Raw Materials SM3 |
|---|---|
| 16 | 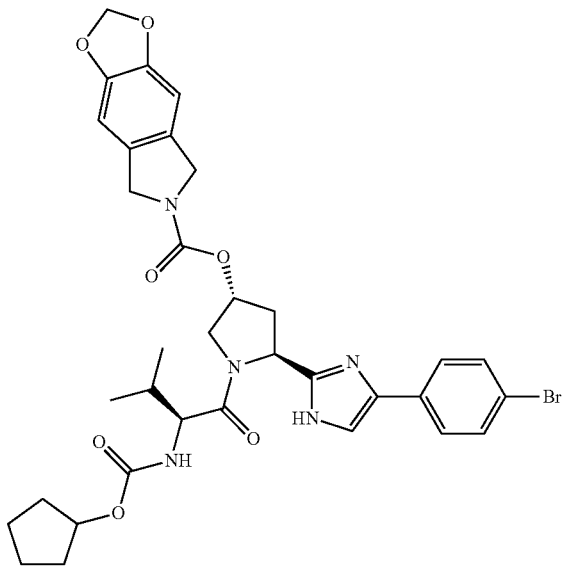 [SMILES: CC(C)[C@H](NC(=O)OC1CCCC1)C(=O)N1C[C@H](OC(=O)N2Cc3cc4c(cc3C2)OCO4)C[C@H]1c1nc(-c2ccc(Br)cc2)c[nH]1]{br}SM-3r |
| 17 | 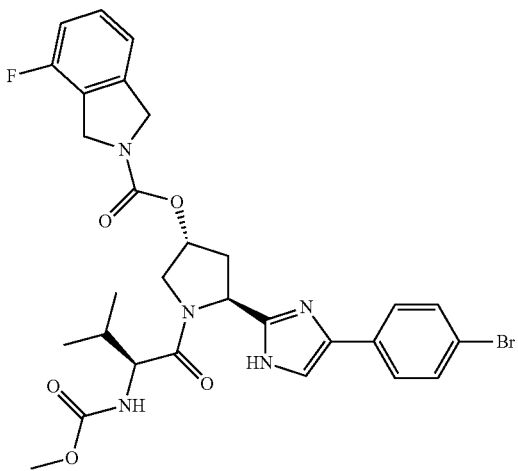 [SMILES: COC(=O)N[C@H](C(=O)N1C[C@H](OC(=O)N2Cc3cccc(F)c3C2)C[C@H]1c1nc(-c2ccc(Br)cc2)c[nH]1)C(C)C]{br}SM-3s |

-continued
Structural FIG. 1: Chemical materials SM3 (SM-3a to SM-3cs)
| No. | Structure of Raw Materials SM3 |
|---|---|
| 18 | 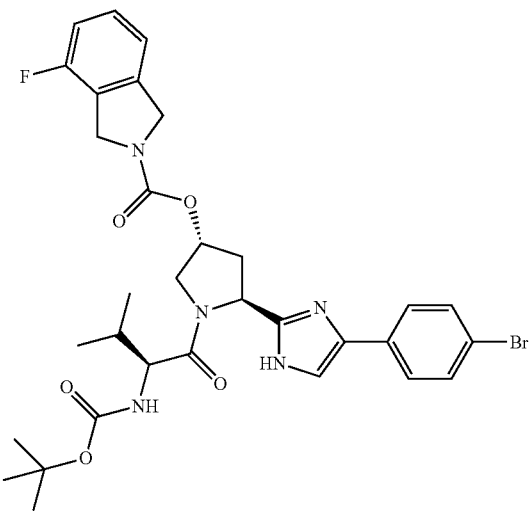 [SMILES: CC(C)[C@H](NC(=O)OC(C)(C)C)C(=O)N1C[C@H](OC(=O)N2Cc3cccc(F)c3C2)C[C@H]1c1nc(-c2ccc(Br)cc2)c[nH]1]<br>SM-3t |
| 19 | 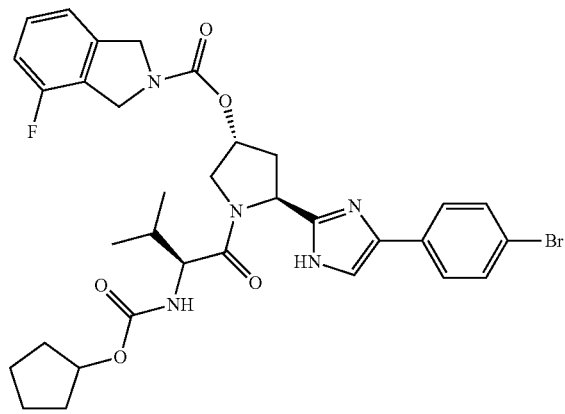 [SMILES: CC(C)[C@H](NC(=O)OC1CCCC1)C(=O)N1C[C@H](OC(=O)N2Cc3cccc(F)c3C2)C[C@H]1c1nc(-c2ccc(Br)cc2)c[nH]1]<br>SM-3u |
| 20 | 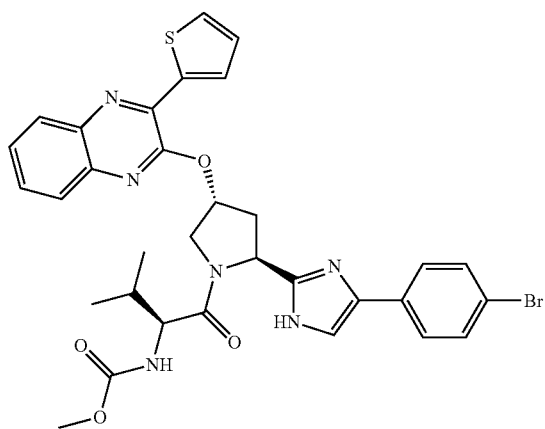 [SMILES: COC(=O)N[C@H](C(=O)N1C[C@H](Oc2nc3ccccc3nc2-c2cccs2)C[C@H]1c1nc(-c2ccc(Br)cc2)c[nH]1)C(C)C]<br>SM-3v |

| Structural FIG. 1: Chemical materials SM3 (SM-3a to SM-3cs) | |
|---|---|
| No. | Structure of Raw Materials SM3 |
| 21 | 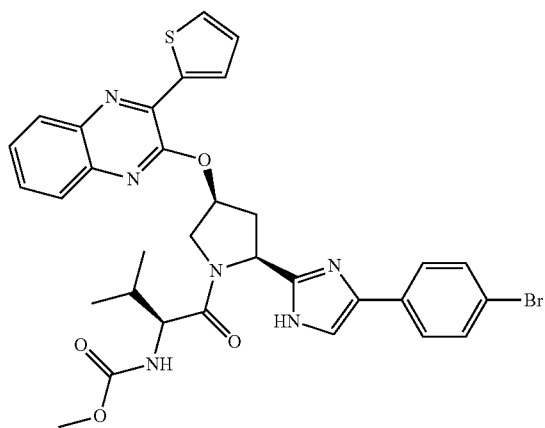 [SMILES: COC(=O)N[C@H](C(=O)N1C[C@@H](Oc2nc3ccccc3nc2-c2cccs2)C[C@H]1c1nc(-c2ccc(Br)cc2)c[nH]1)C(C)C]<br>SM-3w |
| 22 | 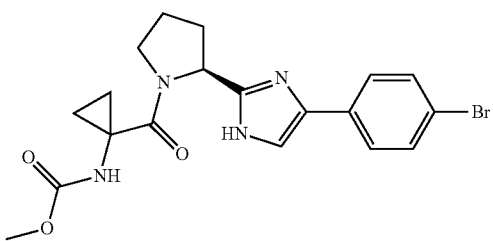 [SMILES: COC(=O)NC1(C(=O)N2CCC[C@H]2c2nc(-c3ccc(Br)cc3)c[nH]2)CC1]<br>SM-3x |
| 23 | 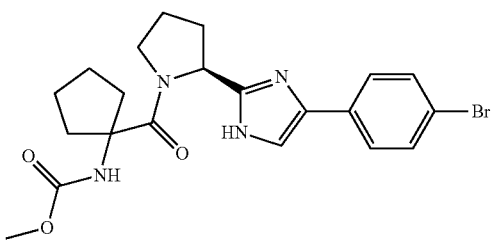 [SMILES: COC(=O)NC1(C(=O)N2CCC[C@H]2c2nc(-c3ccc(Br)cc3)c[nH]2)CCCC1]<br>SM-3y |
| 24 | 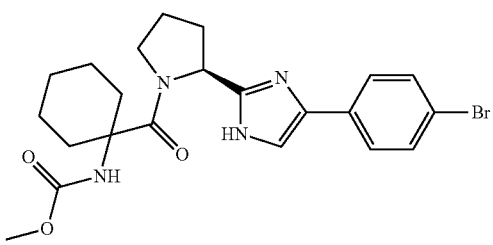 [SMILES: COC(=O)NC1(C(=O)N2CCC[C@H]2c2nc(-c3ccc(Br)cc3)c[nH]2)CCCCC1]<br>SM-3z |

| Structural FIG. 1: Chemical materials SM3 (SM-3a to SM-3cs) | |
|---|---|
| No. | Structure of Raw Materials SM3 |
| 25 | 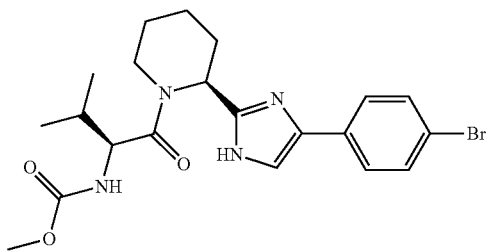 [SMILES: COC(=O)N[C@H](C(=O)N1CCCC[C@H]1c1nc(-c2ccc(Br)cc2)c[nH]1)C(C)C]<br>SM-3aa |
| 26 | 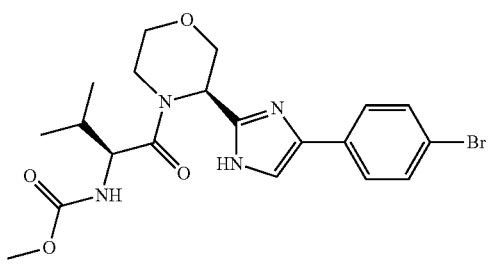 [SMILES: COC(=O)N[C@H](C(=O)N1CCOC[C@H]1c1nc(-c2ccc(Br)cc2)c[nH]1)C(C)C]<br>SM-3ab |
| 27 | 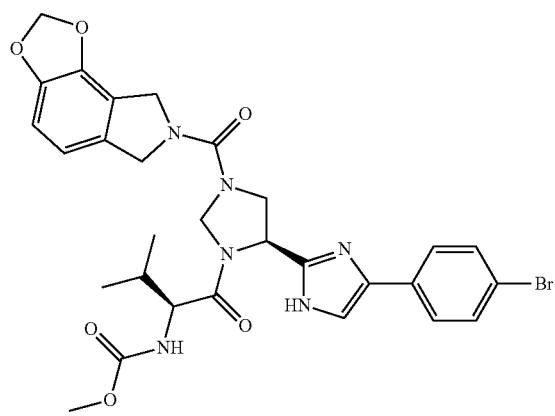 [SMILES: COC(=O)N[C@H](C(=O)N1CN(C(=O)N2Cc3ccc4c(c3C2)OCO4)C[C@H]1c1nc(-c2ccc(Br)cc2)c[nH]1)C(C)C]<br>SM-3ac |
| 28 | 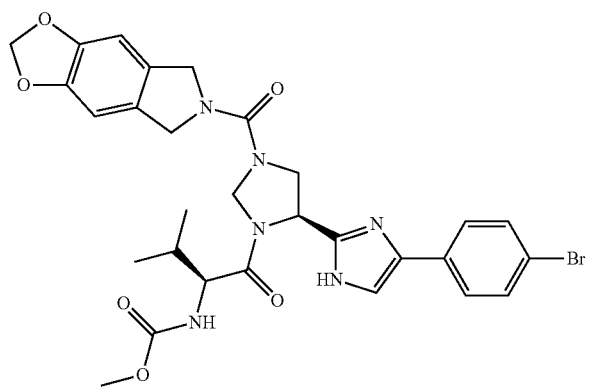 [SMILES: COC(=O)N[C@H](C(=O)N1CN(C(=O)N2Cc3cc4c(cc3C2)OCO4)C[C@H]1c1nc(-c2ccc(Br)cc2)c[nH]1)C(C)C]<br>SM-3ad |

| No. | Structure of Raw Materials SM3 |
|---|---|
| 29 | 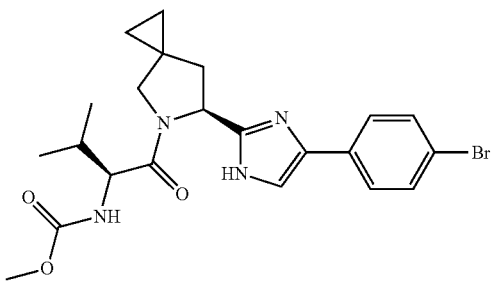 [SMILES: COC(=O)N[C@H](C(=O)N1CC2(CC2)C[C@H]1c1nc(-c2ccc(Br)cc2)c[nH]1)C(C)C]<br>SM-3ae |
| 30 | 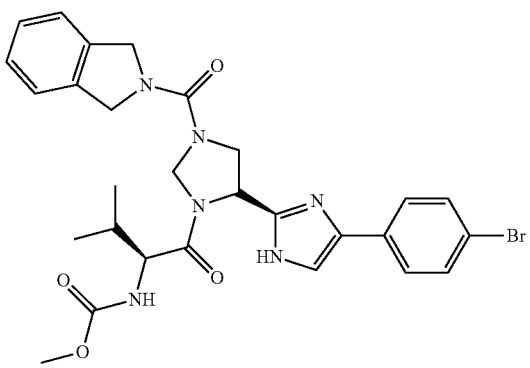<br>SM-3af |
| 31 | 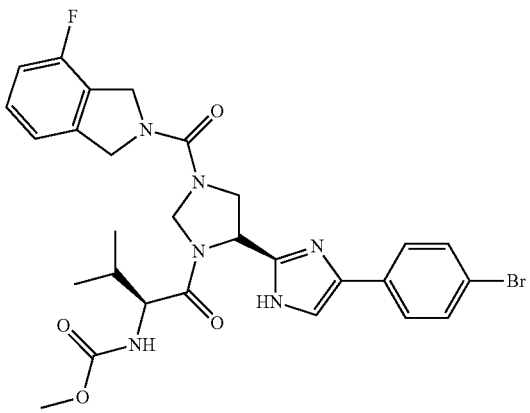<br>SM-3ag |
Structural FIG. 1: Chemical materials SM3 (SM-3a to SM-3cs) -continued

| Structural FIG. 1: Chemical materials SM3 (SM-3a to SM-3cs) | |
|---|---|
| No. | Structure of Raw Materials SM3 |
| 32 | 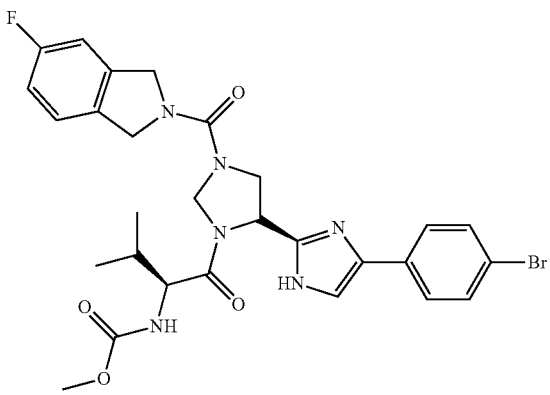<br>SM-3ah |
| 33 | 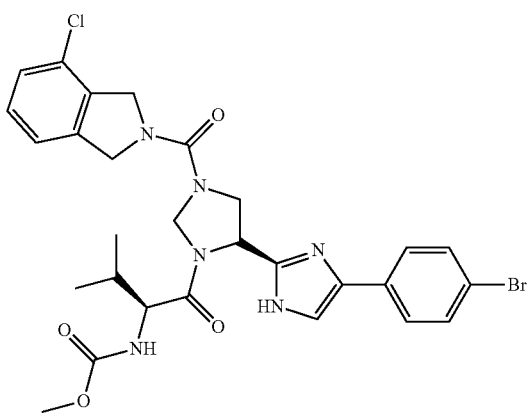<br>SM-3ai |
| 34 | 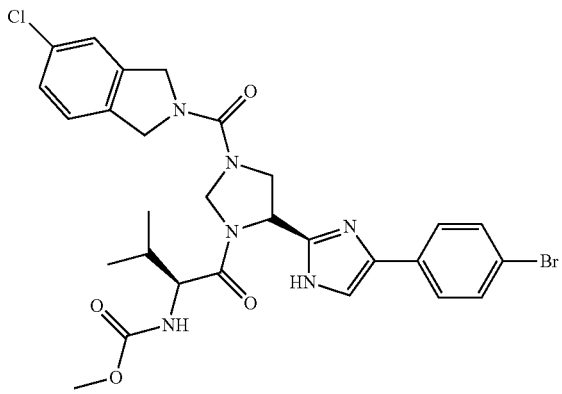<br>SM-3aj |

-continued
| Structural FIG. 1: Chemical materials SM3 (SM-3a to SM-3cs) |
|---|
| No. Structure of Raw Materials SM3 |
35 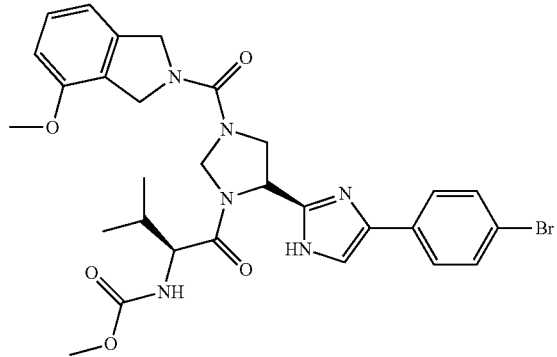
SM-3ak
36 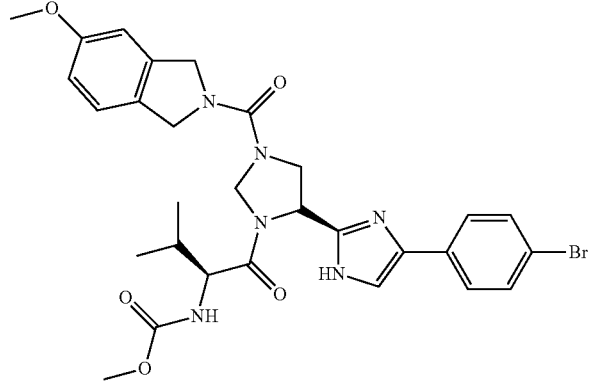
SM-3am
37 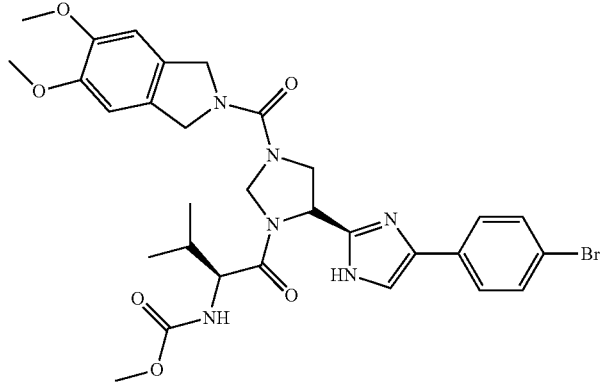
SM-3an
38 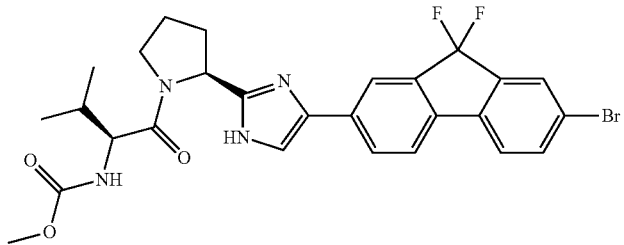 [SMILES: COC(=O)N[C@H](C(=O)N1CC=C[C@H]1c1nc(-c2ccc3c(c2)C(F)(F)c2cc(Br)ccc2-3)c[nH]1)C(C)C]
SM-3ap

Structural FIG. 1: Chemical materials SM3 (SM-3a to SM-3cs)
| No. | Structure of Raw Materials SM3 |
|---|---|
| 39 | 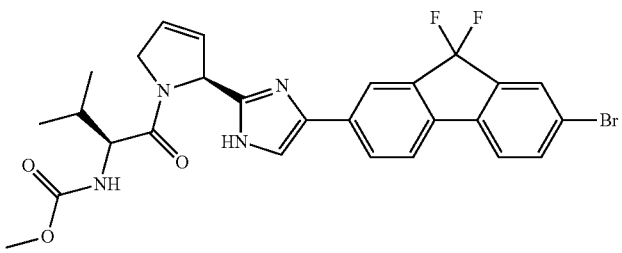<br>SM-3aq |
| 40 | 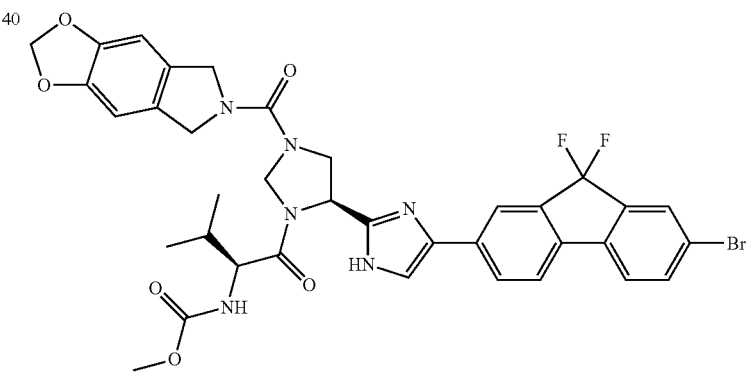<br>SM-3ar |
| 41 | 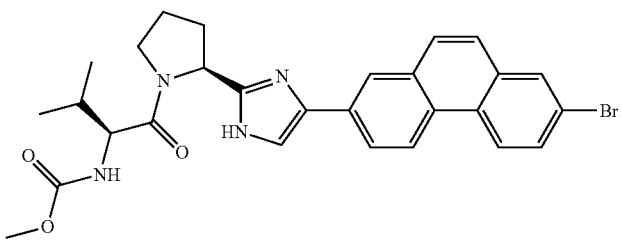 [SMILES: COC(=O)N[C@H](C(=O)N1CCC[C@H]1c1nc(-c2ccc3c(ccc4cc(Br)ccc43)c2)c[nH]1)C(C)C]<br>SM-3as |
| 42 | 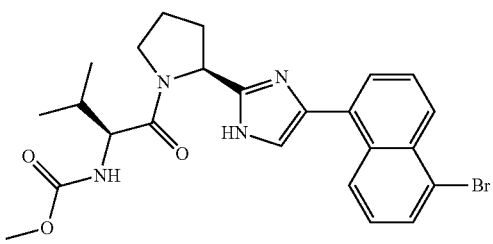 [SMILES: COC(=O)N[C@H](C(=O)N1CCC[C@H]1c1nc(-c2cccc3c(Br)cccc23)c[nH]1)C(C)C]<br>SM-3at |

| | Structural FIG. 1: Chemical materials SM3 (SM-3a to SM-3cs) |
|---|---|
| No. | Structure of Raw Materials SM3 |
| 43 | 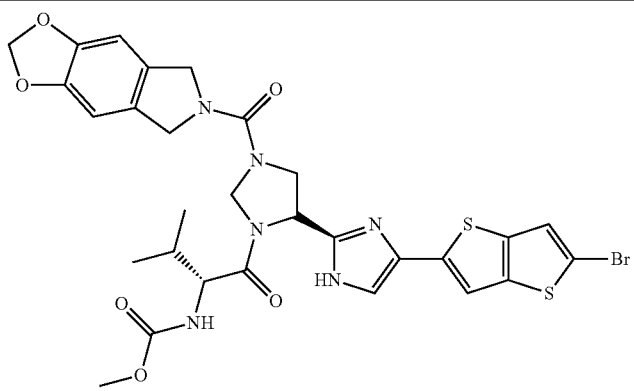<br>SM-3au |
| 44 | 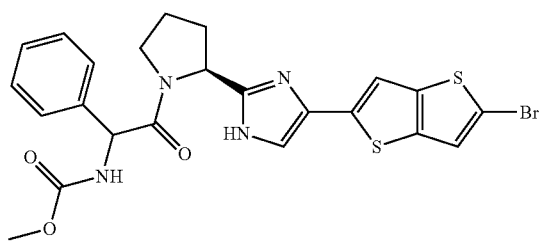 [SMILES: COC(=O)NC(C(=O)N1CCC[C@H]1c1nc(-c2cc3sc(Br)cc3s2)c[nH]1)c1ccccc1]<br>SM-3av |
| 45 | 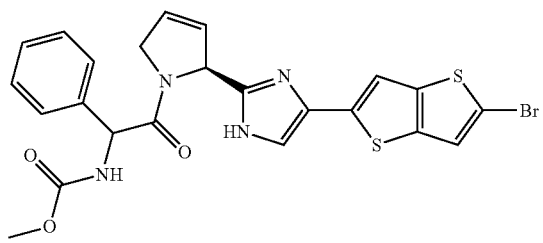 [SMILES: COC(=O)NC(C(=O)N1CC=C[C@H]1c1nc(-c2cc3sc(Br)cc3s2)c[nH]1)c1ccccc1]<br>SM-3aw |
| 46 | 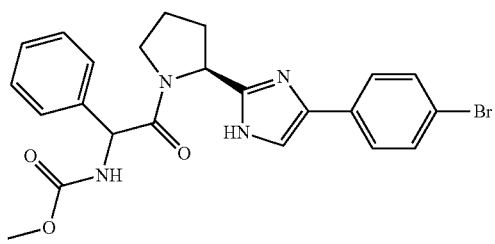 [SMILES: COC(=O)NC(C(=O)N1CCC[C@H]1c1nc(-c2ccc(Br)cc2)c[nH]1)c1ccccc1]<br>SM-3ax |
| 47 | 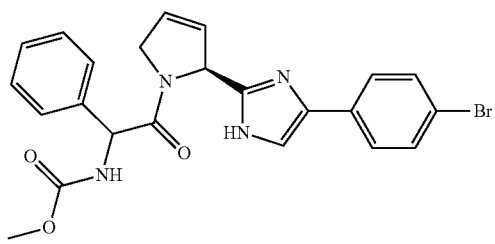 [SMILES: COC(=O)NC(C(=O)N1CC=C[C@H]1c1nc(-c2ccc(Br)cc2)c[nH]1)c1ccccc1]<br>SM-3ay |

-continued
| | Structural FIG. 1: Chemical materials SM3 (SM-3a to SM-3cs) |
|---|---|
| No. | Structure of Raw Materials SM3 |
48
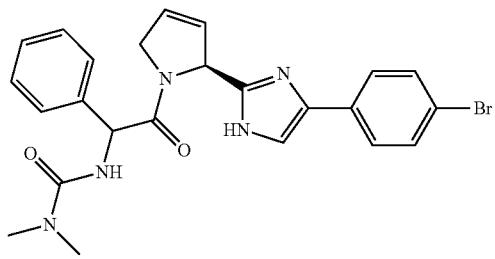 [SMILES: CN(C)C(=O)NC(C(=O)N1CC=C[C@H]1c1nc(-c2ccc(Br)cc2)c[nH]1)c1ccccc1]
SM-3az
49
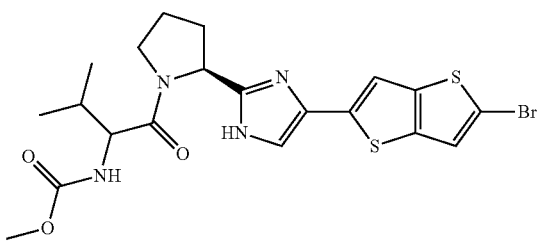 [SMILES: COC(=O)NC(C(=O)N1CCC[C@H]1c1nc(-c2cc3sc(Br)cc3s2)c[nH]1)C(C)C]
SM-3ba
50
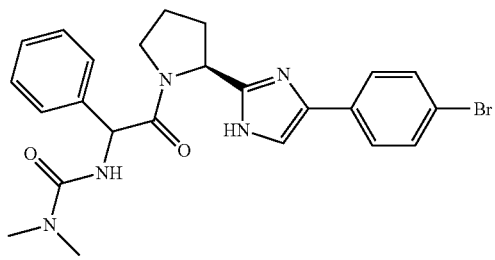 [SMILES: CN(C)C(=O)NC(C(=O)N1CC=C[C@H]1c1nc(-c2ccc(Br)cc2)c[nH]1)c1ccccc1]
SM-3bb
51
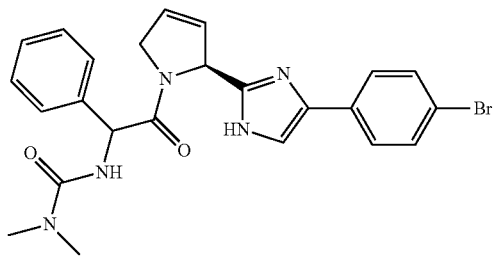
SM-3bc
52
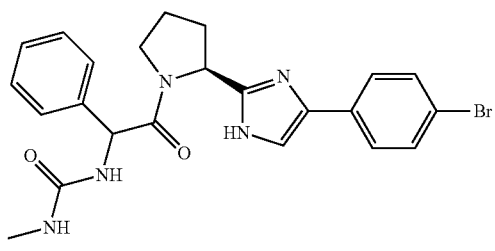 [SMILES: CNC(=O)NC(C(=O)N1CCC[C@H]1c1nc(-c2ccc(Br)cc2)c[nH]1)c1ccccc1]
SM-3bd -continued
Structural FIG. 1: Chemical materials SM3 (SM-3a to SM-3cs)
| No. | Structure of Raw Materials SM3 |
|---|---|
| 53 | 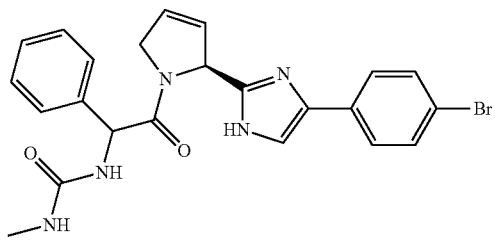 [SMILES: CNC(=O)NC(C(=O)N1CC=C[C@H]1c1nc(-c2ccc(Br)cc2)c[nH]1)c1ccccc1]<br>SM-3be |
| 54 | 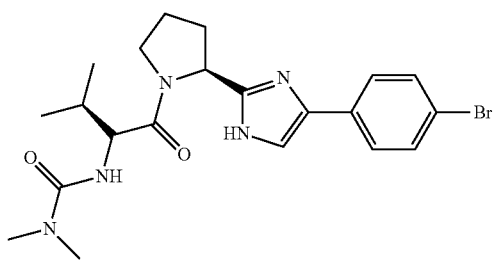<br>SM-3bf |
| 55 | 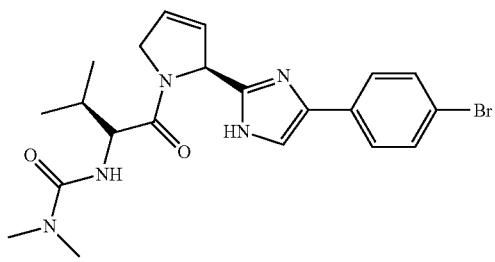<br>SM-3bg |
| 56 | 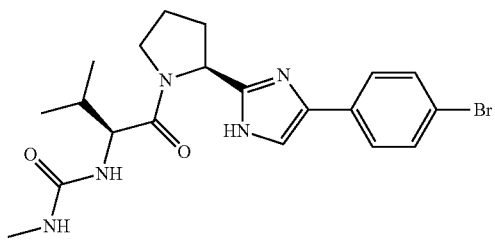 [SMILES: CNC(=O)N[C@H](C(=O)N1CCC[C@H]1c1nc(-c2ccc(Br)cc2)c[nH]1)C(C)C]<br>SM-3bh |
| 57 | 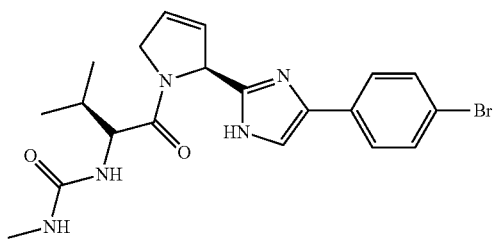<br>SM-3bi |

| Structural FIG. 1: Chemical materials SM3 (SM-3a to SM-3cs) | |
|---|---|
| No. | Structure of Raw Materials SM3 |
| 58 | 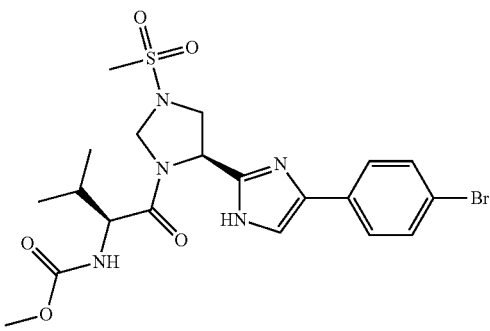 [SMILES: COC(=O)N[C@H](C(=O)N1CN(S(C)(=O)=O)C[C@H]1c1nc(-c2ccc(Br)cc2)c[nH]1)C(C)C]<br>SM-3bj |
| 59 | 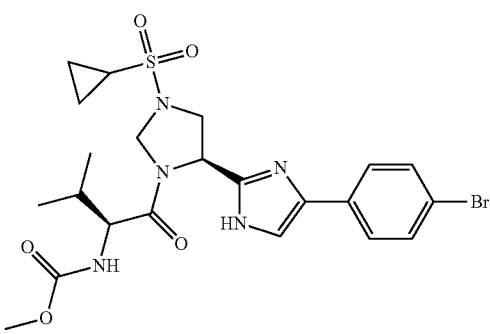 [SMILES: COC(=O)N[C@H](C(=O)N1CN(S(=O)(=O)C2CC2)C[C@H]1c1nc(-c2ccc(Br)cc2)c[nH]1)C(C)C]<br>SM-3bk |
| 60 | 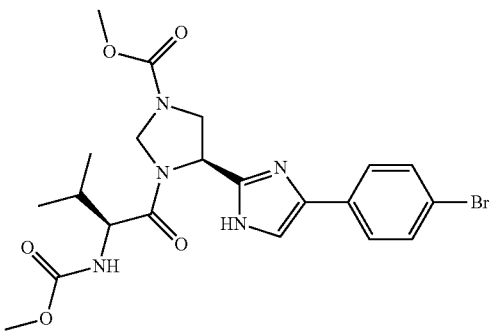 [SMILES: COC(=O)N[C@H](C(=O)N1CN(C(=O)OC)C[C@H]1c1nc(-c2ccc(Br)cc2)c[nH]1)C(C)C]<br>SM-3bm |
| 61 | 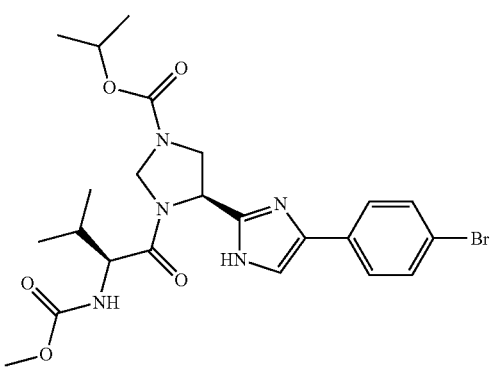 [SMILES: COC(=O)N[C@H](C(=O)N1CN(C(=O)OC(C)C)C[C@H]1c1nc(-c2ccc(Br)cc2)c[nH]1)C(C)C]<br>SM-3bn |

| Structural FIG. 1: Chemical materials SM3 (SM-3a to SM-3cs) | |
|---|---|
| No. | Structure of Raw Materials SM3 |
| 62 | 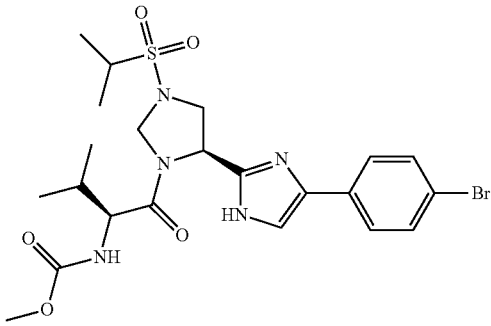 [SMILES: COC(=O)N[C@H](C(=O)N1CN(S(=O)(=O)C(C)C)C[C@H]1c1nc(-c2ccc(Br)cc2)c[nH]1)C(C)C]<br>SM-3bp |
| 63 | 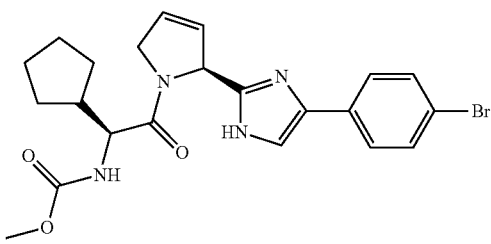 [SMILES: COC(=O)N[C@H](C(=O)N1CC=C[C@H]1c1nc(-c2ccc(Br)cc2)c[nH]1)C1CCCC1]<br>SM-3bq |
| 64 | 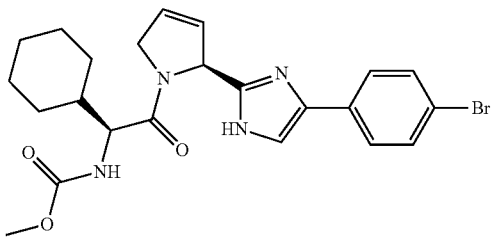 [SMILES: COC(=O)N[C@H](C(=O)N1CC=C[C@H]1c1nc(-c2ccc(Br)cc2)c[nH]1)C1CCCCC1]<br>SM-3br |
| 65 | 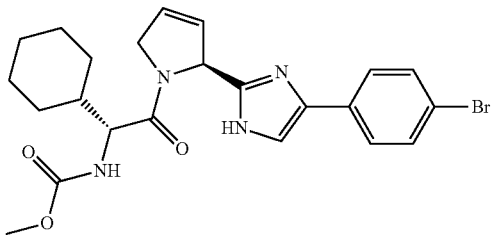 [SMILES: COC(=O)N[C@@H](C(=O)N1CC=C[C@H]1c1nc(-c2ccc(Br)cc2)c[nH]1)C1CCCCC1]<br>SM-3bs |
| 66 | 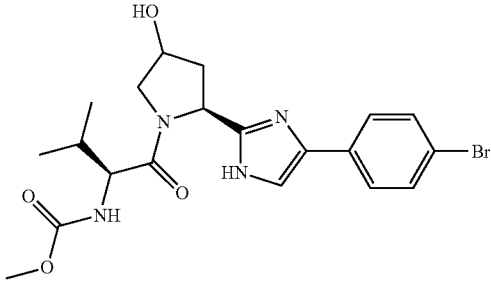 [SMILES: COC(=O)N[C@H](C(=O)N1CC(O)C[C@H]1c1nc(-c2ccc(Br)cc2)c[nH]1)C(C)C]<br>SM-3bt |

Structural FIG. 1: Chemical materials SM3 (SM-3a to SM-3cs)
| No. | Structure of Raw Materials SM3 |
|---|---|
| 67 | 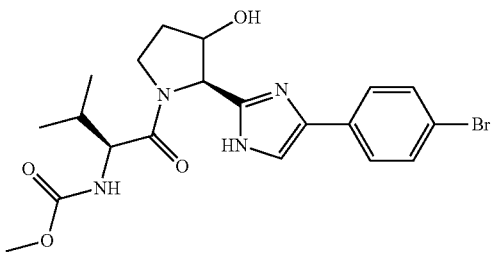 [SMILES: COC(=O)N[C@H](C(=O)N1CCC(O)[C@H]1c1nc(-c2ccc(Br)cc2)c[nH]1)C(C)C]<br>SM-3bu |
| 68 | 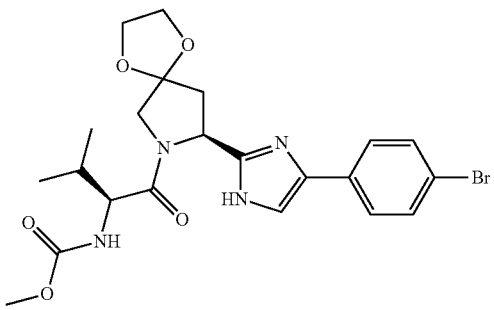 [SMILES: COC(=O)N[C@H](C(=O)N1CC2(C[C@H]1c1nc(-c3ccc(Br)cc3)c[nH]1)OCCO2)C(C)C]<br>SM-3bv |
| 69 | 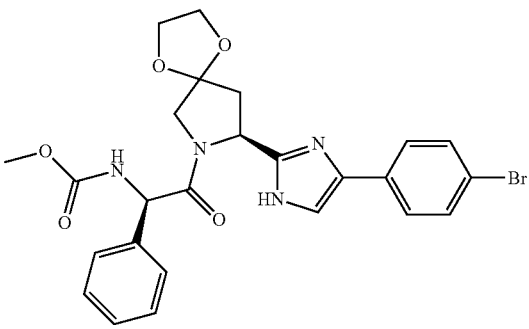 [SMILES: COC(=O)N[C@@H](C(=O)N1CC2(C[C@H]1c1nc(-c3ccc(Br)cc3)c[nH]1)OCCO2)c1ccccc1]<br>SM-3bw |
| 70 | 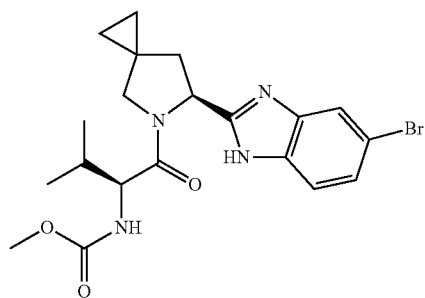 [SMILES: COC(=O)N[C@H](C(=O)N1CC2(CC2)C[C@H]1c1nc2cc(Br)ccc2[nH]1)C(C)C]<br>SM-3bx |

| | Structural FIG. 1: Chemical materials SM3 (SM-3a to SM-3cs) |
|---|---|
| No. | Structure of Raw Materials SM3 |
| 71 | 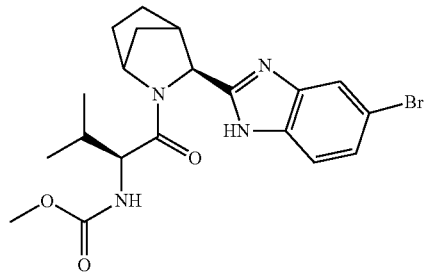 [SMILES: COC(=O)N[C@H](C(=O)N1C2CCC(C2)[C@H]1c1nc2cc(Br)ccc2[nH]1)C(C)C]
SM-3by |
| 72 | 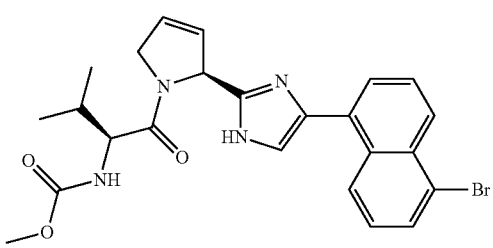 [SMILES: COC(=O)N[C@H](C(=O)N1CC=C[C@H]1c1nc(-c2cccc3c(Br)cccc23)c[nH]1)C(C)C]
SM-3bz |
| 73 | 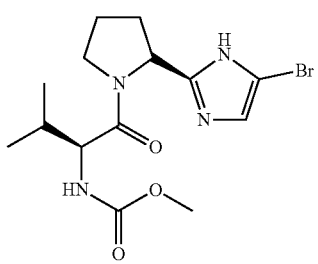
SM-3ca |
| 74 | 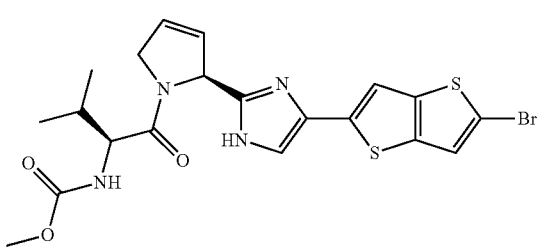 [SMILES: COC(=O)N[C@H](C(=O)N1CC=C[C@H]1c1nc(-c2cc3sc(Br)cc3s2)c[nH]1)C(C)C]
SM-3cb |
| 75 | 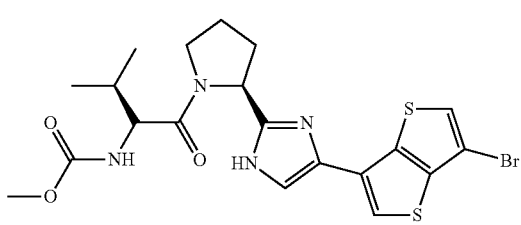
SM-3cc |

-continued
Structural FIG. 1: Chemical materials SM3 (SM-3a to SM-3cs)
| No. | Structure of Raw Materials SM3 |
|---|---|
| 76 | 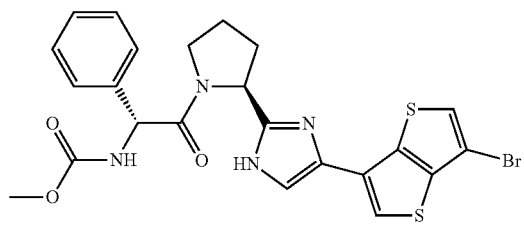 [SMILES: COC(=O)N[C@@H](C(=O)N1CCC[C@H]1c1nc(-c2csc3c(Br)csc23)c[nH]1)c1ccccc1]<br>SM-3cd |
| 77 | 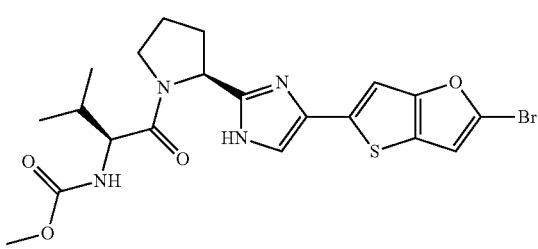 [SMILES: COC(=O)N[C@H](C(=O)N1CCC[C@H]1c1nc(-c2cc3oc(Br)cc3s2)c[nH]1)C(C)C]<br>SM-3ce |
| 78 | 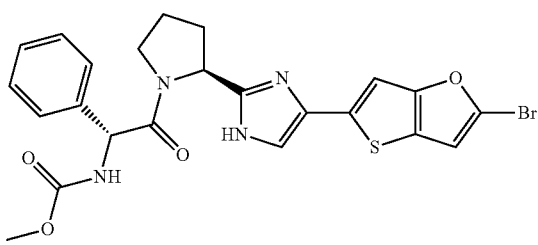<br>SM-3cf |
| 79 | 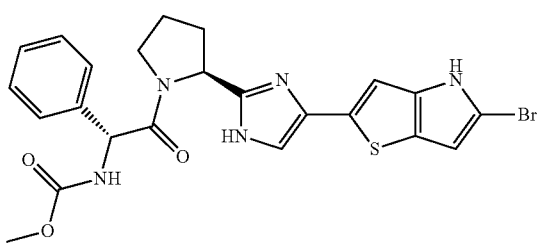 [SMILES: COC(=O)N[C@@H](C(=O)N1CCC[C@H]1c1nc(-c2cc3[nH]c(Br)cc3s2)c[nH]1)c1ccccc1]<br>SM-3cg |
| 80 | 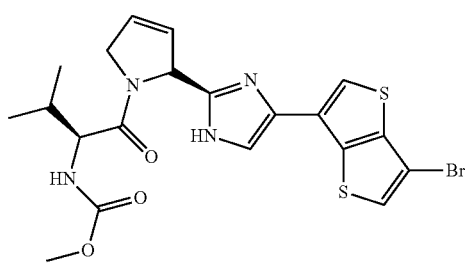<br>SM-3ch |

Structural FIG. 1: Chemical materials SM3 (SM-3a to SM-3cs)
| No. | Structure of Raw Materials SM3 |
|---|---|
| 81 | 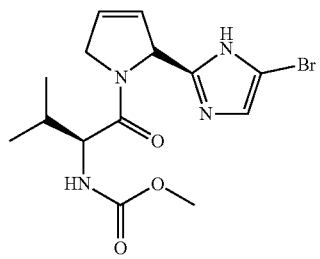<br>SM-3ci |
| 82 | 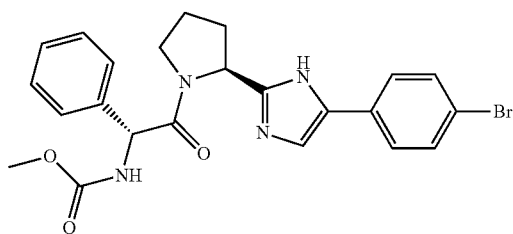 [SMILES: COC(=O)N[C@@H](C(=O)N1CCC[C@H]1c1ncc(-c2ccc(Br)cc2)[nH]1)c1ccccc1]<br>SM-3cj |
| 83 | 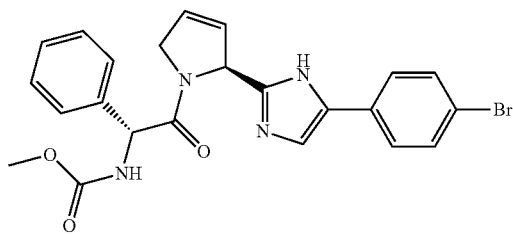 [SMILES: COC(=O)N[C@@H](C(=O)N1CC=C[C@H]1c1ncc(-c2ccc(Br)cc2)[nH]1)c1ccccc1]<br>SM-3ck |
| 84 | 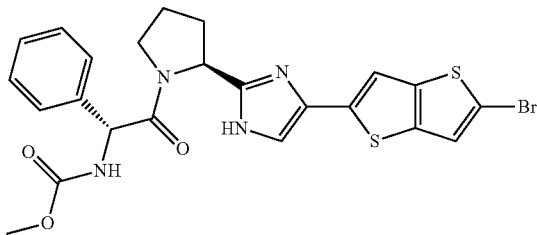<br>SM-3cm |
| 85 | 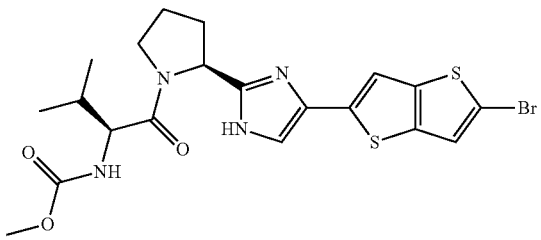<br>SM-3cn |

| | |
|---|---|
| Structural FIG. 1: Chemical materials SM3 (SM-3a to SM-3cs) | |
| No. | Structure of Raw Materials SM3 |
| 86 | 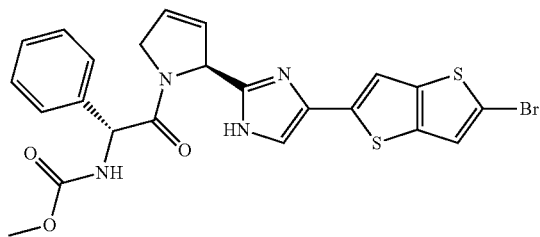<br>SM-3cp |
| 87 | 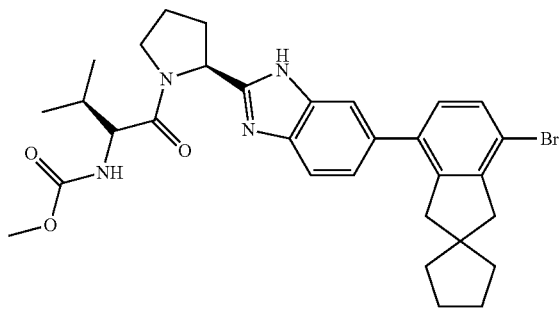<br>SM-3cq |
| 88 | 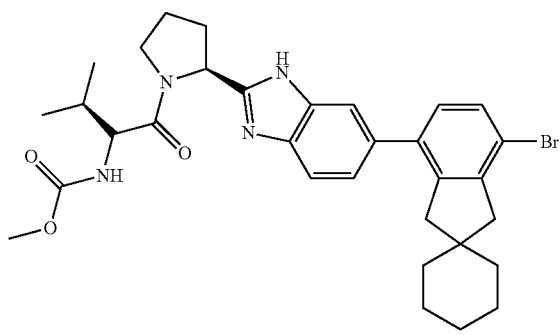<br>SM-3cr |
| 89 | 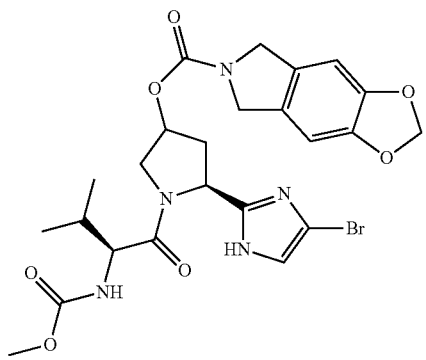 [SMILES: COC(=O)N[C@H](C(=O)N1CC(OC(=O)N2Cc3cc4c(cc3C2)OCO4)C[C@H]1c1nc(Br)c[nH]1)C(C)C]<br>SM-3cs |

Chemical materials SM4 (SM-4a to SM-4bk) in structural figure 2 are the critical compounds in present disclosure, the structures of them were shown as follows:
| Structural FIG. 2: Chemical materials SM4 (SM-4a to SM-4bk) | |
|---|---|
| No. | Structure of Raw Materials SM4 |
| 1 | 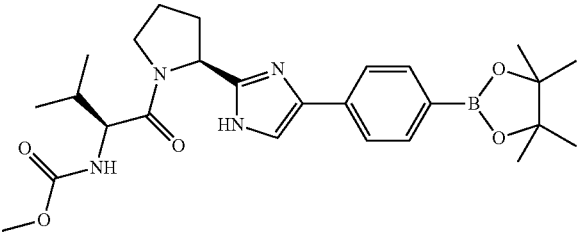<br>SM-4a |
| 2 | 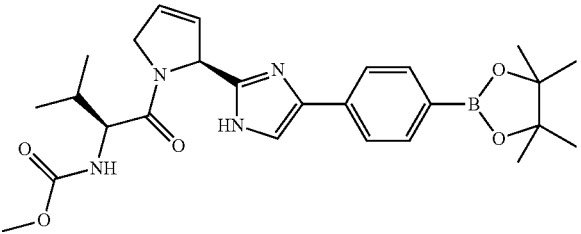<br>SM-4b |
| 3 | 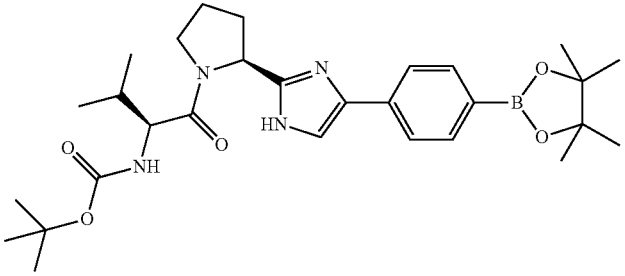<br>SM-4c |
| 4 | 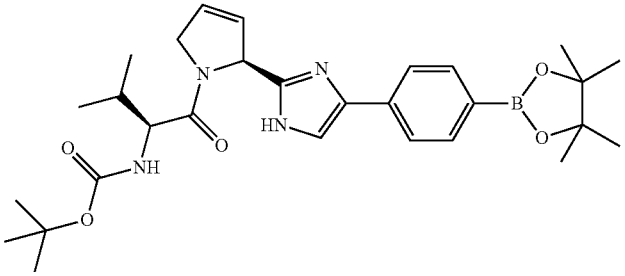<br>SM-4d |

| Structural FIG. 2: Chemical materials SM4 (SM-4a to SM-4bk) | |
|---|---|
| No. | Structure of Raw Materials SM4 |
| 5 | 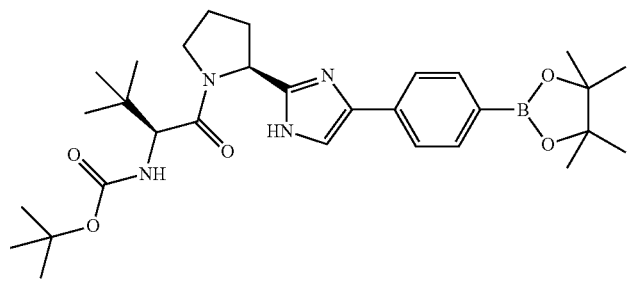<br>SM-4e |
| 6 | 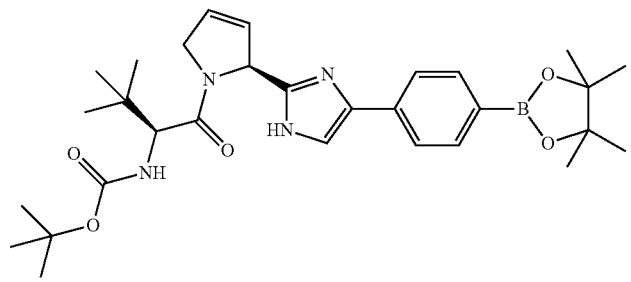<br>SM-4f |
| 7 | 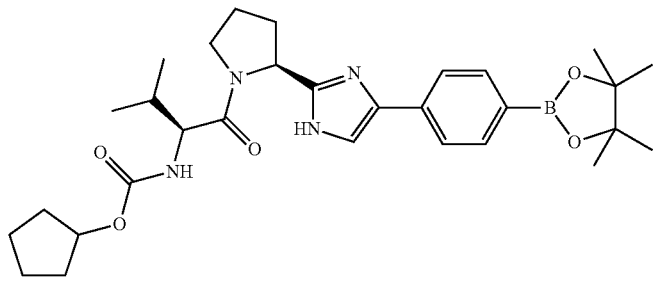<br>SM-4g |
| 8 | 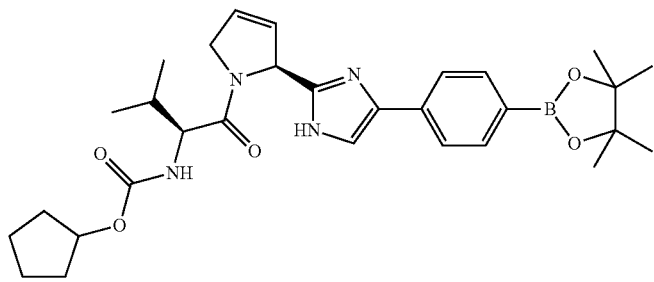<br>SM-4h |

Structural FIG. 2: Chemical materials SM4 (SM-4a to SM-4bk)
| No. | Structure of Raw Materials SM4 |
|---|---|
| 9 | 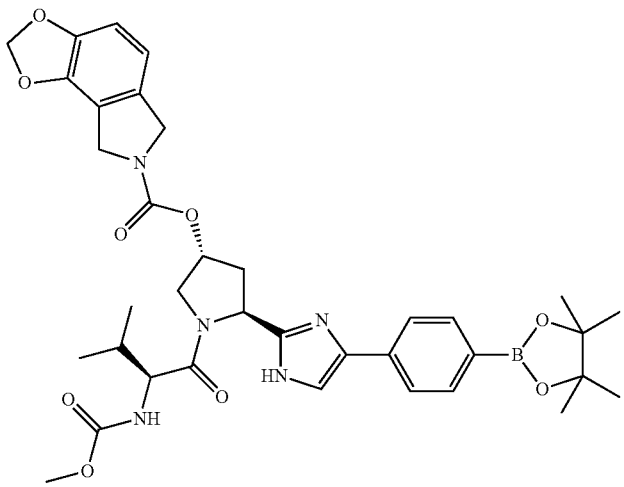 SM-4i |
| 10 | 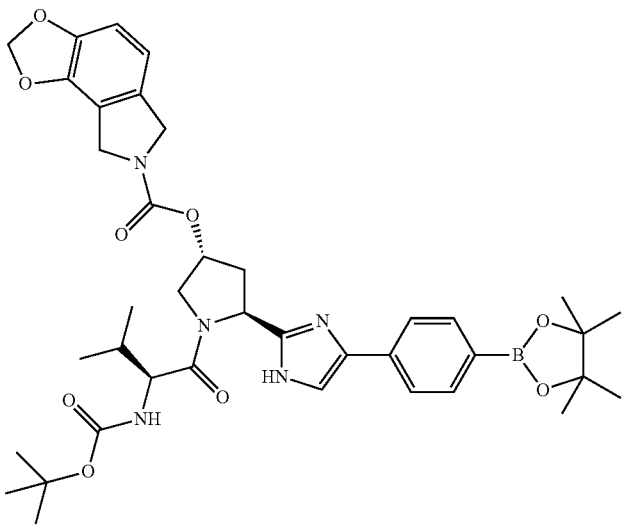 SM-4j |

Structural FIG. 2: Chemical materials SM4 (SM-4a to SM-4bk)
| No. | Structure of Raw Materials SM4 |
|---|---|
| 11 | 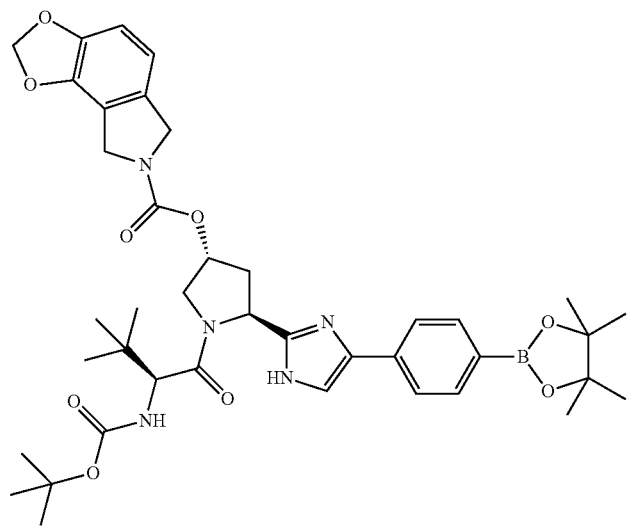<br>SM-4k |
| 12 | 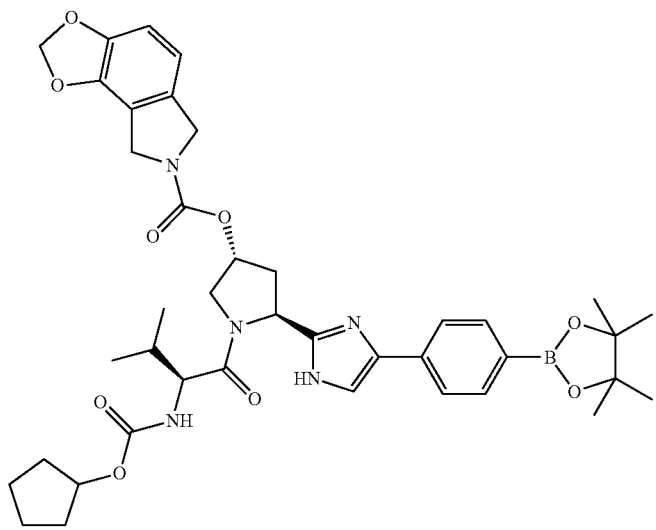<br>SM-4m |

| Structural FIG. 2: Chemical materials SM4 (SM-4a to SM-4bk) | |
|---|---|
| No. | Structure of Raw Materials SM4 |
13
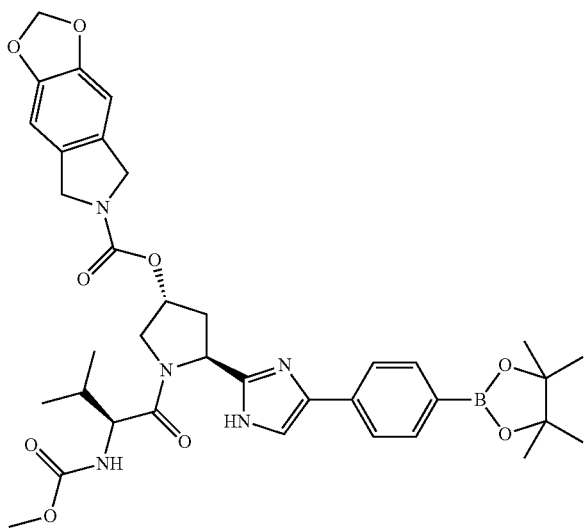
SM-4n
14
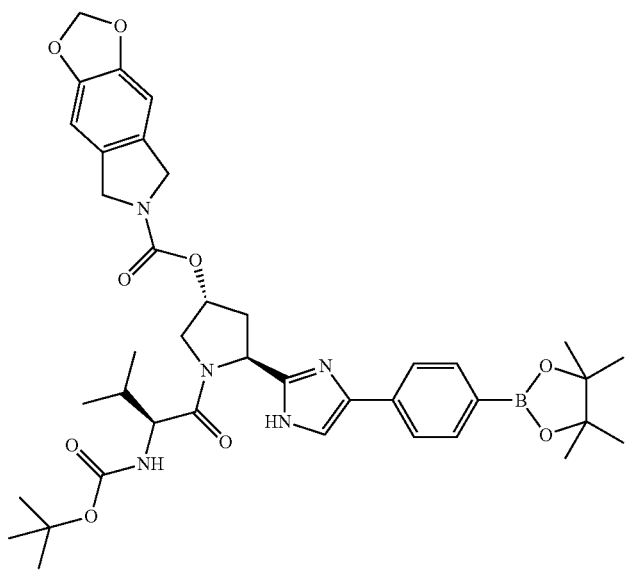
SM-4p

| Structural FIG. 2: Chemical materials SM4 (SM-4a to SM-4bk) | |
|---|---|
| No. | Structure of Raw Materials SM4 |
15
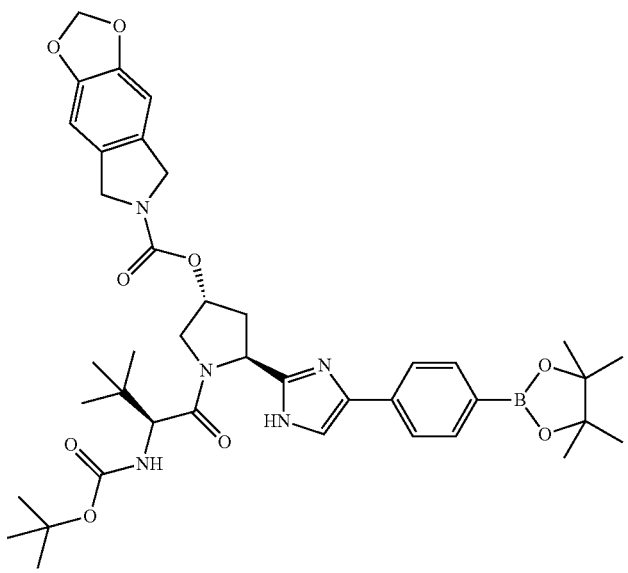
SM-4q
16
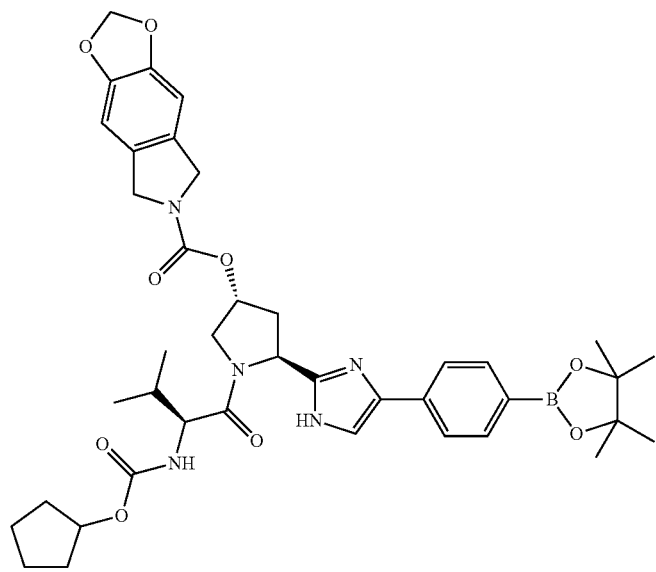
SM-4r Structural FIG. 2: Chemical materials SM4 (SM-4a to SM-4bk)
| No. | Structure of Raw Materials SM4 |
|---|---|
| 17 | 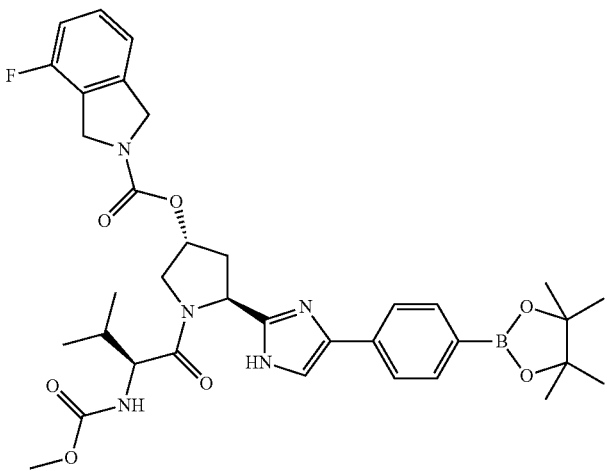<br>SM-4s |
| 18 | 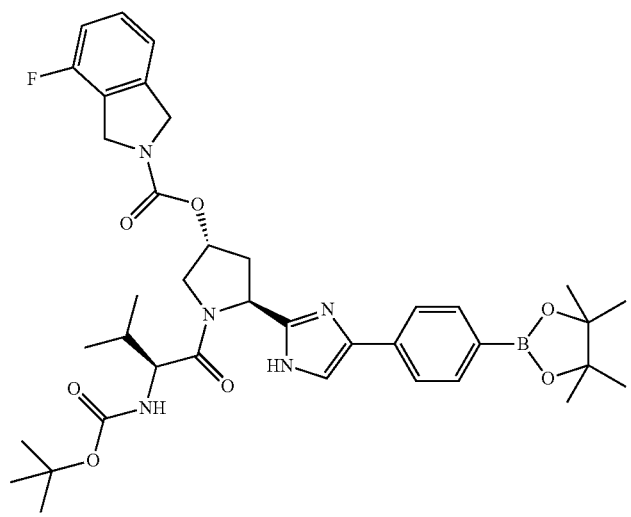<br>SM-4t |

Structural FIG. 2: Chemical materials SM4 (SM-4a to SM-4bk)
| No. | Structure of Raw Materials SM4 |
|---|---|
| 19 | 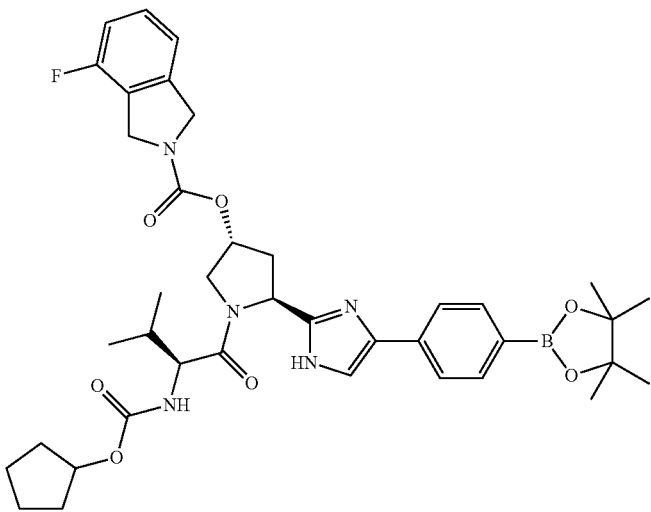<br>SM-4u |
| 20 | 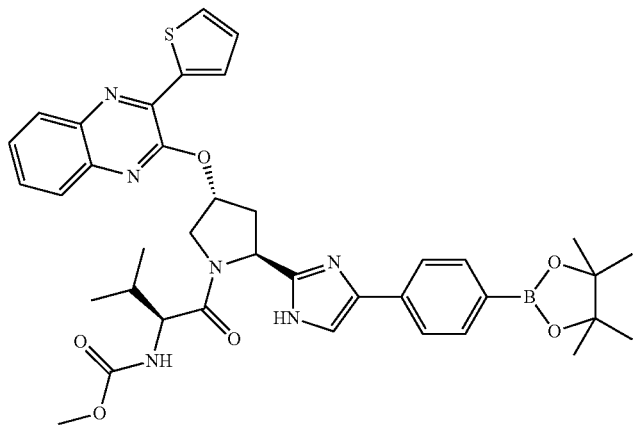<br>SM-4v |
| 21 | 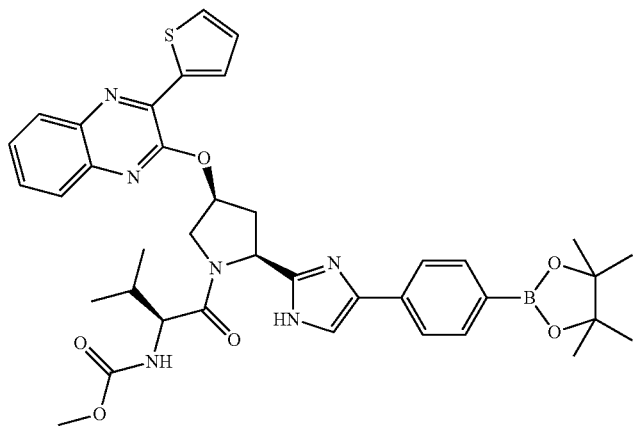<br>SM-4w |

Structural FIG. 2: Chemical materials SM4 (SM-4a to SM-4bk)
| No. | Structure of Raw Materials SM4 |
|---|---|
| 22 | 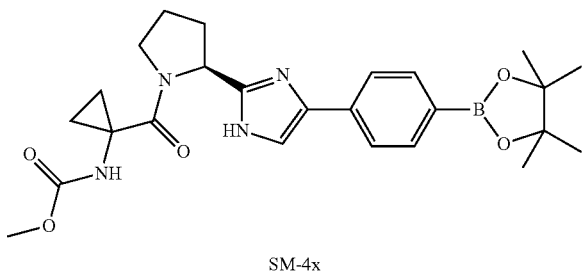<br>SM-4x |
| 23 | 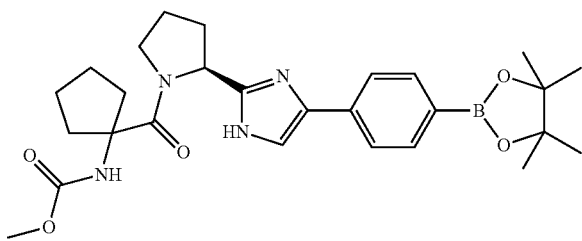<br>SM-4y |
| 24 | 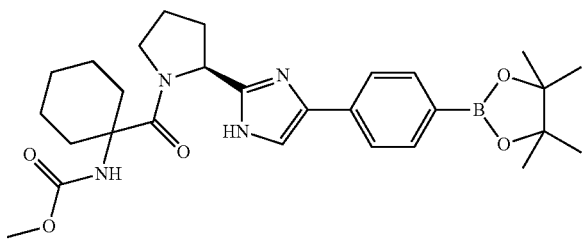<br>SM-4z |
| 25 | 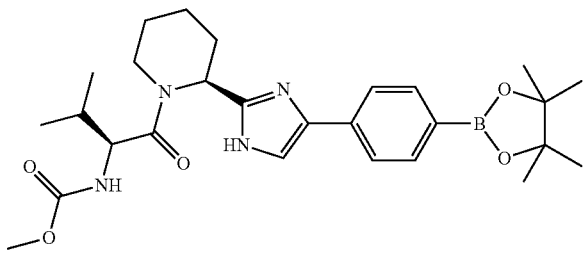<br>SM-4aa |
| 26 | 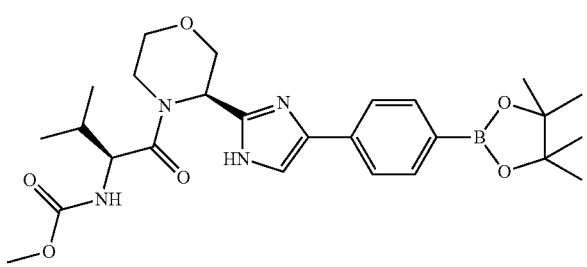<br>SM-4ab |

81
-continued
Structural FIG. 2: Chemical materials SM4 (SM-4a to SM-4bk)
| No. | Structure of Raw Materials SM4 |
|---|---|
| 27 | 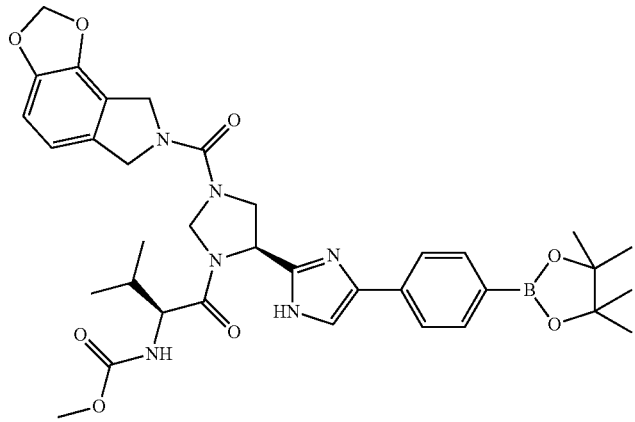 SM-4ac |
| 28 | 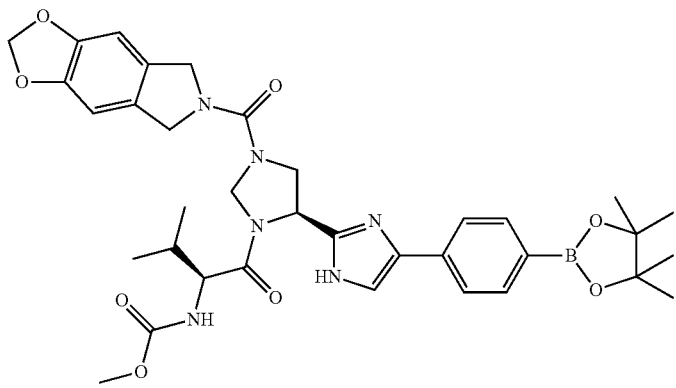 SM-4ad |
| 29 | 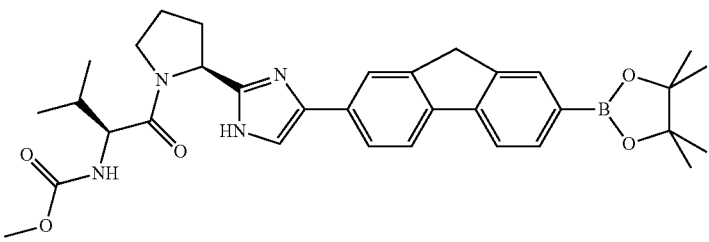 SM-4ae |
| 30 | 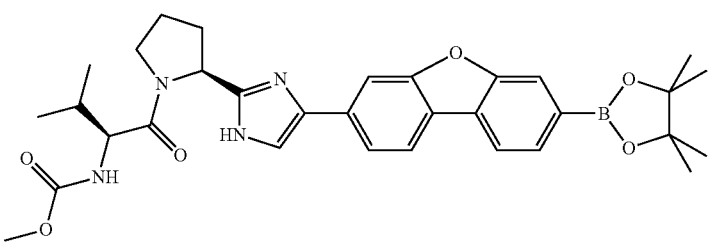 SM-4af |

-continued
Structural FIG. 2: Chemical materials SM4 (SM-4a to SM-4bk)
| No. | Structure of Raw Materials SM4 |
|---|---|
| 31 | 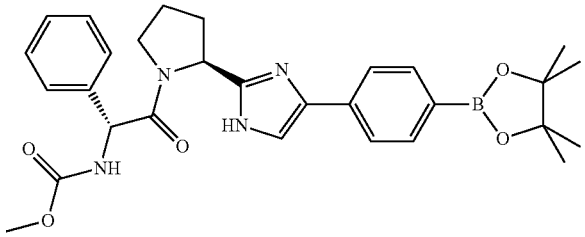<br>SM-4ag |
| 32 | 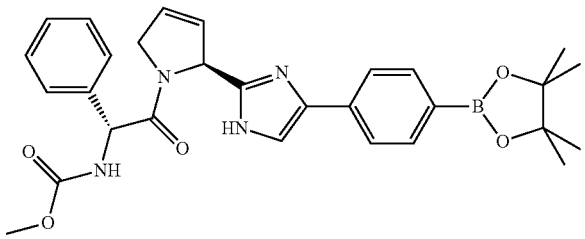<br>SM-4ah |
| 33 | 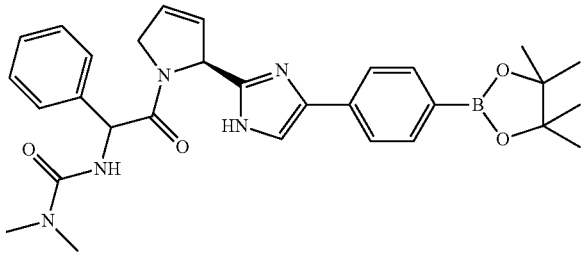<br>SM-4ai |
| 34 | 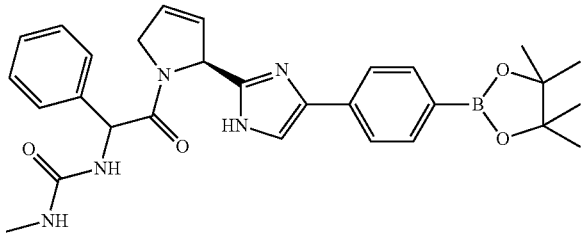<br>SM-4aj |
| 35 | 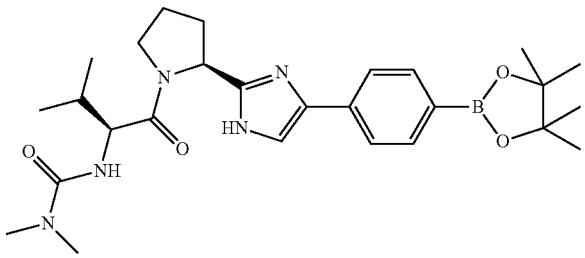<br>SM-4ak |

Structural FIG. 2: Chemical materials SM4 (SM-4a to SM-4bk)
| No. | Structure of Raw Materials SM4 |
|---|---|
| 36 | 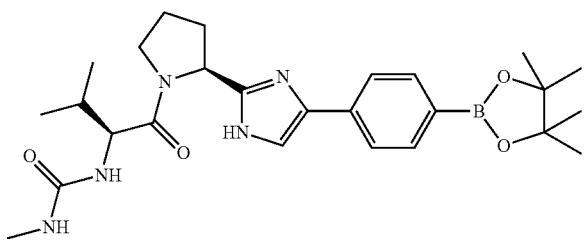<br>SM-4am |
| 37 | 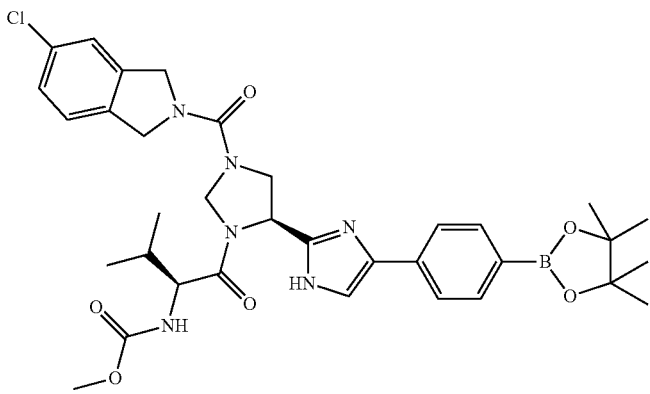<br>SM-4an |
| 38 | 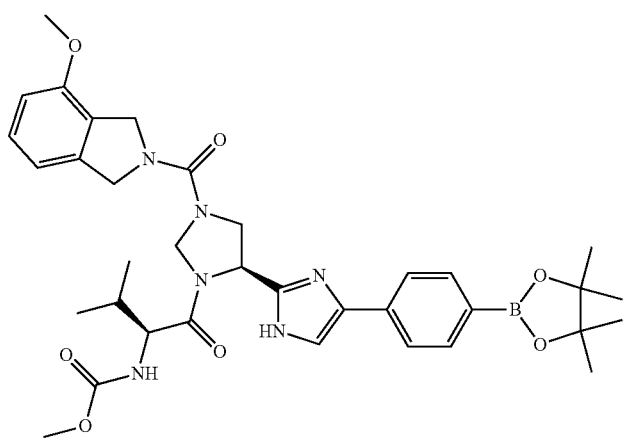<br>SM-4ap |

87 -continued
Structural FIG. 2: Chemical materials SM4 (SM-4a to SM-4bk)
| No. | Structure of Raw Materials SM4 |
|---|---|
| 39 | 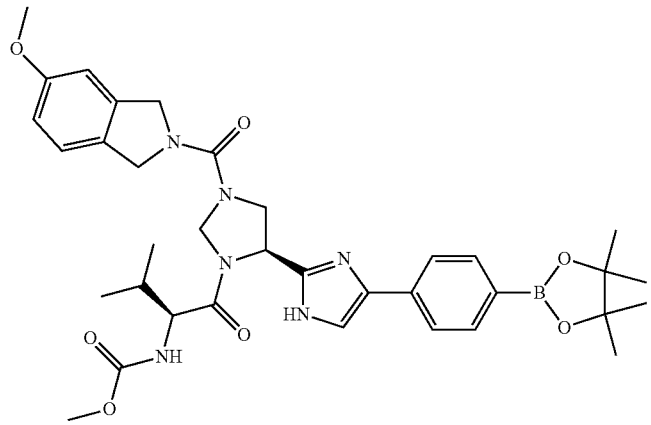<br>SM-4aq |
| 40 | 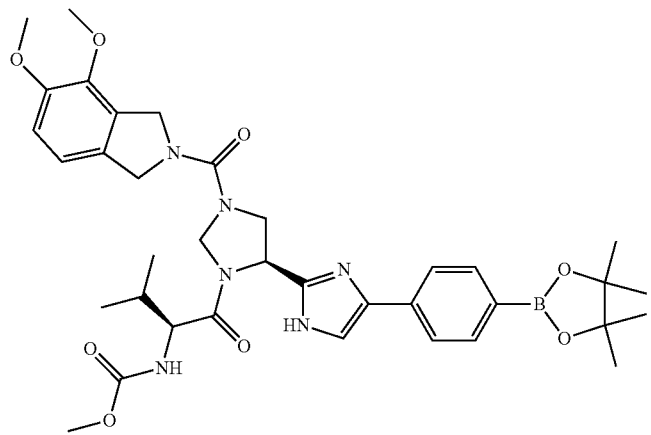<br>SM-4ar |
| 41 | 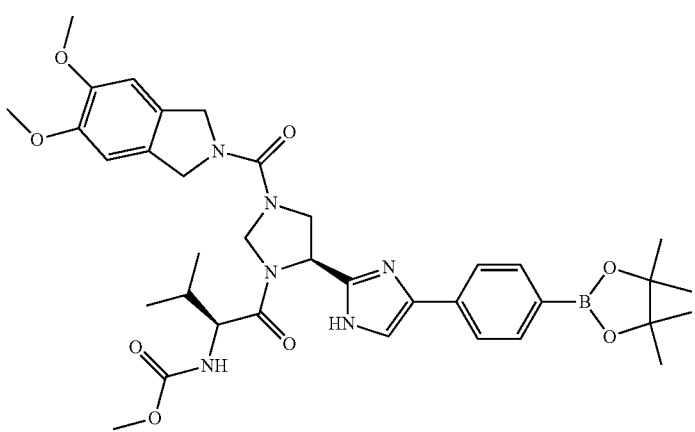<br>SM-4as |

Structural FIG. 2: Chemical materials SM4 (SM-4a to SM-4bk)
| No. | Structure of Raw Materials SM4 |
|---|---|
| 42 | 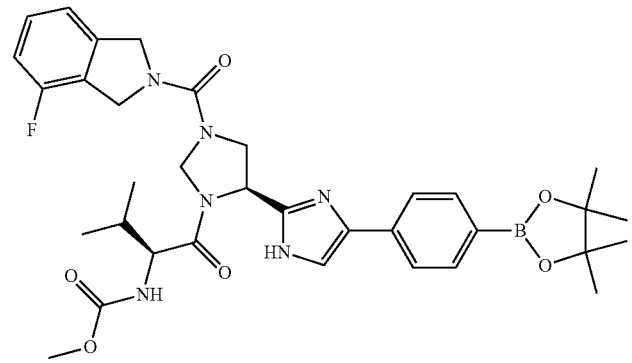<br>SM-4at |
| 43 | 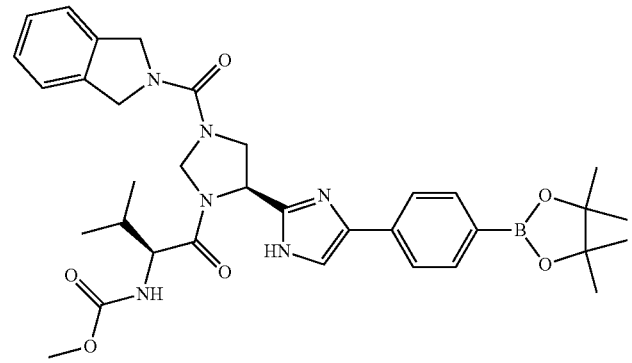<br>SM-4au |
| 44 | 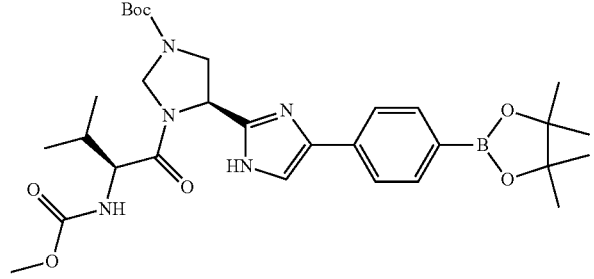<br>SM-4av |
| 45 | 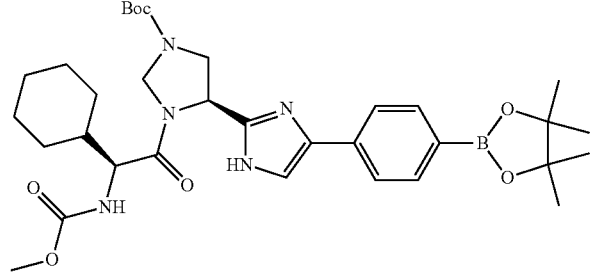<br>SM-4aw |

| No. | Structure of Raw Materials SM4 |
|---|---|
| 46 | 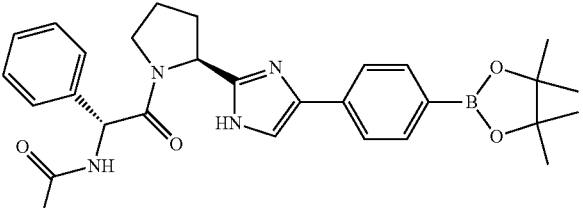<br>SM-4ax |
| 47 | 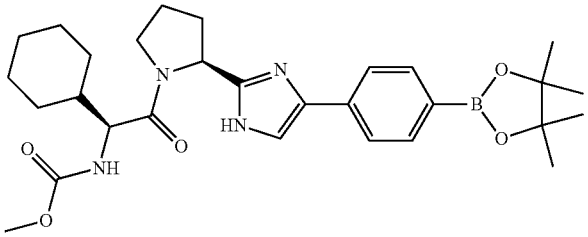<br>SM-4ay |
| 48 | 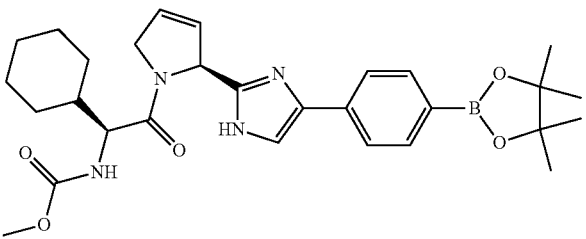<br>SM-4az |
| 49 | 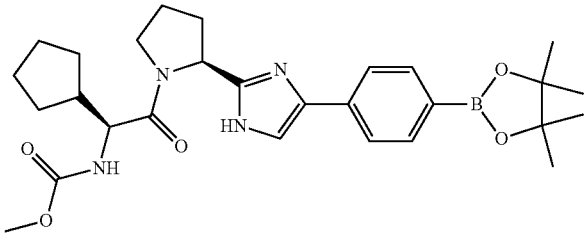<br>SM-4ba |
| 50 | 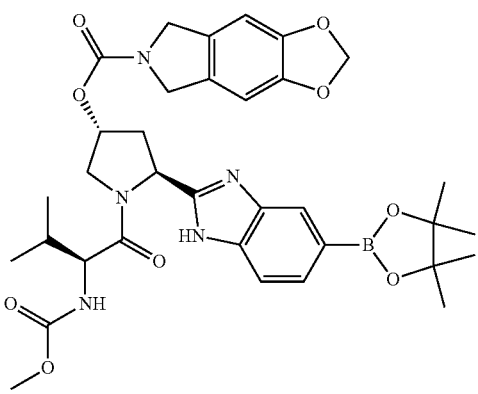<br>SM-4bb |

| No. | Structure of Raw Materials SM4 |
|---|---|
| 51 | 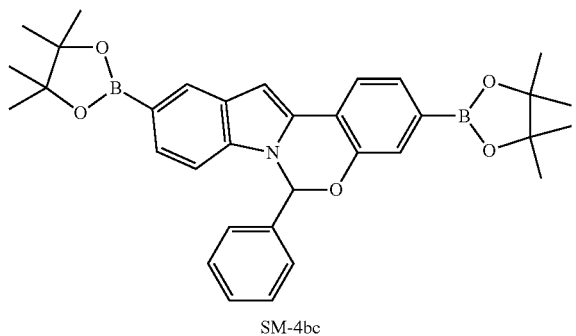<br>SM-4bc |
| 52 | 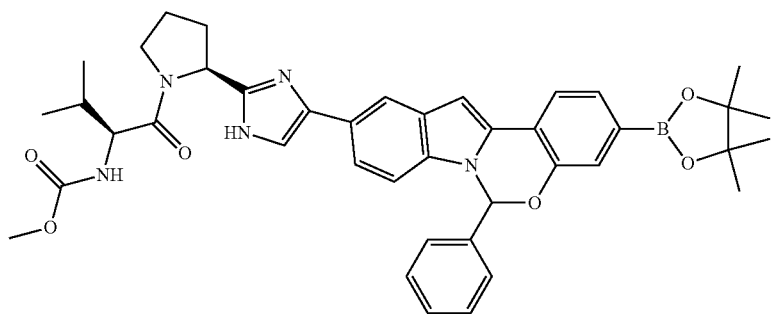<br>SM-4bd |
| 53 | 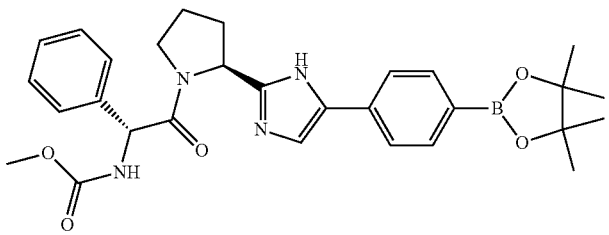<br>SM-4be |
| 54 | 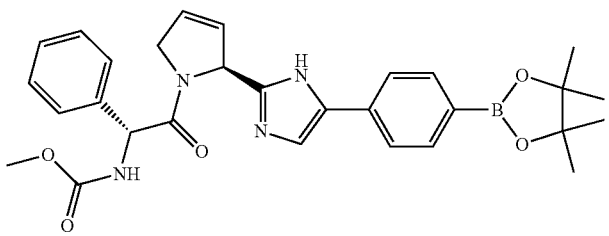<br>SM-4bf |

95
96
-continued
Structural FIG. 2: Chemical materials SM4 (SM-4a to SM-4bk)
| No. | Structure of Raw Materials SM4 |
|---|---|
| 55 | 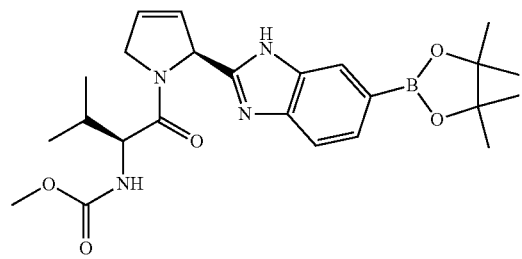<br>SM-4bg |
| 56 | 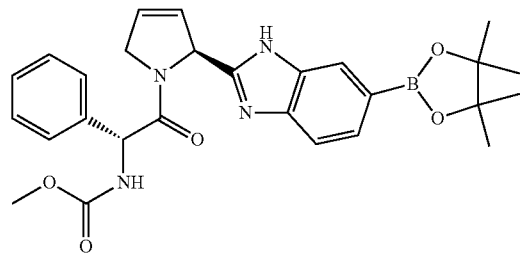<br>SM-4bh |
| 57 | 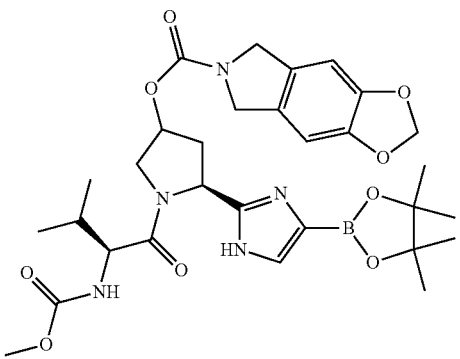<br>SM-4bi |
| 58 | 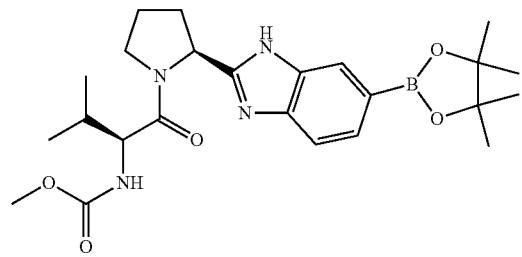<br>SM-4bj |

Structural FIG. 2: Chemical materials SM4 (SM-4a to SM-4bk)
| No. | Structure of Raw Materials SM4 |
|---|---|
| 59 | 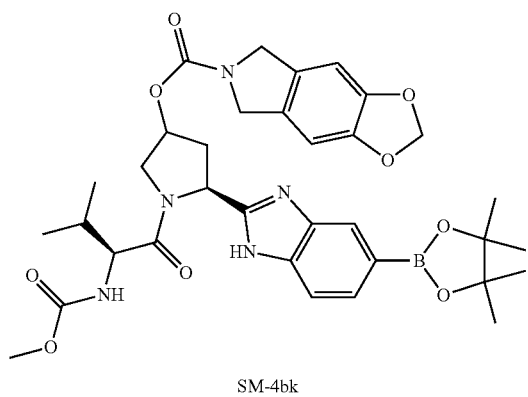 SM-4bk |
The designed antiviral compounds 6a-6ep (Ia) and 6fa-6fy (Ib) were synthesized and listed in structural figure 3 by the synthetic methods 1-3 described above.
Structural FIG. 3a: The Target Antiviral Compounds 6a-6ep
| No. | Prepared Compounds 6a-6ep of Formula Ia |
|---|---|
| Ia-1 | 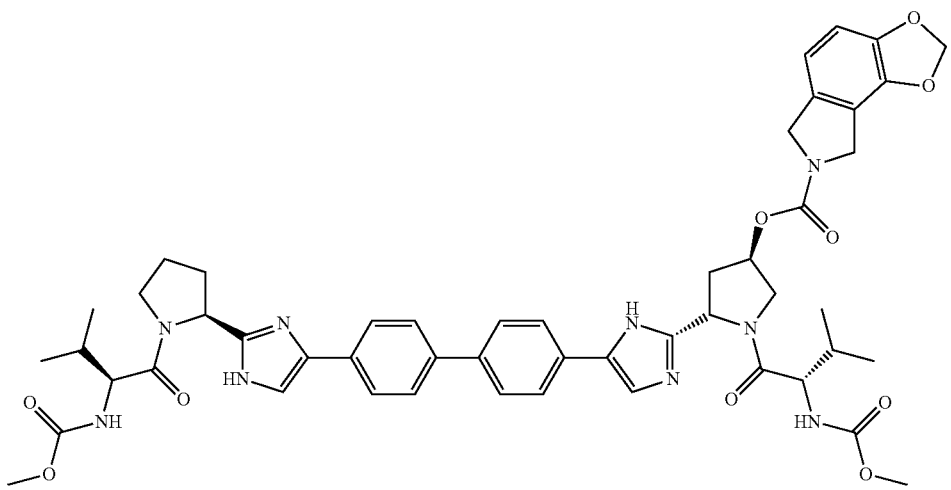 6a |

US 9,334,291 B2
99 / 100
-continued
Structural FIG. 3a: The Target Antiviral Compounds 6a-6ep
| No. | Prepared Compounds 6a-6ep of Formula Ia |
|---|---|
Ia-2
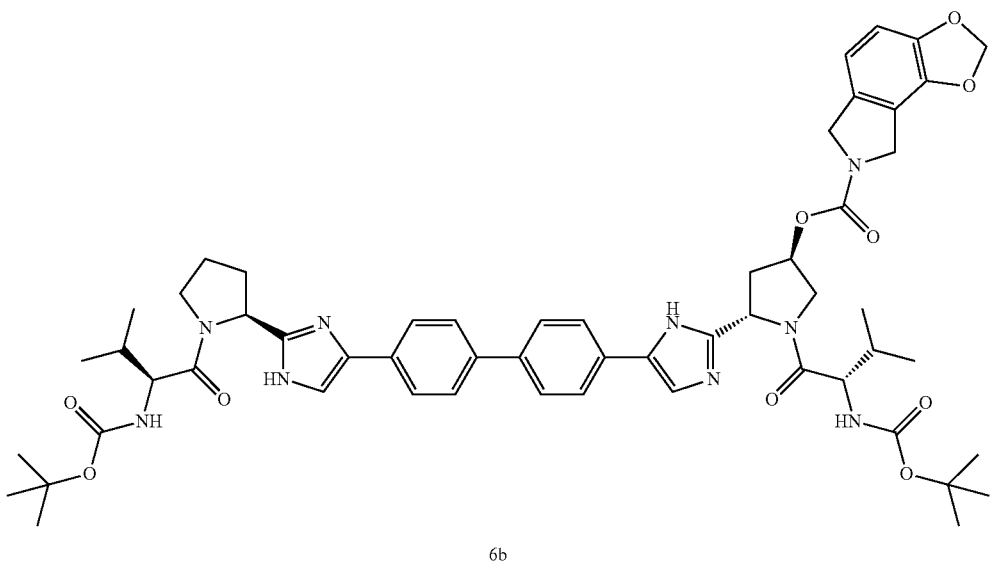 [SMILES: CC(C)[C@H](NC(=O)OC(C)(C)C)C(=O)N1CCC[C@H]1c1nc(-c2ccc(-c3ccc(-c4cnc([C@@H]5C[C@@H](OC(=O)N6Cc7ccc8c(c7C6)OCO8)CN5C(=O)[C@@H](NC(=O)OC(C)(C)C)C(C)C)[nH]4)cc3)cc2)c[nH]1]
6b
Ia-3
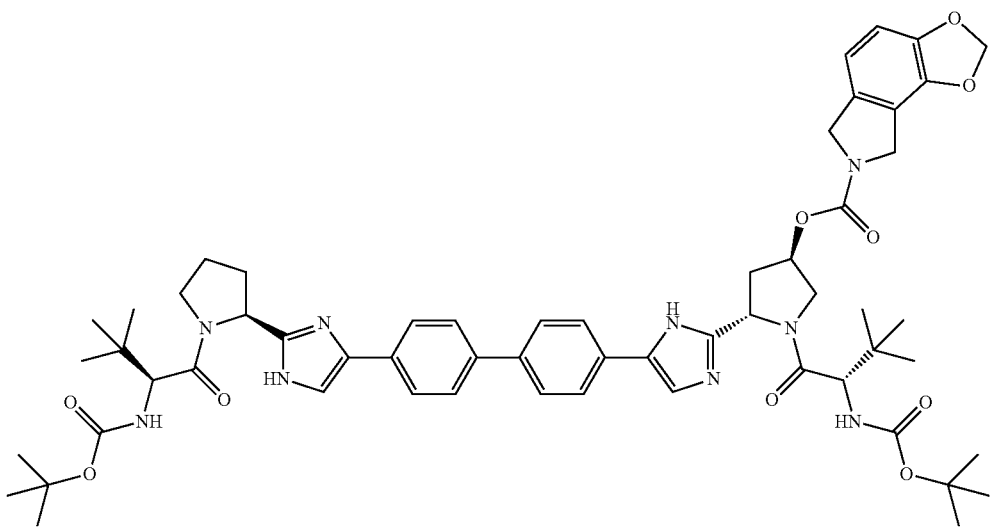
6c US 9,334,291 B2
-continued
Structural FIG. 3a: The Target Antiviral Compounds 6a-6ep
| No. | Prepared Compounds 6a-6ep of Formula Ia |
|---|---|
Ia-4
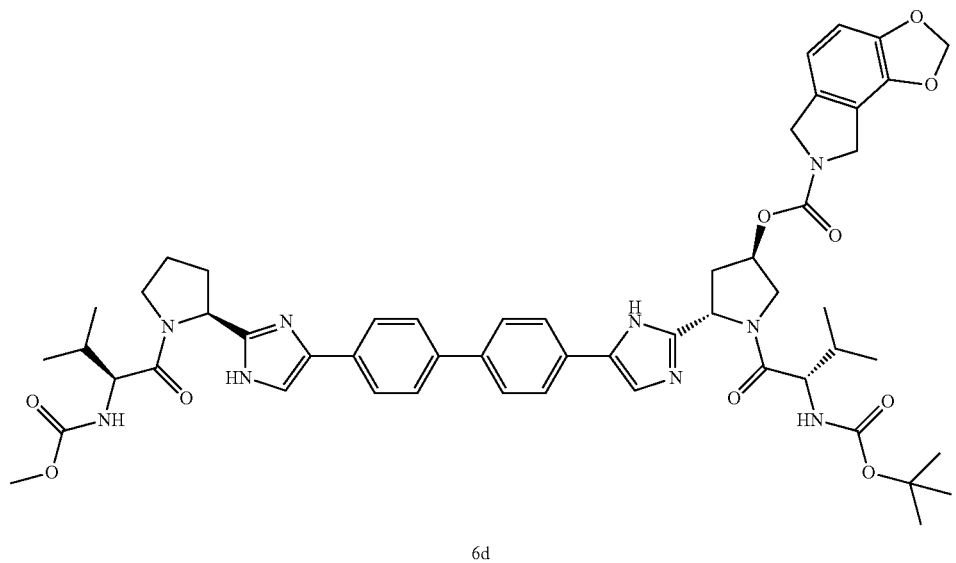 [SMILES: COC(=O)N[C@H](C(=O)N1CCC[C@H]1c1nc(-c2ccc(-c3ccc(-c4cnc([C@@H]5C[C@@H](OC(=O)N6Cc7ccc8c(c7C6)OCO8)CN5C(=O)[C@@H](NC(=O)OC(C)(C)C)C(C)C)[nH]4)cc3)cc2)c[nH]1)C(C)C]
6d
Ia-5
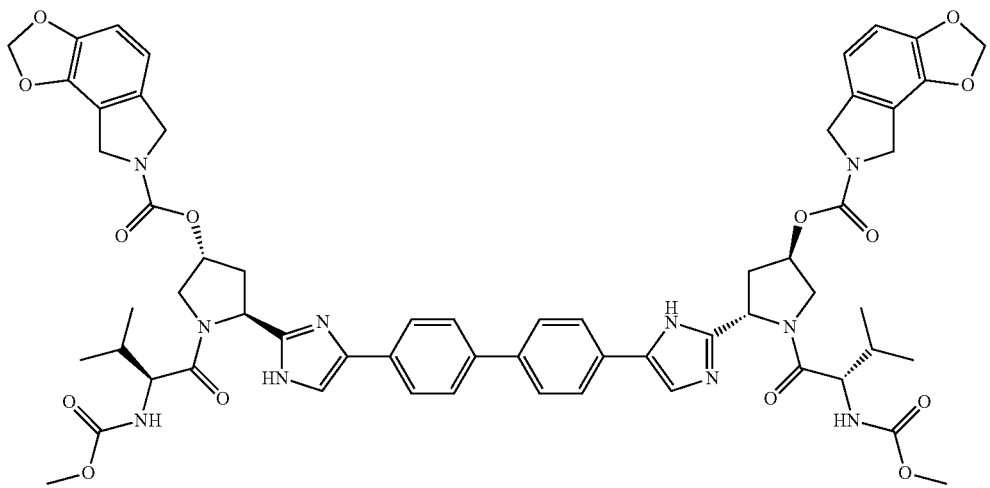
6e

Structural FIG. 3a: The Target Antiviral Compounds 6a-6ep
| No. | Prepared Compounds 6a-6ep of Formula Ia |
|---|---|
| Ia-6 | 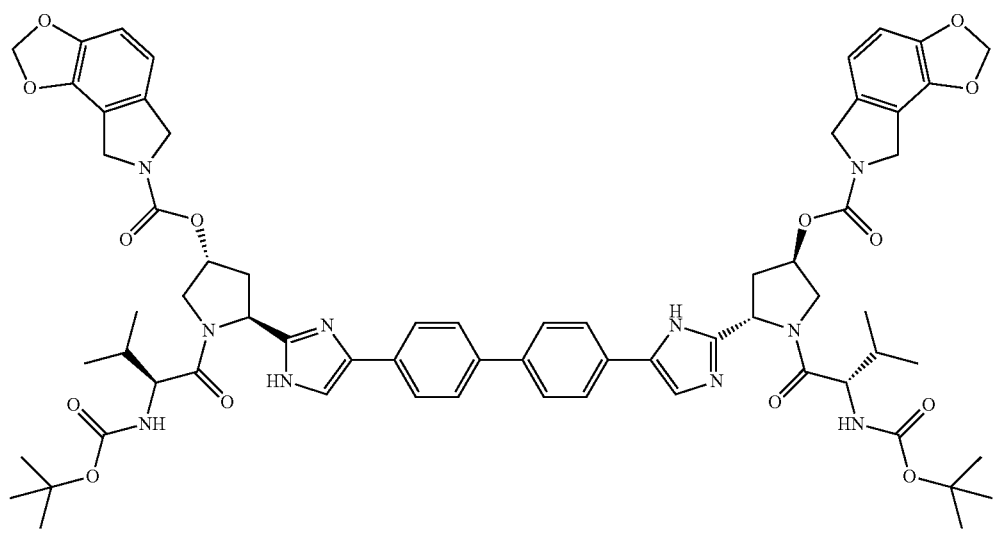<br>6f |
| Ia-7 | 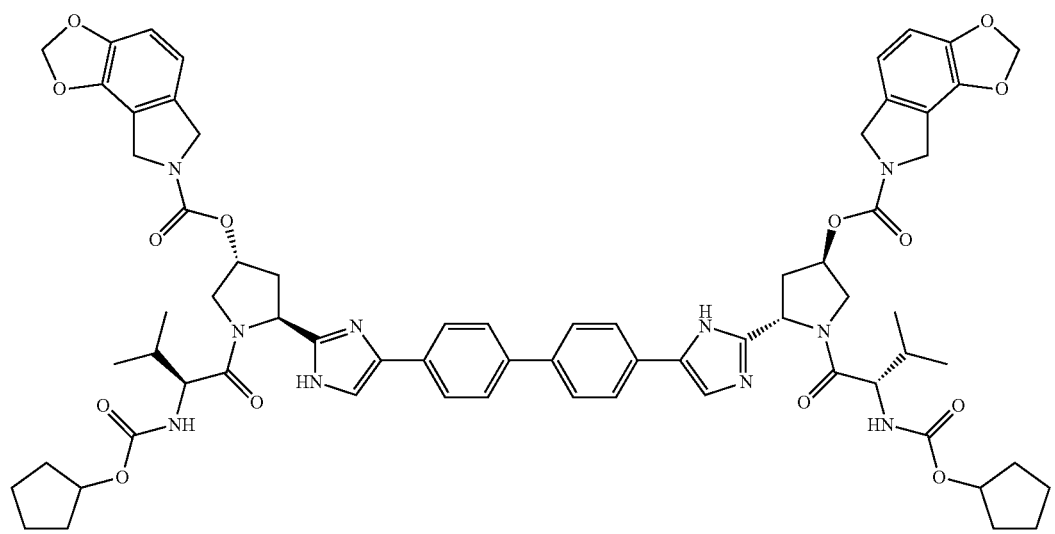<br>6g |

US 9,334,291 B2
105 106
-continued
Structural FIG. 3a: The Target Antiviral Compounds 6a-6ep
| No. | Prepared Compounds 6a-6ep of Formula Ia |
|---|---|
| Ia-8 | 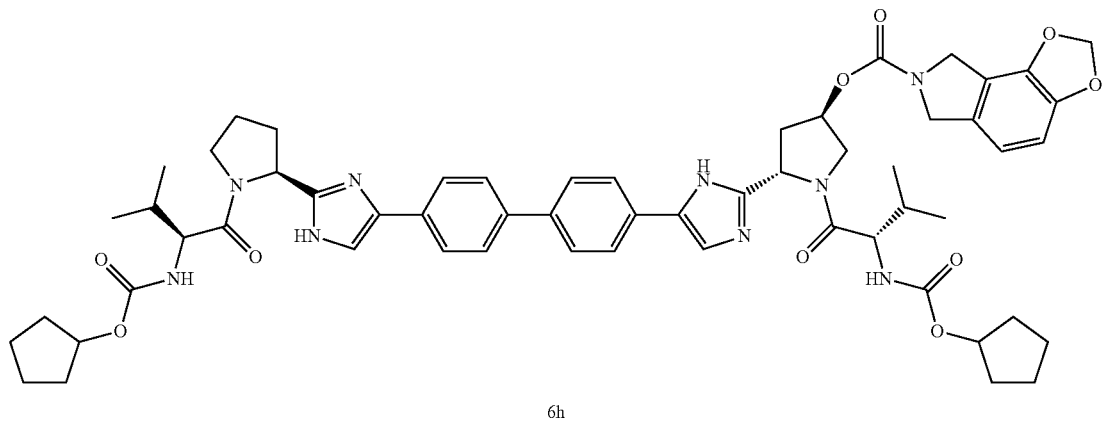 [SMILES: CC(C)[C@H](NC(=O)OC1CCCC1)C(=O)N1CCC[C@H]1c1nc(-c2ccc(-c3ccc(-c4cnc([C@@H]5C[C@@H](OC(=O)N6Cc7ccc8c(c7C6)OCO8)CN5C(=O)[C@@H](NC(=O)OC5CCCC5)C(C)C)[nH]4)cc3)cc2)c[nH]1]<br>6h |
| Ia-9 | 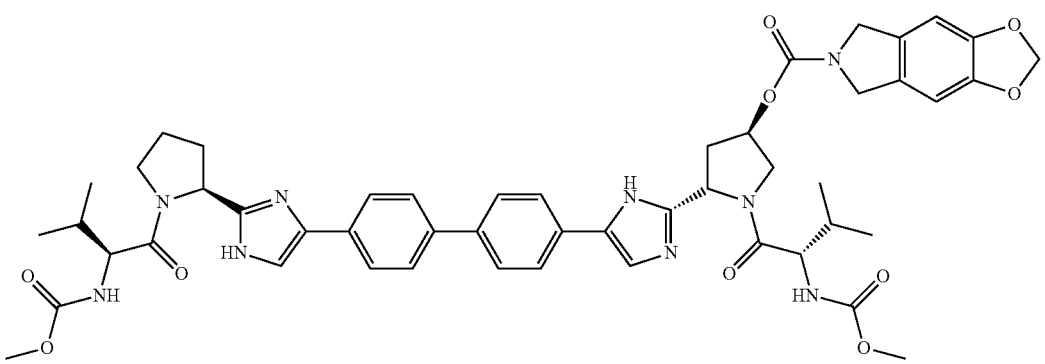<br>6i |
| Ia-10 | 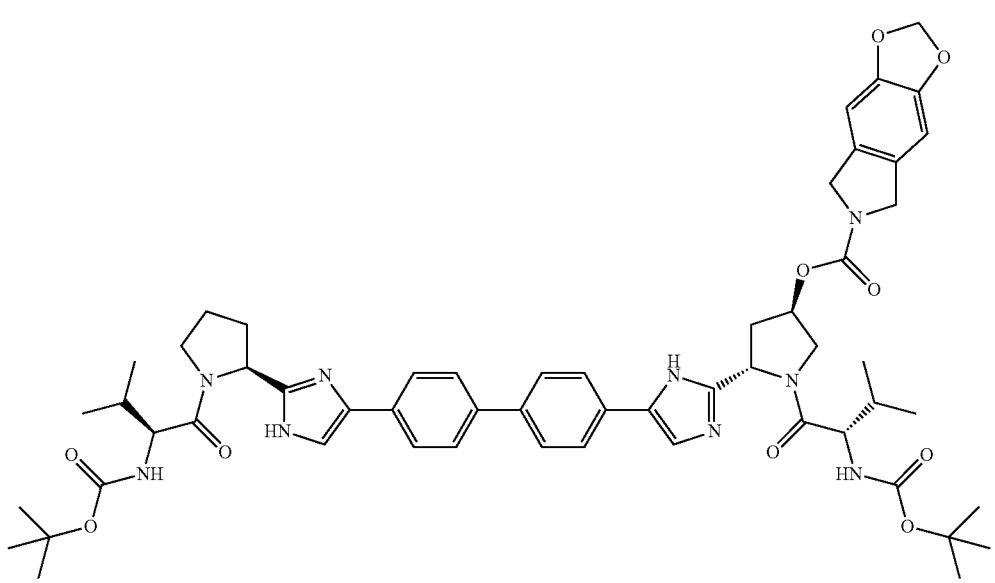<br>6j |

US 9,334,291 B2
107 108
-continued
Structural FIG. 3a: The Target Antiviral Compounds 6a-6ep
| No. | Prepared Compounds 6a-6ep of Formula Ia |
|---|---|
Ia-11
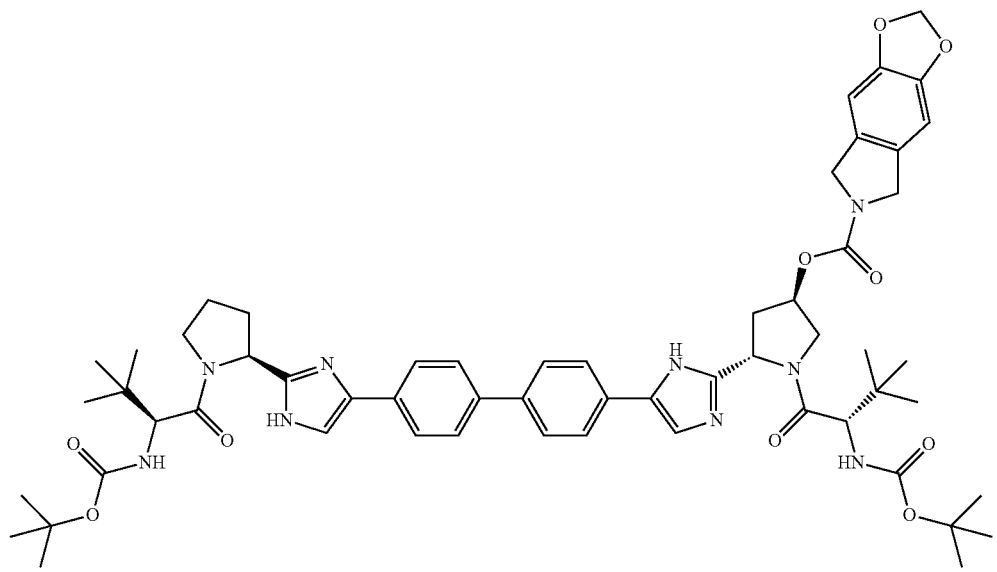
6k
Ia-12
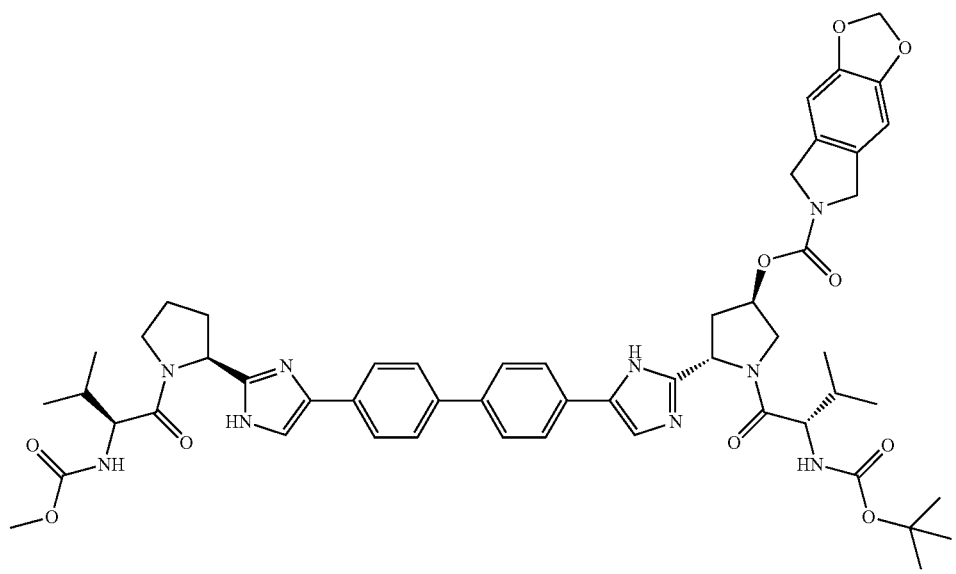
6m

| Structural FIG. 3a: The Target Antiviral Compounds 6a-6ep | |
|---|---|
| No. | Prepared Compounds 6a-6ep of Formula Ia |
| Ia-13 | 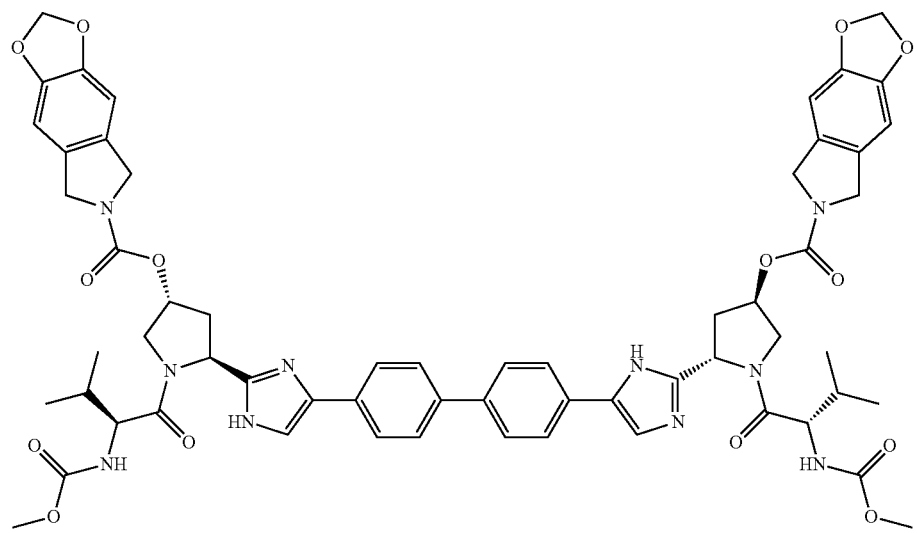<br>6n |
| Ia-14 | 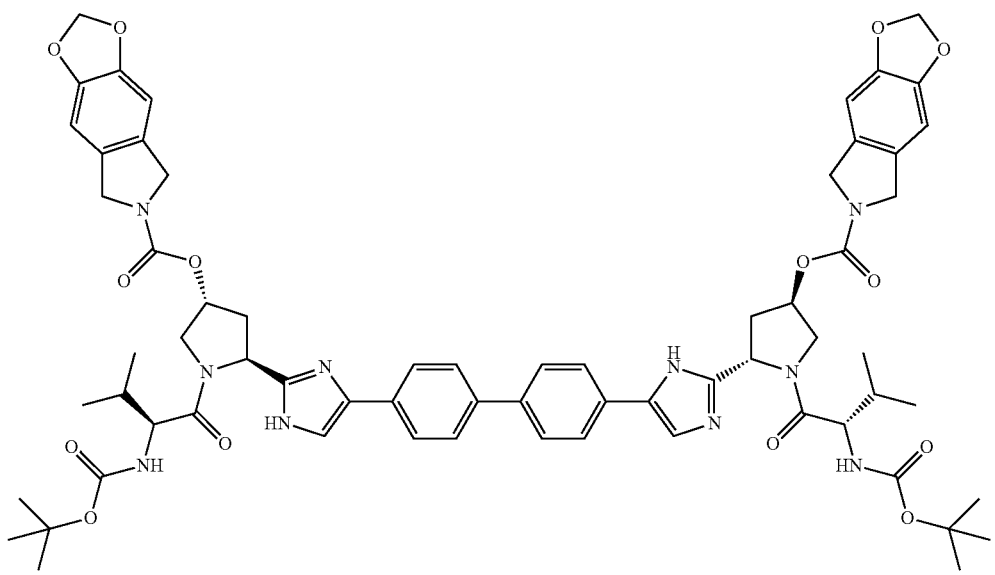<br>6p |

| Structural FIG. 3a: The Target Antiviral Compounds 6a-6ep | |
|---|---|
| No. | Prepared Compounds 6a-6ep of Formula Ia |
Ia-15
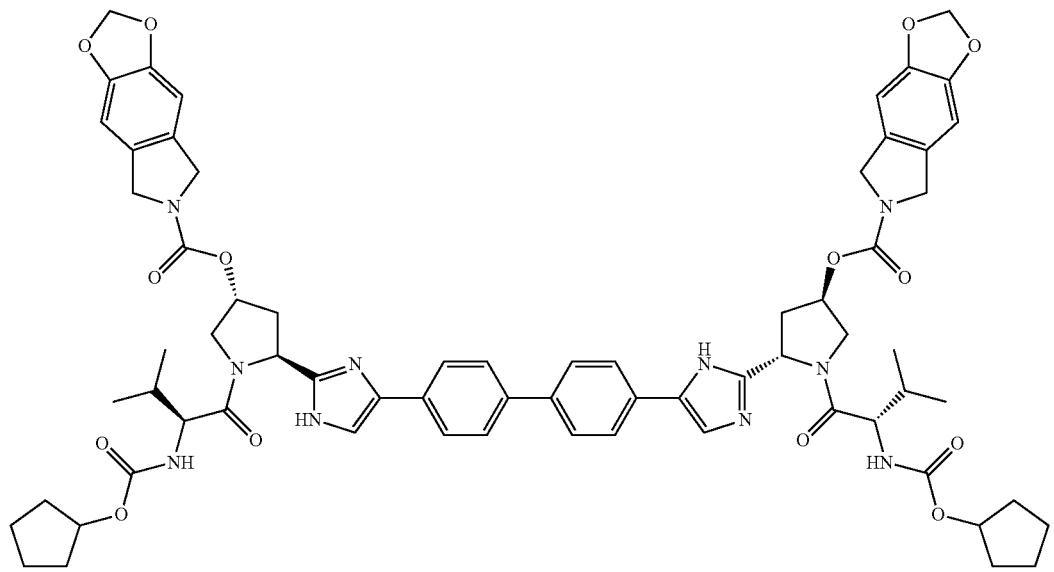
6q
Ia-16
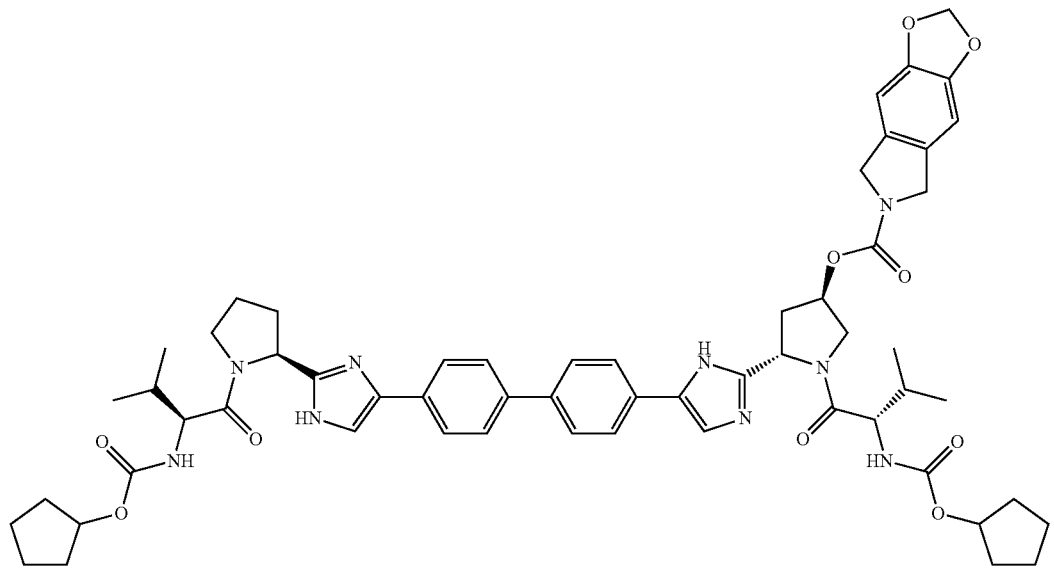
6r Structural FIG. 3a: The Target Antiviral Compounds 6a-6ep
| No. | Prepared Compounds 6a-6ep of Formula Ia |
|---|---|
Ia-17
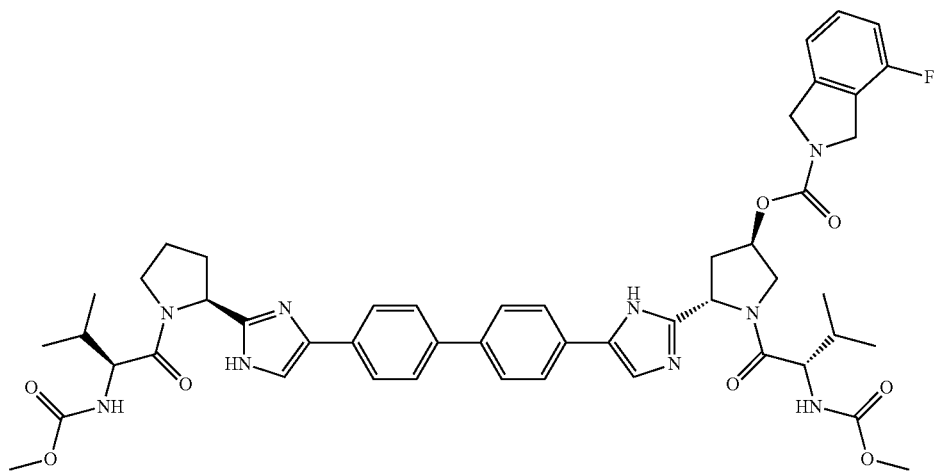
6s
Ia-18
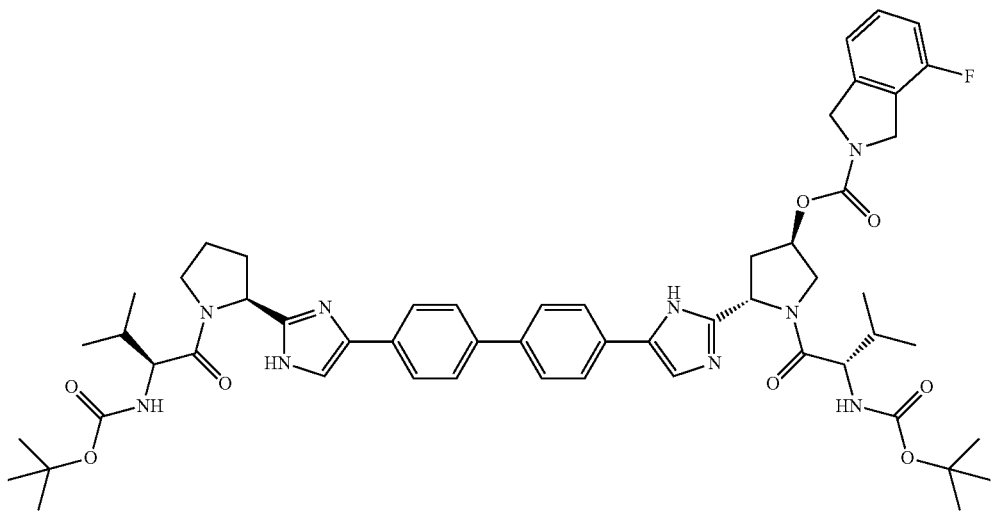
6t

| No. | Prepared Compounds 6a-6ep of Formula Ia |
|---|---|
| Ia-19 | 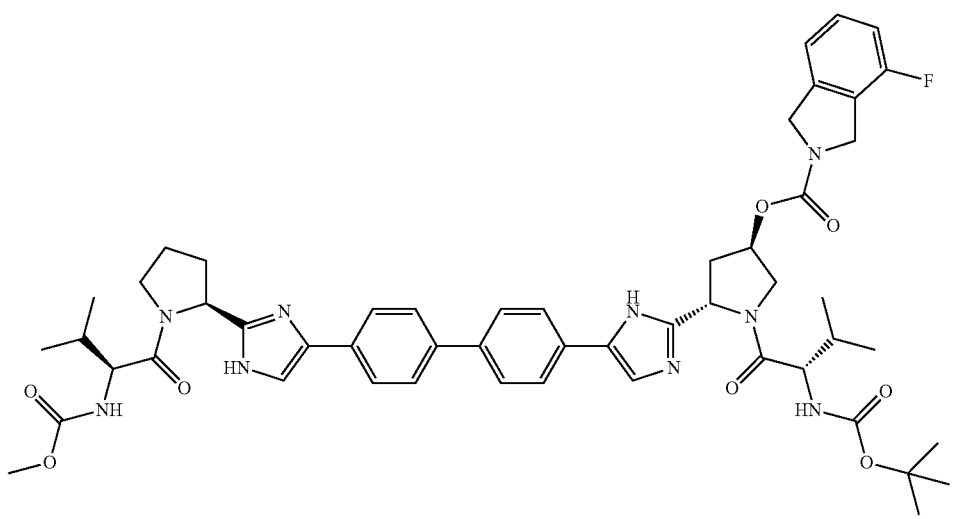<br>6u |
| Ia-20 | 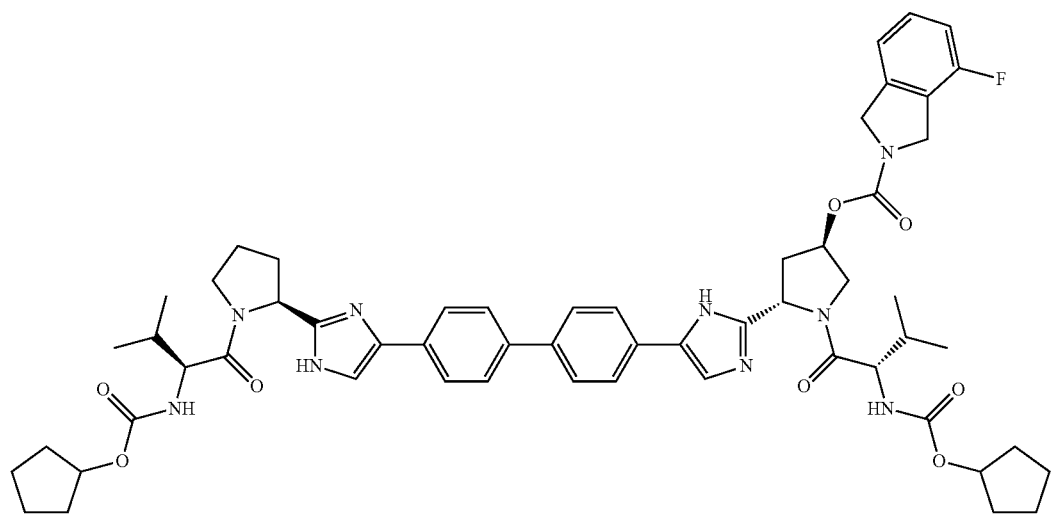<br>6v |

US 9,334,291 B2
-continued
Structural FIG. 3a: The Target Antiviral Compounds 6a-6ep
| No. | Prepared Compounds 6a-6ep of Formula Ia |
|---|---|
Ia-21
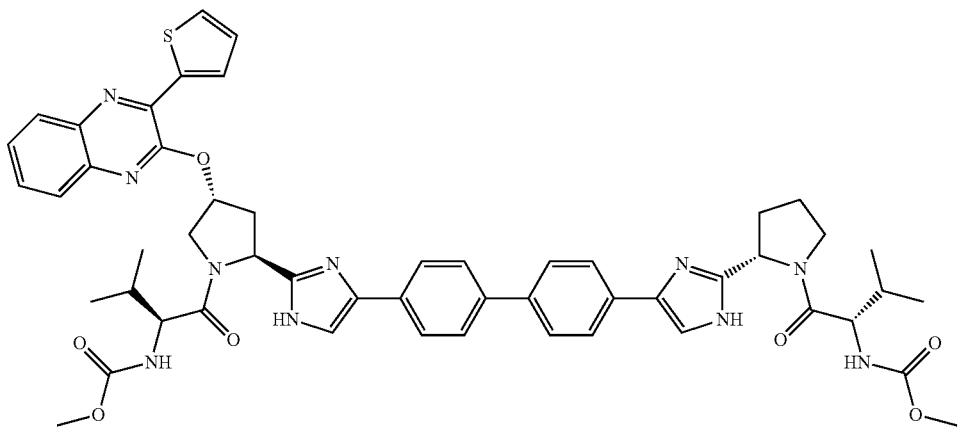
6w
Ia-22
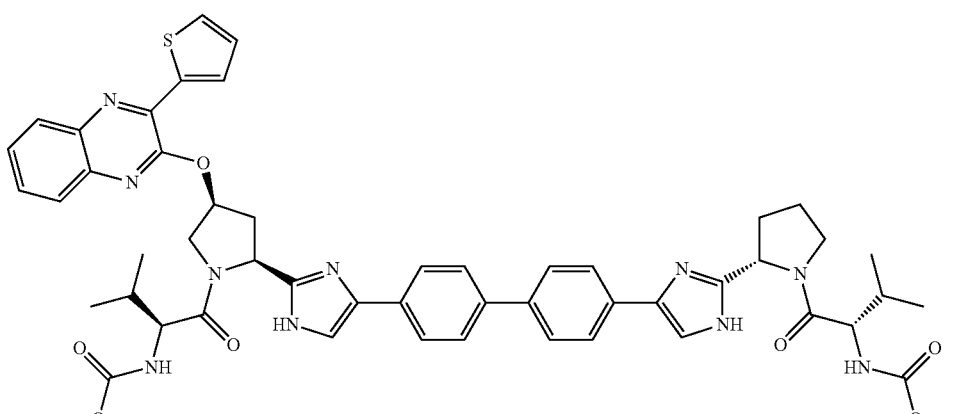
6x
Ia-23
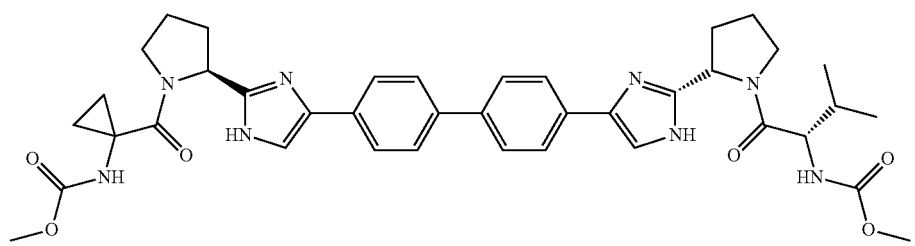
6y

| No. | Structural FIG. 3a: The Target Antiviral Compounds 6a-6ep |
|---|---|
| | Prepared Compounds 6a-6ep of Formula Ia |
Ia-24
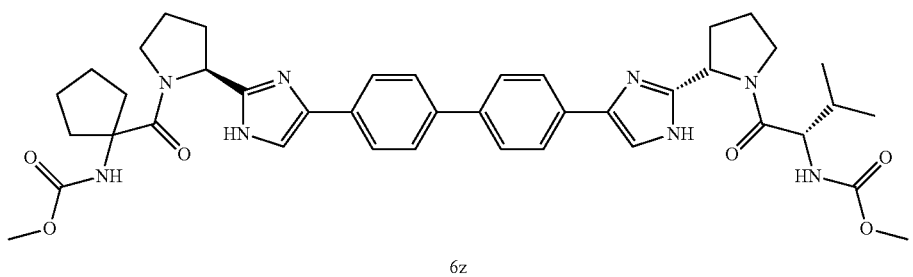
6z
Ia-25
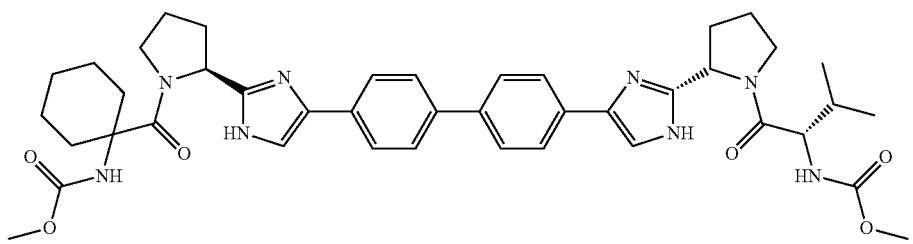
6aa
Ia-26
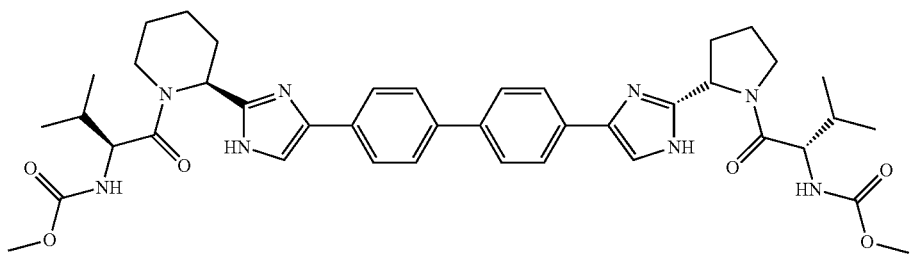
6ab
Ia-27
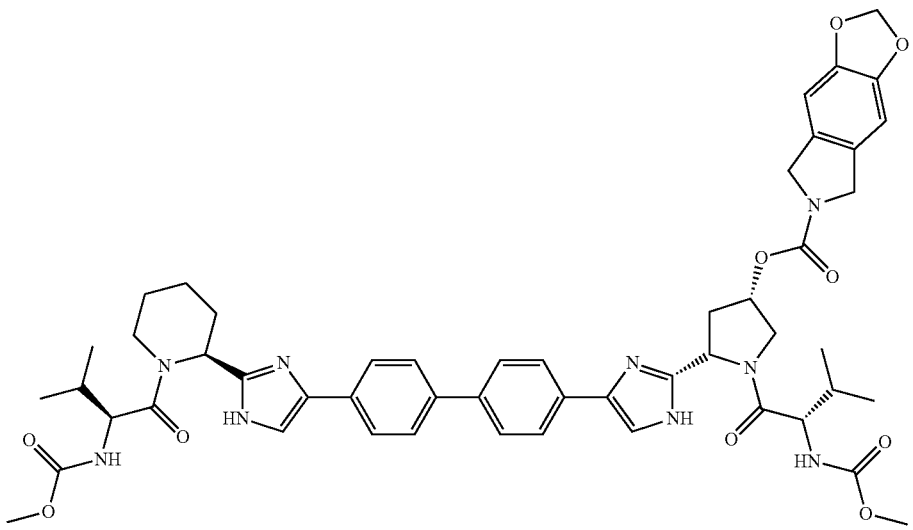
6ac Structural FIG. 3a: The Target Antiviral Compounds 6a-6ep
| No. | Prepared Compounds 6a-6ep of Formula Ia |
|---|---|
Ia-28
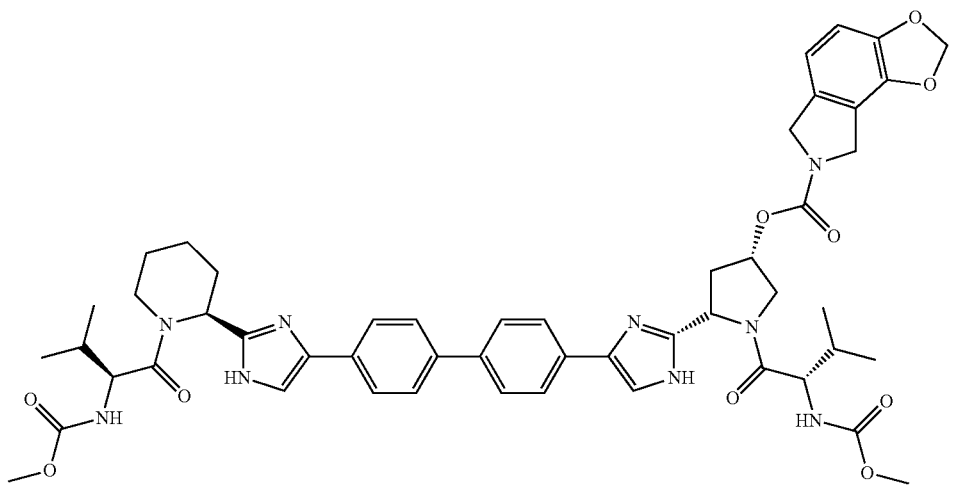
6ad
Ia-29
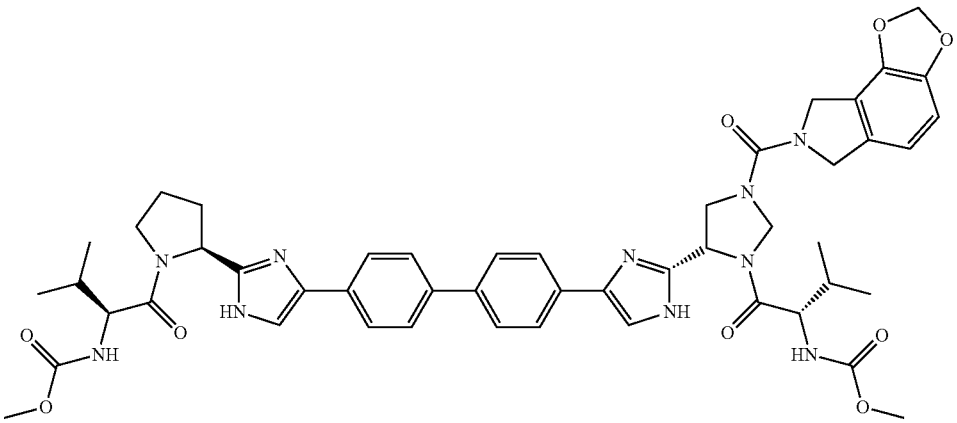
6ae
Ia-30
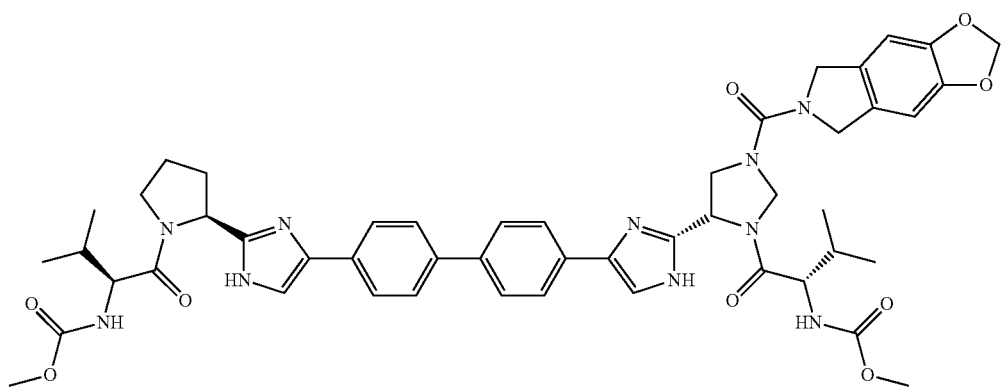
6af Structural FIG. 3a: The Target Antiviral Compounds 6a-6ep
| No. | Prepared Compounds 6a-6ep of Formula Ia |
|---|---|
| Ia-31 | 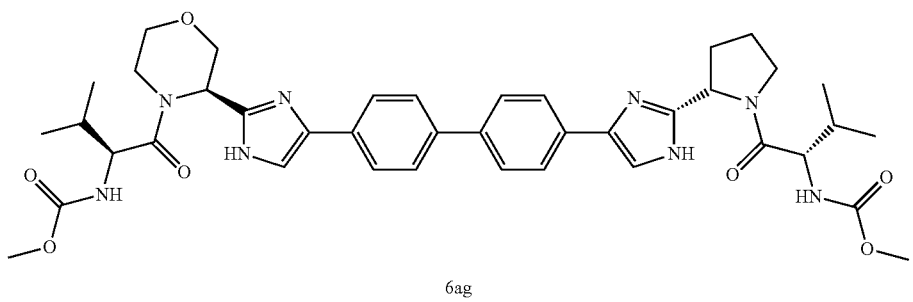 6ag |
| Ia-32 | 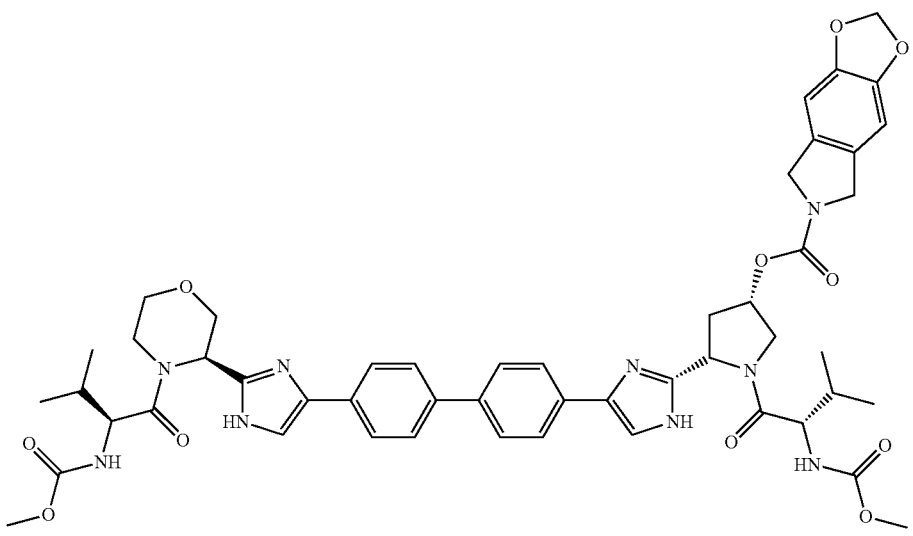 6ah |
| Ia-33 | 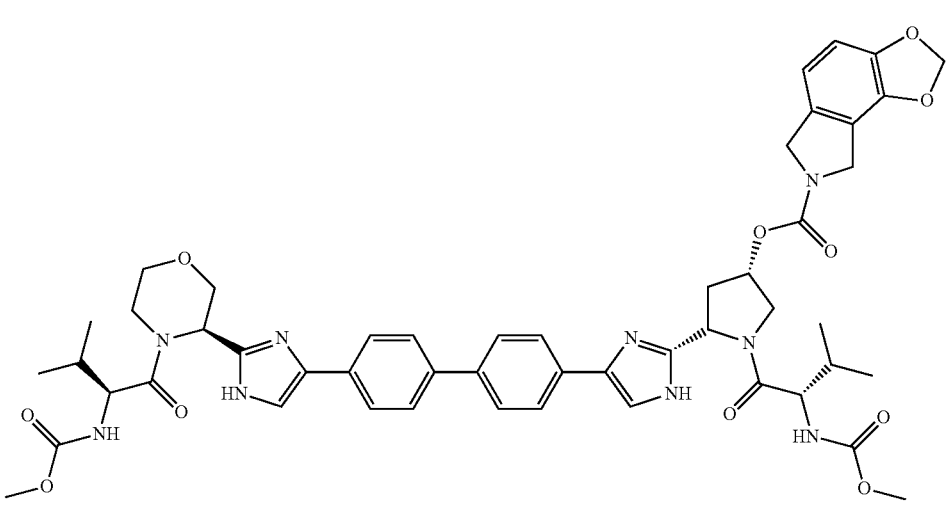 6ai |

Structural FIG. 3a: The Target Antiviral Compounds 6a-6ep
| No. | Prepared Compounds 6a-6ep of Formula Ia |
|---|---|
| Ia-34 | 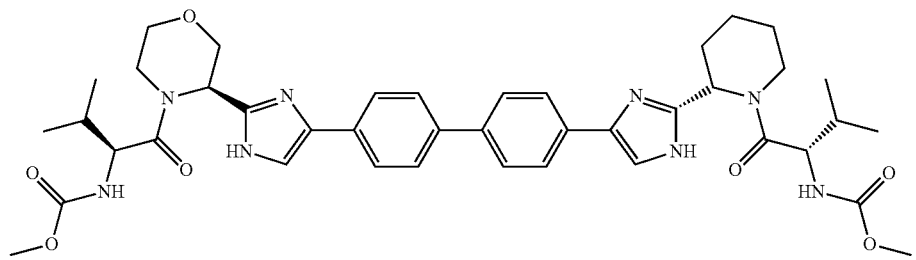 6aj |
| Ia-35 | 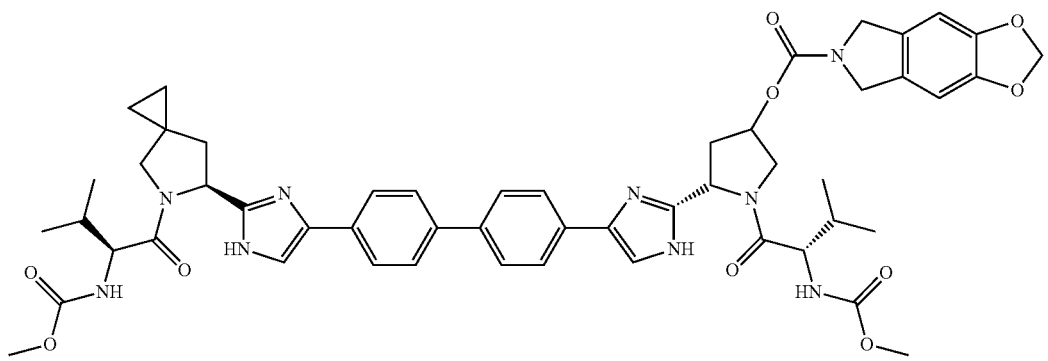 6ak |
| Ia-36 | 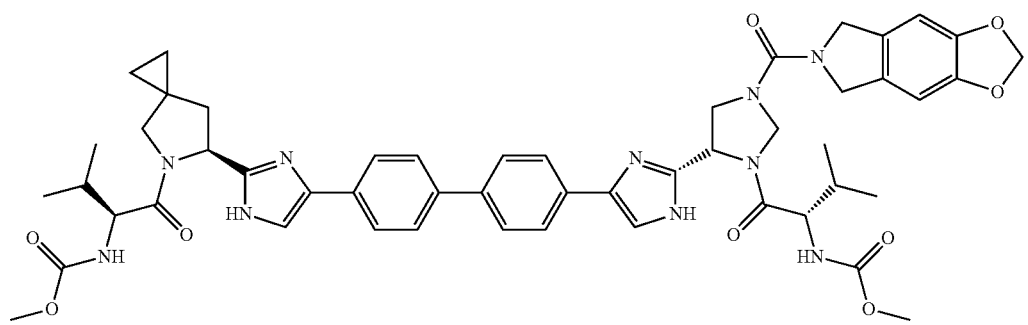 6am |

127 128
-continued
Structural FIG. 3a: The Target Antiviral Compounds 6a-6ep
| No. | Prepared Compounds 6a-6ep of Formula Ia |
|---|---|
Ia-37
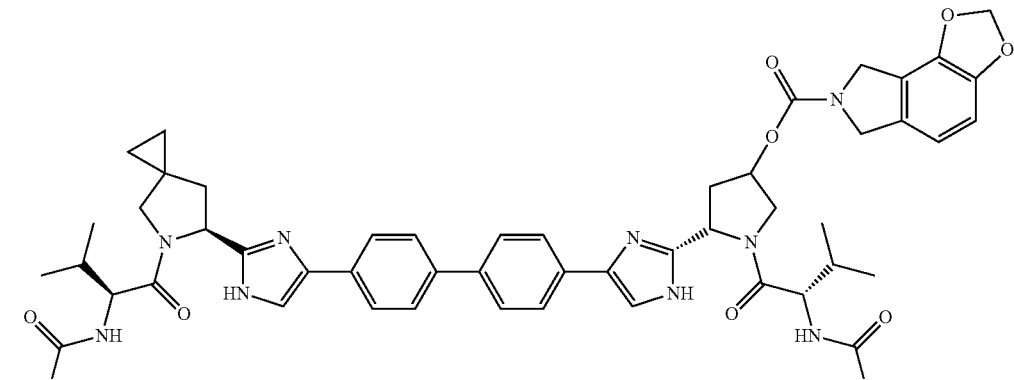
6an
Ia-38
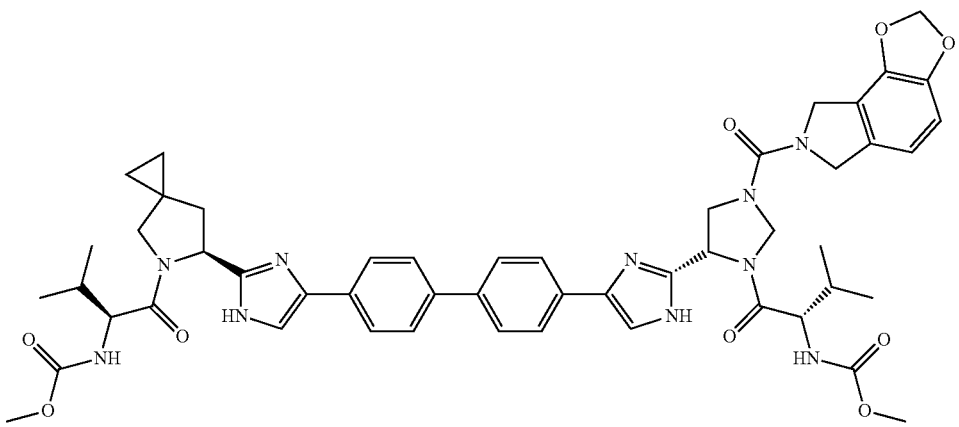
6ap
Ia-39
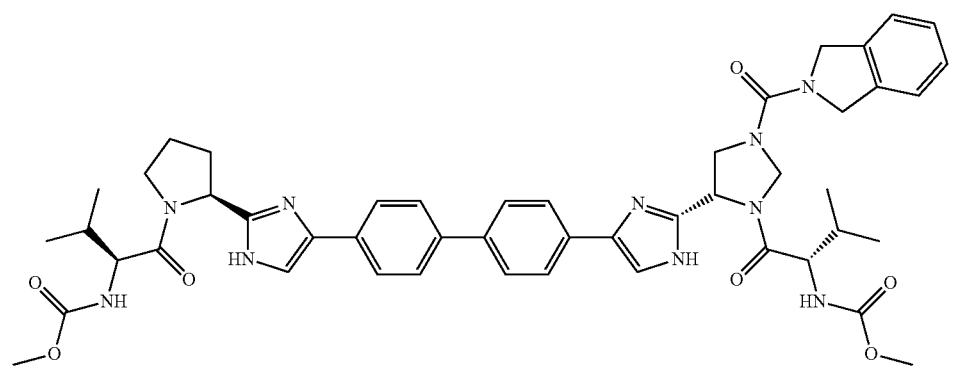
6aq -continued
Structural FIG. 3a: The Target Antiviral Compounds 6a-6ep
| No. | Prepared Compounds 6a-6ep of Formula Ia |
|---|---|
Ia-40
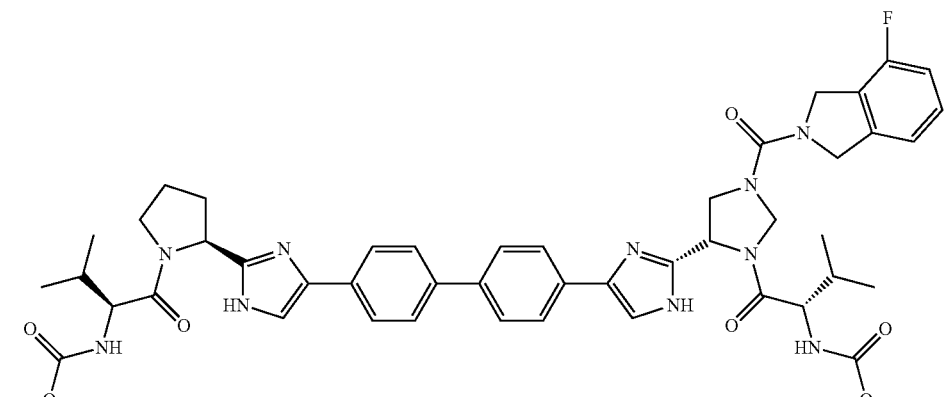
6ar
Ia-41
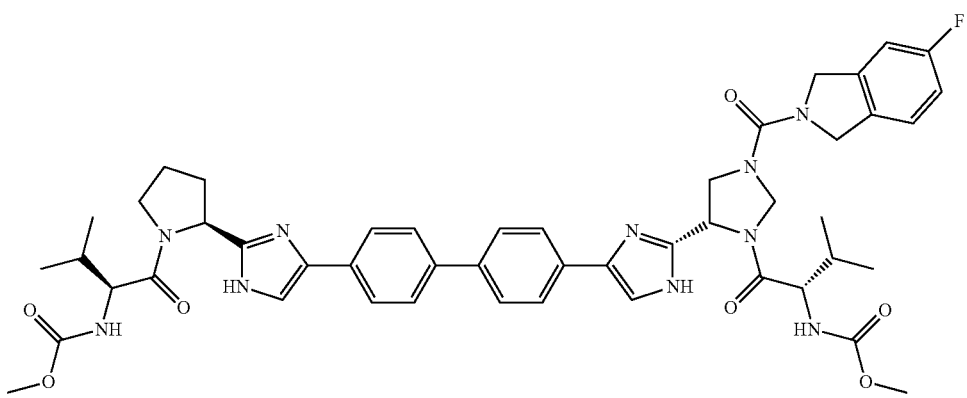
6as
Ia-42
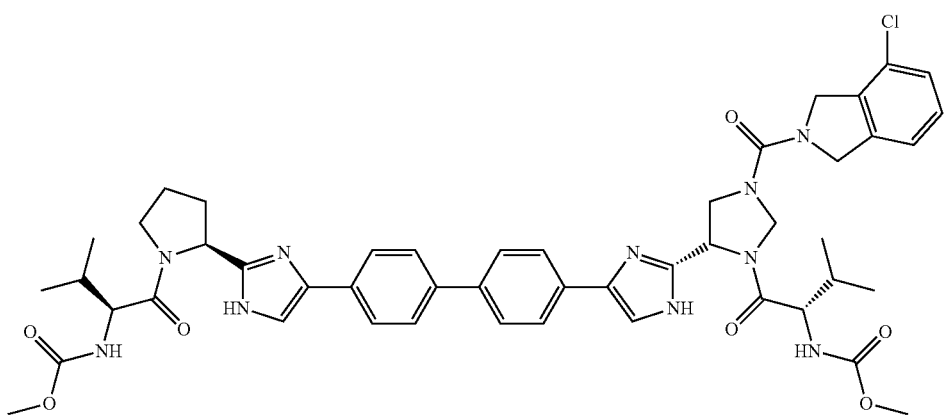
6at

Structural FIG. 3a: The Target Antiviral Compounds 6a-6ep
| No. | Prepared Compounds 6a-6ep of Formula Ia |
|---|---|
| Ia-43 | 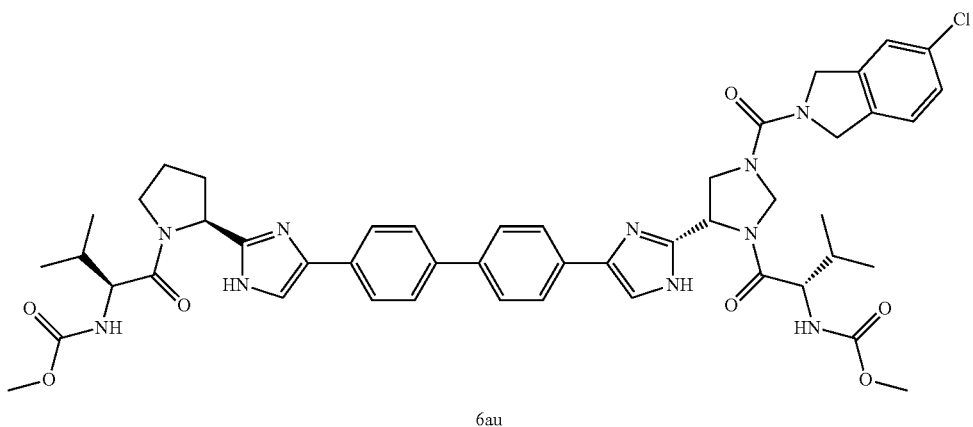 6au |
| Ia-44 | 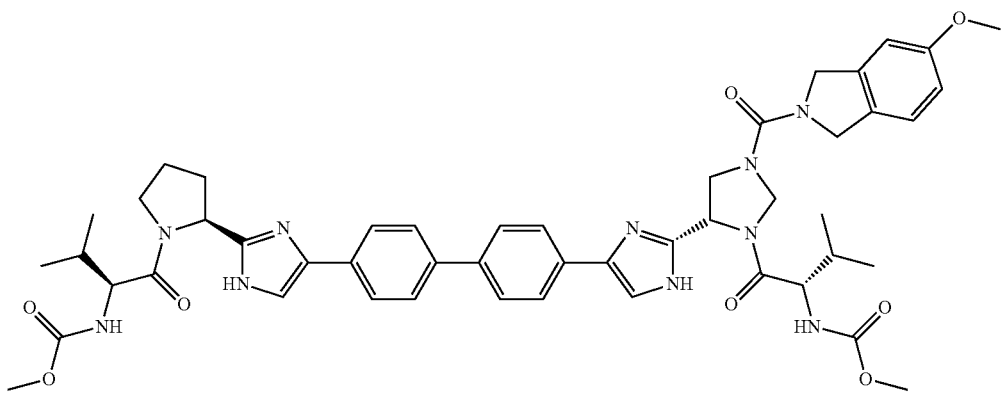 6av |
| Ia-45 | 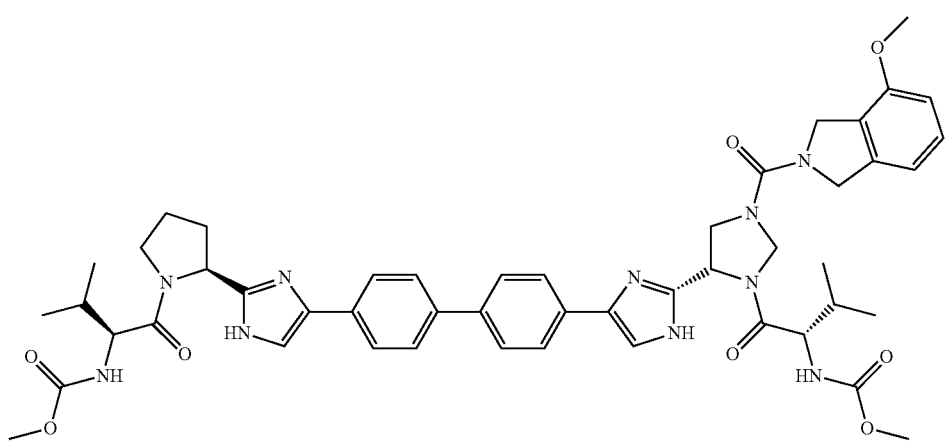 6aw |

US 9,334,291 B2
Structural FIG. 3a: The Target Antiviral Compounds 6a-6ep
| No. | Prepared Compounds 6a-6ep of Formula Ia |
|---|---|
| Ia-46 | 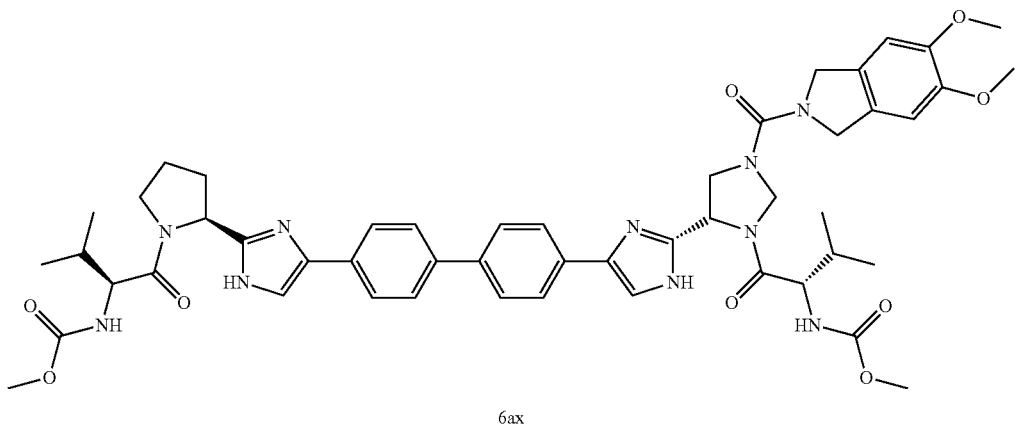<br>6ax |
| Ia-47 | 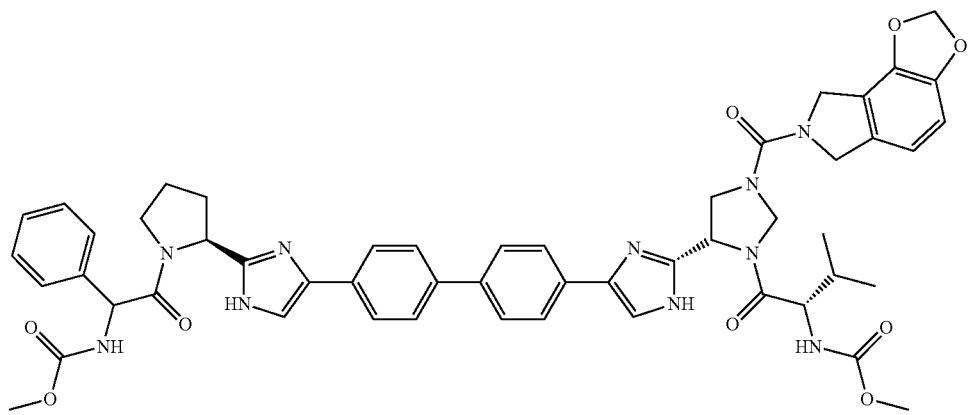<br>6ay |
| Ia-48 | 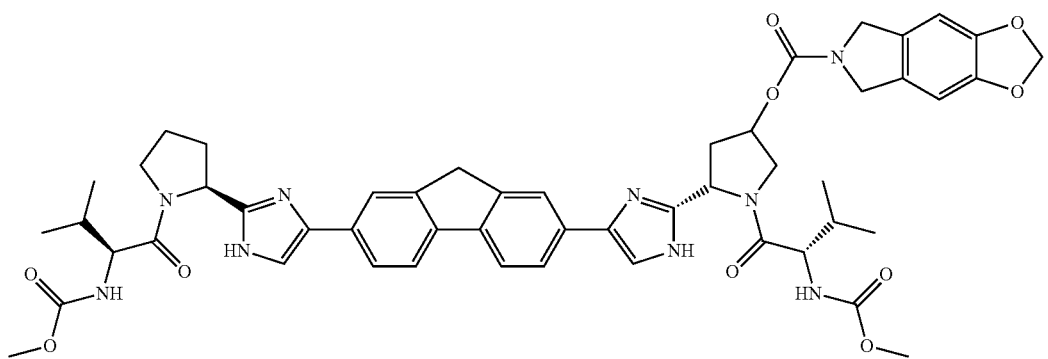<br>6az |

Structural FIG. 3a: The Target Antiviral Compounds 6a-6ep
| No. | Prepared Compounds 6a-6ep of Formula Ia |
|---|---|
| Ia-49 | 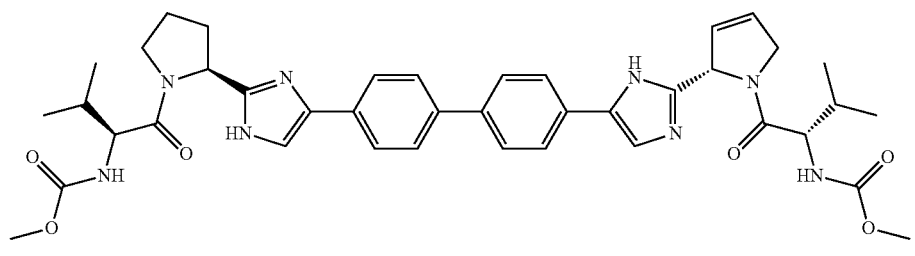<br>6ba |
| Ia-50 | 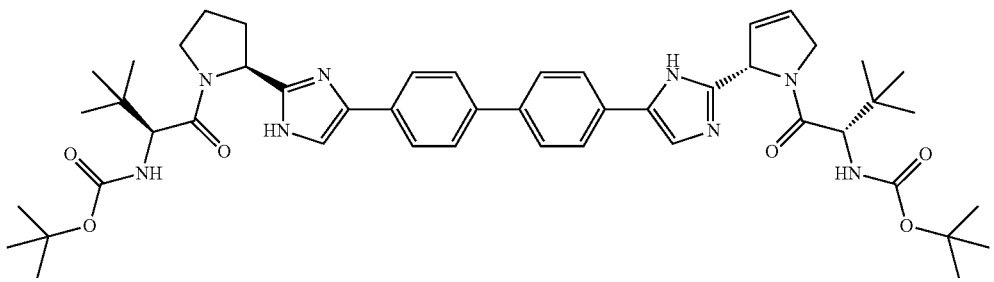<br>6bb |
| Ia-51 | 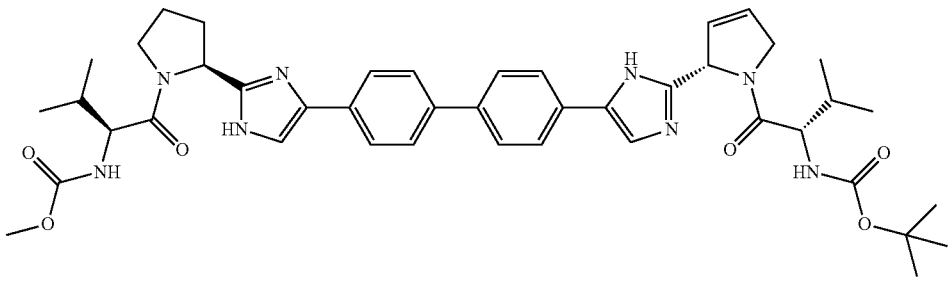<br>6bc |
| Ia-52 | 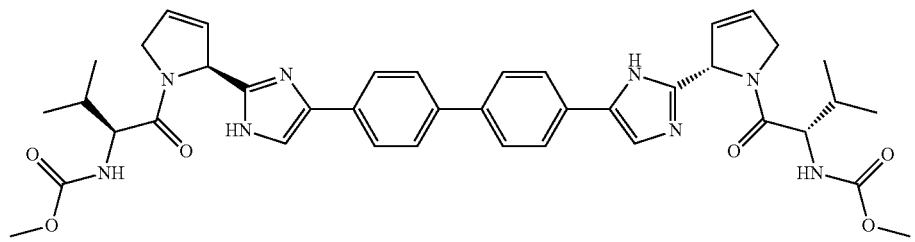<br>6bd |

Structural FIG. 3a: The Target Antiviral Compounds 6a-6ep
| No. | Prepared Compounds 6a-6ep of Formula Ia |
|---|---|
| Ia-53 | 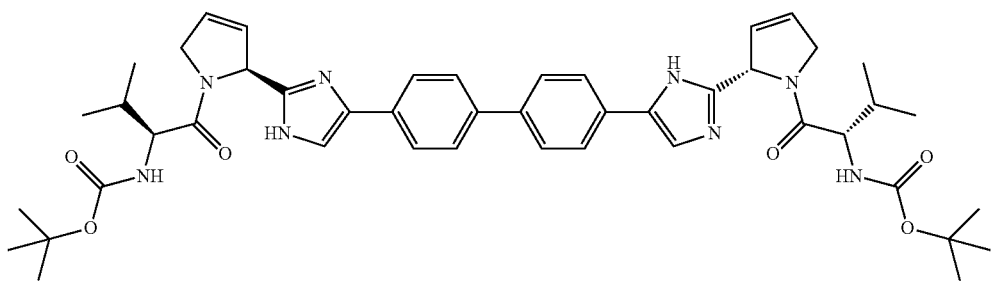<br>6be |
| Ia-54 | 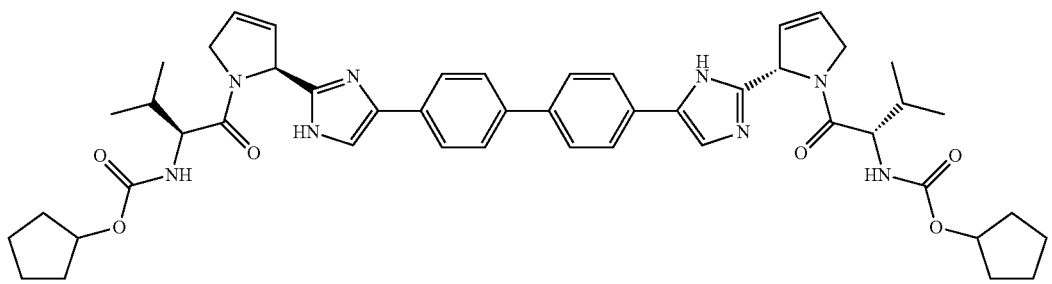<br>6bf |
| Ia-55 | 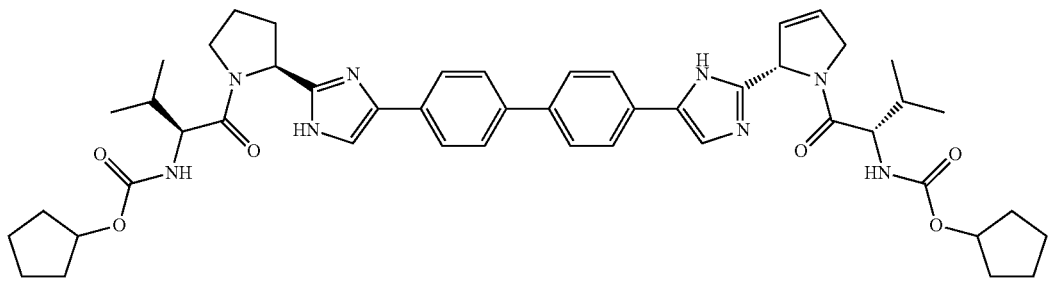<br>6bg |
| Ia-56 | 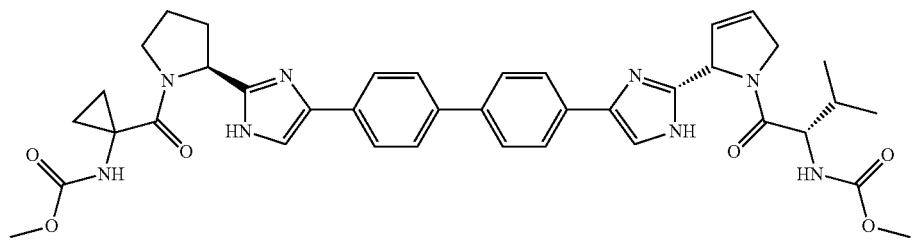<br>6bh |

-continued
Structural FIG. 3a: The Target Antiviral Compounds 6a-6ep
| No. | Prepared Compounds 6a-6ep of Formula Ia |
|---|---|
| Ia-57 | 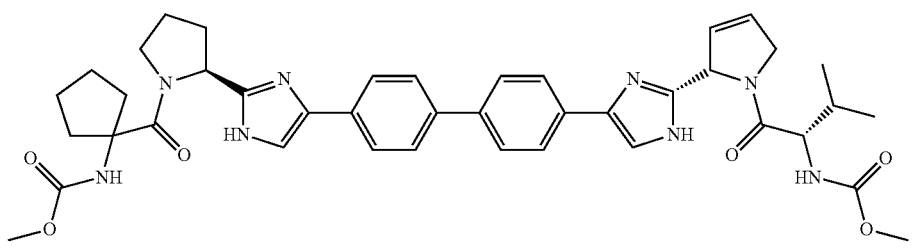 <br> 6bi |
| Ia-58 | 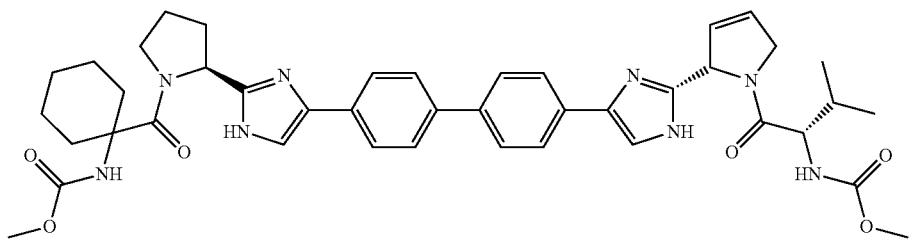 <br> 6bj |
| Ia-59 | 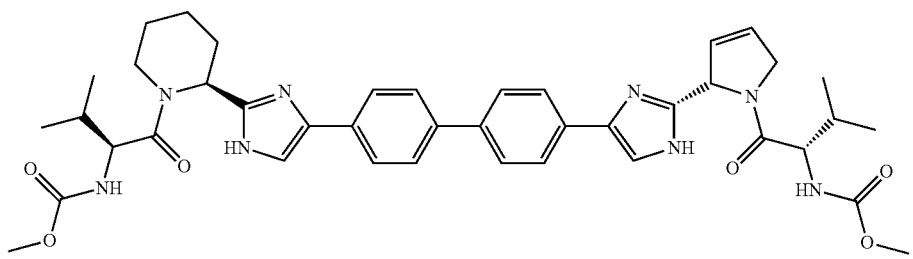 <br> 6bk |
| Ia-60 | 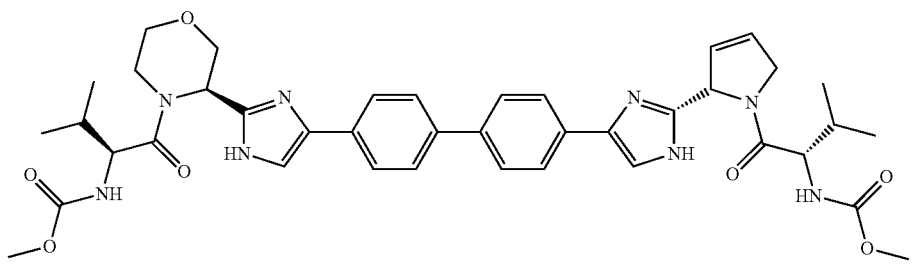 <br> 6bm |

Structural FIG. 3a: The Target Antiviral Compounds 6a-6ep
| No. | Prepared Compounds 6a-6ep of Formula Ia |
|---|---|
| Ia-61 | 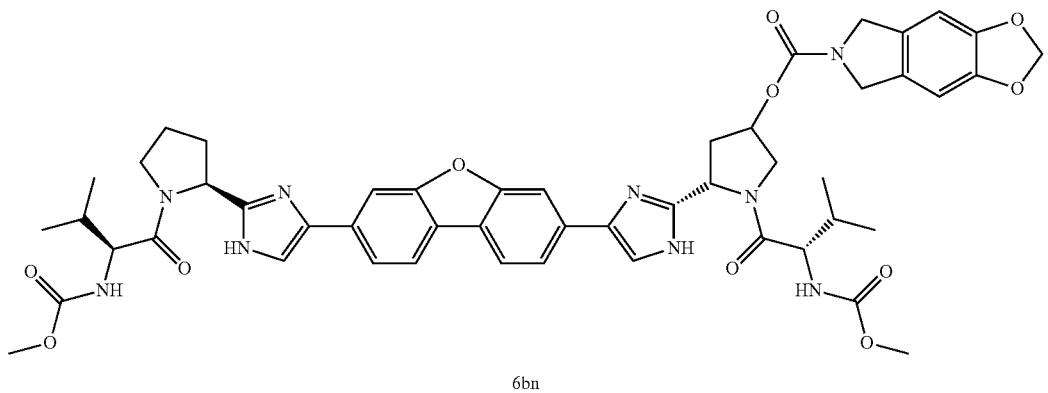<br>6bn |
| Ia-62 | 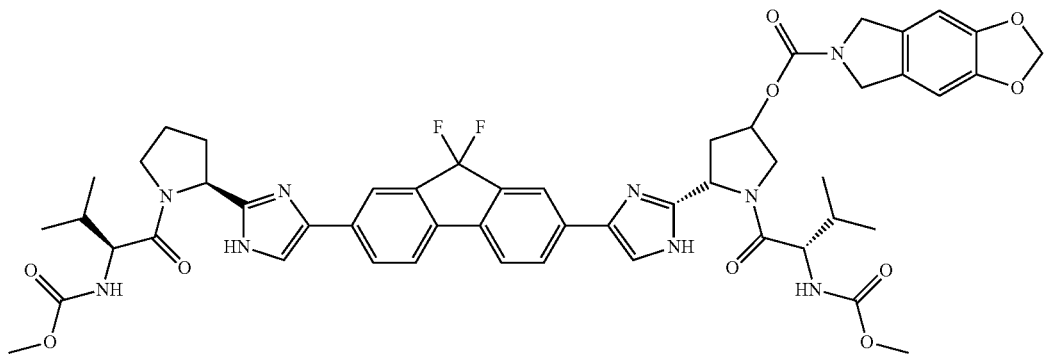<br>6bp |
| Ia-63 | 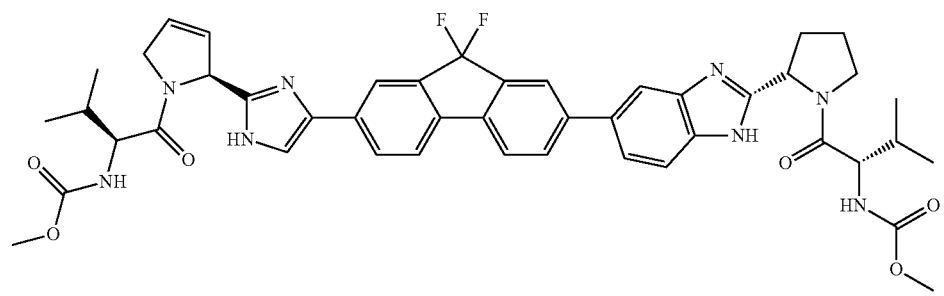<br>6bq |

Structural FIG. 3a: The Target Antiviral Compounds 6a-6ep
| No. | Prepared Compounds 6a-6ep of Formula Ia |
|---|---|
| Ia-64 | 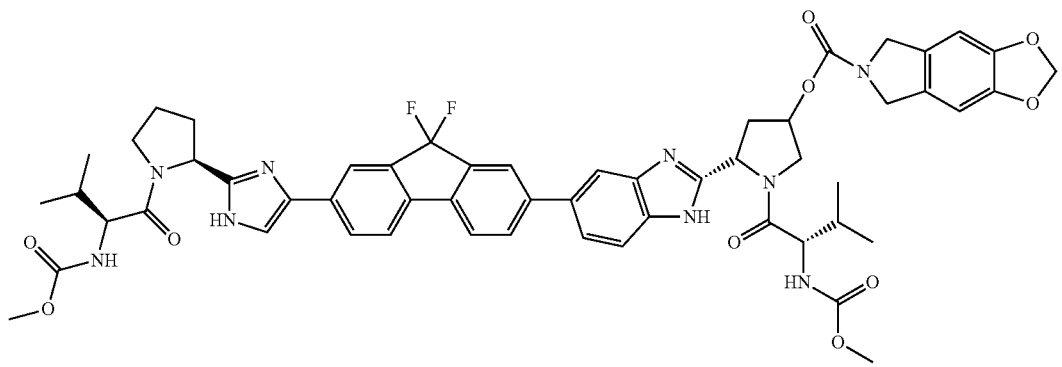<br>6br |
| Ia-65 | 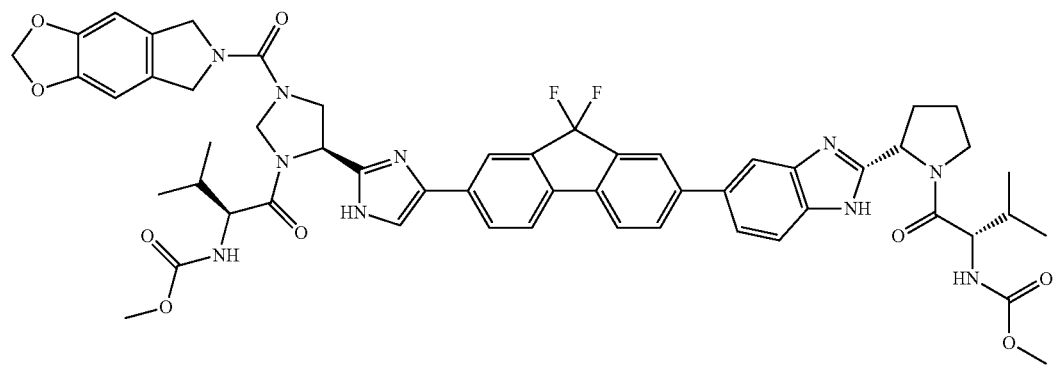<br>6bs |
| Ia-66 | 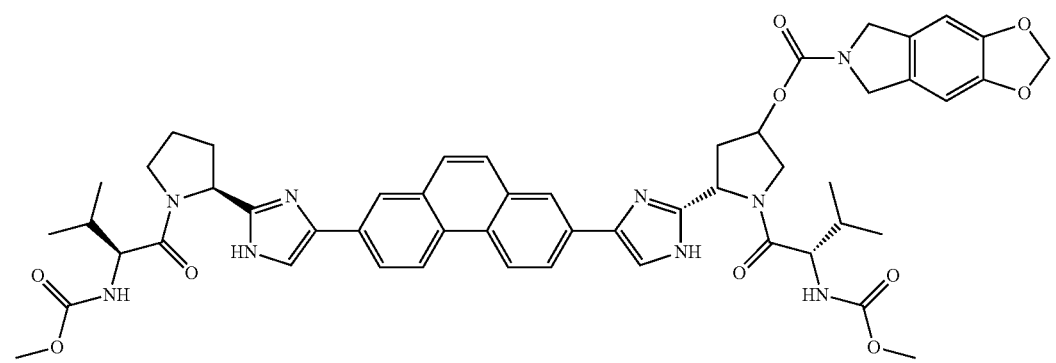<br>6bt |

Structural FIG. 3a: The Target Antiviral Compounds 6a-6ep
| No. | Prepared Compounds 6a-6ep of Formula Ia |
|---|---|
| Ia-67 | 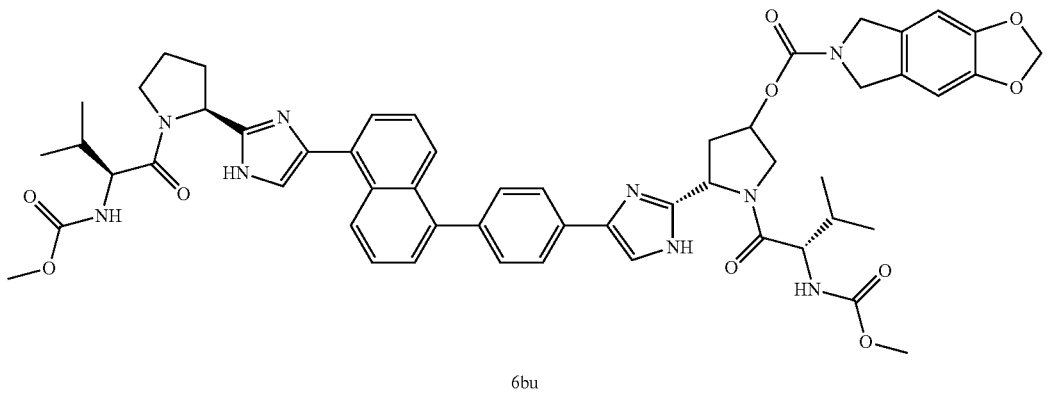 6bu |
| Ia-68 | 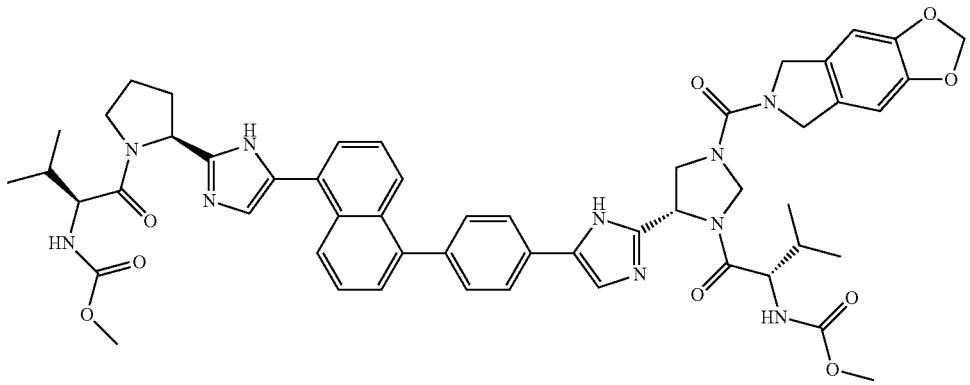 6bv |
| Ia-69 | 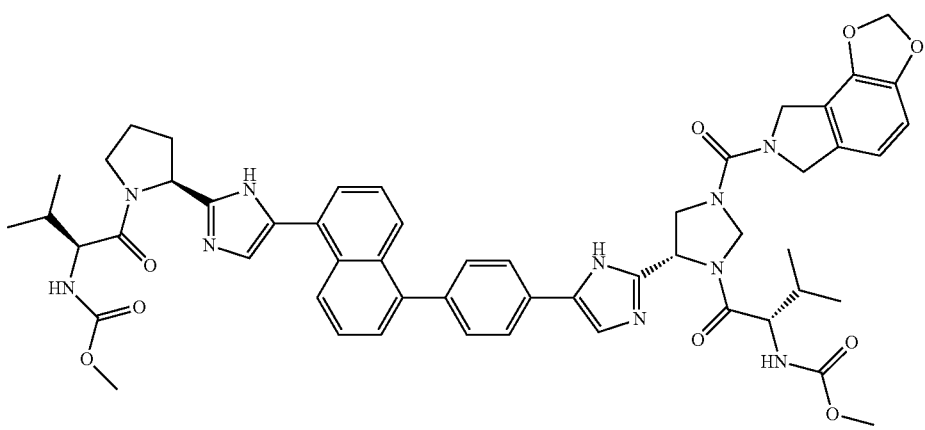 6bw |

| | Structural FIG. 3a: The Target Antiviral Compounds 6a-6ep |
|---|---|
| No. | Prepared Compounds 6a-6ep of Formula Ia |
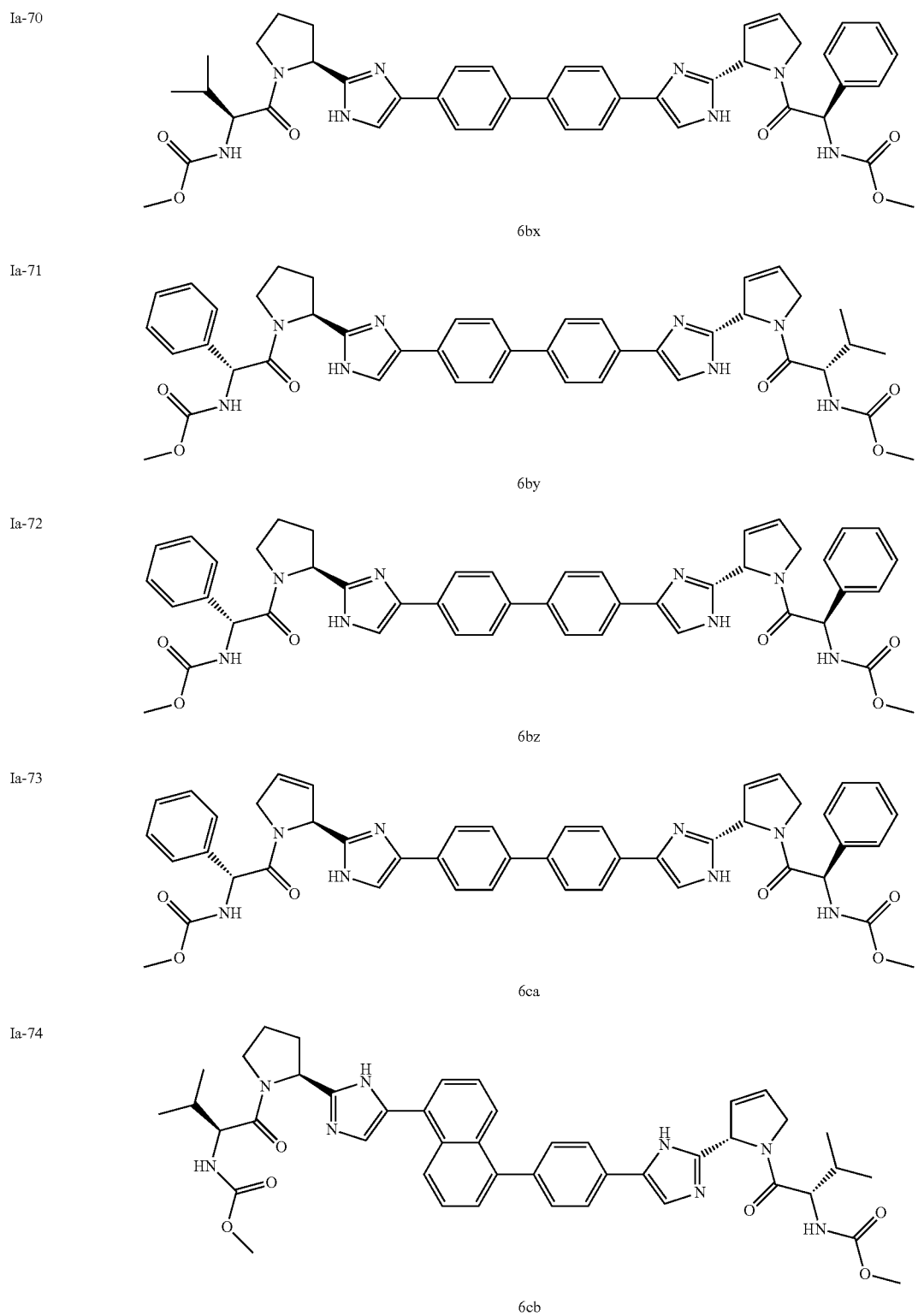
Ia-70  6bx
Ia-71  6by
Ia-72  6bz
Ia-73  6ca
Ia-74  6cb US 9,334,291 B2
149                                                                                       150
-continued
Structural FIG. 3a: The Target Antiviral Compounds 6a-6ep
| No. | Prepared Compounds 6a-6ep of Formula Ia |
|---|---|
Ia-75
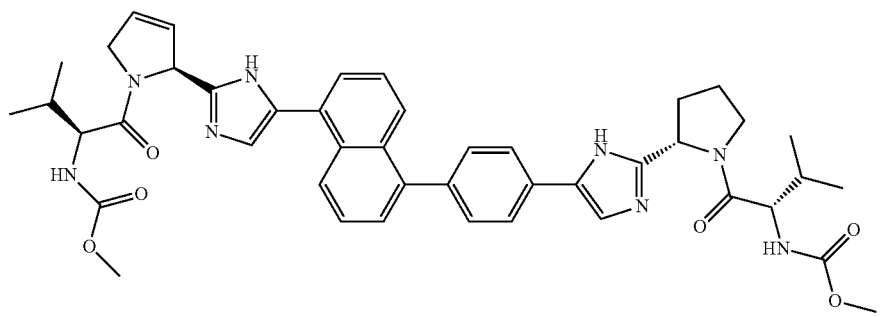
6cc
Ia-76
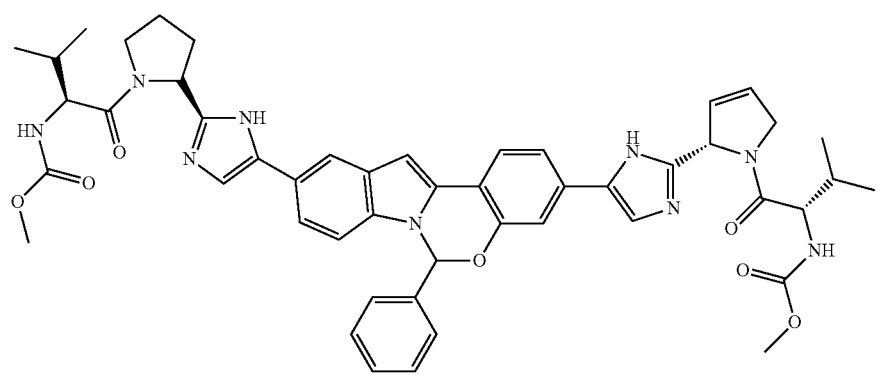
6cd
Ia-77
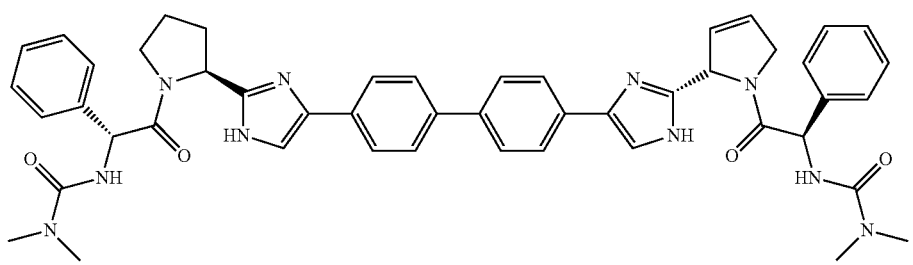
6ce
Ia-78
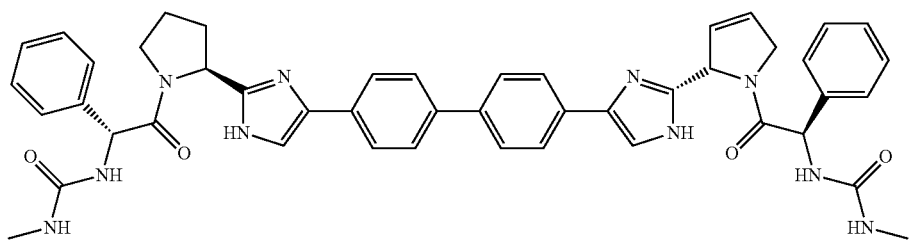
6cf

| No. | Prepared Compounds 6a-6ep of Formula Ia |
|---|---|
| Ia-79 | 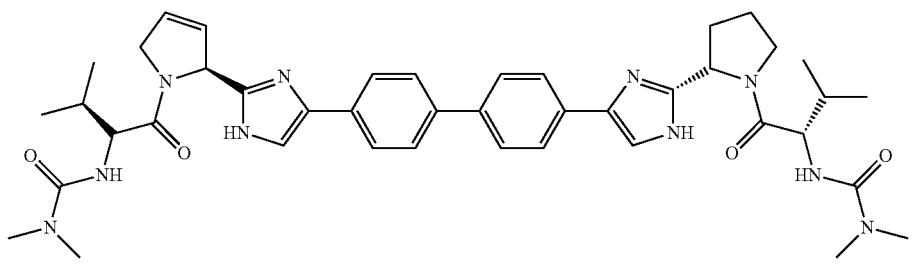 6cg |
| Ia-80 | 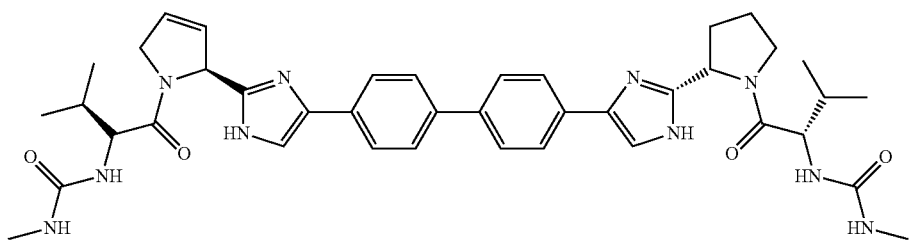 6ch |
| Ia-81 | 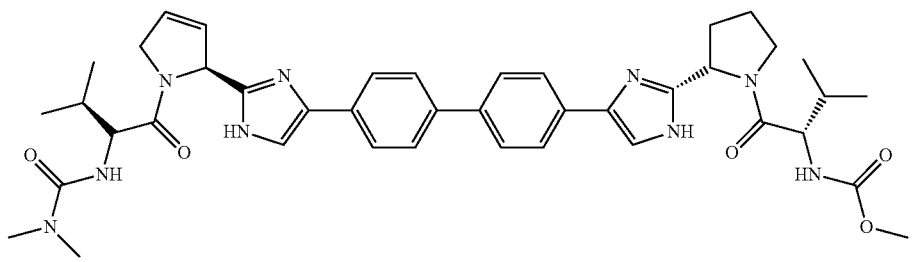 6ci |
| Ia-82 | 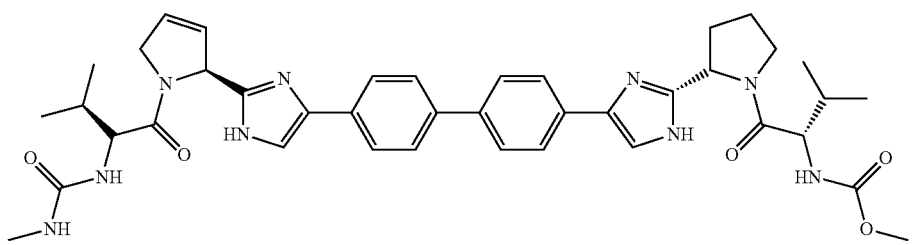 6cj |
| Ia-83 | 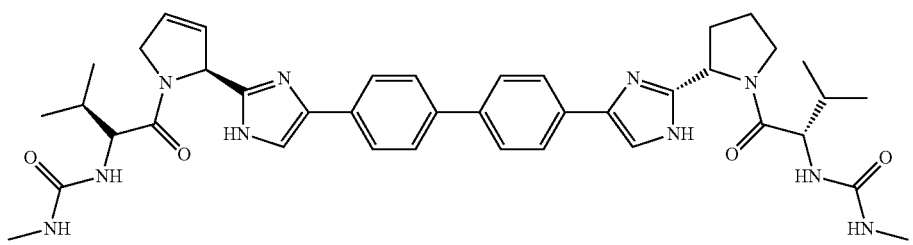 6ck |

US 9,334,291 B2
153   154
-continued
Structural FIG. 3a: The Target Antiviral Compounds 6a-6ep
| No. | Prepared Compounds 6a-6ep of Formula Ia |
|---|---|
Ia-84
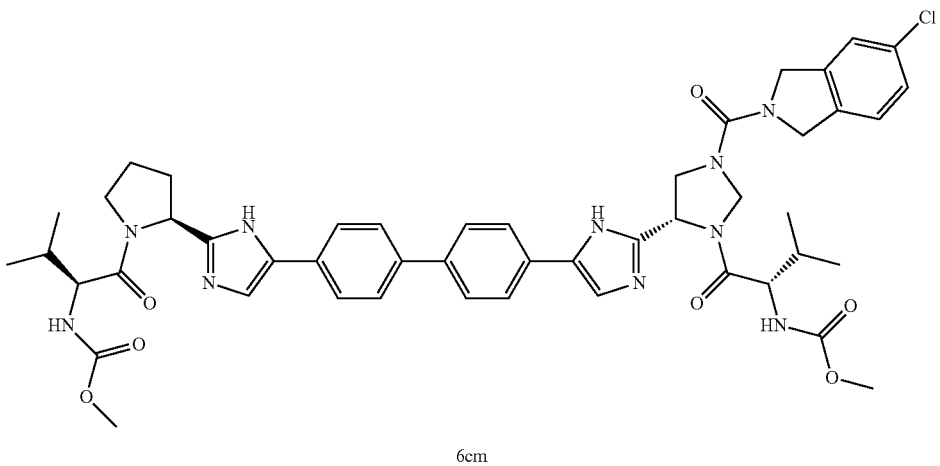 [SMILES: COC(=O)N[C@H](C(=O)N1CCC[C@H]1c1ncc(-c2ccc(-c3ccc(-c4cnc([C@@H]5CN(C(=O)N6Cc7ccc(Cl)cc7C6)CN5C(=O)[C@@H](NC(=O)OC)C(C)C)[nH]4)cc3)cc2)[nH]1)C(C)C]
6cm
Ia-85
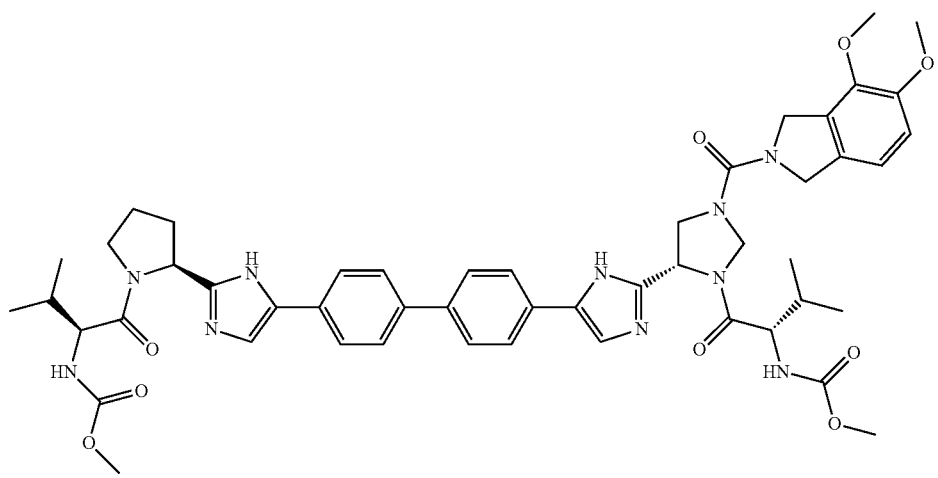
6cq
Ia-86
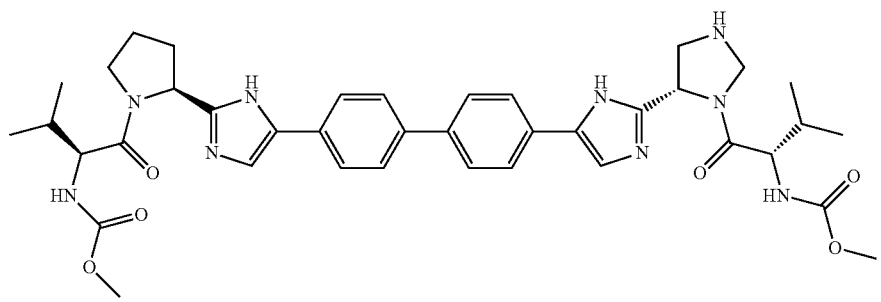
6cu -continued
Structural FIG. 3a: The Target Antiviral Compounds 6a-6ep
| No. | Prepared Compounds 6a-6ep of Formula Ia |
|---|---|
| Ia-87 | 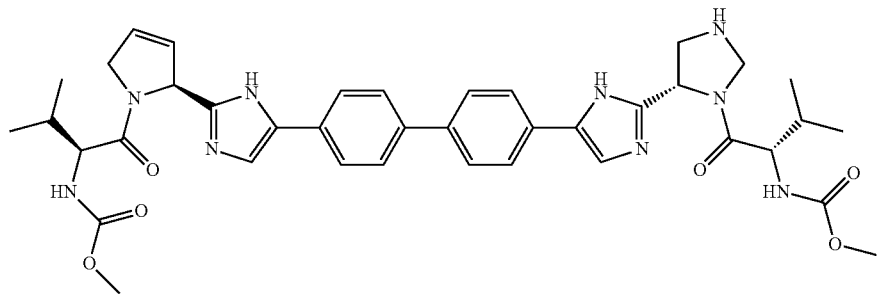<br>6cv |
| Ia-88 | 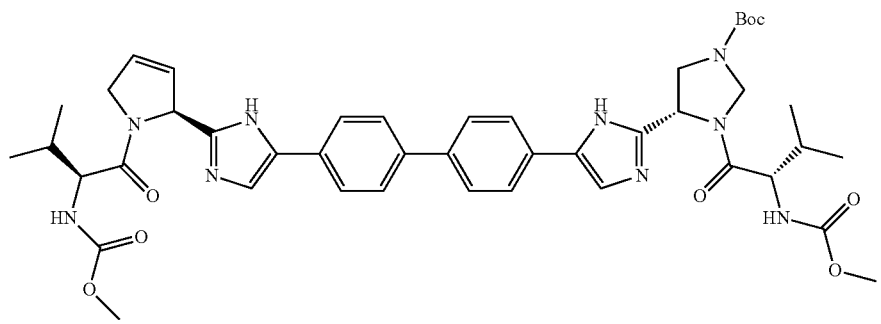<br>6cw |
| Ia-89 | 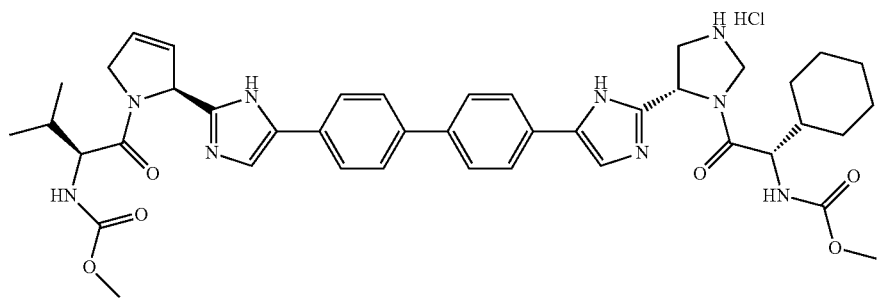<br>6cx |
| Ia-90 | 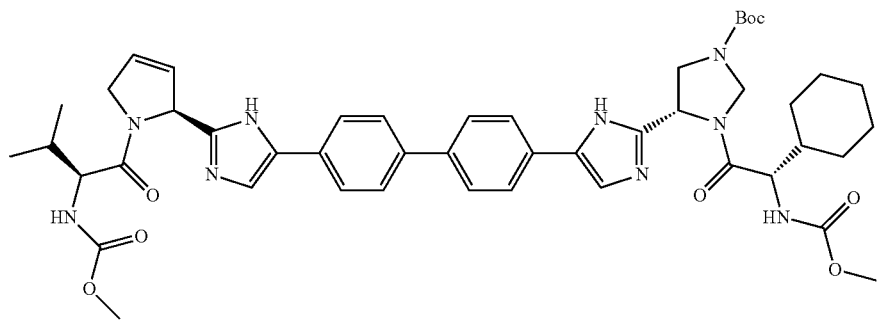<br>6cy |

US 9,334,291 B2
157                                                                 158
-continued
Structural FIG. 3a: The Target Antiviral Compounds 6a-6ep
| No. | Prepared Compounds 6a-6ep of Formula Ia |
|---|---|
Ia-91
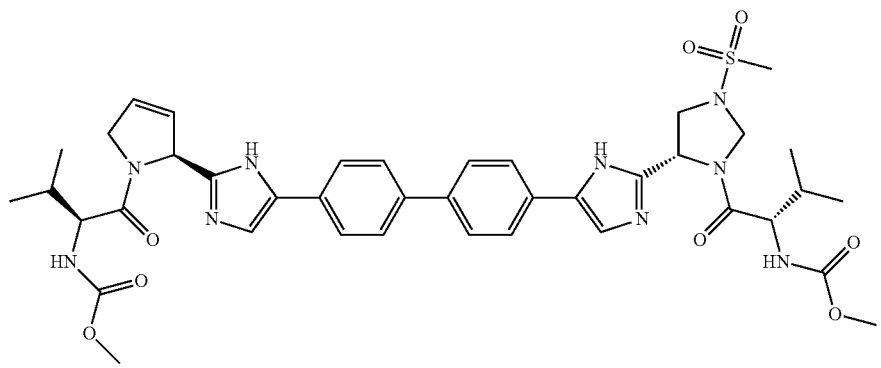
6cz
Ia-92
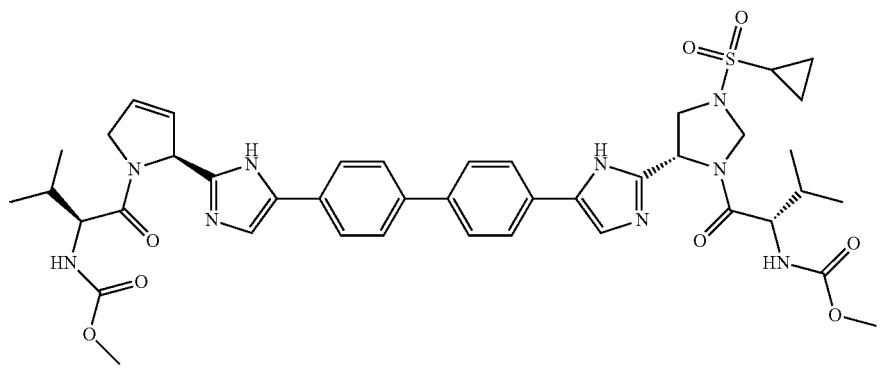
6da
Ia-93
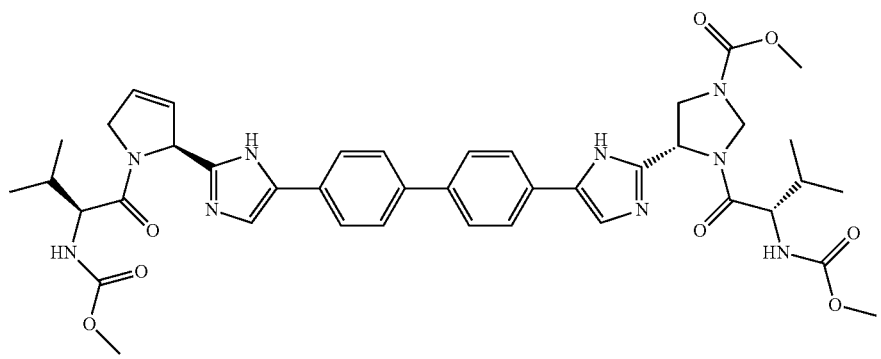
6db US 9,334,291 B2
-continued
Structural FIG. 3a: The Target Antiviral Compounds 6a-6ep
| No. | Prepared Compounds 6a-6ep of Formula Ia |
|---|---|
| Ia-94 | 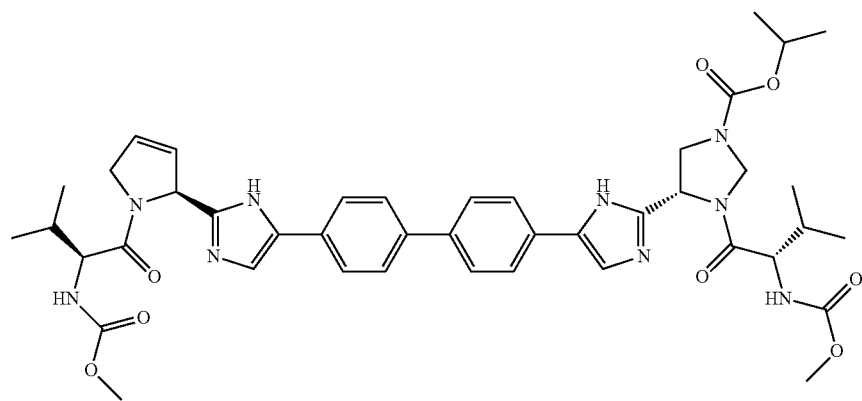<br>6dc |
| Ia-95 | 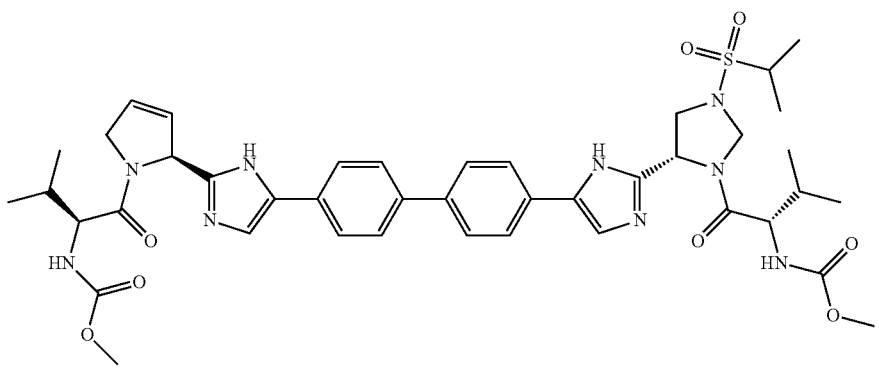<br>6dd |
| Ia-96 | 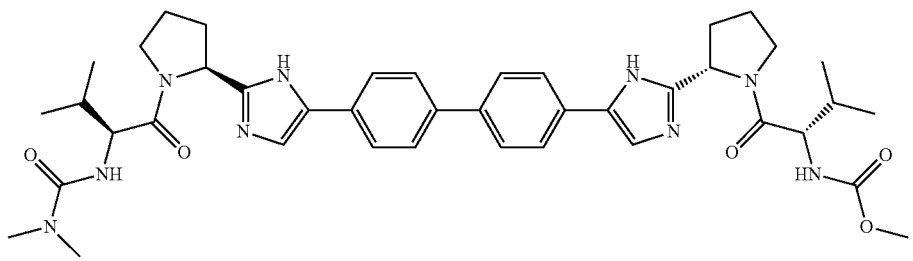<br>6de |
| Ia-97 | 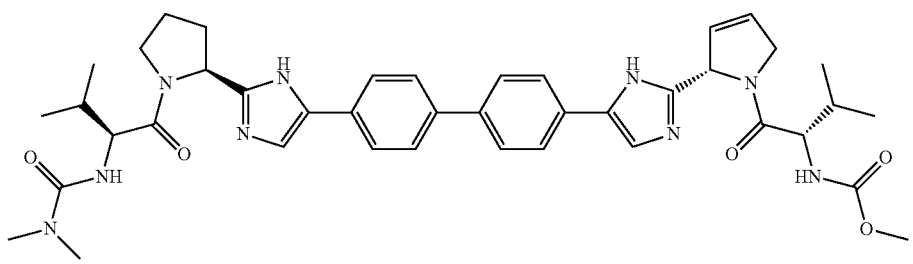<br>6df |

| | |
|---|---|
| Structural FIG. 3a: The Target Antiviral Compounds 6a-6ep | |
| No. | Prepared Compounds 6a-6ep of Formula Ia |
Ia-98
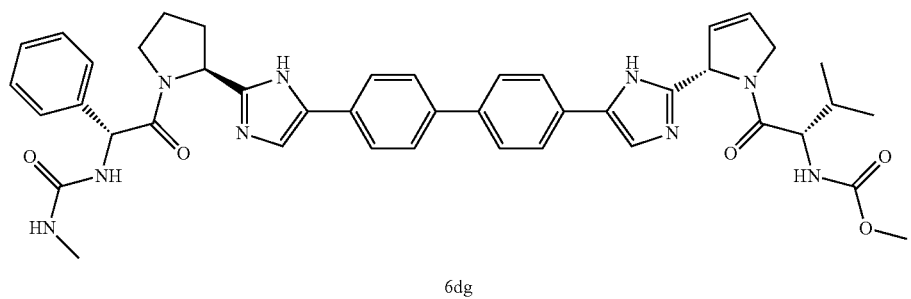 [SMILES: CNC(=O)N[C@@H](C(=O)N1CCC[C@H]1c1ncc(-c2ccc(-c3ccc(-c4cnc([C@@H]5C=CCN5C(=O)[C@@H](NC(=O)OC)C(C)C)[nH]4)cc3)cc2)[nH]1)c1ccccc1]
6dg
Ia-99
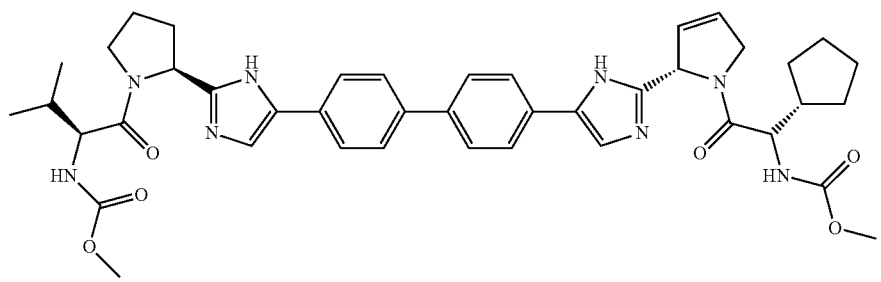
6dh
Ia-100
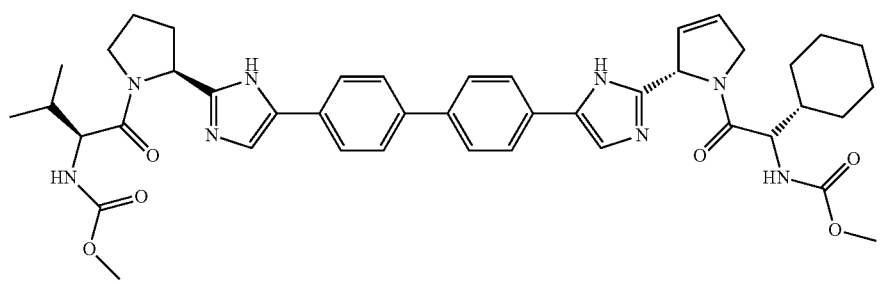
6di
Ia-101
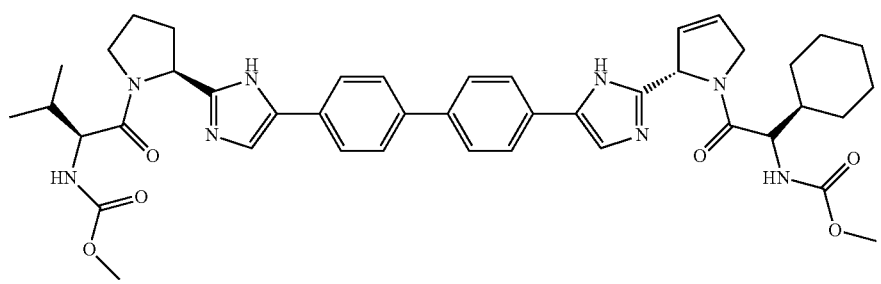
6dj

| | Structural FIG. 3a: The Target Antiviral Compounds 6a-6ep |
|---|---|
| No. | Prepared Compounds 6a-6ep of Formula Ia |
Ia-102
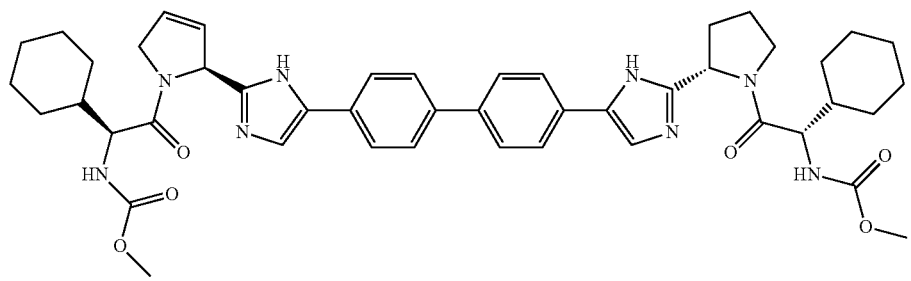
6dk
Ia-103
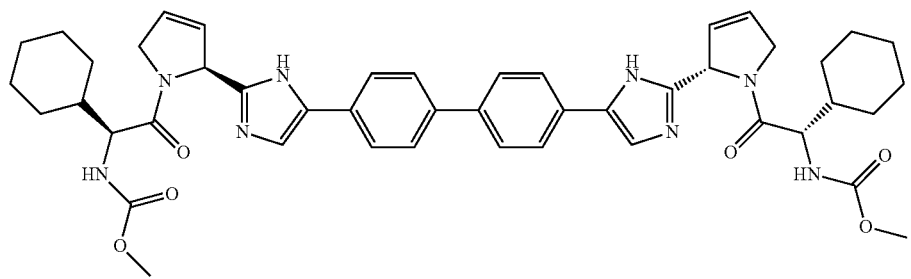
6dm
Ia-104
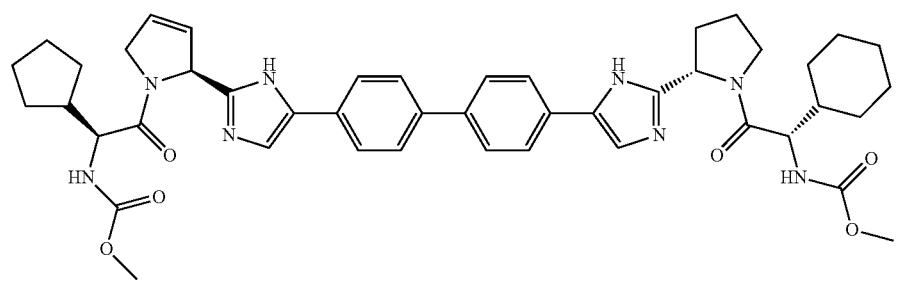
6dn
Ia-105
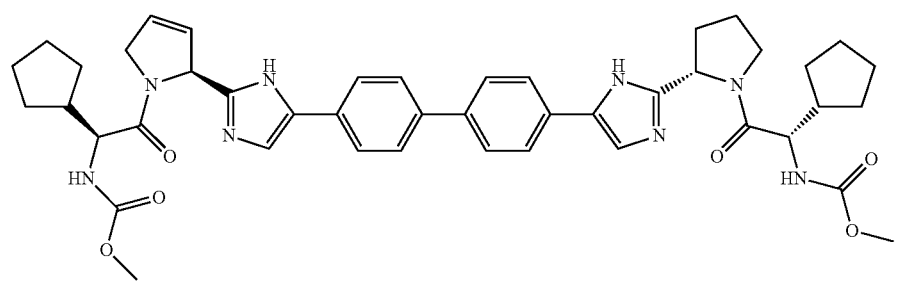
6dp

| | |
|---|---|
| Structural FIG. 3a: The Target Antiviral Compounds 6a-6ep | |
| No. | Prepared Compounds 6a-6ep of Formula Ia |
| Ia-106 | 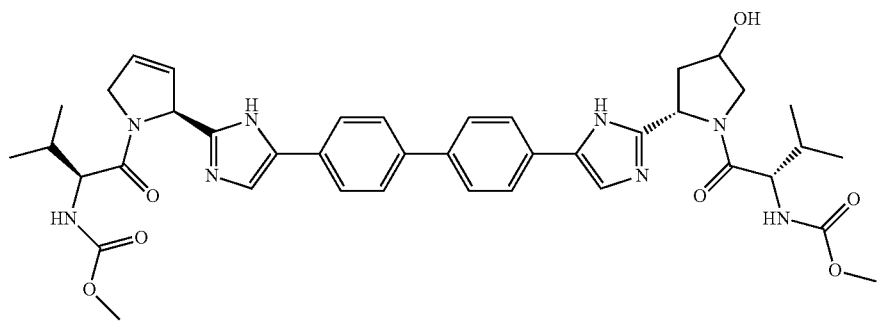 6dq |
| Ia-107 | 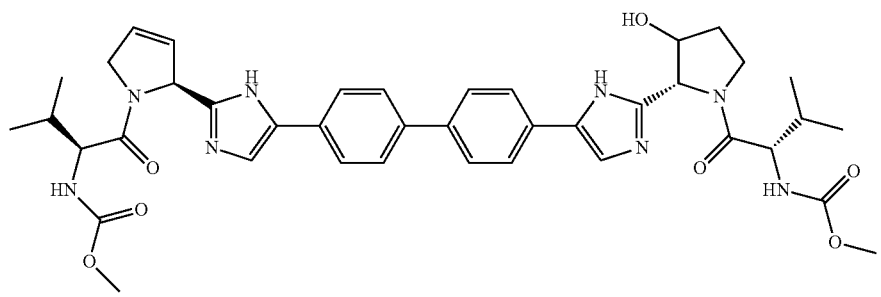 6dr |
| Ia-108 | 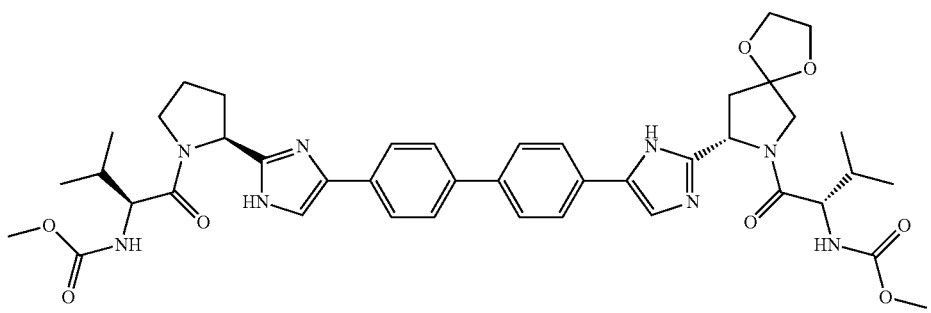 6ds |
| Ia-109 | 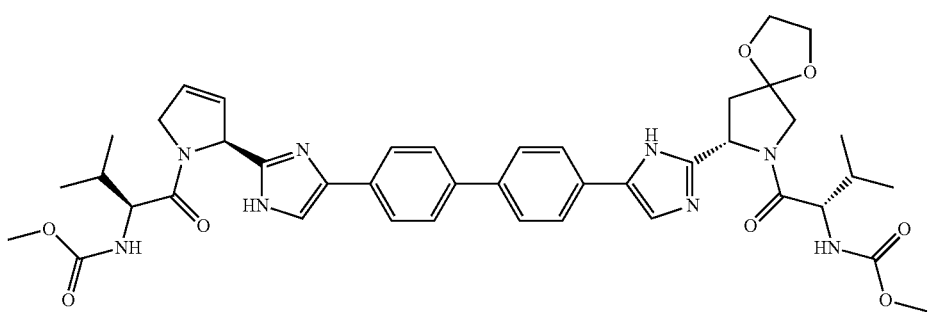 6dt |

-continued
Structural FIG. 3a: The Target Antiviral Compounds 6a-6ep
| No. | Prepared Compounds 6a-6ep of Formula Ia |
|---|---|
Ia-110
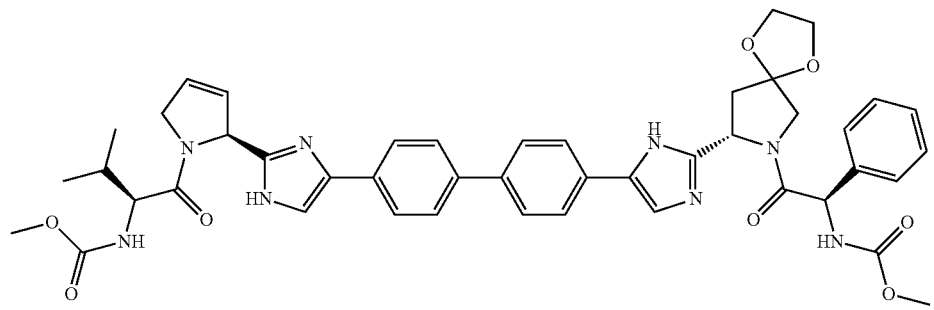
6du
Ia-111
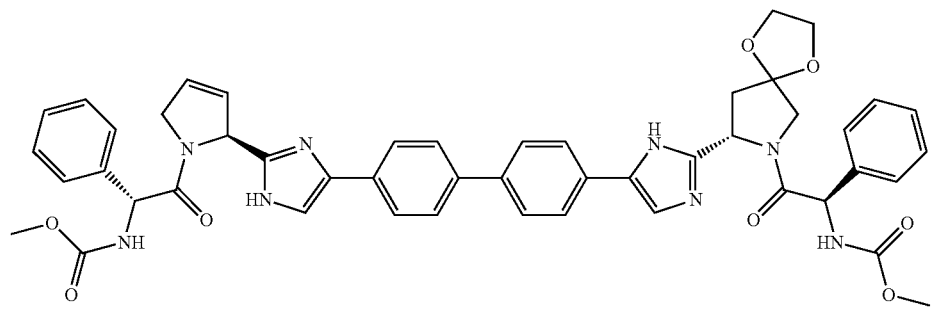
6dv
Ia-112
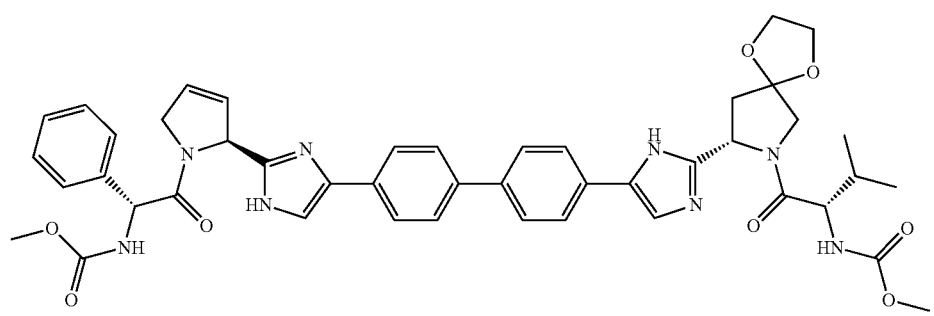
6dw
Ia-113
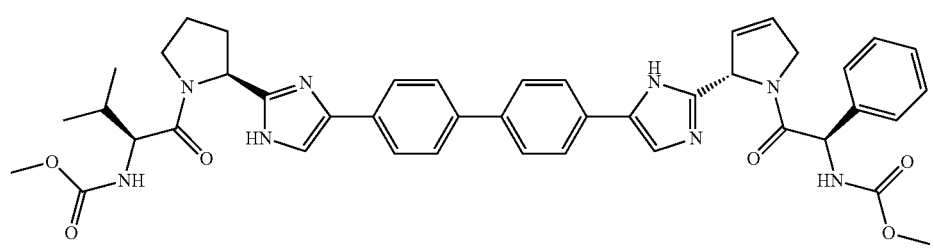
6dy -continued
Structural FIG. 3a: The Target Antiviral Compounds 6a-6ep
| No. | Prepared Compounds 6a-6ep of Formula Ia |
|---|---|
| Ia-114 | 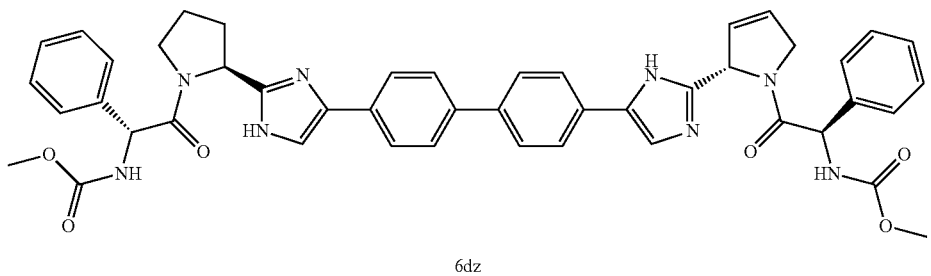<br>6dz |
| Ia-115 | 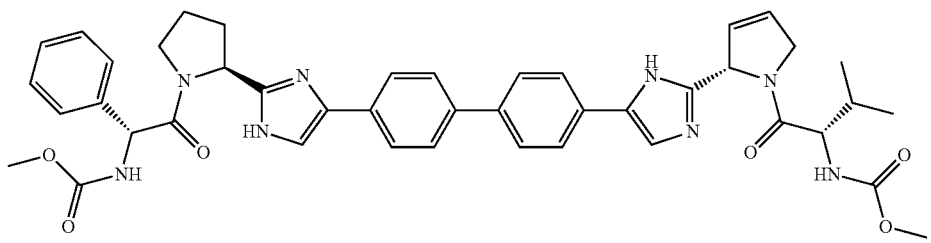<br>6ea |
| Ia-116 | 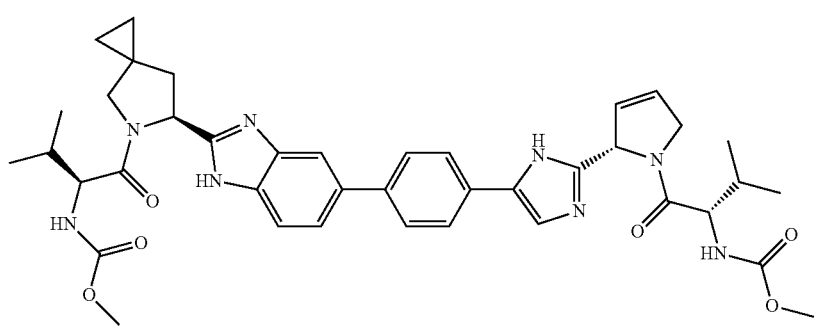<br>6eb |
| Ia-117 | 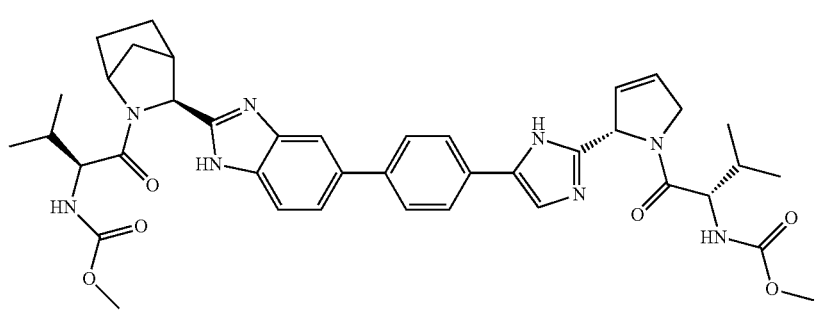<br>6ec |

US 9,334,291 B2
171                                                                                  172
-continued
Structural FIG. 3a: The Target Antiviral Compounds 6a-6ep
| No. | Prepared Compounds 6a-6ep of Formula Ia |
|---|---|
Ia-118
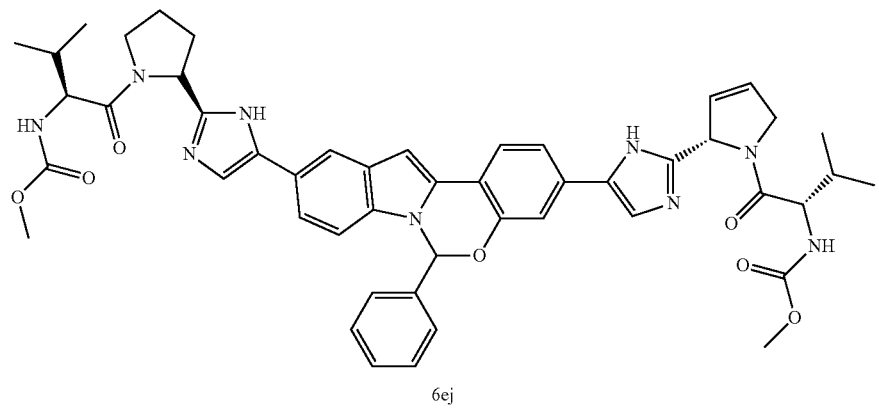
6ej
Ia-119
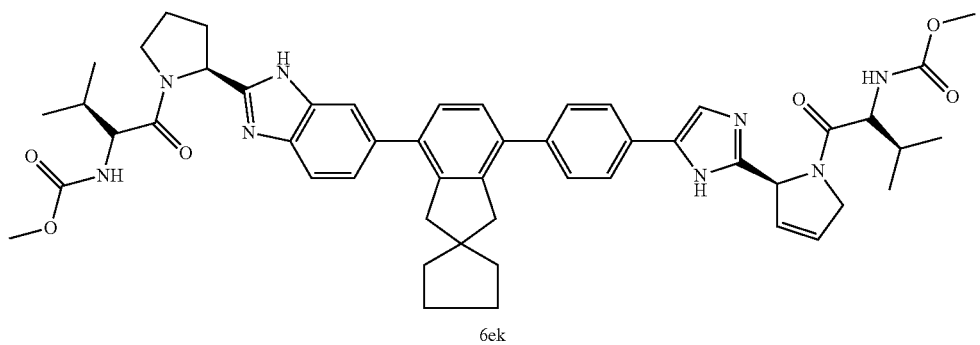
6ek
Ia-120
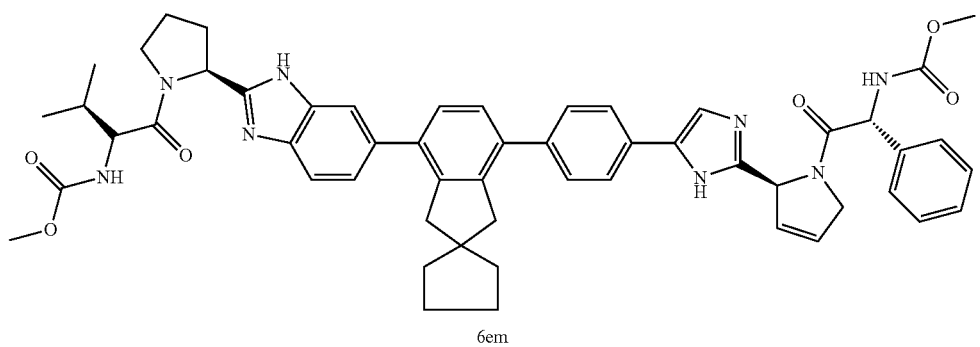
6em
Ia-121
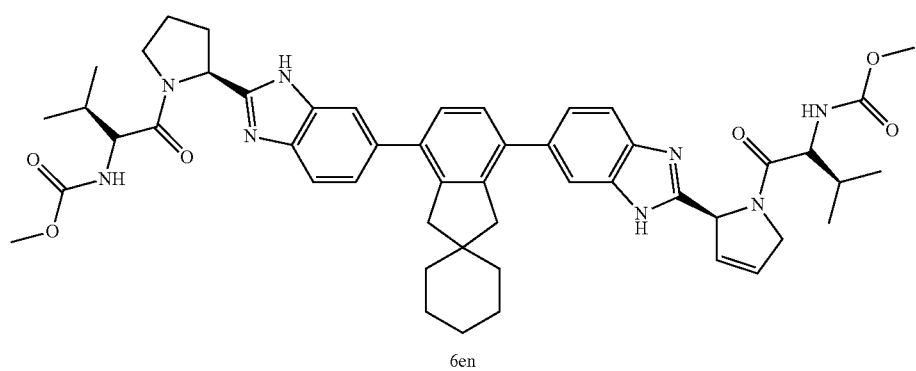
6en

| Structural FIG. 3a: The Target Antiviral Compounds 6a-6ep |
|---|
| No.        Prepared Compounds 6a-6ep of Formula Ia |
Ia-122
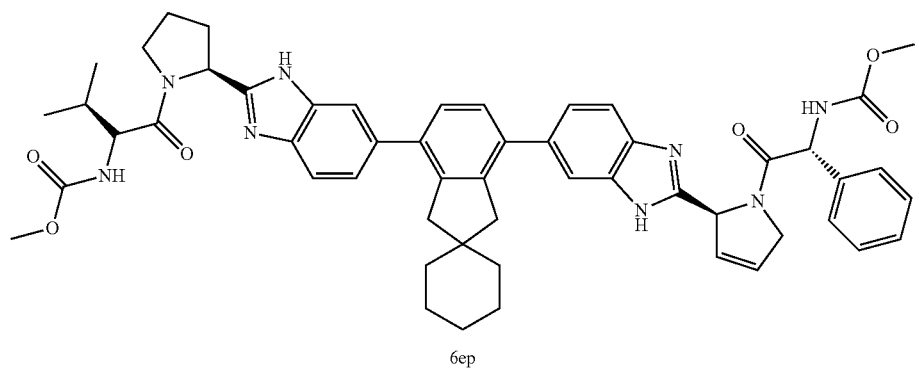
6ep
| Structural FIG. 3b: The Target Antiviral Compounds 6fa-6fy |
|---|
| No.        Prepared Compounds 6fa-6fy of Formula Ib |
Ib-1
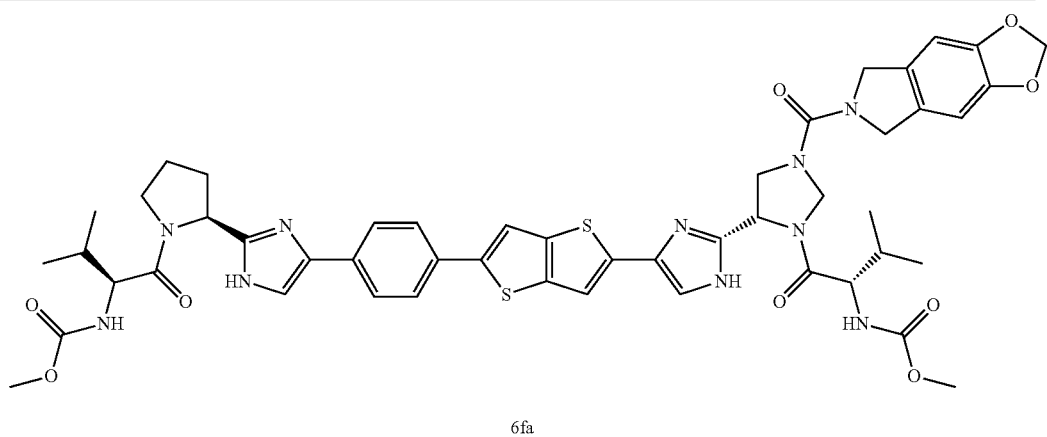
6fa
Ib-2
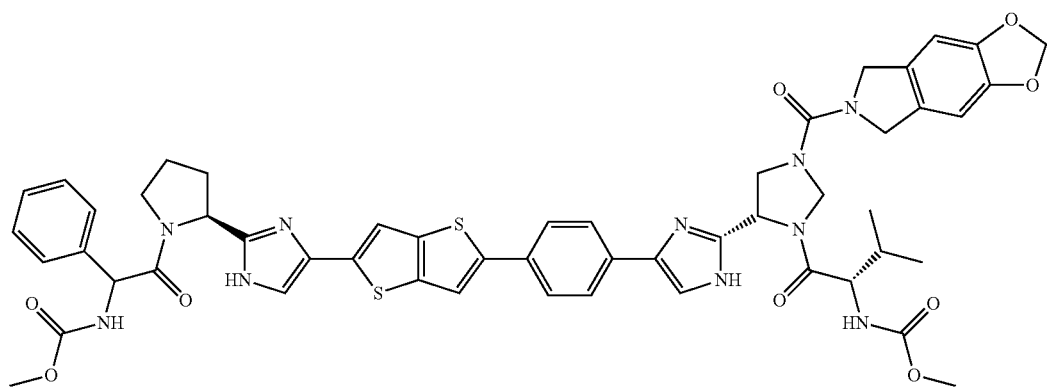
6fb

Structural FIG. 3b: The Target Antiviral Compounds 6fa-6fy
| No. | Prepared Compounds 6fa-6fy of Formula Ib |
|---|---|
| Ib-3 | 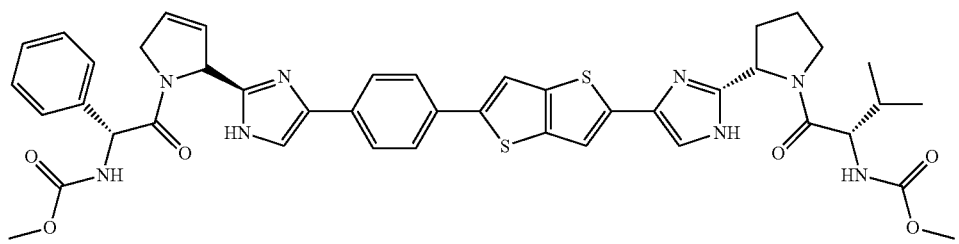<br>6fc |
| Ib-4 | 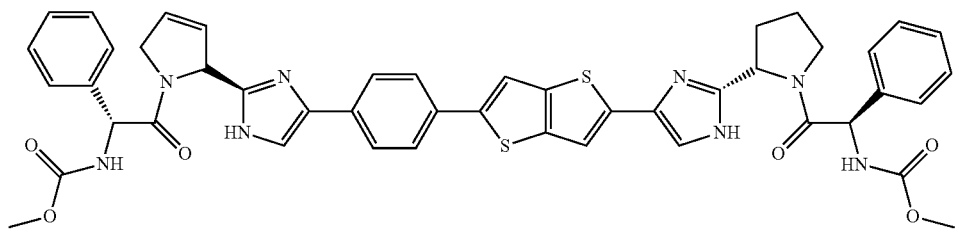<br>6fd |
| Ib-5 | 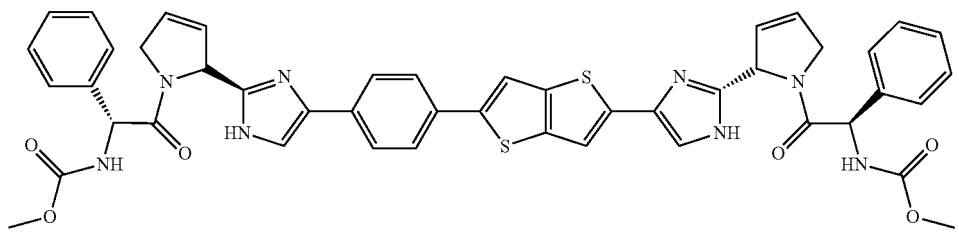<br>6fe |
| Ib-6 | 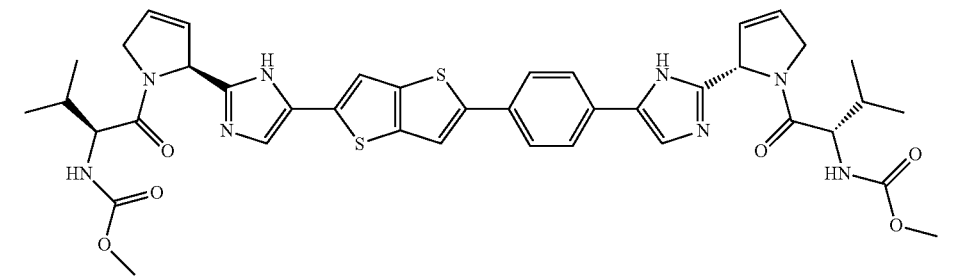 [SMILES: COC(=O)N[C@H](C(=O)N1CC=C[C@H]1c1ncc(-c2ccc(-c3cc4sc(-c5cnc([C@@H]6C=CCN6C(=O)[C@@H](NC(=O)OC)C(C)C)[nH]5)cc4s3)cc2)[nH]1)C(C)C]<br>6ff |
| Ib-7 | 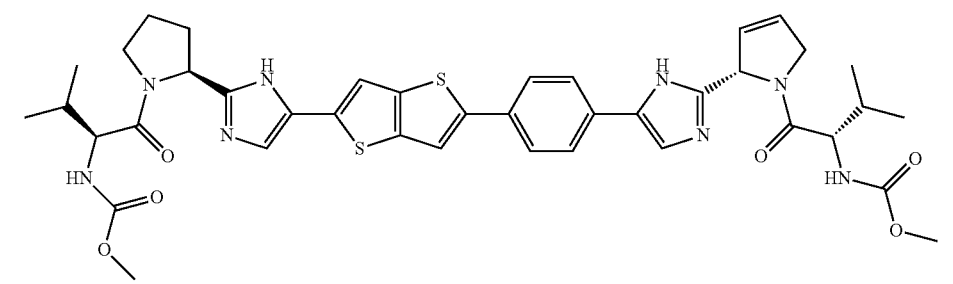 [SMILES: COC(=O)N[C@H](C(=O)N1CC=C[C@H]1c1ncc(-c2ccc(-c3cc4sc(-c5cnc([C@@H]6CCCN6C(=O)[C@@H](NC(=O)OC)C(C)C)[nH]5)cc4s3)cc2)[nH]1)C(C)C]<br>6fg |

Structural FIG. 3b: The Target Antiviral Compounds 6fa-6fy
| No. | Prepared Compounds 6fa-6fy of Formula Ib |
|---|---|
| Ib-8 | 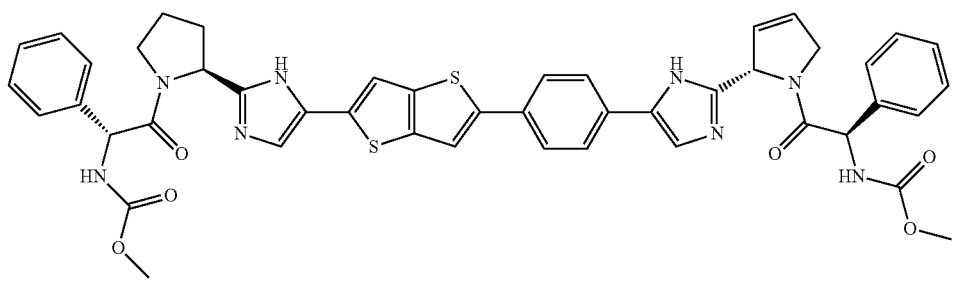 [SMILES: COC(=O)N[C@@H](C(=O)N1CC=C[C@H]1c1ncc(-c2ccc(-c3cc4sc(-c5cnc([C@@H]6CCCN6C(=O)[C@H](NC(=O)OC)c6ccccc6)[nH]5)cc4s3)cc2)[nH]1)c1ccccc1]<br>6fh |
| Ib-9 | 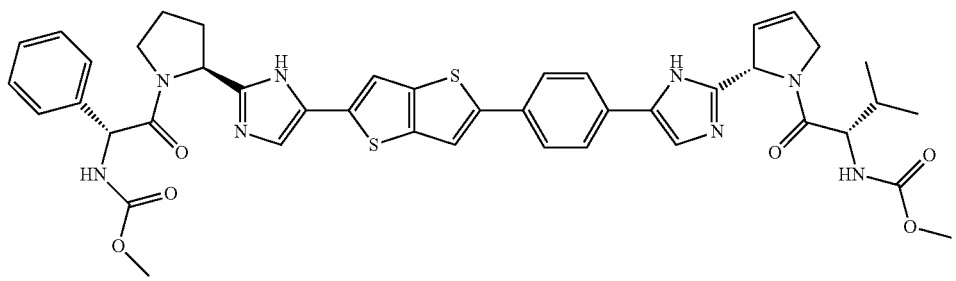 [SMILES: COC(=O)N[C@H](C(=O)N1CC=C[C@H]1c1ncc(-c2ccc(-c3cc4sc(-c5cnc([C@@H]6CCCN6C(=O)[C@H](NC(=O)OC)c6ccccc6)[nH]5)cc4s3)cc2)[nH]1)C(C)C]<br>6fi |
| Ib-10 | 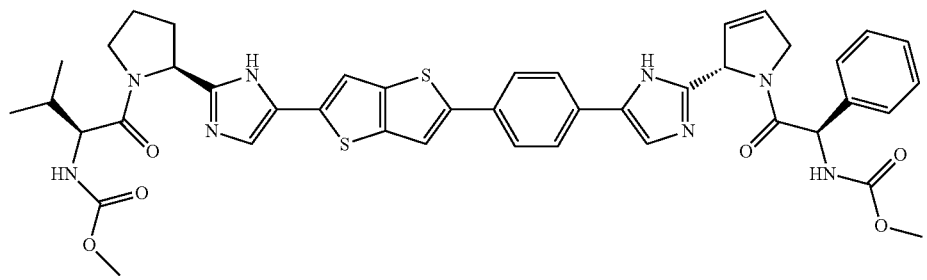<br>6fj |
| Ib-11 | 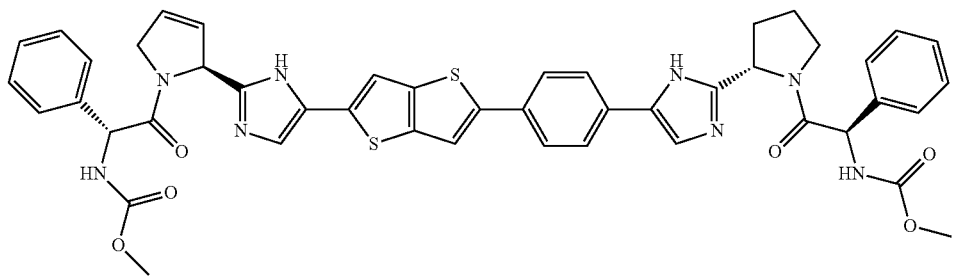 [SMILES: COC(=O)N[C@@H](C(=O)N1CC=C[C@H]1c1ncc(-c2cc3sc(-c4ccc(-c5cnc([C@@H]6CCCN6C(=O)[C@H](NC(=O)OC)c6ccccc6)[nH]5)cc4)cc3s2)[nH]1)c1ccccc1]<br>6fk |

| | Structural FIG. 3b: The Target Antiviral Compounds 6fa-6fy |
|---|---|
| No. | Prepared Compounds 6fa-6fy of Formula Ib |
| Ib-12 | 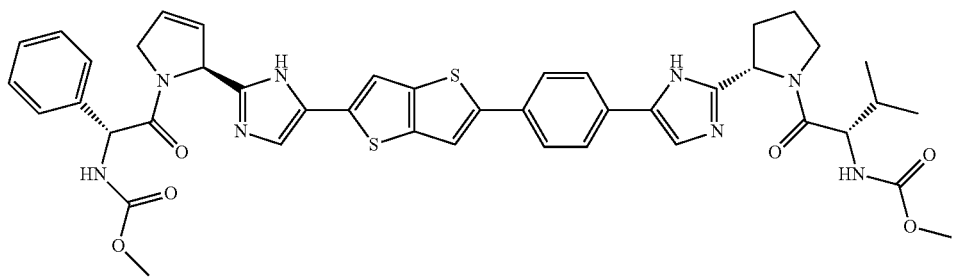 [SMILES: COC(=O)N[C@H](C(=O)N1CCC[C@H]1c1ncc(-c2ccc(-c3cc4sc(-c5cnc([C@@H]6C=CCN6C(=O)[C@H](NC(=O)OC)c6ccccc6)[nH]5)cc4s3)cc2)[nH]1)C(C)C]<br>6fm |
| Ib-13 | 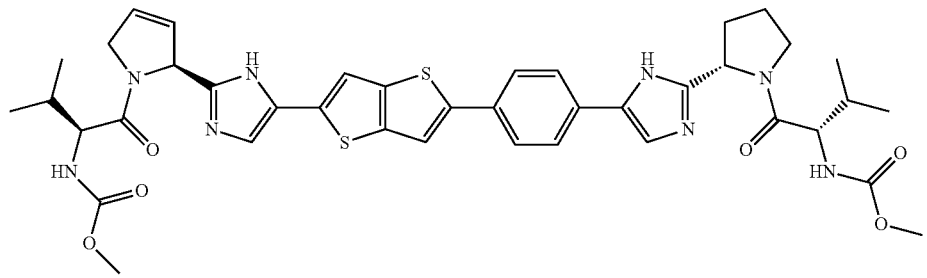 [SMILES: COC(=O)N[C@H](C(=O)N1CC=C[C@H]1c1ncc(-c2cc3sc(-c4ccc(-c5cnc([C@@H]6CCCN6C(=O)[C@@H](NC(=O)OC)C(C)C)[nH]5)cc4)cc3s2)[nH]1)C(C)C]<br>6fn |
| Ib-14 | 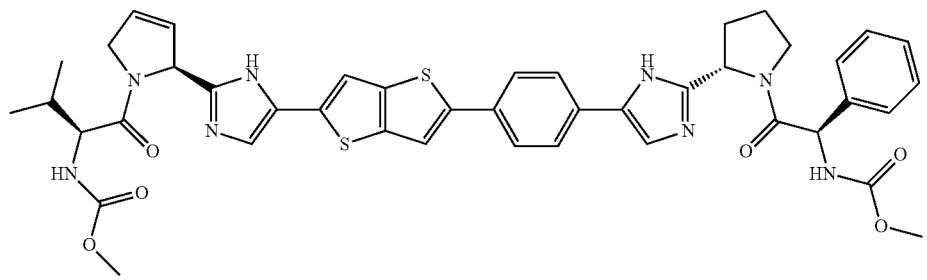 [SMILES: COC(=O)N[C@H](C(=O)N1CC=C[C@H]1c1ncc(-c2cc3sc(-c4ccc(-c5cnc([C@@H]6CCCN6C(=O)[C@H](NC(=O)OC)c6ccccc6)[nH]5)cc4)cc3s2)[nH]1)C(C)C]<br>6fp |
| Ib-15 | 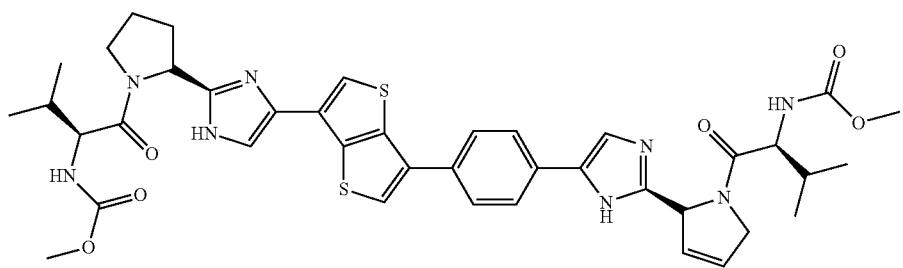<br>6fq |

Structural FIG. 3b: The Target Antiviral Compounds 6fa-6fy
| No. | Prepared Compounds 6fa-6fy of Formula Ib |
|---|---|
| Ib-16 | 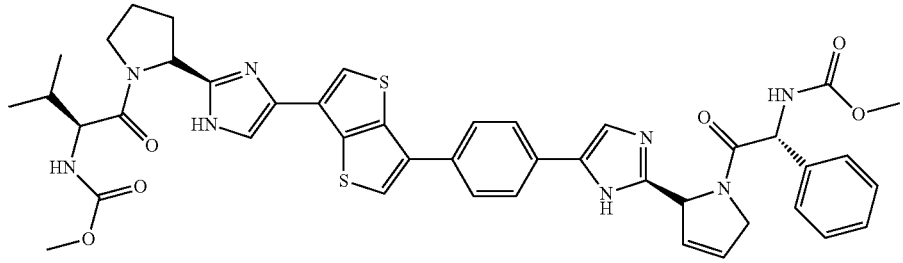<br>6fr |
| Ib-17 | 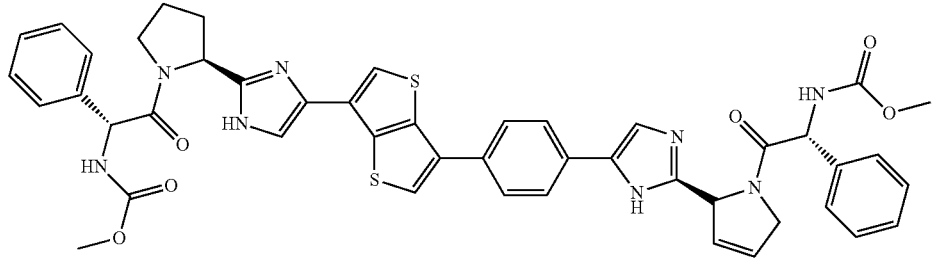<br>6fs |
| Ib-18 | 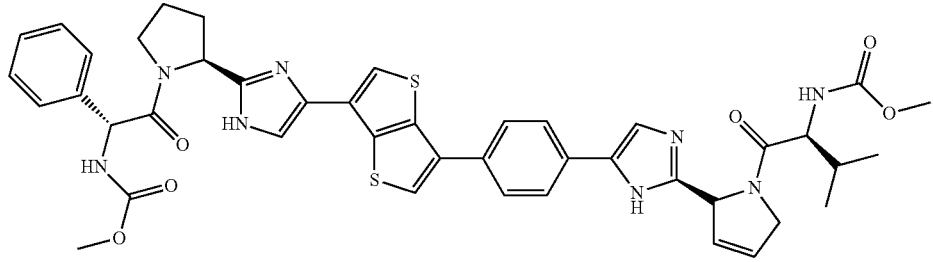<br>6ft |
| Ib-19 | 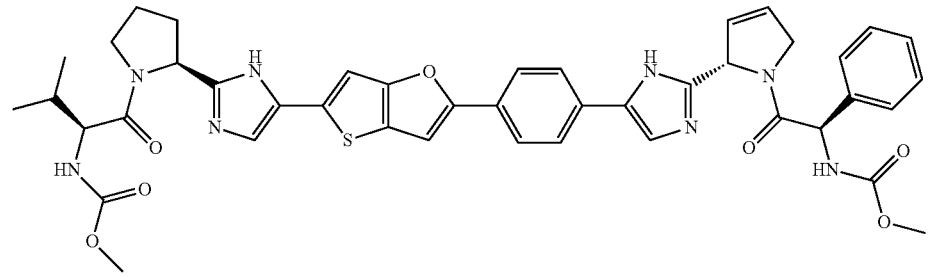<br>6fu |

| | Structural FIG. 3b: The Target Antiviral Compounds 6fa-6fy | |
|---|---|---|
| No. | Prepared Compounds 6fa-6fy of Formula Ib | |
| Ib-20 | 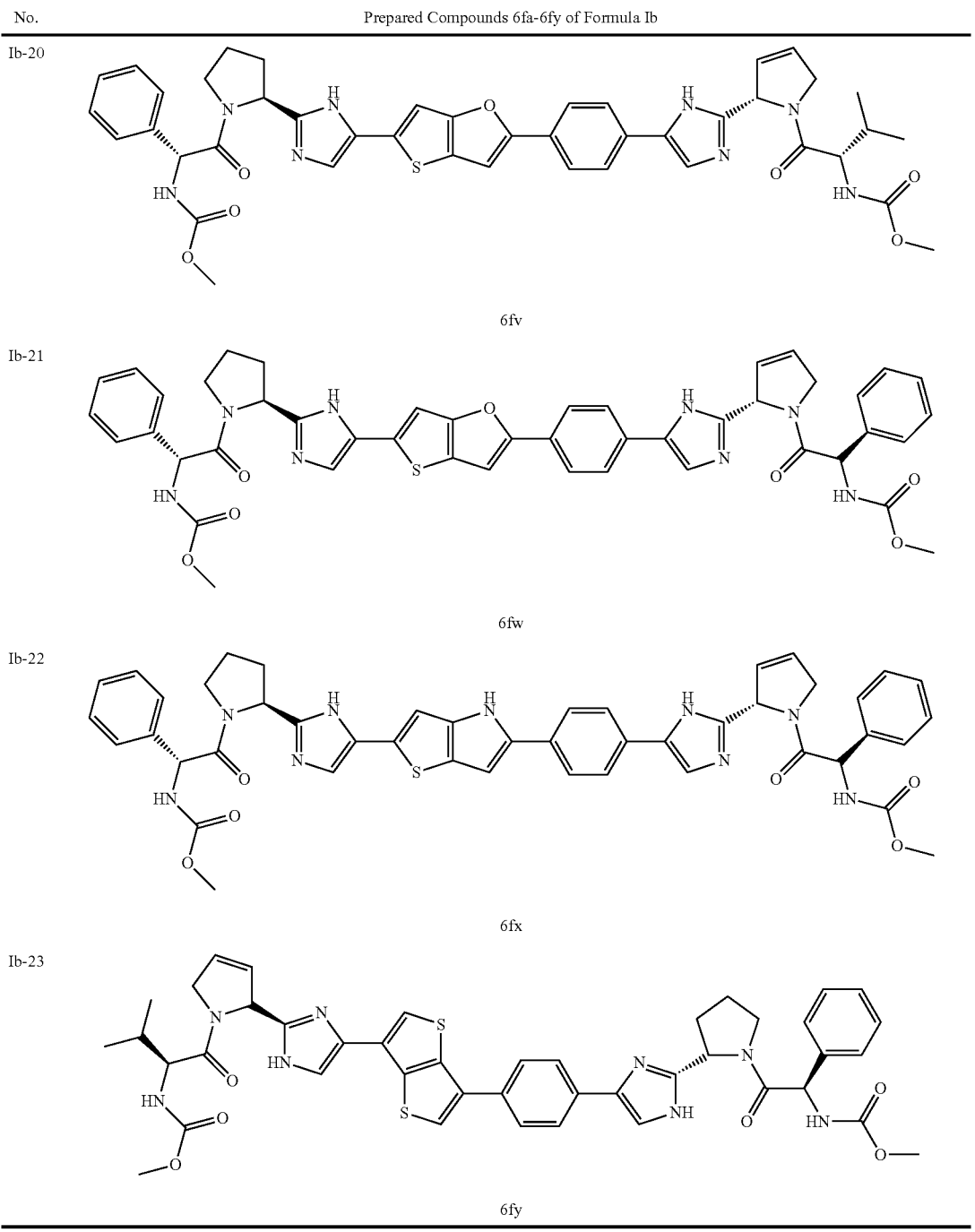 | |
| | 6fv | |
| Ib-21 | | |
| | 6fw | |
| Ib-22 | | |
| | 6fx | |
| Ib-23 | | |
| | 6fy | |

The present invention provides the application of compounds Ia-Ib described above, their stereoisomers, tautomers, esterification or amidation prodrugs and pharmaceutically acceptable salts for development of new drugs inhibiting HCV.

The present disclosure also provided the application of one or more class of compounds Ia-Ib mixtures described above, their stereoisomers, tautomers, esterification or amidation prodrugs and pharmaceutically acceptable salts for development of new drugs inhibiting HCV.

The antiviral compounds (Ia-Ib) mentioned herein may contain a non-aromatic double bond and one or more asymmetric centers. Thus, they can occur as racemates and racemic mixtures, single enantiomers, individual diastereomers, diastereomeric mixtures, tautomers, and cis- or trans-isomeric forms, and/or hydrates. All such isomeric forms are contemplated.

In this invention, some detailed embodiments were illustrated for the further explanation of the invention, but the effective range of the invention was not limited to the detailed embodiments described in present invention. The compounds in present invention could have bis-phenyl or fused bi-heteroaryl groups as well as one or one more heterocyclic chiral centers. Therefore, this kind of compounds could be racemic mixtures, pure diastereoisomers, tautomers. The prepared compounds 6a-6ep (Ia) and 6fa-6fy (Ib) in the invention are chiral heterocycles, in which the optical purity of natural and non-natural amino acids were determined by optical rotation or/and chiral column chromatography. The structural identification of each final compound (including 6a-6ep, 6fa-6fy, and the following reference compounds Ref-1 "BMS790052", Ref-2 "GS-5885", Ref-3 and Ref-4 "IDX719", etc) was each selected to compare the potency and toxicity with the prepared compounds 6a-6ep (Ia) and 6fa-6fy (Ib), respectively.

So far, there is no any effective animal model for scientists to evaluate the efficacy of new compounds by inhibiting the HCV NS5A replicon. The compounds described above in the present invention can be preliminarily screened by evaluating the $IC_{50}$ and/or $EC_{50}$ results for their bioactivity and potency in treating HCV infection by an in vitro assay as follows, then have some highly potent HCV inhibitors selected for further PK and toxicity studies before clinic trial. Other methods will also be apparent for scientists in pharmaceuticals.

Antiviral Assay for Inhibition Activity (EC50):

The study is completed by a new constructed double reporter genes replicon assay system, the capacity of viral replicon in infected cell is determined by detecting the reporter gene *Renilla* luciferase. The relationship of reporter genes, HCV RNA replicon and viral proteins is well linear. 8

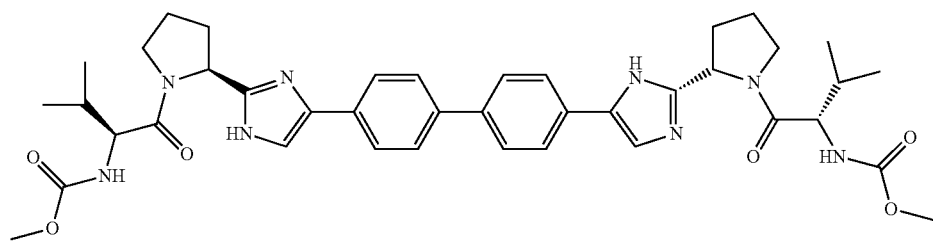

(BMS-790052)

Ref-1

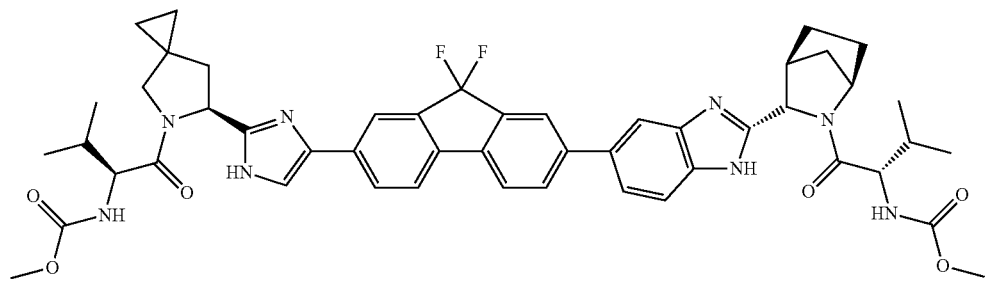

(GS-5885)

Ref-2

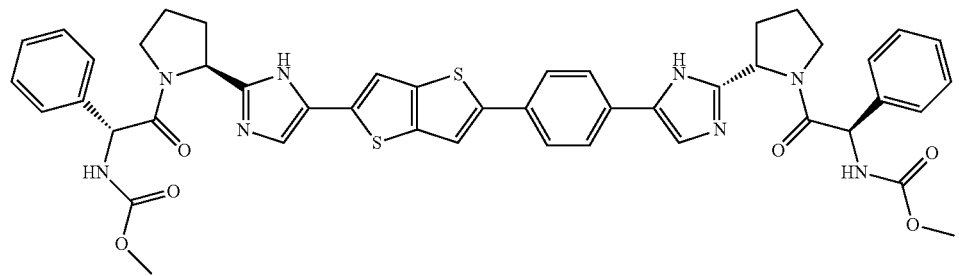

Ref-3

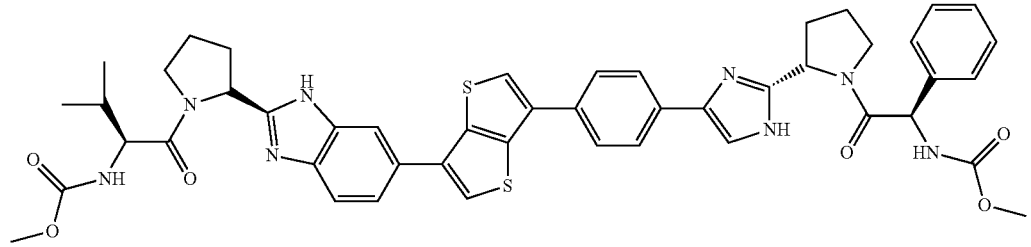

(IDX719)

Ref-4 gradient concentrations for 2-fold dilution, 3 wells, 3 times repetition and 1 or 2 control drugs are set to finally determine EC50 of compound.

Acute Toxicity Study (MTD):

Materials and Methods for MTD Study are as follows:

Test Group:

Animals were fed freely for adaptation more than 1 week. Healthy rats, body weight between 170-190 g, were divided randomly into 3 groups, 5 male and 5 female in each group. Healthy mice, body weight between 18-22 g, were divided randomly into 22 groups, 5 male and 5 female in each group.

MTD Results:

Dozens of highly potent compounds (e.g., 6ba, 6bx, 6by, 6bz, 6fc, 6fd, 6fg, 6fi, 6fm, 6fp, etc.) were tested by MTD, and there were no any test-article related death and no any adverse events observed for each tested compound.

Administration Method:

In rats, the compound weighing 21.00 g, serial number 1-3 respectively, adding 0.7% sodium carboxymethyl cellulose solution 30.00 g, high-speed homogenizer machine 15000 RPM, 10 min mixing, the rats were fed once, oral dose 10000 mg/kg. In mice, the compound weighing 2.00 g, serial number 4-25 respectively, adding 0.7% sodium carboxymethyl cellulose solution 8.00 g, high-speed homogenizer machine 10000 RPM, 10 min mixing, the mice were fed once, oral dose 10000 mg/kg.

Clinical Observation:

Animals were observed every hour after administration in the first day, and behavior observation daily continuous for a week. Dead animals were necropsied, gross pathology of the organs were observed and recorded.

Evaluation of Toxicity:

Toxicity was evaluated by animal mortality, signs of clinical behavior and others. Among all of synthesized compounds 6a-6ep and 6fa-6fy and another reference compound BMS790052, the results of HCV-NS5A inhibition test are listed in the following Table 1; where the scope of potent activity ($EC_{50}$): "A" refers to activity $EC_{50} \geq 50$ nM, "B" refers to activity $EC_{50}$ of 1.0-49.9 nM, and "C" refers to activity $EC_{50}$ of 0.001-0.999 nM.

TABLE 1

Activity of Novel Antiviral Compounds Used as Inhibiting HCV NS5A

| No. | Compound No. | $EC_{50}$ For GT-1a of NS5A Replicon |
|---|---|---|
| 1 | 6a | C |
| 2 | 6b | A |
| 3 | 6c | A |
| 4 | 6d | b |
| 5 | 6e | A |
| 6 | 6f | A |
| 7 | 6g | A |
| 8 | 6h | A |
| 9 | 6i | C |
| 10 | 6j | A |
| 11 | 6k | A |
| 12 | 6m | B |
| 13 | 6n | A |
| 14 | 6p | A |
| 15 | 6q | A |
| 16 | 6r | A |
| 17 | 6s | C |
| 18 | 6t | A |
| 19 | 6u | B |
| 20 | 6v | A |
| 21 | 6w | A |
| 22 | 6x | C |
| 23 | 6y | C |
| 24 | 6z | C |
| 25 | 6aa | C |
| 26 | 6ab | C |
| 27 | 6ac | C |
| 28 | 6ad | C |
| 29 | 6ae | C |
| 30 | 6af | C |
| 31 | 6ag | C |
| 32 | 6ah | C |
| 33 | 6ai | C |
| 34 | 6aj | C |
| 35 | 6ak | C |
| 36 | 6am | C |
| 37 | 6an | C |
| 38 | 6ap | C |
| 39 | 6aq | C |
| 40 | 6ar | C |
| 41 | 6as | C |
| 42 | 6at | C |
| 43 | 6au | C |
| 44 | 6av | C |
| 45 | 6aw | C |
| 46 | 6ax | C |
| 47 | 6ay | C |
| 48 | 6az | C |
| 49 | 6ba | C |
| 50 | 6bb | A |
| 51 | 6bc | B |
| 52 | 6bd | C |
| 53 | 6be | C |
| 54 | 6bf | A |
| 55 | 6bg | A |
| 56 | 6bh | C |
| 57 | 6bi | C |
| 58 | 6bj | C |
| 59 | 6bk | C |
| 60 | 6bm | C |
| 61 | 6bn | C |
| 62 | 6bp | C |
| 63 | 6bq | C |
| 64 | 6br | C |
| 65 | 6bs | A |
| 66 | 6bt | C |
| 67 | 6bu | C |
| 68 | 6bv | A |
| 69 | 6bw | A |
| 70 | 6bx | C |
| 71 | 6by | C |
| 72 | 6bz | C |
| 73 | 6ca | C |
| 74 | 6cb | A |
| 75 | 6cc | A |
| 76 | 6cd | A |
| 77 | 6ce | C |
| 78 | 6cf | C |
| 79 | 6cg | C |
| 80 | 6ch | C |
| 81 | 6ci | C |
| 82 | 6cj | C |
| 83 | 6ck | C |
| 84 | 6cm | C |
| 85 | 6cq | B |
| 86 | 6cu | C |
| 87 | 6cv | C |
| 88 | 6cw | C |
| 89 | 6cx | C |
| 90 | 6cy | C |
| 91 | 6cz | C |
| 92 | 6da | C |
| 93 | 6db | C |
| 94 | 6dc | C |
| 95 | 6dd | C |
| 96 | 6de | C |
| 97 | 6df | C |
| 98 | 6dg | C |

TABLE 1-continued

Activity of Novel Antiviral Compounds Used as Inhibiting HCV NS5A

| No. | Compound No. | $EC_{50}$ For GT-1a of NS5A Replicon |
|---|---|---|
| 99 | 6dh | C |
| 100 | 6di | C |
| 101 | 6dj | B |
| 102 | 6dk | C |
| 103 | 6dm | C |
| 104 | 6dn | C |
| 105 | 6dp | C |
| 106 | 6dq | C |
| 107 | 6dr | C |
| 108 | 6ds | C |
| 109 | 6dt | C |
| 110 | 6du | C |
| 111 | 6dv | C |
| 112 | 6dw | C |
| 113 | 6dx | C |
| 114 | 6dy | C |
| 115 | 6dz | C |
| 116 | 6ea | C |
| 117 | 6eb | C |
| 118 | 6ec | C |
| 119 | 6ej | C |
| 120 | 6ek | B |
| 121 | 6em | B |
| 122 | 6en | B |
| 123 | 6ep | B |
| 124 | 6fa | C |
| 125 | 6fb | C |
| 126 | 6fc | C |
| 127 | 6fd | C |
| 128 | 6fe | C |
| 129 | 6ff | C |
| 130 | 6fg | C |
| 131 | 6fh | C |
| 132 | 6fi | C |
| 133 | 6fj | C |
| 134 | 6fk | C |
| 135 | 6fm | C |
| 136 | 6fn | C |
| 137 | 6fp | C |
| 138 | 6fq | C |
| 139 | 6fr | C |
| 140 | 6fs | C |
| 141 | 6ft | C |
| 142 | 6fu | C |
| 143 | 6fv | C |
| 144 | 6fw | C |
| 145 | 6fx | C |
| 146 | 6fy | C |
| 147 | Ref-1 | C |
| 148 | Ref-2 | C |
| 149 | Ref-3 | C |
| 150 | Ref-4 | C |

TABLE 2

Antiviral Activity ($EC_{50}$) of Several Selected Anitviral Compounds Used as HCV NS5A Inhibitors with Excellent Potency and Safety

| Compound ID | $EC_{50}$ for Replicon (pM) of GT-1a to GT-6a | | | | | | |
|---|---|---|---|---|---|---|---|
| | 1a | 1b | 2a | 3a | 4a | 5a | 6a |
| 6ba | 39 | 12 | 16 | 173 | 10 | 23 | 221 |
| 6dy | 11 | 14 | 6 | 15 | 8 | 23 | 24 |
| 6fd | 21 | 11 | 5 | 15 | 8 | 23 | 111 |
| 6fi | 20 | 5 | 7 | 26 | 5 | 13 | 55 |
| 6fm | 9 | 13 | 8 | 24 | 12 | 29 | 23 |
| Ref-1 | 52 | 21 | 29 | 218 | 11 | 36 | 118 |
| Ref-2 | 88 | N/A | N/A | N/A | N/A | N/A | N/A |
| Ref-3 | 51 | N/A | N/A | N/A | N/A | N/A | N/A |

Note:
N/A: Not Available in Table 2.

The activity screening results in Tables 1 and 2 show that: (1) many prepared compounds have excellent HCV inhibition activity (picomolar potency), (2) Several of fused-heteroaryl core based compounds 6fa-6fy (Ib) have picomolar pan-genotypic activity for all GT-1a to GT-6a, better than the referred compound BMS790052.

Overall, most of new prepared poly-aryl and fused-heteroaryl compounds in this invention have been evaluated with high potency to inhibit HCV. Moreover, the present invention explores the insight relationship between the structures of new antiviral compounds and potency of HCV NS5A inhibition, which provides valuable clue to develop an effective HCV inhibitor among the discovered novel compounds Ia-Ib. In summary, based on the detail experimental results in Table 2, there were several "Me-Better" and a "Best-in-Class" antiviral compounds discovered with excellent "potency, safety, PK and metabolic stability" in each class of novel optimized compounds Ia and Ib by incorporating new

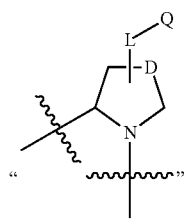

and/or

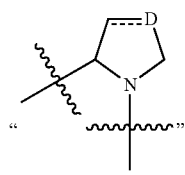

functional groups, especially by incorporating

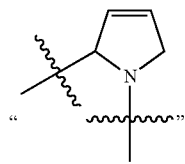

in Ia-Ib (wherein D=CH) instead of

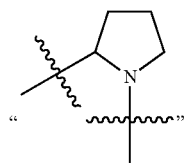

group in comparison with other compounds in previously reported papers and patents, which appears very competitive and/or much better than other reference compounds (e.g., compared with "Ref-1 to Ref-4", respectively) and provides several highly valuable lead compounds for further development of a highly competitive HCV NS5A inhibitor later.

In the following section were the detailed examples of the synthesis and biological activities of different kinds of compounds and their intermediates.

Instruments and Materials Related to Examples are as Follows

Infrared (IR) spectra were recorded on Thermo Nicolet company Fourier Transform AVATAR™ 360 E.S.P™ spectrophotometer (Unit: cm$^{-1}$).

$^1$H-NMR spectra were recorded on a Varian Mercury Plus 400 or 500 (400 or 500 MHz) spectrometer. Chemical shifts are reported in ppm from tetramethylsilane (TMS) with the solvent resonance as the internal standard (CHCl$_3$: 7.26 ppm). Data are reported as follows: chemical shift, multiplicity (s: single, d: doublet, t: triplet, q: quartet, br: broad, m: multiplet) and coupling constants.

Unless otherwise noted, mass spectra were obtained at Finnigan LCQ Advantage of liquid chromatography-mass spectrometer analysis, all reactions were conducted in oven and flame-dried glassware with vacuum-line techniques under an inert atmosphere of dry Ar. Solid metal organic compounds were stored in Ar in a drying box.

THF was distilled from sodium metal and benzophenone. DCM, pentane and hexane were distilled form calcium hydride. Special raw material and intermediate in the invention were ordered by contract synthesis from Zannan SciTech Co., Let in China, others reagents were purchased from Shanghai reagent company, Aldrich, Acros etc. As intermediates or products during the synthesis is not required for the reaction and other tests the next step, the synthesis is repeated until a sufficient number of times. The invention of the prepared compounds of HCV protease (HCV NS5A) inhibitory activity test was performed by CRO service units such as WuXi AppTec etc.

Abbreviations of chemical materials, reagnets, and solvents related to the present invention are listed as follows:
AIBN: azobisisobutyronitrile
Boc: tert-butoxycarbonyl
(Boc)$_2$O: di-tert-butyl carbonate
CDI: N,N'-carbonyldiimidazole imidazole
DBU: 1,8-Diazabicyclo[5.4.0]undec-7-ene
HATU: 2-(7-benzotriazole azo)-N,N,N',N-tetramethyl urea phosphate hexafluoride
NBS: N-bromosuccinimide
DMAP: 4-dimethylaminopyridine
DIEA: N, N-diisopropyl ethylamine
Pd/C: Palladium carbon
HMTA: hexamethylene tetramine
HOAc: acetic acid
TFA: trifluoroacetic acid
TsOH: p-toluenesulfonate
ACN: acetonitrile
DCM: dichloromethane
DMF: N, N-dimethylformamide
DMSO: dimethyl sulfoxide
Et$_2$O: diethyl ether
EA: ethyl acetate
PE: petroleum ether
THF: tetrahydrofuran
TBME: tert-butyl methyl ether Example 1

Synthesis of Compound 6a

The starting materials SM-3a (0.10 g, 0.2 mmol) and SM-4i (0.15 g, 0.2 mmol, 1.0 eq.) were dissolved in 5 mL DMF in a 25 mL 3-neck flask, then the potassium carbonate (0.6 mmol, 3.0 eq.) and water (3 mL) were added with stirring. Under argon protection, the reaction mixture was heated to 100° C., then tetrakis(triphenylphosphine) palladium (0.01 g) was added in one portion. The mixture was stirred at 100° C. until HPLC showed that the reaction was completed. The reaction mixture was filtered, then water was added and extracted with ethyl acetate, combined the organic phase, washed with brine, purified by column chromatography to obtain a yellow solid 6a (61 mg, yield: 31%).

$^1$H NMR for the product 6a (300 MHz, CDCl$_3$): δ 7.49-7.84 (m, 8H), 7.22-7.24 (m, 2H), 6.65-6.78 (m, 2H), 5.98-5.99 (m, 2H), 5.51-5.55 (m, 2H), 5.43-5.51 (m, 2H), 5.27-5.31 (m, 1H), 4.60-4.72 (m, 4H), 4.12-4.38 (m, 3H), 3.85-3.91 (m, 1H), 3.64-3.74 (m, 4H), 3.49 (s, 3H), 2.54-2.61 (m, 1H), 2.36-2.42 (m, 1H), 1.91-2.28 (m, 5H), 0.85-0.91 (m, 12H). Confirmed by MS, ESI-MS [(M+H)$^+$] for 6a: m/z calculated 944.4. founded 944.5.

Example 2

Synthesis of Compound 6b

Compound 6b was prepared by the same coupling reaction procedure as in example 1. By using the reagent SM-3c (0.24 mmol) and SM-4j (0.24 mmol) instead of SM-3a and SM-4i, a yellow solid product 6b (62 mg, yield: 25%) was obtained.

$^1$H NMR for the product 6b (500 MHz, CDCl$_3$): δ 7.48-7.84 (m, 8H), 6.66-6.77 (m, 2H), 5.98 (m, 2H), 5.14-5.57 (m, 5H), 4.60-4.72 (m, 4H), 4.13-4.32 (m, 3H), 3.84 (m, 2H), 3.71 (m, 1H), 3.37 (m, 1H), 2.58 (m, 1H), 1.93-2.36 (m, 8H), 1.25-1.45 (m, 20H), 0.87-1.13 (m, 12H). Confirmed by MS, ESI-MS [(M+H)$^+$] for 6b: m/z calculated 1028.5. founded 1028.6.

Example 3

Synthesis of Compound 6c

Compound 6c was prepared by the same coupling reaction procedure as in example 1. By using the reagent SM-3e (0.24 mmol) and SM-4k (0.24 mmol) instead of SM-3a and SM-4i, a yellow solid 6c (78 mg, yield: 31%) was obtained.

Confirmed by MS, ESI-MS [(M+H)$^+$] for 6c: m/z calculated 1056.6. founded 1056.7.

Example 4

Synthesis of Compound 6d

Compound 6d was prepared by the same coupling reaction procedure as in example 1. By using the reagent SM-3a (0.29 mmol) and SM-4j (0.29 mmol) instead of SM-3a and SM-4i, a yellow solid 6d (160 mg, yield: 57%) was obtained.

$^1$H NMR for the product 6d (300 MHz, CDCl$_3$): δ 7.31-7.79 (m, 8H), 7.22-7.27 (m, 2H), 6.66-6.78 (m, 2H), 5.98-5.99 (m, 2H), 5.28-5.56 (m, 4H), 4.62-4.69 (m, 4H), 4.20-4.59 (m, 3H), 3.88-3.97 (m, 1H), 3.62-3.75 (m, 4H), 1.78-2.01 (m, 8H), 1.36-1.46 (m, 9H), 0.89-0.94 (m, 12H). Confirmed by MS, ESI-MS [(M+H)$^+$] for 6d: m/z calculated 986.5. founded 986.6.

Example 5

Synthesis of Compound 6e

Compound 6e was prepared by the same coupling reaction procedure as in example 1. By using the reagent SM-3i (0.14 mmol) and SM-4j (0.14 mmol) instead of SM-3a and SM-4i, a yellow solid 6e (48 mg, yield: 30%) was obtained.

$^1$H NMR for the product 6e (500 MHz, CDCl$_3$): δ 7.82 (brs, 2H), 7.50-7.61 (m, 6H), 6.66-6.78 (m, 4H), 5.98 (s, 2H), 5.97 (s, 2H), 5.55 (brs, 2H), 5.39-5.46 (m, 4H), 4.60-4.74 (m, 8H), 4.21-4.25 (m, 4H), 3.84-3.85 (m, 2H), 3.49 (s, 6H), 2.57 (m, 2H), 1.93-1.94 (m, 2H), 1.73 (m, 4H), 1.32 (m, 1H), 1.12 (m, 1H), 0.82-0.88 (m, 12H). Confirmed by MS, ESI-MS [(M+H)$^+$] for 6e: m/z calculated 1149.5. founded 1149.6.

Example 6

Synthesis of Compound 6f

Compound 6f was prepared by the same coupling reaction procedure as in example 1. By using the reagent SM-3j (0.2 mmol) and SM-4j (0.2 mmol) instead of SM-3a and SM-4i, a yellow solid 6f (110 mg, yield: 42%) was obtained $^1$H NMR for the product 6f (500 MHz, CDCl$_3$): δ 7.62-7.83 (m, 8H), 6.68-6.78 (m, 4H), 5.96-5.98 (m, 4H), 5.55 (s, 2H), 5.47 (s, 2H), 5.15 (m, 2H), 4.61-4.72 (m, 8H), 4.12-4.22 (m, 4H), 3.85 (m, 2H), 3.49 (s, 6H), 2.58 (m, 2H), 1.74-1.92 (m, 4H), 1.25-1.35 (m, 20H), 1.12 (m, 2H), 0.84 (s, 12H). Confirmed by MS, ESI-MS [(M+H)$^+$] for 6f: m/z calculated 1233.6. founded 1233.6.

Example 7

Synthesis of Compound 6g

Compound 6g was prepared by the same coupling reaction procedure as in example 1. By using the reagent SM-3m (0.1 mmol) and SM-4m (0.1 mmol) instead of SM-3a and SM-4i, a yellow solid 6g (18 mg, yield: 17%) was obtained.

$^1$H NMR for the product 6g (400 MHz, CD$_3$OD): δ 7.38-7.34 (m, 1H), 7.00-6.96 (m, 2H), 6.11-6.03 (m, 1H), 5.43-5.39 (m, 1H), 5.29-5.27 (m, 1H), 4.65-4.64 (m, 2H), 4.62 (s, 2H), 4.57 (s, 2H). Confirmed by MS, ESI-MS [(M+H)$^+$] for 6g: m/z calculated 1257.6. founded 1257.6.

Example 8

Synthesis of Compound 6h

Compound 6h was prepared by the same coupling reaction procedure as in example 1. By using the reagent SM-3g (0.1 mmol) and SM-4m (0.1 mmol) instead of SM-3a and SM-4i, a yellow solid 6h (21 mg, yield: 20%) was obtained.

$^1$H NMR for the product 6h (400 MHz, CD$_3$OD): δ 7.38-7.34 (m, 1H), 7.00-6.96 (m, 2H), 6.11-6.03 (m, 1H), 5.43-5.39 (m, 1H), 5.29-5.27 (m, 1H), 4.65-4.64 (m, 2H), 4.62 (s, 2H), 4.57 (s, 2H). Confirmed by MS, ESI-MS [(M+H)$^+$] for 6h: m/z calculated 1052.5. founded 1052.6.

Example 9

Synthesis of Compound 6i

Compound 6i was prepared by the same coupling reaction procedure as in example 1. By using the reagent SM-3a (0.2 mmol) and SM-4n (0.2 mmol) instead of SM-3a and SM-4i, a yellow solid 6i (105 mg, yield: 55%) was obtained.

$^1$H NMR for the product 6i (500 MHz, CDCl$_3$): δ 7.62-7.83 (m, 8H), 6.72 (s, 1H), 6.66 (s, 1H), 5.97 (s, 2H), 5.44-5.54 (m, 4H), 5.28 (m, 1H), 4.57-4.69 (m, 4H), 4.34 (m, 1H), 4.25 (m, 1H), 4.17 (m, 1H), 3.83-3.86 (m, 2H), 3.74-3.76 (m, 1H), 3.70 (s, 3H), 3.65 (m, 1H), 3.50 (s, 3H), 2.57 (m, 1H), 2.36 (m, 1H), 2.20 (m, 1H), 2.09-2.10 (m, 1H), 1.79-1.98 (m, 5H), 1.04-1.16 (m, 2H), 0.84-0.89 (m, 12H). Confirmed by MS, ESI-MS [(M+H)$^+$] for 6i: m/z calculated 944.4. founded 944.5.

Example 10

Synthesis of Compound 6j

Compound 6j was prepared by the same coupling reaction procedure as in example 1. By using the reagent SM-3c (0.2 mmol) and SM-4p (0.2 mmol) instead of SM-3a and SM-4i, a yellow solid 6j (45 mg, yield: 20%) was obtained.

$^1$H NMR for the product 6j (500 MHz, CDCl$_3$): δ 7.83 (m, 2H), 7.51-7.64 (m, 6H), 6.72 (s, 1H), 6.64 (s, 1H), 5.97 (m, 2H), 5.14-5.56 (m, 5H), 4.55-4.67 (m, 4H), 4.13-4.31 (m, 3H), 3.82 (m, 2H), 3.48-3.60 (m, 2H), 2.57 (m, 1H), 2.32 (m, 1H), 1.72-2.07 (m, 7H), 1.08-1.32 (m, 20H), 0.84-0.90 (m, 12H). Confirmed by MS, ESI-MS [(M+H)$^+$] for 6j: m/z calculated 1028.5. founded 1028.6.

Example 11

Synthesis of Compound 6k

Compound 6k was prepared by the same coupling reaction procedure as in example 1. By using the reagent SM-3e (0.2 mmol) and SM-4q (0.2 mmol) instead of SM-3a and SM-4i, a yellow solid 6k (45 mg, yield: 20%) was obtained.

$^1$H NMR for the product 6k (500 MHz, CDCl$_3$): δ 7.62-7.81 (m, 8H), 6.71 (s, 1H), 6.62 (s, 1H), 5.97 (s, 2H), 5.16-5.50 (m, 5H), 4.58-4.66 (m, 4H), 4.28-4.35 (m, 2H), 4.21-4.23 (d, J=9.5 Hz, 1H), 3.90 (m, 1H), 3.78 (m, 1H), 3.66 (m, 1H), 3.42 (m, 1H), 2.58 (m, 1H), 2.34 (m, 1H), 2.01-2.09 (m, 2H), 1.49-1.64 (m, 5H), 1.32 (s, 9H), 1.26 (s, 9H), 0.82-0.93 (m, 18H). Confirmed by MS, ESI-MS [(M+H)$^+$] for 6k: m/z calculated 1056.6. founded 1056.7.

Example 12

Synthesis of Compound 6m

Compound 6m was prepared by the same coupling reaction procedure as in example 1. By using the reagent SM-3a (0.2 mmol) and SM-4p (0.2 mmol) instead of SM-3a and SM-4i, a yellow solid 6m (155 mg, yield: 79%) was obtained.

$^1$H NMR for the product 6m (500 MHz, CDCl$_3$): δ 7.58-7.82 (m, 8H), 6.71 (s, 1H), 6.64 (s, 1H), 5.97 (s, 2H), 5.46-5.55 (m, 3H), 5.18-5.28 (m, 2H), 4.56-4.66 (m, 4H), 4.35 (m, 1H), 4.15-4.24 (m, 2H), 3.84-3.89 (m, 2H), 3.67-3.75 (m, 5H), 2.58 (m, 1H), 2.37 (m, 1H), 2.22 (m, 1H), 2.10 (m, 1H), 1.91-2.05 (m, 3H), 1.36 (s, 9H), 1.07-1.13 (m, 4H), 0.84-0.90 (m, 12H). Confirmed by MS, ESI-MS [(M+H)$^+$] for 6m: m/z calculated 986.5. founded 986.6.

Example 13

Synthesis of Compound 6n

Compound 6n was prepared by the same coupling reaction procedure as in example 1. By using the reagent SM-3n (0.2 mmol) and SM-4n (0.2 mmol) instead of SM-3a and SM-4i, a yellow solid 6n (54 mg, yield: 19%) was obtained.

$^1$H NMR for the product 6n (500 MHz, CDCl$_3$): δ 7.83 (brs, 2H), 7.50-7.63 (m, 6H), 6.72 (s, 2H), 6.66 (s, 2H), 5.97 (s, 4H), 5.36-5.54 (m, 6H), 4.57-4.68 (m, 8H), 4.24-4.27 (m, 2H), 4.16-4.19 (m, 2H), 3.84-3.85 (m, 2H), 3.51 (s, 6H), 2.55-2.59 (m, 2H), 1.92-1.94 (m, 2H), 1.66-1.68 (m, 4H), 1.32 (m, 1H), 1.12 (m, 1H), 0.84-0.88 (m, 12H). Confirmed by MS, ESI-MS [(M+H)$^+$] for 6n: m/z calculated 1149.6. founded 1149.6.

Example 14

Synthesis of Compound 6p

Compound 6p was prepared by the same coupling reaction procedure as in example 1. By using the reagent SM-3p (0.2 mmol) and SM-4p (0.2 mmol) instead of SM-3a and SM-4i, a yellow solid 6p (124 mg, yield: 50%) was obtained.
$^1$H NMR for the product 6p (500 MHz, CDCl$_3$): δ 7.83 (brs, 2H), 7.51-7.63 (m, 6H), 6.71 (s, 2H), 6.64 (s, 2H), 5.97 (s, 4H), 5.48-5.54 (m, 4H), 5.17 (m, 2H), 4.55-4.66 (m, 8H), 4.14-4.22 (m, 4H), 3.59-3.84 (m, 2H), 2.58 (m, 2H), 1.69-2.05 (m, 6H), 1.26-1.36 (m, 20H), 0.84-0.90 (m, 12H). Confirmed by MS, ESI-MS [(M+H)$^+$] for 6p: m/z calculated 1233.6. founded 1233.6.

Example 15

Synthesis of Compound 6q

Compound 6q was prepared by the same coupling reaction procedure as in example 1. By using the reagent SM-3r (0.2 mmol) and SM-4r (0.2 mmol) instead of SM-3a and SM-4i, a yellow solid 6q (46 mg, yield: 21%) was obtained.
$^1$H NMR for the product 6q (500 MHz, CDCl$_3$): δ 7.83-7.84 (m, 2H), 7.52-7.63 (m, 6H), 6.72 (s, 2H), 6.65 (s, 2H), 5.97 (s, 4H), 5.43-5.53 (m, 4H), 5.21 (m, 2H), 4.57-4.77 (m, 8H), 4.29 (m, 4H), 3.80-3.82 (m, 2H), 3.49 (m, 2H), 2.57 (m, 2H), 1.88-1.91 (m, 2H), 1.59-1.70 (m, 16H), 1.12-1.33 (m, 6H), 0.81-0.85 (m, 12H). Confirmed by MS, ESI-MS [(M+H)$^+$] for 6q: m/z calculated 1257.6. founded 1257.7.

Example 16

Synthesis of Compound 6r

Compound 6r was prepared by the same coupling reaction procedure as in example 1. By using the reagent SM-3g (0.1 mmol) and SM-4r (0.1 mmol) instead of SM-3a and SM-4i, a yellow solid 6r (49 mg, yield: 47%) was obtained.
$^1$H NMR for the product 6r (500 MHz, CDCl$_3$): δ 7.85-7.84 (m, 2H), 7.60 (m, 6H), 6.72 (s, 1H), 5.97 (s, 2H), 5.54 (m, 2H), 5.10-5.31 (m, 5H), 4.57-4.78 (m, 4H), 4.22-4.34 (m, 3H), 3.86 (m, 2H), 3.68 (m, 1H), 3.15-3.46 (m, 1H), 2.58 (m, 1H), 2.36 (m, 1H), 2.22-2.24 (m, 2H), 1.99-2.11 (m, 5H), 1.15-1.50 (m, 18H), 0.74-0.90 (m, 12H). Confirmed by MS, ESI-MS [(M+H)$^+$] for 6r: m/z calculated 1052.5. founded 1052.6.

Example 17

Synthesis of Compound 6s

Compound 6s was prepared by the same coupling reaction procedure as in example 1. By using the reagent SM-3a (0.2 mmol) and SM-4s (0.2 mmol) instead of SM-3a and SM-4i, a yellow solid 6s (55 mg, yield: 31%) was obtained.
$^1$H NMR for the product 6s (500 MHz, CDCl$_3$): δ 7.57-7.67 (m, 4H), 7.21-7.25 (m, 2H), 6.93-7.07 (m, 3H), 5.55-5.57 (m, 2H), 5.46-5.47 (m, 2H), 5.24-5.27 (m, 1H), 4.69-4.84 (m, 4H), 4.32-4.36 (m, 1H), 4.22 (m, 1H), 4.10-4.14 (m, 1H), 3.84-3.86 (m, 1H), 3.68-3.73 (m, 6H), 3.43-3.46 (m, 3H), 2.94-2.95 (m, 1H), 2.56-2.58 (m, 1H), 2.33-2.35 (m, 1H), 2.20-2.22 (m, 1H), 2.08-2.11 (m, 1H), 1.92-2.02 (m, 3H), 0.84-0.89 (m, 12H). Confirmed by MS, ESI-MS [(M+H)$^+$] for 6s: m/z calculated 918.4. founded 918.5.

Example 18

Synthesis of Compound 6t

Compound 6t was prepared by the same coupling reaction procedure as in example 1. By using the reagent SM-3c (0.2 mmol) and SM-4t (0.2 mmol) instead of SM-3a and SM-4i, a yellow solid 6t (132 mg, yield: 65%) was obtained.
$^1$H NMR for the product 6t (500 MHz, CDCl$_3$): δ 7.72-7.82 (m, 2H), 7.59 (s, 4H), 6.95-7.07 (m, 3H), 5.48-5.55 (m, 3H), 5.13-5.30 (m, 4H), 4.71-4.81 (m, 4H), 4.20-4.32 (m, 4H), 3.84-3.47 (m, 5H), 2.59-2.59 (m, 1H), 1.89-2.34 (m, 5H), 1.26 (s, 18H), 0.85-0.88 (m, 12H). Confirmed by MS, ESI-MS [(M+H)$^+$] for 6t: m/z calculated 1002.5. founded 1002.6.

Example 19

Synthesis of Compound 6u

Compound 6u was prepared by the same coupling reaction procedure as in example 1. By using the reagent SM-3a (0.2 mmol) and SM-4t (0.2 mmol) instead of SM-3a and SM-4i, a yellow solid 6u (64 mg, yield: 35%) was obtained.
$^1$H NMR for the product 6u (500 MHz, CDCl$_3$): δ 7.58 (s, 4H), 7.21-7.23 (m, 1H), 6.95-7.06 (m, 3H), 6.80-6.82 (m, 1H), 5.46-5.53 (m, 3H), 5.23-5.30 (m, 3H), 4.71-4.80 (m, 3H), 4.32-4.33 (m, 1H), 4.19-4.20 (m, 1H), 3.82-3.85 (m, 1H), 3.65-3.74 (m, 4H), 2.94-2.96 (m, 1H), 2.88-2.89 (m, 1H), 2.62 (s, 4H), 2.33-2.34 (m, 1H), 2.18-2.22 (m, 2H), 1.89-2.10 (m, 4H), 1.25-1.31 (m, 9H), 0.83-0.8 (m, 12H). Confirmed by MS, ESI-MS [(M+H)$^+$] for 6u: m/z calculated 960.5. founded 960.6.

Example 20

Synthesis of Compound 6v

Compound 6v was prepared by the same coupling reaction procedure as in example 1. By using the reagent SM-3g (0.1 mmol) and SM-4u (0.1 mmol) instead of SM-3a and SM-4i, a yellow solid 6v (38 mg, yield: 37%) was obtained.
$^1$H NMR for the product 6v (500 MHz, CDCl$_3$): δ 7.77-7.82 (m, 3H), 7.54-7.62 (m, 5H), 6.95-7.08 (m, 3H), 6.02-6.05 (m, 1H), 5.83-5.85 (m, 1H), 5.52 (s, 1H), 5.39-5.44 (m, 2H), 5.30-5.32 (m, 1H), 5.22-5.24 (m, 1H), 5.06-5.08 (m, 1H), 4, 68-4.86 (m, 5H), 4.42-4.44 (m, 1H), 4.32-4.36 (m, 1H), 4.24-4.25 (m, 2H), 3.97-4.00 (m, 1H), 3.88-3.91 (m, 1H), 2.66-2.68 (m, 1H), 2.42-2.45 (m, 1H), 2.31-2.34 (m, 1H), 2.19-2.30 (m, 2H), 2.12-2.18 (m, 1H), 1.63-1.84 (m, 16H), 1.24-1.26 (m, 2H), 1.09-1.16 (m, 4H), 0.86-0.96 (m, 6H). Confirmed by MS, ESI-MS [(M+H)$^+$] for 6v: m/z calculated 1026.5. founded 1026.6.

Example 21

Synthesis of Compound 6w

Compound 6w was prepared by the same coupling reaction procedure as in example 1. By using the reagent SM-3v (0.2 mmol) and SM-4a (0.2 mmol) instead of SM-3a and SM-4i, a yellow solid 6w (75 mg, yield: 38%) was obtained.
$^1$H NMR for the product 6w (500 MHz, CDCl$_3$): δ 8.11 (m, 1H), 8.01-8.00 (m, 1H), δ7.84-7.79 (m, 2H), 7.64-7.45 (m, 10H), 7.21-7.13 (m, 3H), 5.61-5.58 (m, 1H), 5.53-5.51 (m, 1H), 5.45-5.43 (m, 1H), 5.27-5.25 (m, 1H), 4.51-4.48 (m, 1H), 4.35-4.27 (m, 2H), 4.13-4.09 (m, 1H), 3.85-3.84 (m, 1H), 3.67 (s, 3H), 3.40 (s, 3H), 2.20-2.96 (m, 8H), 0.89-0.83 (m, 12H). Confirmed by MS, ESI-MS [(M+H)$^+$] for 6w: m/z calculated 965.4. founded 965.5.

Example 22

Synthesis of Compound 6x

Compound 6x was prepared by the same coupling reaction procedure as in example 1. By using the reagent SM-3w (0.2 mmol) and SM-4a (0.2 mmol) instead of SM-3a and SM-4i, a yellow solid 6x (68 mg, yield: 35%) was obtained.

$^1$H NMR for the product 6x (500 MHz, CDCl$_3$): δ 8.04-8.02 (m, 1H), δ7.90-7.88 (m, 1H), 7.68-7.52 (m, 11H), 7.36-7.32 (m, 2H), 7.22-7.24 (m, 2H), 5.55-5.48 (m, 3H), 5.28 (m, 2H), 4.42-4.34 (m, 2H), 3.88-3.86 (m, 2H), 3.71 (s, 6H), 2.40-2.01 (m, 8H), 0.92-0.89 (m, 12H). Confirmed by MS, ESI-MS [(M+H)$^+$] for 6x: m/z calculated 965.4. founded 965.5.

Example 23

Synthesis of Compound 6y

Compound 6y was prepared by the same coupling reaction procedure as in example 1. By using the reagent SM-3x (0.2 mmol) and SM-4a (0.2 mmol) instead of SM-3a and SM-4i, a yellow solid 6y (28 mg, yield: 19%) was obtained.

$^1$H NMR for the product 6y (500 MHz, CDCl$_3$): δ 7.68-7.47 (m, 7H), 7.33-7.18 (m, 3H), 5.54-5.53 (m, 1H), 5.35-5.25 (m, 2H), 4.35-4.30 (m, 1H), 3.87-3.85 (m, 1H), 3.76-3.69 (m, 6H), 3.30 (m, 1H), 2.91 (m, 1H), 2.38-2.35 (m, 2H), 2.34-1.92 (m, 7H), 1.38-1.20 (m, 12H), 0.95-0.85 (m, 6H). Confirmed by MS, ESI-MS [(M+H)$^+$] for 6y: m/z calculated 723.4. Founded 723.5.

Example 24

Synthesis of Compound 6z

Compound 6z was prepared by the same coupling reaction procedure as in example 1. By using the reagent SM-3y (0.2 mmol) and SM-4a (0.2 mmol) instead of SM-3a and SM-4i, a yellow solid 6z (76 mg, yield: 50%) was obtained.

$^1$H NMR for the product 6z (500 MHz, CDCl$_3$): δ 7.76-7.56 (m, 7H), 7.34-7.21 (m, 3H), 5.51-5.26 (m, 3H), 4.34-4.33 (m, 1H), 3.84-3.60 (m, 7H), 3.51 (m, 1H), 2.76-2.74 (m, 1H), 2.40-2.33 (m, 2H), 2.38-1.95 (m, 13H), 1.26-1.23 (m, 4H), 0.93-0.86 (m, 6H). Confirmed by MS, ESI-MS [(M+H)$^+$] for 6z: m/z calculated 751.4. founded 751.5.

Example 25

Synthesis of Compound 6aa

Compound 6aa was prepared by the same coupling reaction procedure as in example 1. By using the reagent SM-3z (0.2 mmol) and SM-4a (0.2 mmol) instead of SM-3a and SM-4i, a yellow solid 6aa (52 mg, yield: 34%) was obtained.

$^1$H NMR for the product 6aa (500 MHz, CDCl$_3$): δ 7.82-7.49 (m, 6H), 7.34-7.19 (m, 4H), 5.54-5.49 (m, 1H), 5.36-5.27 (m, 1H), 4.37-4.28 (m, 1H), 3.57-3.55 (m, 6H), 2.98 (m, 1H), 2.34-2.33 (m, 2H), 2.27-1.57 (m, 12H), 1.44-1.21 (m, 8H), 0.94-0.87 (m, 6H). Confirmed by MS, ESI-MS [(M+H)$^+$] for 6aa: m/z calculated 765.4. founded 765.5.

Example 26

Synthesis of Compound 6ab

Compound 6ab was prepared by the same coupling reaction procedure as in example 1. By using the reagent SM-3aa (0.2 mmol) and SM-4a (0.2 mmol) instead of SM-3a and SM-4i, a yellow solid 6ab (991 mg, yield: 65%) was obtained.

$^1$H NMR for the product 6ab (500 MHz, CDCl$_3$): δ 7.85-7.76 (m, 2H), 7.67-7.56 (m, 5H), 7.40-7.37 (m, 2H), 7.22-7.16 (m, 1H), 5.51-5.45 (m, 2H), 5.40-5.30 (m, 2H), 4.45-4.36 (m, 2H), 3.88-3.86 (m, 2H), 3.71 (s, 6H), 2.87-2.85 (m, 1H), 2.51-1.74 (m, 11H), 1.10-0.80 (m, 12H). Confirmed by MS, ESI-MS [(M+H)$^+$] for 6ab: m/z calculated 753.4. founded 753.5.

Example 27

Synthesis of Compound 6ac

Compound 6ac was prepared by the same coupling reaction procedure as in example 1. By using the reagent SM-3aa (0.2 mmol) and SM-4n (0.2 mmol) instead of SM-3a and SM-4i, a yellow solid 6ac (64 mg, yield: 42%) was obtained.

$^1$H NMR for the product 6ac (500 MHz, CDCl$_3$): δ 7.81-7.45 (m, 8H), 7.37-7.22 (m, 4H), 6.72-6.62 (m, 2H), 5.97-5.93 (m, 2H), 5.55-5.35 (m, 3H), 4.71-4.57 (m, 4H), 4.26-4.12 (m, 2H), 3.77-3.70 (m, 3H), 3.51-3.43 (m, 3H), 2.83 (m, 1H), 2.57-2.47 (m, 2H), 2.07-1.77 (m, 9H), 1.12-1.11 (m, 6H), 0.84-0.82 (m, 6H). Confirmed by MS, ESI-MS [(M+H)$^+$] for 6ac: m/z calculated 958.4. founded 958.5.

Example 28

Synthesis of Compound 6ad

Compound 6ad was prepared by the same coupling reaction procedure as in example 1. By using the reagent SM-3aa (0.20 mmol) and SM-4i (0.20 mmol) instead of SM-3a and SM-4i, a yellow solid 6ad (64 mg, yield: 33%) was obtained.

$^1$H NMR for the product 6ad (500 MHz, CDCl$_3$): δ 7.80-7.46 (m, 8H), 7.37-7.22 (m, 4H), 6.78-6.66 (m, 2H), 5.98-5.97 (m, 2H), 5.56-5.34 (m, 3H), 4.75-4.59 (m, 4H), 4.25-4.17 (m, 2H), 3.86-3.64 (m, 3H), 3.49-3.46 (m, 3H), 2.82 (m, 1H), 2.58-2.47 (m, 2H), 2.08-1.76 (m, 9H), 1.12-1.11 (m, 6H), 0.86-0.84 (m, 6H). Confirmed by MS, ESI-MS [(M+H)$^+$] for 6ad: m/z calculated 958.4. founded 958.5.

Example 29

Synthesis of Compound 6ae

Compound 6ae was prepared by the same coupling reaction procedure as in example 1. By using the reagent SM-3a (0.2 mmol) and SM-4ac (0.2 mmol) instead of SM-3a and SM-4i, a yellow solid 6ae (32 mg, yield: 17%) was obtained.

$^1$H NMR for the product 6ae (500 MHz, CDCl$_3$): δ 7.81-7.55 (m, 8H), 7.34-7.22 (m, 4H), 6.80-6.69 (m, 2H), 5.99-5.97 (m, 1H), 5.57-5.56 (m, 1H), 5.32-5.17 (m, 2H), 4.93-4.72 (m, 4H), 4.35-4.25 (m, 2H), 3.74-3.69 (m, 6H), 2.96 (m, 1H), 2.37-2.36 (m, 1H), 2.24-1.76 (m, 8H), 1.16-0.79 (m, 12H). Confirmed by MS, ESI-MS [(M+H)$^+$] for 6ae: m/z calculated 929.4. founded 929.5.

Example 30

Synthesis of Compound 6af

Compound 6af was prepared by the same coupling reaction procedure as in example 1. By using the reagent SM-3a (0.2 mmol) and SM-4ad (0.2 mmol) instead of SM-3a and SM-4i, a yellow solid 6af (19 mg, yield: 10%) was obtained.

$^1$H NMR for the product 6af (500 MHz, CDCl$_3$): δ 7.77-7.54 (m, 8H), 7.28-7.22 (m, 2H), 6.73-6.68 (m, 2H), 6.00-5.98 (m, 2H), 5.61-5.46 (m, 2H), 5.35-5.22 (m, 2H), 4.85-4.75 (m, 4H), 4.365-4.10 (m, 2H), 3.72-3.70 (m, 6H), 2.95 (m, 1H), 2.39 (m, 1H), 2.03-1.81 (m, 8H), 1.10-0.90 (m, 12H). Confirmed by MS, ESI-MS [(M+H)$^+$] for 6af: m/z calculated 929.4. founded 929.5.

Example 31

Synthesis of Compound 6ag

Compound 6ag was prepared by the same coupling reaction procedure as in example 1. By using the reagent SM-3ab (0.2 mmol) and SM-4a (0.2 mmol) instead of SM-3a and SM-4i, a yellow solid 6ag (99 mg, yield: 65%) was obtained.

$^1$H NMR for the product 6ag (500 MHz, CDCl$_3$): δ 7.83-7.53 (m, 7H), 7.47-7.19 (m, 3H), 5.50-5.48 (m, 1H), 5.27-5.26 (m, 1H), 5.08-5.03 (m, 1H), 4.54-4.48 (m, 1H), 4.40-4.33 (m, 1H), 4.01-3.82 (m, 3H), 3.70 (m, 6H), 2.95-2.90 (m, 1H), 2.38-2.37 (m, 1H), 2.23-1.83 (m, 8H), 1.27-1.11 (m, 6H), 0.97-0.86 (m, 6H). Confirmed by MS, ESI-MS [(M+H)$^+$] for 6ag: m/z calculated 755.4. founded 755.5.

Example 32

Synthesis of Compound 6ah

Compound 6ah was prepared by the same coupling reaction procedure as in example 1. By using the reagent SM-3ab (0.2 mmol) and SM-4n (0.2 mmol) instead of SM-3a and SM-4i, a yellow solid 6ah (22 mg, yield: 14%) was obtained.

$^1$H NMR for the product 6ah (500 MHz, CDCl$_3$): δ 7.80-7.59 (m, 8H), 7.27 (m, 2H), 6.71-6.65 (m, 2H), 5.96 (s, 2H), 5.46-5.38 (m, 3H), 5.08-5.03 (m, 1H), 4.68-4.53 (m, 5H), 3.79-3.70 (m, 3H), 3.57-3.50 (m, 3H), 2.91-2.84 (m, 2H), 2.15-1.88 (m, 10H), 1.26-1.11 (m, 6H), 0.93-0.86 (m, 6H). Confirmed by MS, ESI-MS [(M+H)$^+$]: m/z calculated 960.4. Founded 960.5.

Example 33

Synthesis of Compound 6ai

Compound 6ai was prepared by the same coupling reaction procedure as in example 1. By using the reagent SM-3ab (0.2 mmol) and SM-4i (0.2 mmol) instead of SM-3a and SM-4i, a yellow solid 6ai (38 mg, yield: 25%) was obtained.

$^1$H NMR for the product 6ai (500 MHz, CDCl$_3$): δ 7.80-7.58 (m, 8H), 7.28-7.23 (m, 2H), 6.78-6.66 (m, 2H), 5.98-5.97 (m, 2H), 5.47-5.37 (m, 3H), 5.08-5.04 (m, 1H), 4.75-4.53 (m, 5H), 4.24-4.21 (m, 2H), 3.79-3.65 (m, 3H), 3.57-3.49 (m, 3H), 2.92 (m, 1H), 2.57 (m, 1H), 2.15-1.73 (m, 8H), 1.28-1.11 (m, 6H), 0.83-0.75 (m, 6H). Confirmed by MS, ESI-MS [(M+H)$^+$] for 6ai: m/z calculated 960.4. founded 960.5.

Example 34

Synthesis of Compound 6aj

Compound 6aj was prepared by the same coupling reaction procedure as in example 1. By using the reagent SM-3ab (0.2 mmol) and SM-4aa (0.2 mmol) instead of SM-3a and SM-4i, a yellow solid 6aj (67 mg, yield: 43%) was obtained.

$^1$H NMR for the product 6aj (500 MHz, CDCl$_3$): δ 7.85-7.39 (m, 8H), 5.58-5.54 (m, 1H), 5.41-5.35 (m, 1H), 5.09-5.05 (m, 1H), 4.60 (m, 1H), 4.54-4.40 (m, 2H), 4.31-4.30 (m, 1H), 4.20-4.18 (m, 1H), 4.02 (m, 1H), 3.80 (m, 3H), 3.72-3.43 (m, 3H), 3.04-3.03 (m, 2H), 2.98-2.84 (m, 2H), 2.45 (m, 1H), 2.30 (m, 1H), 1.76-1.62 (m, 2H), 1.49-1.33 (m, 2H), 1.15-1.12 (m, 6H), 0.95-0.87 (m, 6H). Confirmed by MS, ESI-MS [(M+H)$^+$] for 6aj: m/z calculated 769.4. founded 769.5.

Example 35

Synthesis of Compound 6ak

Compound 6ak was prepared by the same coupling reaction procedure as in example 1. By using the reagent SM-3ae (0.2 mmol) and SM-4n (0.2 mmol) instead of SM-3a and SM-4i, a yellow solid 6ak (yield: 51%) was obtained.

Confirmed by MS, ESI-MS [(M+H)$^+$] for 6ak: m/z calculated 970.4. founded 970.6.

Example 36

Synthesis of Compound 6am

Compound 6am was prepared by the same coupling reaction procedure as in example 1. By using the reagent SM-3ae (0.2 mmol) and SM-4ad (0.2 mmol) instead of SM-3a and SM-4i, a yellow solid 6am (yield: 53%) was obtained.

Confirmed by MS, ESI-MS [(M+H)$^+$] for 6am: m/z calculated 955.4. founded 955.6.

Example 37

Synthesis of Compound 6an

Compound 6an was prepared by the same coupling reaction procedure as in example 1. By using the reagent SM-3ae (0.2 mmol) and SM-4i (0.2 mmol) instead of SM-3a and SM-4i, a yellow solid 6an (yield: 52%) was obtained.

Confirmed by MS, ESI-MS [(M+H)$^+$]: m/z calculated 970.4. founded 970.6.

Example 38

Synthesis of Compound 6ap

Compound 6ap was prepared by the same coupling reaction procedure as in example 1. By using the reagent SM-3ae (0.2 mmol) and SM-4ac (0.2 mmol) instead of SM-3a and SM-4i, a yellow solid 6ap (yield: 53%) was obtained.

Confirmed by MS, ESI-MS [(M+H)⁺] for 6ap: m/z calculated 955.4. founded 955.6.

Example 39

Synthesis of Compound 6aq

Compound 6aq was prepared by the same coupling reaction procedure as in example 1. By using the reagent SM-3af (0.2 mmol) and SM-4a (0.2 mmol) instead of SM-3a and SM-4i, a yellow solid 6aq (yield: 53%) was obtained.
Confirmed by MS, ESI-MS [(M+H)⁺] for 6aq: m/z calculated 885.4. founded 885.5.

Example 40

Synthesis of Compound 6ar

Compound 6ar was prepared by the same coupling reaction procedure as in example 1. By using the reagent SM-3ag (0.2 mmol) and SM-4a (0.2 mmol) instead of SM-3a and SM-4i, a yellow solid 6ar (yield: 55%) was obtained.
$^1$H-NMR of the product 6ar (500 MHz, CDCl$_3$): δ 7.53-7.76 (m, 9H), 7.18-7.29 (m, 3H), 6.96-7.08 (m, 2H), 5.60-5.70 (m, 2H), 5.20-5.46 (m, 4H), 4.80-5.03 (m, 5H), 4.24-4.36 (m, 2H), 3.86-4.11 (m, 2H), 3.68-3.72 (m, 6H), 2.92 (m, 1H), 2.38 (m, 1H), 2.22 (m, 1H), 2.00-2.11 (m, 4H), 0.88-0.93 (m, 12H). ESI-MS [(M+H)⁺] for 6ar: m/z calculated 903.4. found 903.5.

Example 41

Synthesis of Compound 6as

Compound 6as was prepared by the same coupling reaction procedure as in example 1. By using the reagent SM-3ah (0.2 mmol) and SM-4a (0.2 mmol) instead of SM-3a and SM-4i, a yellow solid 6as (yield: 54%) was obtained.
Confirmed by MS, ESI-MS [(M+H)⁺] for 6as: m/z calculated 903.4. founded 903.5.

Example 42

Synthesis of Compound 6at

Compound 6at was prepared by the same coupling reaction procedure as in example 1. By using the reagent SM-3ai (0.2 mmol) and SM-4a (0.2 mmol) instead of SM-3a and SM-4i, a yellow solid 6at (yield: 51%) was obtained.
Confirmed by MS, ESI-MS [(M+H)⁺] for 6at: m/z calculated 919.4. founded 919.5.

Example 43

Synthesis of Compound 6au

Compound 6au was prepared by the same coupling reaction procedure as in example 1. By using the reagent SM-3aj (0.2 mmol) and SM-4a (0.2 mmol) instead of SM-3a and SM-4i, a yellow solid 6au (yield: 52%) was obtained.
Confirmed by MS, ESI-MS [(M+H)⁺] for 6au: m/z calculated 919.4. founded 919.5.

Example 44

Synthesis of Compound 6av

Compound 6av was prepared by the same coupling reaction procedure as in example 1. By using the reagent SM-3am (0.2 mmol) and SM-4a (0.2 mmol) instead of SM-3a and SM-4i, a yellow solid 6av (yield: 63%) was obtained.
$^1$H-NMR of the product 6av (500 MHz, CDCl$_3$): δ 7.54-7.80 (m, 9H), 7.17-7.22 (m, 3H), 6.76-6.85 (m, 3H), 5.60-5.72 (m, 2H), 5.19-5.44 (m, 4H), 4.82-4.92 (m, 5H), 3.97-4.34 (m, 4H), 3.79-3.82 (m, 3H), 3.68-3.73 (m, 6H), 2.95 (m, 1H), 2.37 (m, 1H), 2.20-2.21 (m, 1H), 1.98-2.11 (m, 4H), 0.88-0.95 (m, 12H). ESI-MS [(M+H)⁺] for 6av: m/z calculated 915.4. found 915.5.

Example 45

Synthesis of Compound 6aw

Compound 6aw was prepared by the same coupling reaction procedure as in example 1. By using the reagent SM-3ak (0.2 mmol) and SM-4a (0.2 mmol) instead of SM-3a and SM-4i, a yellow solid 6aw (yield: 61%) was obtained.
$^1$H-NMR of the product 6aw (500 MHz, CDCl$_3$): δ 7.48-7.80 (m, 9H), 7.16-7.25 (m, 4H), 6.83-6.84 (m, 1H), 6.72-6.73 (m, 1H), 5.70-5.78 (m, 2H), 5.22-5.41 (m, 4H), 4.74-4.98 (m, 5H), 4.28-4.30 (m, 2H), 4.01-4.13 (m, 2H), 3.81 (s, 3H), 3.64-3.66 (m, 6H), 2.92 (m, 1H), 2.38 (m, 1H), 2.17-2.18 (m, 1H), 1.94-2.07 (m, 4H), 0.85-0.91 (m, 12H). ESI-MS [(M+H)⁺] for 6aw: m/z calculated 915.4. found 915.5.

Example 46

Synthesis of Compound 6ax

Compound 6ax was prepared by the same coupling reaction procedure as in example 1. By using the reagent SM-3an (0.2 mmol) and SM-4a (0.2 mmol) instead of SM-3a and SM-4i, a yellow solid 6ax (yield: 54%) was obtained.
$^1$H-NMR of the product 6ax (500 MHz, CDCl$_3$): δ 7.54-7.84 (m, 9H), 7.23 (s, 1H), 7.20 (s, 1H), 6.79 (s, 2H), 6.74 (s, 1H), 6.81-6.87 (m, 2H), 5.58-5.70 (m, 2H), 5.46 (m, 1H), 5.19-5.34 (m, 3H), 4.72-4.92 (m, 5H), 3.97-4.35 (m, 4H), 3.86-3.89 (m, 6H), 3.69-3.74 (m, 6H), 2.96 (m, 1H), 2.38 (m, 1H), 2.22 (m, 1H), 1.99-2.12 (m, 4H), 0.89-0.96 (m, 12H). ESI-MS [(M+H)⁺] for 6ax: m/z calculated 945.4. found 945.5.

Example 47

Synthesis of Compound 6ay

Compound 6ay was prepared by the same coupling reaction procedure as in example 1. By using the reagent SM-3ac (0.2 mmol) and SM-4ag (0.2 mmol) instead of SM-3a and SM-4i, a yellow solid 6ay (yield: 53%) was obtained.
Confirmed by MS, ESI-MS [(M+H)⁺] for 6ay: m/z calculated 963.4. founded 963.5.

Example 48

Synthesis of Compound 6az

Compound 6az was prepared by the same coupling reaction procedure as in example 1. By using the reagent SM-3n (0.2 mmol) and SM-4ae (0.2 mmol) instead of SM-3a and SM-4i, a yellow solid 6az (yield: 56%) was obtained.

Confirmed by MS, ESI-MS [(M+H)$^+$] for 6az: m/z calculated 956.4. founded 956.5.

Example 49

Synthesis of Compound 6ba

Compound 6ba was prepared by the same coupling reaction procedure as in example 1. By using the reagent SM-3a (0.5 mmol) and SM-4b (0.5 mmol) instead of SM-3a and SM-4i, a yellow solid 6ba (118 mg, yield: 32%) was obtained.

$^1$H NMR for the product 6ba (500 MHz, CDCl$_3$): δ 7.59-7.18 (m, 10H), 6.26 (m, 1H), 6.09 (m, 1H), 6.00 (m, 1H), 5.50 (m, 1H), 5.27 (m, 1H), 4.76 (m, 1H), 4.52 (m, 1H), 4.36 (m, 1H), 4.30 (m, 1H), 3.86 (m, 1H), 3.71 (s, 6H), 2.38-2.00 (m, 6H), 0.91 (d, 6H), 0.89 (d, 6H). ESI-MS [(M+H)$^+$] for 6dx: m/z calculated 737.4. found 737.5.

Example 50

Synthesis of Compound 6bb

Compound 6bb was prepared by the same coupling reaction procedure as in example 1. By using the reagent SM-3e (0.2 mmol) and SM-4f (0.2 mmol) instead of SM-3a and SM-4i, a yellow solid 6bb (47 mg, yield: 27%) was obtained.

$^1$H NMR for the product 6bb (500 MHz, CDCl$_3$): δ 7.57-7.72 (m, 4H), 7.16-7.23 (m, 2H), 6.29 (s, 1H), 6.00-6.07 (m, 2H), 5.24-5.36 (m, 3H), 4.75, 4.76 (d, 1H), 4.45-4.57 (m, 2H), 4.27-4.36 (m, 2H), 3.88 (s, 1H), 3.67-3.68 (m, 1H), 2.20-2.34 (m, 2H), 1.99-2.09 (m, 2H), 1.46 (s, 18H), 0.93 (m, 18H). Confirmed by MS, ESI-MS [(M+H)$^+$] for 6bb: m/z calculated 849.5. founded 849.6.

Example 51

Synthesis of Compound 6bc

Compound 6bc was prepared by the same coupling reaction procedure as in example 1. By using the reagent SM-3a (0.2 mmol) and SM-4d (0.2 mmol) instead of SM-3a and SM-4i, a yellow solid 6bc (32 mg, yield: 20%) was obtained.

$^1$H NMR for the product 6bc (500 MHz, CDCl$_3$): δ 7.46-7.54 (m, 4H), 7.15-7.24 (m, 2H), 6.29 (s, 1H), 6.07-6.08 (m, 1H), 6.00 (s, 1H), 5.50-5.52 (m, 1H), 5.23-5.27 (m, 2H), 4.69-4.72 (m, 1H), 4.25-4.47 (m, 3H), 3.83-3.86 (m, 1H), 3.70 (s, 3H), 2.34-2.38 (m, 1H), 1.95-2.23 (m, 5H), 1.46 (s, 6H), 0.88-0.93 (m, 12H). Confirmed by MS, ESI-MS [(M+H)$^+$] for 6bc: m/z calculated 779.4. founded 779.5.

Example 52

Synthesis of Compound 6bd

Compound 6bd was prepared by the same coupling reaction procedure as in example 1. By using the reagent SM-3b (0.2 mmol) and SM-4b (0.2 mmol) instead of SM-3a and SM-4i, a yellow solid 6bd (yield: 33%) was obtained.

$^1$H NMR for the product 6bd (500 MHz, CDCl$_3$): δ 7.77-7.80 (m, 2H), 7.56-7.60 (m, 4H), 7.20-7.23 (m, 2H), 6.30-6.33 (m, 2H), 6.08-6.09 (m, 2H), 5.99 (s, 2H), 5.34-5.39 (m, 2H), 4.72-4.74 (m, 2H), 4.42-4.45 (m, 2H), 4.27-4.30 (m, 2H), 3.71 (s, 6H), 1.96-2.01 (m, 2H), 1.25-1.34 (m, 6H), 0.87-0.90 (m, 6H). Confirmed by MS, ESI-MS [(M+H)$^+$] for 6bd: m/z calculated 735.4. founded 735.4.

Example 53

Synthesis of Compound 6be

Compound 6be was prepared by the same coupling reaction procedure as in example 1. By using the reagent SM-3d (0.2 mmol) and SM-4d (0.2 mmol) instead of SM-3a and SM-4i, a yellow solid 6be (yield: 42%) was obtained.

$^1$H NMR for the product 6be (500 MHz, CDCl$_3$): δ 7.70-7.76 (m, 2H), 7.47-7.60 (m, 4H), 7.21-7.25 (m, 2H), 6.28-6.32 (m, 2H), 6.07-6.08 (m, 2H), 6.01 (s, 2H), 5.21-5.23 (m, 2H), 4.69-4.72 (m, 2H), 4.44-4.47 (m, 2H), 4.25-4.29 (m, 2H), 1.94-1.99 (m, 2H), 1.46 (s, 18H), 0.82-0.89 (m, 12H). Confirmed by MS, ESI-MS [(M+H)$^+$] for 6be: m/z calculated 819.5. founded 819.5.

Example 54

Synthesis of Compound 6bf

Compound 6bf was prepared by the same coupling reaction procedure as in example 1. By using the reagent SM-3h (0.2 mmol) and SM-4h (0.2 mmol) instead of SM-3a and SM-4i, a yellow solid 6bf (yield: 34%) was obtained.

$^1$H NMR for the product 6bf (500 MHz, CDCl$_3$): δ 7.47-7.63 (m, 6H), 7.15-7.23 (m, 2H), 7.21-7.24 (m, 2H), 6.07-6.08 (m, 2H), 6.00 (s, 2H), 5.30-5.32 (m, 2H), 5.08-5.09 (m, 2H), 4.73-4.76 (m, 2H), 4.48-4.51 (m, 2H), 4.27-4.30 (m, 2H), 1.94-2.00 (m, 2H), 1.83-1.86 (m, 4H), 1.71 (s, 8H), 1.58 (s, 4H), 0.90-0.91 (m, 12H). Confirmed by MS, ESI-MS [(M+H)$^+$] for 6bf: m/z calculated 843.5. founded 843.6.

Example 55

Synthesis of Compound 6bg

Compound 6bg was prepared by the same coupling reaction procedure as in example 1. By using the reagent SM-3g (0.2 mmol) and SM-4h (0.2 mmol) instead of SM-3a and SM-4i, a yellow solid 6bg (yield: 15%) was obtained.

$^1$H NMR for the product 6bg (400 MHz, CD$_3$OD): δ 7.38-7.34 (m, 1H), 7.00-6.96 (m, 2H), 6.11-6.03 (m, 1H), 5.43-5.39 (m, 1H), 5.29-5.27 (m, 1H), 4.65-4.64 (m, 2H), 4.62 (s, 2H), 4.57 (s, 2H). Confirmed by MS, ESI-MS [(M+H)$^+$] for 6bg: m/z calculated 845.5. founded 845.6.

Example 56

Synthesis of Compound 6bh

Compound 6bh was prepared by the same coupling reaction procedure as in example 1. By using the reagent SM-3x (0.2 mmol) and SM-4b (0.2 mmol) instead of SM-3a and SM-4i, a yellow solid 6bh (yield: 57.5%) was obtained.

$^1$H NMR for the product 6bh (500 MHz, CDCl$_3$): δ 7.66-7.52 (m, 8H), 7.20 (m, 2H), 6.23 (m, 1H), 6.23 (m, 1H), 6.06-6.05 (m, 1H), 5.98 (m, 1H), 5.73 (m, 1H), 5.53-5.52 (m, 1H), 5.35 (m, 1H), 4.74-4.71 (m, 1H), 4.49-4.47 (m, 1H), 4.29-4.26 (m, 1H), 3.77-3.69 (m, 6H), 2.33-2.32 (m, 1H), 2.09-1.95 (m, 4H), 1.32-1.24 (m, 4H), 0.91-0.80 (m, 6H). Confirmed by MS, ESI-MS [(M+H)$^+$] for 6bh: m/z calculated 721.3. founded 721.5.

Example 57

Synthesis of Compound 6bi

Compound 6bi was prepared by the same coupling reaction procedure as in example 1. By using the reagent SM-3y (0.2 mmol) and SM-4b (0.2 mmol) instead of SM-3a and SM-4i, a yellow solid 6bi (yield: 43%) was obtained.

$^1$H NMR for the product 6bi (500 MHz, CDCl$_3$): δ 7.76-7.55 (m, 8H), 7.26-7.23 (m, 2H), 6.29-6.28 (m, 1H), 6.08-6.07 (m, 1H), 5.99 (m, 1H), 5.51-5.49 (m, 1H), 5.37 (m, 1H), 4.75-4.72 (m, 1H), 4.47-4.44 (m, 1H), 4.30-4.27 (m, 1H), 3.72-3.70 (m, 6H), 2.77-2.74 (m, 1H), 2.39-2.34 (m, 1H), 2.15-1.73 (m, 10H), 1.26 (m, 1H), 0.90-0.85 (m, 6H). Confirmed by MS, ESI-MS [(M+H)$^+$] for 6bi: m/z calculated 749.4. founded 749.5.

Example 58

Synthesis of Compound 6bj

Compound 6bj was prepared by the same coupling reaction procedure as in example 1. By using the reagent SM-3z (0.2 mmol) and SM-4b (0.2 mmol) instead of SM-3a and SM-4i, a yellow solid 6bj (yield: 33%) was obtained.

$^1$H NMR for the product 6bj (500 MHz, CDCl$_3$): δ 7.75-7.46 (m, 6H), 7.35-7.24 (m, 4H), 6.08-5.99 (m, 1H), 5.52-5.48 (m, 1H), 4.75-4.72 (m, 1H), 4.47-4.44 (m, 1H), 4.30-4.28 (m, 1H), 3.76-3.58 (m, 6H), 2.39 (m, 2H), 2.14-1.55 (m, 11H), 1.26 (m, 6H), 0.94-0.88 (m, 6H). Confirmed by MS, ESI-MS [(M+H)$^+$] for 6bj: m/z calculated 763.4. founded 763.5.

Example 59

Synthesis of Compound 6bk

Compound 6bk was prepared by the same coupling reaction procedure as in example 1. By using the reagent SM-3aa (0.2 mmol) and SM-4b (0.2 mmol) instead of SM-3a and SM-4i, a yellow solid 6bk (yield: 61%) was obtained.

$^1$H NMR for the product 6bk (500 MHz, CDCl$_3$): δ 7.81-7.52 (m, 6H), 7.38-7.20 (m, 4H), 6.09 (m, 1H), 6.0 (m, 1H), 5.43 (m, 1H), 4.73-4.70 (m, 1H), 4.48-4.43 (m, 1H), 4.32-4.29 (m, 1H), 3.70-3.63 (m, 6H), 2.85-2.83 (m, 1H), 2.09-1.48 (m, 11H), 1.11 (m, 6H), 0.92-0.85 (m, 6H). Confirmed by MS, ESI-MS [(M+H)$^+$] for 6bk: m/z calculated 751.3. founded 751.5.

Example 60

Synthesis of Compound 6bm

Compound 6bm was prepared by the same coupling reaction procedure as in example 1. By using the reagent SM-3ab (0.2 mmol) and SM-4b (0.2 mmol) instead of SM-3a and SM-4i, a yellow solid 6bm (yield: 54%) was obtained.

$^1$H NMR for the product 6bm (500 MHz, CDCl$_3$): δ 7.76-7.42 (m, 9H), 7.28-7.21 (m, 1H), 6.24 (m, 1H), 6.10-6.09 (m, 1H), 5.99 (m, 1H), 5.45-5.46 (m, 1H), 5.13-5.04 (m, 1H), 4.74-4.71 (m, 1H), 4.53-4.52 (m, 2H), 4.41-4.28 (m, 2H), 4.14-4.00 (m, 2H), 3.70 (m, 6H), 2.94 (m, 1H), 2.11-1.99 (m, 3H), 1.27-1.12 (m, 6H), 0.95-0.87 (m, 6H). Confirmed by MS, ESI-MS [(M+H)$^+$] for 6bm: m/z calculated 753.4. founded 753.5.

Example 61

Synthesis of Compound 6bn

Compound 6bn was prepared by the same coupling reaction procedure as in example 1. By using the reagent SM-3cs (0.2 mmol) and SM-4af (0.2 mmol) instead of SM-3a and SM-4i, a yellow solid 6bn (yield: 61%) was obtained.

Confirmed by MS, ESI-MS [(M+H)$^+$] for 6bn: m/z calculated 958.4. founded 958.5.

Example 62

Synthesis of Compound 6 bp

Compound 6 bp was prepared by the same coupling reaction procedure as in example 1. By using the reagent SM-3ap (0.2 mmol) and SM-4bi (0.2 mmol) instead of SM-3a and SM-4i, a yellow solid 6 bp (yield: 56%) was obtained.

Confirmed by MS, ESI-MS [(M+H)$^+$] for 6 bp: m/z calculated 992.4. founded 992.5.

Example 63

Synthesis of Compound 6bq

Compound 6bq was prepared by the same coupling reaction procedure as in example 1. By using the reagent SM-3aq (0.2 mmol) and SM-4bj (0.2 mmol) instead of SM-3a and SM-4i, a yellow solid 6bq (yield: 53%) was obtained.

Confirmed by MS, ESI-MS [(M+H)$^+$] for 6bq: m/z calculated 835.4. founded 835.5.

Example 64

Synthesis of Compound 6br

Compound 6br was prepared by the same coupling reaction procedure as in example 1. By using the reagent SM-3ap (0.2 mmol) and SM-4bk (0.2 mmol) instead of SM-3a and SM-4i, a yellow solid 6br (yield: 52%) was obtained.

Confirmed by MS, ESI-MS [(M+H)$^+$] for 6br: m/z calculated 1042.4. founded 1042.5.

Example 65

Synthesis of Compound 6bs

Compound 6bs was prepared by the same coupling reaction procedure as in example 1. By using the reagent SM-3ar (0.2 mmol) and SM-4bj (0.2 mmol) instead of SM-3a and SM-4i, a yellow solid 6bs (yield: 54%) was obtained.

Confirmed by MS, ESI-MS [(M+H)$^+$] for 6bs: m/z calculated 1027.4. founded 1027.5.

Example 66

Synthesis of Compound 6bt

Compound 6bt was prepared by the same coupling reaction procedure as in example 1. By using the reagent SM-3as (0.2 mmol) and SM-4bi (0.2 mmol) instead of SM-3a and SM-4i, a yellow solid 6bt (yield: 52%) was obtained.

Confirmed by MS, ESI-MS [(M+H)$^+$] for 6bt: m/z calculated 968.4. founded 968.5.

Example 67

Synthesis of Compound 6bu

Compound 6bu was prepared by the same coupling reaction procedure as in example 1. By using the reagent SM-3at (0.2 mmol) and SM-4n (0.2 mmol) instead of SM-3a and SM-4i, a yellow solid 6bu (yield: 56%) was obtained.

Confirmed by MS, ESI-MS [(M+H)$^+$] for 6bu: m/z calculated 994.4. founded 994.5.

Example 68

Synthesis of Compound 6bv

Compound 6bv was prepared by the same coupling reaction procedure as in example 1. By using the reagent SM-3at (0.2 mmol) and SM-4ad (0.2 mmol) instead of SM-3a and SM-4i, a yellow solid 6bv (yield: 53%) was obtained.

Confirmed by MS, ESI-MS [(M+H)$^+$] for 6bv: m/z calculated 979.4. founded 979.5.

Example 69

Synthesis of Compound 6bw

Compound 6bw was prepared by the same coupling reaction procedure as in example 1. By using the reagent SM-3av (0.2 mmol) and SM-4ad (0.2 mmol) instead of SM-3a and SM-4i, a yellow solid 6bw (yield: 52%) was obtained.

Confirmed by MS, ESI-MS [(M+H)$^+$] for 6bw: m/z calculated 979.4. founded 979.5.

Example 70

Synthesis of Compound 6bx

Compound 6bx was prepared by the same coupling reaction procedure as in example 1. By using the reagent SM-3ay (0.2 mmol) and SM-4a (0.2 mmol) instead of SM-3a and SM-4i, a yellow solid 6bx (yield: 54%) was obtained.

Confirmed by MS, ESI-MS [(M+H)$^+$] for 6bx: m/z calculated 771.4. founded 771.4.

Example 71

Synthesis of Compound 6by

Compound 6by was prepared by the same coupling reaction procedure as in example 1. By using the reagent SM-3b (0.2 mmol) and SM-4ag (0.2 mmol) instead of SM-3a and SM-4i, a yellow solid 6by (yield: 56%) was obtained.

Confirmed by MS, ESI-MS [(M+H)$^+$] for 6by: m/z calculated 771.4. founded 771.4.

Example 72

Synthesis of Compound 6bz

Compound 6bz was prepared by the same coupling reaction procedure as in example 1. By using the reagent SM-3ax (0.2 mmol) and SM-4ah (0.2 mmol) instead of SM-3a and SM-4i, a yellow solid 6bz (yield: 61%) was obtained.

Confirmed by MS, ESI-MS [(M+H)$^+$] for 6bz: m/z calculated 805.3. founded 805.4.

Example 73

Synthesis of Compound 6ca

Compound 6ca was prepared by the same coupling reaction procedure as in example 1. By using the reagent SM-3ay (0.2 mmol) and SM-4ah (0.2 mmol) instead of SM-3a and SM-4i, a yellow solid 6ca (yield: 53%) was obtained.

Confirmed by MS, ESI-MS [(M+H)$^+$] for 6ca: m/z calculated 803.3. founded 803.4.

Example 74

Synthesis of Compound 6cb

Compound 6cb was prepared by the same coupling reaction procedure as in example 1. By using the reagent SM-3at (0.2 mmol) and SM-4b (0.2 mmol) instead of SM-3a and SM-4i, a yellow solid 6cb (yield: 51%) was obtained.

Confirmed by MS, ESI-MS [(M+H)$^+$] for 6cb: m/z calculated 787.4. founded 787.5. 实施例 75.

Example 75

Synthesis of Compound 6cc

Compound 6cc was prepared by the same coupling reaction procedure as in example 1. By using the reagent SM-3bz (0.2 mmol) and SM-4a (0.2 mmol) instead of SM-3a and SM-4i, a yellow solid 6cc (yield: 58%) was obtained.

Confirmed by MS, ESI-MS [(M+H)$^+$] for 6cc: m/z calculated 787.4. founded 787.5.

Example 76

Synthesis of Compound 6cd

Compound 6cd was prepared by the same coupling reaction procedure as in example 1. By using the reagent SM-3ci (0.2 mmol) and SM-4bd (0.2 mmol) instead of SM-3a and SM-4i, a yellow solid 6cd (yield: 43%) was obtained.

Confirmed by MS, ESI-MS [(M+H)$^+$] for 6cd: m/z calculated 880.4. founded 880.5.

Example 77

Synthesis of Compound 6ce

Compound 6ce was prepared by the same coupling reaction procedure as in example 1. By using the reagent SM-3bb (0.2 mmol) and SM-4ai (0.2 mmol) instead of SM-3a and SM-4i, a yellow solid 6ce (yield: 57%) was obtained.

Confirmed by MS, ESI-MS [(M+H)$^+$] for 6ce: m/z calculated 831.4. founded 831.5.

Example 78

Synthesis of Compound 6cf

Compound 6cf was prepared by the same coupling reaction procedure as in example 1. By using the reagent SM-3bd (0.2 mmol) and SM-4aj (0.2 mmol) instead of SM-3a and SM-4i, a yellow solid 6cf (yield: 56%) was obtained.

Confirmed by MS, ESI-MS [(M+H)$^+$] for 6cf: m/z calculated 803.3. founded 803.4.

Example 79

Synthesis of Compound 6cg

Compound 6cg was prepared by the same coupling reaction procedure as in example 1. By using the reagent SM-3bg (0.2 mmol) and SM-4ak (0.2 mmol) instead of SM-3a and SM-4i, a yellow solid 6cg (yield: 52%) was obtained.

Confirmed by MS, ESI-MS [(M+H)$^+$] for 6cg: m/z calculated 763.4. founded 763.5.

Example 80

Synthesis of Compound 6ch

Compound 6ch was prepared by the same coupling reaction procedure as in example 1. By using the reagent SM-3bi (0.2 mmol) and SM-4am (0.2 mmol) instead of SM-3a and SM-4i, a yellow solid 6ch (yield: 53%) was obtained.

Confirmed by MS, ESI-MS [(M+H)$^+$] for 6ch: m/z calculated 735.4. founded 735.5.

Example 81

Synthesis of Compound 6ci

Compound 6ci was prepared by the same coupling reaction procedure as in example 1. By using the reagent SM-3bg (0.2 mmol) and SM-4a (0.2 mmol) instead of SM-3a and SM-4i, a yellow solid 6ci (yield: 53%) was obtained.

Confirmed by MS, ESI-MS [(M+H)$^+$] for 6ci: m/z calculated 750.4. founded 750.5.

Example 82

Synthesis of Compound 6cj

Compound 6cj was prepared by the same coupling reaction procedure as in example 1. By using the reagent SM-3bi (0.2 mmol) and SM-4a (0.2 mmol) instead of SM-3a and SM-4i, a yellow solid 6cj (yield: 59%) was obtained.

Confirmed by MS, ESI-MS [(M+H)$^+$] for 6cj: m/z calculated 736.4. founded 736.5.

Example 83

Synthesis of Compound 6ck

Compound 6ck was prepared by the same coupling reaction procedure as in example 1. By using the reagent SM-3bi (0.2 mmol) and SM-4am (0.2 mmol) instead of SM-3a and SM-4i, a yellow solid 6ck (yield: 53%) was obtained.

Confirmed by MS, ESI-MS [(M+H)$^+$] for 6ck: m/z calculated 735.4. founded 735.5.

Example 84

Synthesis of Compound 6 cm

Compound 6 cm was prepared by the same coupling reaction procedure as in example 1, in which the SM-3a (0.2 mmol) and SM-4an (0.2 mmol) were used instead of SM-3a and SM-4i, and the product 6 cm was obtained as a yellow solid, yield: 54%.

$^1$H-NMR of the product 6 cm (500 MHz, CDCl$_3$): δ 7.74-7.80 (m, 1H), 7.53-7.62 (m, 8H), 7.26-7.28 (m, 3H), 7.18-7.22 (m, 3H), 5.56-5.67 (m, 2H), 5.44 (m, 1H), 4.74-4.94 (m, 5H), 4.34 (m, 1H), 4.23 (m, 1H), 4.08 (m, 1H), 3.85 (m, 1H), 3.67-3.73 (m, 6H), 2.92 (m, 1H), 2.37 (m, 1H), 2.22 (m, 1H), 2.00-2.11 (m, 4H), 0.90-0.91 (m, 12H). ESI-MS [(M+H)$^+$] for 6 cm: m/z calculated 919.4. found 919.5.

Example 85

Synthesis of Compound 6cq

Compound 6cq was prepared by the same coupling reaction procedure as in example 1, in which the SM-3a (0.2 mmol) and SM-4ar (0.2 mmol) were used instead of SM-3a and SM-4i, and the product 6cq was obtained as a yellow solid, yield: 43%.

$^1$H-NMR of the product 6cq (500 MHz, CDCl$_3$): δ 7.46-7.75 (m, 9H), 7.12-7.30 (m, 3H), 6.81-6.87 (m, 2H), 5.64-5.74 (m, 2H), 5.17-5.41 (m, 4H), 4.56-4.93 (m, 5H), 3.94-4.30 (m, 4H), 3.81-3.85 (m, 6H), 3.63-3.65 (m, 6H), 2.83 (m, 1H), 2.33 (m, 1H), 2.17 (m, 1H), 1.96-2.07 (m, 4H), 0.86-0.89 (m, 12H). ESI-MS [(M+H)$^+$] for 6cq: m/z calculated 945.5. found 945.7.

Example 86

Synthesis of Compound 6cu

Compound 6cu was prepared by the same coupling reaction procedure as in example 1, followed by cleavage of Boc group and neutralization workup, in which SM-3a (1.45 mmol) and SM-4av (1.45 mmol) were used instead of SM-3a and SM-4i. The coupling product first obtained (yield: 25%) was subsequently treated with 10 mL 3N HCl/Et$_2$O at room temperature, followed by basification and preparative TLC purification to afford compound 6cu (100 mg) as a yellow solid, yield: 37%.

$^1$H-NMR of the product 6cu (500 MHz, CDCl$_3$): δ 7.50-7.78 (m, 9H), 7.02-7.35 (m, 3H), 5.67 (m, 2H), 5.13-5.26 (m, 2H), 4.69-4.75 (m, 2H), 4.35-4.41 (m, 2H), 4.13-4.14 (m, 1H), 3.88 (m, 1H), 3.71 (s, 6H), 3.35 (m, 1H), 2.18-2.39 (m, 2H), 2.00-2.11 (m, 4H), 0.91 (s, 12H). ESI-MS [(M+H)$^+$] for 6cu: m/z calculated 740.4. found 740.5.

Example 87

Synthesis of Compound 6cv

Compound 6cv was prepared by prepared by the same coupling reaction procedure as in example 1, followed by cleavage of Boc group and neutralization workup, in which SM-3b (0.34 mmol) and SM-4av (0.34 mmol) were used instead of SM-3a and SM-4i. The coupling product first obtained was subsequently treated with 10 mL HCl/Et$_2$O (3N) at room temperature, followed by basification and preparative TLC purification to afford compound 6cv (80 mg) as a yellow solid, yield after two steps: 32%.

ESI-MS [(M+H)$^+$] for 6cv: m/z calculated 738.4. found 738.5.

Example 88

Synthesis of Compound 6cw

Compound 6cw was prepared by the same coupling reaction procedure as in example 1, in which SM-3b (0.34 mmol) and SM-4av (0.34 mmol) were used instead of SM-3a and SM-4i, and the product 6cw was obtained as a yellow solid, yield: 35%.

ESI-MS [(M+H)⁺] for 6cw: m/z calculated 838.4. found 838.6.

Example 89

Synthesis of Compound 6cx

Compound 6cx was prepared by the same coupling reaction procedure as in example 1, followed by cleavage of Boc group, in which SM-3b (0.2 mmol) and SM-4aw (0.2 mmol) were used instead of SM-3a and SM-4i. The coupling product first obtained (13 mg, yield: 10%) was subsequently taken of 10 mg and treated with 10 mL 3N HCl/Et$_2$O at room temperature, followed by vacuum concentration to afford product 6cx (32%).

ESI-MS [(M+H)⁺] for 6cx: m/z calculated 778.5. found 778.6.

Example 90

Synthesis of Compound 6cy

Compound 6cy was prepared by the same coupling reaction procedure as in example 1, in which SM-3b (0.2 mmol) and SM-4aw (0.2 mmol) were used instead of SM-3a and SM-4i, and the product 6cy was obtained as a yellow solid, yield: 23%.

ESI-MS [(M+H)⁺] for 6cy: m/z calculated 878.5. found 878.6.

Example 91

Synthesis of Compound 6cz

Compound 6cz was prepared by the same coupling reaction procedure as in example 1, in which SM-3bj (0.2 mmol) and SM-4b (0.2 mmol) were used instead of SM-3a and SM-4i, and the product 6cz was obtained as a yellow solid, yield: 29%.

¹H-NMR of the product 6cz (500 MHz, CDCl$_3$): δ 7.62-7.78 (m, 10H), 5.98-6.09 (m, 2H), 5.43-5.59 (m, 2H), 4.49-4.60 (m, 4H), 3.70-3.75 (m, 8H), 3.01 (s, 3H), 2.78 (m, 1H), 0.89-0.91 (m, 12H). ESI-MS [(M+H)⁺] for 6cz: m/z calculated 816.3. found 816.5.

Example 92

Synthesis of Compound 6da

Compound 6da was prepared by the same coupling reaction procedure as in example 1, in which SM-3bk (0.2 mmol) and SM-4b (0.2 mmol) were used instead of SM-3a and SM-4i, and the product 6da was obtained as a yellow solid, yield: 32%.

ESI-MS [(M+H)⁺] for 6da: m/z calculated 842.4. found 842.5.

Example 93

Synthesis of Compound 6db

Compound 6db was prepared by the same coupling reaction procedure as in example 1, in which SM-3bm (0.2 mmol) and SM-4b (0.2 mmol) were used instead of SM-3a and SM-4i, and the product 6db was obtained as a yellow solid, yield: 22%.

ESI-MS [(M+H)⁺] for 6db: m/z calculated 796.4. found 796.6.

Example 94

Synthesis of Compound 6dc

Compound 6dc was prepared by the same coupling reaction procedure as in example 1, in which SM-3bn (0.2 mmol) and SM-4b (0.2 mmol) were used instead of SM-3a and SM-4i, and the product 6dc was obtained as a yellow solid, yield: 33%.

ESI-MS [(M+H)⁺] for 6dc: m/z calculated 824.4. found 824.5.

Example 95

Synthesis of Compound 6dd

Compound 6dd was prepared by the same coupling reaction procedure as in example 1, in which SM-3 bp (0.2 mmol) and SM-4b (0.2 mmol) were used instead of SM-3a and SM-4i, and the product 6dd was obtained as a yellow solid, yield: 28%.

ESI-MS [(M+H)⁺] for 6dd: m/z calculated 844.4. found 844.5.

Example 96

Synthesis of Compound 6de

Compound 6de was prepared by the same coupling reaction procedure as in example 1, in which SM-3bf (0.2 mmol) and SM-4a (0.2 mmol) were used instead of SM-3a and SM-4i, and the product 6de was obtained as a yellow solid, yield: 35%.

¹H-NMR of the product 6de (500 MHz, CDCl$_3$): δ 7.81 (m, 1H), 7.53-7.59 (m, 8H), 7.34 (s, 1H), 7.24 (s, 1H), 7.19 (s, 1H), 5.55-5.56 (d, J=8.5 Hz, 1H), 5.10-5.12 (d, J=8.5 Hz, 1H), 4.48-4.51 (t, J=7.5 Hz, 1H), 4.33-4.36 (m, 1H), 3.97 (m, 1H), 3.85 (m, 1H), 3.70 (s, 3H), 3.45 (m, 1H), 3.14 (m, 1H), 2.95 (s, 6H). 2.34-2.39 (m, 2H), 2.19-2.24 (m, 2H), 1.97-2.10 (m, 6H), 0.86-0.91 (m, 12H). ESI-MS [(M+H)⁺] for 6de: m/z calculated 752.4. found 752.5.

Example 97

Synthesis of Compound 6df

Compound 6df was prepared by the same coupling reaction procedure as in example 1, in which SM-3bf (0.2 mmol) and SM-4b (0.2 mmol) were used instead of SM-3a and SM-4i, and the product 6df was obtained as a yellow solid, yield: 35%.

¹H-NMR of the product 6df (500 MHz, CDCl$_3$): δ 7.82-7.86 (m, 1H), 7.54-7.68 (m, 8H), 7.34 (s, 1H), 7.19-7.23 (m, 2H), 6.24-6.28 (m, 1H), 5.98-6.08 (m, 2H), 5.44-5.53 (m, 1H), 5.26 (m, 1H), 5.08-5.09 (m, 1H), 4.71 (m, 1H), 4.49-4.51 (m, 1H), 4.28-4.34 (m, 1H), 3.94-3.95 (m, 1H), 3.70 (s, 3H), 3.43 (m, 1H), 3.15 (m, 1H), 2.92 (s, 6H), 1.97-2.20 (m, 6H), 1.05-1.10 (m, 6H), 0.88 (s, 6H). ESI-MS [(M+H)⁺] for 6df: m/z calculated 750.4. found 750.5.

Example 98

Synthesis of Compound 6dg

Compound 6dg was prepared by the same coupling reaction procedure as in example 1, in which SM-3b (0.2 mmol)

and SM-4ax (0.2 mmol) were used instead of SM-3a and SM-4i, and the product 6dg was obtained as a yellow solid, yield: 36%.

$^1$H-NMR of the product 6dg (500 MHz, CDCl$_3$): δ 7.10-7.71 (m, 17H), 5.97-6.15 (m, 3H), 5.41-5.55 (m, 3H), 4.73 (m, 1H), 4.48-4.55 (m, 1H), 4.26 (m, 1H), 4.03 (m, 1H), 3.69 (s, 3H), 3.30 (m, 1H), 2.72 (m, 1H), 2.44 (s, 3H), 1.97-2.27 (m, 6H), 0.88-0.99 (m, 6H). ESI-MS [(M+H)$^+$] for 6dg: m/z calculated 770.4. found 770.5.

Example 99

Synthesis of Compound 6dh

Compound 6dh was prepared by the same coupling reaction procedure as in example 1, in which SM-3bq (0.2 mmol) and SM-4a (0.2 mmol) were used instead of SM-3a and SM-4i, and the product 6dh was obtained as a yellow solid, yield: 22%.

ESI-MS [(M+H)$^+$] for 6dh: m/z calculated 763.4. found 763.5.

Example 100

Synthesis of Compound 6di

Compound 6di was prepared by the same coupling reaction procedure as in example 1, in which SM-3br (0.2 mmol) and SM-4a (0.2 mmol) were used instead of SM-3a and SM-4i, and the product 6di was obtained as a yellow solid, yield: 38%.

ESI-MS [(M+H)$^+$] for 6di: m/z calculated 777.4. found 777.4.

Example 101

Synthesis of Compound 6dj

Compound 6dj was prepared by the same coupling reaction procedure as in example 1, in which SM-3bs (0.2 mmol) and SM-4a (0.2 mmol) were used instead of SM-3a and SM-4i, and the product 6dj was obtained as a yellow solid, yield: 46%.

$^1$H-NMR of the product 6dj (500 MHz, CDCl$_3$): δ 7.59-7.47 (m, 10H), 6.26 (m, 1H), 6.08 (m, 1H), 5.99 (m, 1H), 5.26 (s, 1H), 4.77 (m, 1H), 4.54 (m, 1H), 4.35 (m, 1H), 4.28 (m, 1H), 3.87 (m, 1H), 3.73 (s, 6H), 2.39 (m, 2H), 2.21-1.69 (m, 14H), 1.26 (d, 6H). ESI-MS [(M+H)$^+$] for 6dj: m/z calculated 777.4. found 777.5.

Example 102

Synthesis of Compound 6dk

Compound 6dk was prepared by the same coupling reaction procedure as in example 1, in which SM-3br (0.2 mmol) and SM-4ay (0.2 mmol) were used instead of SM-3a and SM-4i, and the product 6dk was obtained as a yellow solid, yield: 36%.

ESI-MS [(M+H)$^+$] for 6dk: m/z calculated 817.4. found 817.6.

Example 103

Synthesis of Compound 6dm

Compound 6dm was prepared by the same coupling reaction procedure as in example 1, in which SM-3br (0.2 mmol) and SM-4az (0.2 mmol) were used instead of SM-3a and SM-4i, and the product 6dm was obtained as a yellow solid, yield: 38%.

ESI-MS [(M+H)$^+$] for 6dm: m/z calculated 815.4. found 815.5.

Example 104

Synthesis of Compound 6dn

Compound 6dn was prepared by the same coupling reaction procedure as in example 1, in which SM-3bq (0.2 mmol) and SM-4ay (0.2 mmol) were used instead of SM-3a and SM-4i, and the product 6dn was obtained as a yellow solid, yield: 30%.

ESI-MS [(M+H)$^+$] for 6dn: m/z calculated 803.4. found 803.5.

Example 105

Synthesis of Compound 6dp

Compound 6dp was prepared by the same coupling reaction procedure as in example 1, in which SM-3bq (0.2 mmol) and SM-4ba (0.2 mmol) were used instead of SM-3a and SM-4i, and the product 6dp was obtained as a yellow solid, yield: 28%.

$^1$H-NMR of the product 6dp (500 MHz, CDCl$_3$): δ 8.02 (s, 1H), 7.85-7.55 (m, 9H), 6.34 (m, 1H), 6.09 (m, 1H), 5.99 (m, 1H), 5.42 (m, 1H), 5.36 (m, 1H), 4.81 (m, 1H), 4.44 (m, 1H), 4.38 (m, 1H), 3.90 (m, 1H), 3.71 (s, 6H), 3.50 (m, 1H), 2.34-2.01 (m, 16H). ESI-MS [(M+H)$^+$] for 6dp: m/z calculated 789.4. found 789.5.

Example 106

Synthesis of Compound 6dq

Compound 6dq was prepared by the same coupling reaction procedure as in example 1, in which SM-3bt (0.2 mmol) and SM-4b (0.2 mmol) were used instead of SM-3a and SM-4i, and the product 6dq was obtained as a yellow solid, yield: 36%.

$^1$H-NMR of the product 6dq (500 MHz, CDCl$_3$): δ 7.53-7.22 (m, 8H), 6.21 (m, 1H), 6.10 (m, 1H), 6.03 (m, 1H), 5.46 (m, 1H), 5.39 (m, 1H), 4.74 (m, 1H), 4.60 (m, 1H), 4.32 (m, 1H), 4.21 (m, 1H), 3.99 (m, 1H), 3.86 (m, 1H), 3.72 (s, 3H), 3.69 (s, 3H), 2.62 (m, 1H), 2.44 (m, 1H), 2.06-1.72 (m, 6H), 1.26 (d, 12H). ESI-MS [(M+H)$^+$] for 6dq: m/z calculated 753.4. found 753.5.

Example 107

Synthesis of Compound 6dr

Compound 6dr was prepared by the same coupling reaction procedure as in example 1, in which SM-3bu (0.2 mmol) and SM-4b (0.2 mmol) were used instead of SM-3a and SM-4i, and the product 6dr was obtained as a yellow solid, yield: 33%.

ESI-MS [(M+H)$^+$] for 6dr: m/z calculated 753.4. found 753.5.

Example 108

Synthesis of Compound 6ds

Compound 6ds was prepared by the same coupling reaction procedure as in example 1, in which SM-3bv (0.2 mmol)

and SM-4a (0.2 mmol) were used instead of SM-3a and SM-4i, and the product 6ds was obtained as a yellow solid, yield: 38%.

ESI-MS [(M+H)$^+$] for 6ds: m/z calculated 797.4. found 797.5.

Example 109

Synthesis of Compound 6dt

Compound 6dt was prepared by the same coupling reaction procedure as in example 1, in which SM-3bv (0.2 mmol) and SM-4b (0.2 mmol) were used instead of SM-3a and SM-4i, and the product 6dt was obtained as a yellow solid, yield: 41%.

ESI-MS [(M+H)$^+$] for 6dt: m/z calculated 795.4. found 795.5.

Example 110

Synthesis of Compound 6du

Compound 6du was prepared by the same coupling reaction procedure as in example 1, in which SM-3bw (0.2 mmol) and SM-4b (0.2 mmol) were used instead of SM-3a and SM-4i, and the product 6du was obtained as a yellow solid, yield: 39%.

$^1$H-NMR of the product 6du (500 MHz, CDCl$_3$): δ 7.16-7.82 (m, 15H), 5.98-6.26 (m, 3H), 5.35-5.53 (m, 1H), 4.71-4.74 (m, 1H), 4.48-4.51 (m, 1H), 3.91-4.04 (m, 6H), 3.62-3.69 (m, 8H), 2.47-2.38 (m, 1H), 2.04-2.08 (m, 1H), 1.69-2.00 (m, 1H), 1.05-0.87 (m, 6H). ESI-MS [(M+H)$^+$] for 6du: m/z calculated 829.4. found 829.5.

Example 111

Synthesis of Compound 6dv

Compound 6dv was prepared by the same coupling reaction procedure as in example 1, in which SM-3bw (0.2 mmol) and SM-4ah (0.2 mmol) were used instead of SM-3a and SM-4i, and the product 6dv was obtained as a yellow solid, yield: 34%.

ESI-MS [(M+H)$^+$] for 6dv: m/z calculated 863.3. found 863.5.

Example 112

Synthesis of Compound 6dw

Compound 6dw was prepared by the same coupling reaction procedure as in example 1, in which SM-3bv (0.2 mmol) and SM-4ah (0.2 mmol) were used instead of SM-3a and SM-4i, and the product 6dv was obtained as a yellow solid, yield: 37%.

ESI-MS [(M+H)$^+$] for 6dw: m/z calculated 829.4. found 829.4.

Example 113

Synthesis of Compound 6dy

Compound 6dy was prepared by the same coupling reaction procedure as in example 1, in which SM-3ay (0.2 mmol) and SM-4a (0.2 mmol) were used instead of SM-3a and SM-4i, and the product 6dy was obtained as a yellow solid, yield: 42%.

$^1$H-NMR of the product 6dy (500 MHz, CDCl$_3$): δ 7.65-7.18 (m, 15H), 6.23 (m, 1H), 6.01 (m, 1H), 5.89 (m, 1H), 5.50 (m, 1H), 5.39 (m, 1H), 5.25 (m, 1H), 4.52 (m, 1H), 4.34 (m, 1H), 4.12 (m, 1H), 3.84 (m, 1H), 3.67 (s, 3H), 3.61 (s, 3H), 2.34-1.83 (m, 6H), 1.23 (d, 6H). ESI-MS [(M+H)$^+$] for 6dy: m/z calculated 771.4. found 771.4.

Example 114

Synthesis of Compound 6dz

Compound 6dz was prepared by the same coupling reaction procedure as in example 1, in which SM-3ck (0.2 mmol) and SM-4bf (0.2 mmol) were used instead of SM-3a and SM-4i, and the product 6dy was obtained as a yellow solid, yield: 38%.

$^1$H-NMR of the product 6dz (500 MHz, CDCl$_3$): δ 7.71-7.40 (m, 20H), 6.28 (m, 1H), 6.04 (m, 1H), 5.99 (m, 1H), 5.50 (m, 1H), 5.39 (m, 1H), 4.54 (m, 1H), 4.12 (m, 1H), 3.98 (m, 1H), 3.68 (s, 3H), 3.65 (s, 3H), 2.23-1.82 (m, 6H). ESI-MS [(M+H)$^+$] for 6dz: m/z calculated 805.3. found 805.5.

Example 115

Synthesis of Compound 6ea

Compound 6ea was prepared by the same coupling reaction procedure as in example 1, in which SM-3ay (0.2 mmol) and SM-4b (0.2 mmol) were used instead of SM-3a and SM-4i, and the product 6ea was obtained as a yellow solid, yield: 33%.

$^1$H-NMR of the product 6ea (500 MHz, CDCl$_3$): δ 7.67-7.20 (m, 13H), 6.26 (s, 1H), 6.15 (s, 1H), 6.08 (m, 1H), 5.99 (m, 1H), 5.59 (m, 1H), 5.46 (m, 1H), 5.31 (m, 1H), 4.76 (m, 1H), 4.48 (m, 1H), 4.30 (m, 1H), 3.70 (s, 3H), 3.65 (s, 3H), 3.22 (m, 1H), 2.24-1.92 (m, 6H), 1.26 (d, 6H). ESI-MS [(M+H)$^+$] for 6ea: m/z calculated 771.4. found 771.5.

Example 116

Synthesis of Compound 6eb

Compound 6eb was prepared by the same coupling reaction procedure as in example 1, in which SM-3bx (0.2 mmol) and SM-4b (0.2 mmol) were used instead of SM-3a and SM-4i, and the product 6eb was obtained as a yellow solid, yield: 37%.

ESI-MS [(M+H)$^+$] for 6eb: m/z calculated 737.4. found 737.4.

Example 117

Synthesis of Compound 6ec

Compound 6eb was prepared by the same coupling reaction procedure as in example 1, in which SM-3by (0.2 mmol) and SM-4b (0.2 mmol) were used instead of SM-3a and SM-4i, and the product 6ec (30 mg) was obtained as a yellow solid, yield: 43%.

ESI-MS [(M+H)$^+$] for 6ec: m/z calculated 737.4. found 737.5.

Example 118

Synthesis of Compound 6ej

Compound 6ej was prepared by the same coupling reaction procedure as in example 1, in which SM-3ci (0.2 mmol) and SM-4bd (0.2 mmol) were used instead of SM-3a and SM-4i, and the product 6ej (76 mg) was obtained as a yellow solid, yield: 43%.

ESI-MS [(M+H)$^+$] for 6ej: m/z calculated 880.4. found 880.5.

Example 119

Synthesis of Compound 6ek

Compound 6ek was prepared by the same coupling reaction procedure as in example 1, in which SM-3cq (0.2 mmol) and SM-4b (0.2 mmol) were used instead of SM-3a and SM-4i, and the product 6ek (81 mg) was obtained as a yellow solid, yield: 46%.

ESI-MS [(M+H)$^+$] for 6ek: m/z calculated 881.5. found 881.5.

Example 120

Synthesis of Compound 6em

Compound 6em was prepared by the same coupling reaction procedure as in example 1, in which SM-3cq (0.2 mmol) and SM-4bf (0.2 mmol) were used instead of SM-3a and SM-4i, and the product 6em (75 mg) was obtained as a yellow solid, yield: 41%.

ESI-MS [(M+H)$^+$] for 6em: m/z calculated 915.5. found 915.5.

Example 121

Synthesis of Compound 6en

Compound 6en was prepared by the same coupling reaction procedure as in example 1, in which SM-3cr (0.2 mmol) and SM-4bg (0.2 mmol) were used instead of SM-3a and SM-4i, and the product 6en (94 mg) was obtained as a yellow solid, yield: 54%.

ESI-MS [(M+H)$^+$] for 6en: m/z calculated 869.5. found 869.5.

Example 122

Synthesis of Compound 6ep

Compound 6ep was prepared by the same coupling reaction procedure as in example 1, in which SM-3by (0.2 mmol) and SM-4b (0.2 mmol) were used instead of SM-3a and SM-4i, and the product 6ep (71 mg) was obtained as a yellow solid, yield: 39%.

ESI-MS [(M+H)$^+$] for 6ej: m/z calculated 903.5. found 903.5.

Example 123

Synthesis of Compound 6fa

Compound 6fa was prepared by the same coupling reaction procedure as in example 1. By using the reagent SM-3au (0.2 mmol) and SM-4a (0.2 mmol) instead of SM-3a and SM-4i, a yellow solid 6fa was obtained (105 mg, yield: 53%).

Confirmed by MS, ESI-MS [(M+H)$^+$] for 6fa: m/z calculated 991.3. founded 991.4.

Example 124

Synthesis of Compound 6fb

Compound 6th was prepared by the same coupling reaction procedure as in example 1. By using the reagent SM-3av (0.2 mmol) and SM-4ad (0.2 mmol) instead of SM-3a and SM-4i, a yellow solid 6fb was obtained (98 mg, yield: 47%).

Confirmed by MS, ESI-MS [(M+H)$^+$] for 6fb: m/z calculated 1025.3. founded 1025.4.

Example 125

Synthesis of Compound 6fc

Compound 6fc was prepared by the same coupling reaction procedure as in example 1. By using the reagent SM-3ba (0.2 mmol) and SM-4ah (0.2 mmol) instead of SM-3a and SM-4i, a yellow solid 6fc was obtained (87 mg, yield: 52%).

Confirmed by MS, ESI-MS [(M+H)$^+$] for 6fc: m/z calculated 833.3. founded 833.4.

Example 126

Synthesis of Compound 6fd

Compound 6fd was prepared by the same coupling reaction procedure as in example 1. By using the reagent SM-3av (0.2 mmol) and SM-4ah (0.2 mmol) instead of SM-3a and SM-4i, a yellow solid 6fd was obtained (83 mg, yield: 48%).

Confirmed by MS, ESI-MS [(M+H)$^+$] for 6fd: m/z calculated 867.2. founded 867.3.

Example 127

Synthesis of Compound 6fe

Compound 6fe was prepared by the same coupling reaction procedure as in example 1. By using the reagent SM-3aw (0.2 mmol) and SM-4ah (0.2 mmol) instead of SM-3a and SM-4i, a yellow solid 6fe was obtained (95 mg, yield: 54%).

Confirmed by MS, ESI-MS [(M+H)$^+$] for 6fe: m/z calculated 865.2. founded 865.3.

Example 128

Synthesis of Compound 6ff

Compound 6ff was prepared by the same coupling reaction procedure as in example 1. By using the reagent SM-3cb (0.2 mmol) and SM-4b (0.2 mmol) instead of SM-3a and SM-4i, a yellow solid 6ff was obtained (69 mg, yield: 43%).

Confirmed by MS, ESI-MS [(M+H)$^+$] for 6ff: m/z calculated 865.3. founded 865.3.

Example 129

Synthesis of Compound 6fg

Compound 6fg was prepared by the same coupling reaction procedure as in example 1. By using the reagent SM-3cn (0.2 mmol) and SM-4b (0.2 mmol) instead of SM-3a and SM-4i, a yellow solid 6fg was obtained (32 mg, yield: 20%).

¹H NMR for the product 6fg (500 MHz, CDCl₃): δ 7.39-7.10 (m, 8H), 6.09 (s, 1H), 5.99 (s, 1H), 5.49 (s, 1H), 5.25 (s, 1H), 4.74 (m, 1H), 4.38 (m, 1H), 4.32 (m, 1H), 3.91 (s, 1H), 3.71 (s, 6H), 2.38 (m, 2H), 2.19 (m, 2H), 2.09-2.07 (m, 4H), 1.28 (s, 6H), 1.27 (s, 6H). Confirmed by MS, ESI-MS [(M+H)⁺] for 6fg: m/z calculated 799.3. founded 799.3.

Example 130

Synthesis of Compound 6fh

Compound 6fh was prepared by the same coupling reaction procedure as in example 1. By using the reagent SM-3 cm (0.2 mmol) and SM-4bf (0.2 mmol) instead of SM-3a and SM-4i, a yellow solid 6fh was obtained (46 mg, yield: 26%).
¹H NMR for the product 6fh (500 MHz, CDCl₃): δ 7.92-7.27 (m, 18H), 6.24 (s, 1H), 6.19 (s, 1H), 5.97 (s, 1H), 5.89 (s, 1H), 5.48 (m, 1H), 5.28 (s, 1H), 4.55 (m, 1H), 4.10 (s, 1H), 3.76 (s, 6H), 2.32-2.03 (m, 6H). Confirmed by MS, ESI-MS [(M+H)⁺] for 6fh: m/z calculated 867.3. founded 867.3.

Example 131

Synthesis of Compound 6fi

Compound 6fi was prepared by the same coupling reaction procedure as in example 1. By using the reagent SM-3 cm (0.2 mmol) and SM-4b (0.2 mmol) instead of SM-3a and SM-4i, a yellow solid 6fi was obtained (59 mg, yield: 25%).
¹H NMR for the product 6fi (500 MHz, CDCl₃): δ 7.46-7.41 (m, 13H), 6.20 (s, 1H), 6.09 (s, 1H), 5.99 (s, 1H), 5.51 (m, 1H), 5.31 (m, 1H), 4.78 (m, 1H), 4.57 (m, 1H), 4.31 (m, 1H), 3.70 (s, 6H), 3.24 (m, 1H), 2.24-1.92 (m, 6H), 1.28 (s, 6H). Confirmed by MS, ESI-MS [(M+H)⁺] for 6fi: m/z calculated 833.3. founded 833.3.

Example 132

Synthesis of Compound 6fj

Compound 6fj was prepared by the same coupling reaction procedure as in example 1. By using the reagent SM-3cn (0.2 mmol) and SM-4bf (0.2 mmol) instead of SM-3a and SM-4i, a yellow solid 6fj was obtained (53 mg, yield: 35%).
¹H NMR for the product 6fj (500 MHz, CDCl₃): δ 7.47-7.32 (m, 13H), 6.16 (s, 1H), 5.98 (s, 1H), 5.92 (s, 1H), 5.53 (m, 1H), 5.47 (m, 1H), 5.23 (m, 1H), 4.61 (m, 1H), 4.37 (m, 1H), 3.88 (m, 1H), 3.74 (s, 6H), 2.34-2.03 (m, 6H), 1.27 (s, 6H). Confirmed by MS, ESI-MS [(M+H)⁺] for 6fj: m/z calculated 833.3. founded 833.3.

Example 133

Synthesis of Compound 6fk

Compound 6fk was prepared by the same coupling reaction procedure as in example 1. By using the reagent SM-3cp (0.2 mmol) and SM-4be (0.2 mmol) instead of SM-3a and SM-4i, a yellow solid 6fk was obtained (40 mg, yield: 26%).
¹H NMR for the product 6fk (500 MHz, CDCl₃): δ 7.46-7.31 (m, 18H), 6.27 (s, 1H), 6.12 (s, 1H), 5.99 (s, 1H), 5.90 (s, 1H), 5.52 (m, 1H), 5.33 (s, 1H), 4.53 (m, 1H), 4.11 (s, 1H), 3.69 (s, 6H), 2.34-1.99 (m, 6H). Confirmed by MS, ESI-MS [(M+H)⁺] for 6fk: m/z calculated 867.3. founded 867.3.

Example 134

Synthesis of Compound 6fm

Compound 6fm was prepared by the same coupling reaction procedure as in example 1. By using the reagent SM-3cp (0.2 mmol) and SM-4a (0.2 mmol) instead of SM-3a and SM-4i, a yellow solid 6fm was obtained (81 mg, yield: 48%).
¹H NMR for the product 6fm (500 MHz, CDCl₃): δ 7.47-7.40 (m, 13H), 6.24 (s, 1H), 5.97 (s, 1H), 5.90 (s, 1H), 5.58 (m, 1H), 5.27 (s, 1H), 4.62 (m, 1H), 4.36 (m, 1H), 4.12 (m, 1H), 3.88 (m, 1H), 3.73 (s, 6H), 2.18-2.02 (m, 6H), 1.26 (s, 6H). Confirmed by MS, ESI-MS [(M+H)⁺] for 6fm: m/z calculated 833.3. founded 833.3.

Example 135

Synthesis of Compound 6fn

Compound 6fn was prepared by the same coupling reaction procedure as in example 1. By using the reagent SM-3cb (0.2 mmol) and SM-4a (0.2 mmol) instead of SM-3a and SM-4i, a yellow solid 6fn was obtained (63 mg, yield: 38%).
¹H NMR for the product 6fn (500 MHz, CDCl₃): δ 7.55-7.13 (m, 8H), 6.07 (s, 1H), 5.98 (s, 1H), 5.57 (s, 1H), 5.28 (s, 1H), 4.79 (m, 1H), 4.60 (m, 1H), 4.39 (m, 1H), 4.33 (s, 1H), 3.73 (s, 6H), 2.39 (m, 1H), 2.25 (m, 1H), 2.11-2.07 (m, 6H), 1.07 (s, 6H), 0.94 (s, 6H). Confirmed by MS, ESI-MS [(M+H)⁺] for 6fn: m/z calculated 799.3. founded 799.3.

Example 136

Synthesis of Compound 6fp

Compound 6fp was prepared by the same coupling reaction procedure as in example 1. By using the reagent SM-3cb (0.2 mmol) and SM-4be (0.2 mmol) instead of SM-3a and SM-4i, a yellow solid 6fp was obtained (59 mg, yield: 35%).
¹H NMR for the product 6fp (500 MHz, CDCl₃): δ 7.45-7.39 (m, 13H), 6.18 (s, 1H), 6.06 (s, 1H), 5.95 (s, 1H), 5.61 (m, 1H), 5.30 (m, 1H), 4.77 (m, 1H), 4.56 (m, 1H), 4.30 (m, 1H), 3.70 (s, 3H), 3.63 (s, 3H), 3.22 (s, 1H), 2.25-1.91 (m, 6H), 1.26 (s, 6H). Confirmed by MS, ESI-MS [(M+H)⁺] for 6fp: m/z calculated 833.3. founded 833.3.

Example 137

Synthesis of Compound 6fq

Compound 6fq was prepared by the same coupling reaction procedure as in example 1. By using the reagent SM-3cc (0.2 mmol) and SM-4b (0.2 mmol) instead of SM-3a and SM-4i, a yellow solid 6fq was obtained (61 mg, yield: 37%).
Confirmed by MS, ESI-MS [(M+H)⁺] for 6fq: m/z calculated 799.3. founded 799.4.

Example 138

Synthesis of Compound 6fr

Compound 6fr was prepared by the same coupling reaction procedure as in example 1. By using the reagent SM-3cc (0.2 mmol) and SM-4bf (0.2 mmol) instead of SM-3a and SM-4i, a yellow solid 6fr was obtained (59 mg, yield: 35%).

Confirmed by MS, ESI-MS [(M+H)+] for 6fr: m/z calculated 833.3. founded 833.3.

Example 139

Synthesis of Compound 6fs

Compound 6fs was prepared by the same coupling reaction procedure as in example 1. By using the reagent SM-3cd (0.2 mmol) and SM-4bf (0.2 mmol) instead of SM-3a and SM-4i, a yellow solid 6fs was obtained (57 mg, yield: 32%).
Confirmed by MS, ESI-MS [(M+H)+] for 6fs: m/z calculated 867.3. founded 867.5.

Example 140

Synthesis of Compound 6 ft

Compound 6 ft was prepared by the same coupling reaction procedure as in example 1. By using the reagent SM-3cd (0.2 mmol) and SM-4b (0.2 mmol) instead of SM-3a and SM-4i, a yellow solid 6 ft was obtained (57 mg, yield: 34%).
$^1$H NMR for the product 6 ft (500 MHz, CDCl$_3$): δ 7.20-7.66 (m, 13H), 5.99-6.26 (m, 3H), 5.56-5.58 (m, 1H), 5.31-5.32 (m, 1H), 4.73-4.76 (m, 2H), 4.49-4.51 (m, 1H), 3.79-3.82 (m, 2H), 3.68-3.71 (m, 5H), 3.54 (s, 3H), 1.93-2.04 (m, 5H), 0.90-0.91 (m, 6H). Confirmed by MS, ESI-MS [(M+H)+] for 6 ft: m/z calculated 833.3. founded 833.5.

Example 141

Synthesis of Compound 6fu

Compound 6fu was prepared by the same coupling reaction procedure as in example 1. By using the reagent SM-3ce (0.2 mmol) and SM-4bf (0.2 mmol) instead of SM-3a and SM-4i, a yellow solid 6fu was obtained (60 mg, yield: 37%).
Confirmed by MS, ESI-MS [(M+H)+] for 6fu: m/z calculated 817.3. founded 817.3.

Example 142

Synthesis of Compound 6fv

Compound 6fv was prepared by the same coupling reaction procedure as in example 1. By using the reagent SM-3cf (0.2 mmol) and SM-4b (0.2 mmol) instead of SM-3a and SM-4i, a yellow solid 6fv was obtained (52 mg, yield: 32%).
Confirmed by MS, ESI-MS [(M+H)+] for 6fv: m/z calculated 817.3. founded 817.3.

Example 143

Synthesis of Compound 6fw

Compound 6fw was prepared by the same coupling reaction procedure as in example 1. By using the reagent SM-3cf (0.2 mmol) and SM-4bf (0.2 mmol) instead of SM-3a and SM-4i, a yellow solid 6fw was obtained (55 mg, yield: 32%).
Confirmed by MS, ESI-MS [(M+H)+] for 6fw: m/z calculated 851.3. founded 851.3.

Example 144

Synthesis of Compound 6fx

Compound 6fx was prepared by the same coupling reaction procedure as in example 1. By using the reagent SM-3cg (0.2 mmol) and SM-4bf (0.2 mmol) instead of SM-3a and SM-4i, a yellow solid 6fx was obtained (67 mg, yield: 39%).
Confirmed by MS, ESI-MS [(M+H)+] for 6fx: m/z calculated 850.3. founded 850.4.

Example 145

Synthesis of Compound 6fy

Compound 6fy was prepared by the same coupling reaction procedure as in example 1. By using the reagent SM-3ch (0.2 mmol) and SM-4be (0.2 mmol) instead of SM-3a and SM-4i, a yellow solid 6fy was obtained (198 mg, yield: 48%).
Confirmed by MS, ESI-MS [(M+H)+] for 6fy: m/z calculated 833.3. founded 833.4.

Example 146

Synthesis of Compound Ref-3

Compound Ref-3 was prepared by the same coupling reaction procedure as in example 1. By using the reagent SM-3 cm (0.2 mmol) and SM-4be (0.2 mmol) instead of SM-3a and SM-4i, a yellow solid Ref-3 was obtained (69 mg, yield: 40%).
$^1$H NMR for the product Ref-3 (500 MHz, CDCl$_3$): δ 10.53 (s, 1H), 7.75-7.14 (m, 17H), 6.13 (m, 2H), 5.46 (m, 2H), 5.31 (m, 2H), 3.80 (m, 6H), 3.23 (m, 2H), 2.91 (m, 2H), 2.23-1.67 (m, 12H). Confirmed by MS, ESI-MS [(M+H)+] for Ref-3: m/z calculated 869.3. Founded 869.3.

What is claimed is:

1. A compound represented by the formula Ib, or a stereoisomer, tautomer, esterification or amidation prodrug or pharmaceutically acceptable salt thereof:

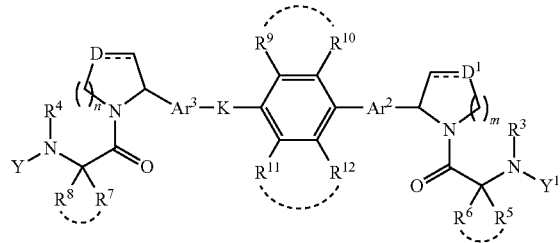

Ib wherein
m=1, 2 or 3;
n=1, 2 or 3;
each dashed line " ----- " is, independently, a single bond or double bond,
wherein at least one of the dashed line connecting D to the adjacent carbon atom and the dashed line connecting D$^1$ to the adjacent carbon atom is a double bond,
wherein when the dashed line connecting D to the adjacent carbon atom is a single bond D is selected from the group consisting of O, S, N(Ra), CH$_2$, CH(OH), and C(Rb)(Rc),
wherein when the dashed line connecting D to the adjacent carbon atom is a double bond D is selected from the group consisting of N, CH, and C(Rb),
wherein when the dashed line connecting D$^1$ to the adjacent carbon atom is a single bond D$^1$ is selected from the group consisting of O, S, N(Ra), CH$_2$, CH(OH), and C(Rb)(Rc), and wherein when the dashed line connecting $D^1$ to the adjacent carbon atom is a double bond $D^1$ is selected from the group consisting of N, CH, and C(Rb);

Ra is H, hydroxyl, $C_1$-$C_{20}$ alkyl, $C_1$-$C_{20}$ cycloalkyl, $C_6$-$C_{20}$ aryl, $C_2$-$C_{20}$ heteroaryl, $C_1$-$C_{20}$ alkoxycarbonyl, $C_3$-$C_{20}$ cycloalkyloxycarbonyl, $C_6$-$C_{20}$ aryloxycarbonyl, $C_2$-$C_{20}$ heterocyclo-oxycarbonyl, $C_1$-$C_{20}$ alkylaminocarbonyl, $C_3$-$C_{20}$ cycloalkylamino-carbonyl, $C_1$-$C_{20}$ alkylamino sulfonamido, $C_2$-$C_{20}$ heterocyclo-aminosulfonyl, or $C_6$-$C_{20}$ arylaminosulfonyl;

Rb and Rc are each, independently, selected from the group consisting of H, halogen, hydroxy, cyano, $C_1$-$C_{20}$ alkyl, $C_3$-$C_{20}$ cycloalkyl, $C_2$-$C_{20}$ heterocyclo, $C_6$-$C_{20}$ aryl, $C_1$-$C_{20}$ alkoxy, $C_1$-$C_{20}$ alkylthio, $C_1$-$C_{20}$ alkoxycarbonyl, $C_6$-$C_{20}$ aryloxy, $C_6$-$C_{20}$ heteroaryloxy, $C_6$-$C_{20}$ fused aryloxy, $C_6$-$C_{20}$ fused heterocyclo-oxy, $C_6$-$C_{20}$ aryloxycarbonyl, $C_2$-$C_{20}$ heterocyclo oxycarbonyl, $C_2$-$C_{20}$ heteroaryl, $C_1$-$C_{20}$ alkylamino, $C_2$-$C_{20}$ heterocycloamino, $C_6$-$C_{20}$ arylamino, $C_1$-$C_{20}$ alkylaminocarbonyl, $C_1$-$C_{20}$ alkylcarbonylamino, $C_1$-$C_{20}$ alkylsulfonamido, $C_2$-$C_{20}$ heterocyclosulfonamido, $C_6$-$C_{20}$ arylsulfonamido, and $C_1$-$C_{20}$ alkylaminosulfonamido;

or Rb and Rc may be linked to form a $C_2$-$C_{20}$ cycloalkyl, $C_2$-$C_{20}$ cycloalkenyl, or $C_1$-$C_{20}$ cycloethereal group;

$Ar^2$ and $Ar^3$ are each, independently, selected from the group consisting of $C_6$-$C_{20}$ aryl, $C_2$-$C_{20}$ heteroaryl, $C_8$-$C_{20}$ fused aryl, and $C_4$-$C_{20}$ fused heteroaryl, K is $C_2$-$C_{20}$ mono-heteroaryl, $C_2$-$C_{20}$ poly-heteroaryl, or $C_2$-$C_{20}$ fused-heteroaryl represented by one of the following structures:

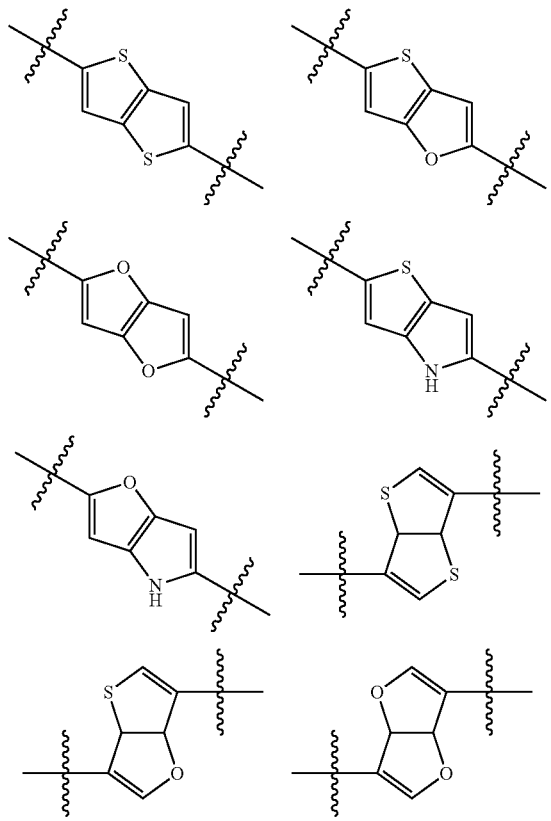

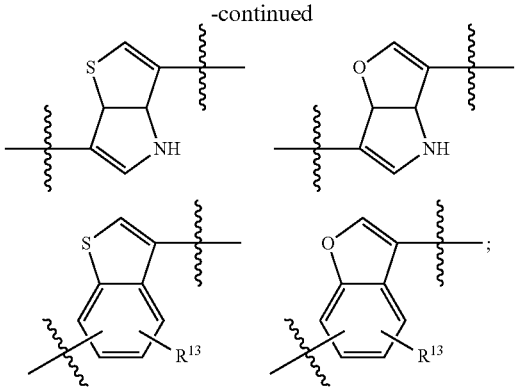

Y and $Y^1$ are each, independently, selected from the group consisting of H, $C_1$-$C_{20}$ alkyl, $C_3$-$C_{20}$ cycloalkyl, $C_6$-$C_{20}$ aryl, $C_1$-$C_{20}$ alkylcarbonyl, $C_6$-$C_{20}$ arylcarbonyl, $C_2$-$C_{20}$ heterocycloalkylcarbonyl, $C_1$-$C_{20}$ alkoxycarbonyl, $C_1$-$C_{20}$ cycloalkyl-oxy-carbonyl, $C_6$-$C_{20}$ aryloxycarbonyl, $C_2$-$C_{20}$ heteroaryloxycarbonyl, $C_1$-$C_{20}$ alkylaminocarbonyl, $C_1$-$C_{20}$ alkylsulfonyl, $C_3$-$C_{20}$ cycloalkylsulfonyl, $C_6$-$C_{20}$ arylsulfonyl, $C_1$-$C_{20}$ alkylamino sulfonyl, $C_3$-$C_{20}$ cycloalkylaminosulfonyl, and $C_6$-$C_{20}$ arylaminosulfonyl group;

$R^3$ and $R^4$ are each, independently, selected from the group consisting of H, $C_1$-$C_{20}$ alkyl, $C_3$-$C_{20}$ cycloalkyl, $C_2$-$C_{20}$ heterocyclo, $C_6$-$C_{20}$ aryl, $C_2$-$C_{20}$ heteroaryl, $C_1$-$C_{20}$ alkoxycarbonyl, $C_6$-$C_{20}$ aryloxycarbonyl, $C_2$-$C_{20}$ heterocyclo-oxy carbonyl, $C_1$-$C_{20}$ alkylaminocarbonyl, $C_1$-$C_{20}$ alkylaminosulfonamido, $C_2$-$C_{20}$ heterocycloamino sulfonyl, and $C_6$-$C_{20}$ arylaminosulfonyl group;

$R^5$, $R^6$, $R^7$ and $R^8$ are each, independently, selected from the group consisting of H, halogen, hydroxy, cyano, amino, $C_1$-$C_{20}$ alkyl, $C_3$-$C_{20}$ cycloalkyl, $C_2$-$C_{20}$ heterocyclo, $C_1$-$C_{20}$ alkoxy, $C_1$-$C_{20}$ alkylamino, $C_2$-$C_{20}$ heterocycloamino, $C_6$-$C_{20}$ aryl, $C_3$-$C_{20}$ heteroaryl, $C_6$-$C_{20}$ arylamino, $C_1$-$C_{20}$ alkoxycarbonylamino, $C_1$-$C_{20}$ alkylaminocarbonylamino, $C_1$-$C_{20}$ alkylsulfonamido, $C_2$-$C_{20}$ heterocyclosulfonamido, $C_6$-$C_{20}$ arylsulfonamido, and $C_1$-$C_{20}$ alkylaminosulfonamido, or $R^5$ and $R^6$ may be linked to each other to form a cyclo group, or $R^7$ and $R^8$ may be linked to each other to form a cyclo group; and $R^9$, $R^{10}$, $R^{11}$ and $R^{12}$ are each, independently, selected from the group consisting of H, halogen, hydroxy, cyano, amino, $C_1$-$C_{20}$ alkyl, $C_3$-$C_{20}$ cycloalkyl, $C_1$-$C_{20}$ alkoxy, $C_1$-$C_{20}$ alkylamino, $C_2$-$C_{20}$ heterocycloamino, $C_6$-$C_{20}$ aryl, $C_3$-$C_{20}$ heteroaryl, $C_6$-$C_{20}$ arylamino, and $C_1$-$C_{20}$ alkoxycarbonylamino, or the $R^9$ and $R^{10}$ may be linked to each other to form a cyclo or spiro group, the $R^{11}$ and $R^{12}$ may be linked to each other to form a cyclo or spiro group; and $R^{13}$ is selected from the group consisting of H, halogen, hydroxy, cyano, amino, $C_1$-$C_{20}$ alkyl, $C_3$-$C_{20}$ cycloalkyl, $C_2$-$C_{20}$ heterocyclo, $C_1$-$C_{20}$ alkoxy, $C_1$-$C_{20}$ alkylamino, $C_2$-$C_{20}$ heterocycloamino, $C_6$-$C_{20}$ aryl, $C_3$-$C_{20}$ heteroaryl, $C_6$-$C_{20}$ arylamino, $C_1$-$C_{20}$ alkoxycarbonylamino, and $C_1$-$C_{20}$ alkylaminocarbonylamino group.

2. The compound according to claim 1, wherein m=1 or 2 and n=1 or 2.

3. The compound according to claim 1, wherein the dashed line connecting $D^1$ to the adjacent carbon atom is a double bond and $D^1$ is CH.

4. The compound according to claim 1, wherein
Ra is H, hydroxy, $C_1$-$C_{12}$ alkyl, $C_1$-$C_{12}$ cycloalkyl, $C_6$-$C_{12}$ aryl, $C_2$-$C_{12}$ heteroaryl, $C_1$-$C_{12}$ alkoxycarbonyl, $C_3$-$C_{12}$ cycloalkyloxycarbonyl, $C_6$-$C_{12}$ aryloxycarbonyl, $C_2$-$C_{12}$ heterocyclo-oxycarbonyl, $C_1$-$C_{12}$ alkylaminocarbonyl, $C_3$-$C_{12}$ cycloalkylaminocarbonyl, $C_1$-$C_{12}$ alkylaminosulfonamido, $C_2$-$C_{12}$ heterocycloaminosulfonyl, or $C_6$-$C_{12}$ arylaminosulfonyl; and the Rb and Rc are each, independently, selected from the group consisting of H, halogen, hydroxy, cyano, $C_1$-$C_{12}$ alkyl, $C_3$-$C_{12}$ cycloalkyl, $C_2$-$C_{12}$ heterocyclo, $C_6$-$C_{12}$ aryl, $C_1$-$C_{12}$ alkoxy, $C_1$-$C_{12}$ alkylthio, $C_1$-$C_{12}$ alkoxycarbonyl, $C_6$-$C_{12}$ aryloxy, $C_6$-$C_{12}$ heteroaryloxy, $C_6$-$C_{12}$ fused aryloxy, $C_6$-$C_{12}$ fused heterocyclo-oxy, $C_6$-$C_{12}$ aryloxycarbonyl, $C_2$-$C_{12}$ heterocyclo oxycarbonyl, $C_2$-$C_{12}$ heteroaryl, $C_1$-$C_{12}$ alkylamino, $C_2$-$C_{12}$ heterocycloamino, $C_6$-$C_{12}$ arylamino, $C_1$-$C_{12}$ alkylaminocarbonyl, $C_1$-$C_{12}$ alkylcarbonylamino, $C_1$-$C_{12}$ alkylsulfonamido, $C_2$-$C_{12}$ heterocyclosulfonamido, $C_6$-$C_{12}$ arylsulfonamido, $C_1$-$C_{12}$ alkylaminosulfonamido; or Rb and Rc could be linked to form $C_2$-$C_{12}$ cycloalkyl, $C_2$-$C_{12}$ cycloalkenyl, or $C_1$-$C_{12}$ cycloethereal group.

5. The compound according to claim 4, wherein
Ra is H, hydroxy, $C_1$-$C_5$ alkoxycarbonyl, $C_3$-$C_6$ cycloalkyloxycarbonyl, $C_3$-$C_{10}$ cycloalkylaminocarbonyl, $C_1$-$C_4$alkylaminosulfonamido, or $C_2$-$C_{10}$ heterocycloaminosulfonyl group; and Rb and Rc may be linked to form $C_2$-$C_5$ cycloalkyl, or $C_1$-$C_2$ cycloethereal group.

6. The compound according to claim 1, wherein K is represented by one of the following structures:

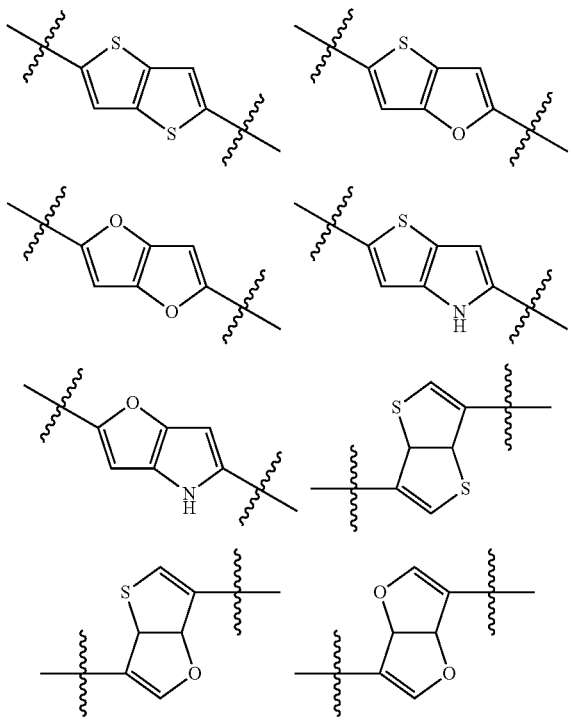

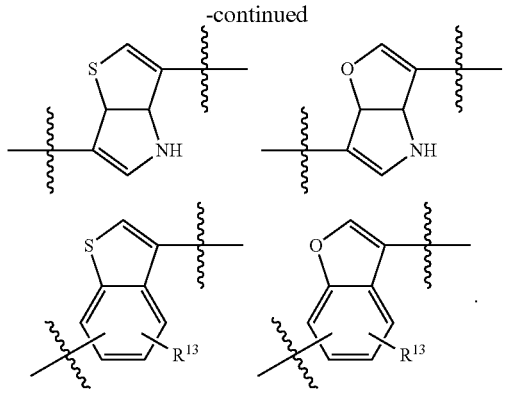

7. The compound according to claim 6, wherein K is represented by one of the following structures:

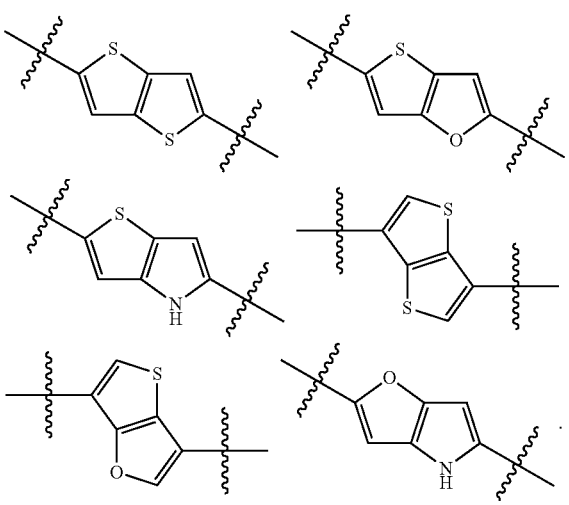

8. The compound according to claim 1, wherein Y and $Y^1$ are each, independently, selected from the group consisting of H, $C_1$-$C_{12}$ alkyl, $C_3$-$C_{12}$ cycloalkyl, $C_6$-$C_{12}$ aryl, $C_1$-$C_{12}$ alkylcarbonyl, $C_6$-$C_{12}$ arylcarbonyl, $C_2$-$C_{12}$ heterocyclocarbonyl, $C_1$-$C_{12}$ alkoxycarbonyl, $C_1$-$C_{12}$ cycloalkyl-oxy-carbonyl, $C_6$-$C_{12}$ aryloxycarbonyl, $C_2$-$C_{12}$ heteroaryloxycarbonyl, $C_1$-$C_{12}$ alkylaminocarbonyl, $C_1$-$C_{12}$ alkylsulfonyl, $C_3$-$C_{12}$ cycloalkylsulfonyl, $C_6$-$C_{12}$ arylsulfonyl, $C_1$-$C_{12}$ alkylamino sulfonyl, $C_3$-$C_{12}$ cycloalkylaminosulfonyl, and $C_6$-$C_{12}$ arylaminosulfonyl group.

9. The compound according to claim 8, wherein Y and $Y^1$ are a $C_1$-$C_5$ alkoxycarbonyl, or $C_1$-$C_5$ alkylaminocarbonyl group.

10. The compound according to claim 1, wherein $R^3$ and $R^4$ are each, independently, selected from the group consisting of H, $C_1$-$C_{12}$ alkyl, $C_3$-$C_{12}$ cycloalkyl, $C_2$-$C_{12}$ heterocyclo, $C_6$-$C_{12}$ aryl, $C_2$-$C_{12}$ heteroaryl, $C_1$-$C_{12}$ alkoxycarbonyl, $C_6$-$C_{12}$ aryloxycarbonyl, $C_2$-$C_{12}$ heterocyclo-oxy carbonyl, $C_1$-$C_{12}$ alkylaminocarbonyl, $C_1$-$C_{12}$ alkylaminosulfonamido, $C_2$-$C_{12}$ heterocycloamino sulfonyl, and $C_6$-$C_{12}$ arylaminosulfonyl group.

11. The compound according to claim 1, wherein
$R^5$, $R^6$, $R^7$ and $R^8$ are each, independently, selected from the group consisting of H, halogen, hydroxy, cyano, amino, $C_1$-$C_{12}$ alkyl, $C_3$-$C_{12}$ cycloalkyl, $C_2$-$C_{12}$ heterocyclo, $C_1$-$C_{12}$ alkoxy, $C_1$-$C_{12}$ alkylamino, $C_2$-$C_{12}$ heterocycloamino, $C_6$-$C_{12}$ aryl, $C_6$-$C_{12}$ arylamino, $C_1$-$C_{12}$ alkoxycarbonylamino, $C_1$-$C_{12}$ alkylaminocarbonylamino, $C_1$-$C_{12}$ alkylsulfonamido, $C_2$-$C_{12}$ heterocyclosulfonamido, $C_6$-$C_{12}$ arylsulfonamido, and $C_1$-$C_{12}$ alkylaminosulfonamido, or $R^5$ and $R^6$ are linked to form a cyclo group, or $R^7$ and $R^8$ are linked to each other to form a cyclo group.

12. The compound according to claim 11, wherein
$R^5$ and $R^7$ are H; and
$R^6$ and $R^8$ are a $C_1$-$C_6$ alkyl, $C_2$-$C_6$ heterocyclo, $C_6$-$C_{10}$ aryl, or $C_3$-$C_8$ heteroaryl group.

13. The compound according to claim 1, wherein $R^9$, $R^{10}$, $R^{11}$ and $R^{12}$ are each, independently, selected from the group consisting of H, halogen, hydroxy, cyano, amino, $C_1$-$C_{12}$ alkyl, $C_3$-$C_{12}$ cycloalkyl, $C_1$-$C_{12}$ alkoxy, $C_1$-$C_{12}$ alkylamino, $C_2$-$C_{12}$ heterocycloamino, $C_6$-$C_{12}$ aryl, $C_3$-$C_{12}$ heteroaryl, $C_6$-$C_{20}$ arylamino, and $C_1$-$C_{12}$ alkoxycarbonylamino, or $R^9$ and $R^{10}$ may be linked to each to form a cyclo or spiro group, and $R^{11}$ and $R^{12}$ may be linked to each other to form a cyclo or spiro group.

14. The compound according to claim 13, wherein $R^9$, $R^{10}$, $R^{11}$ and $R^{12}$ are H.

15. The compound according to claim 1, which is represented by one of the following structures:

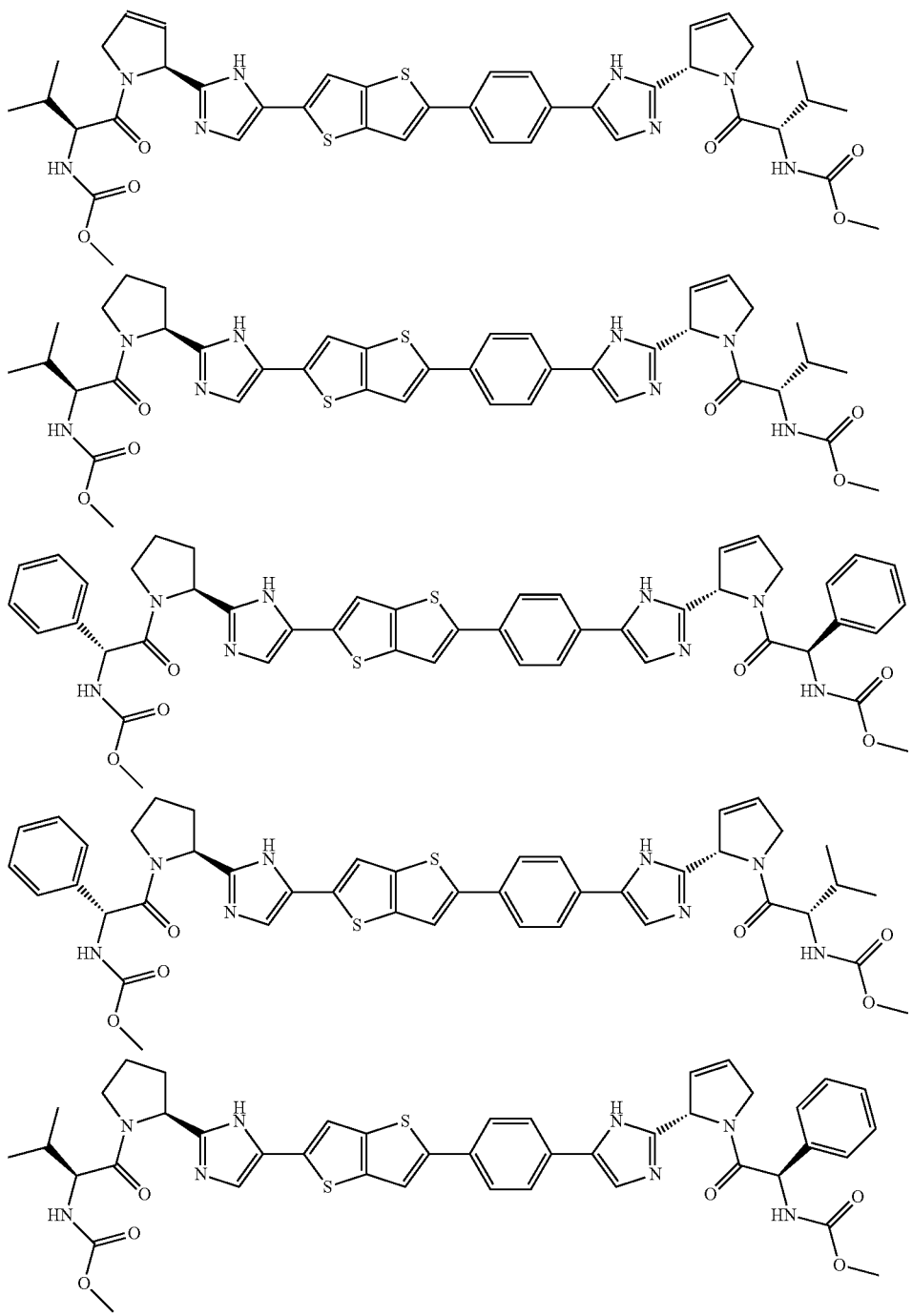

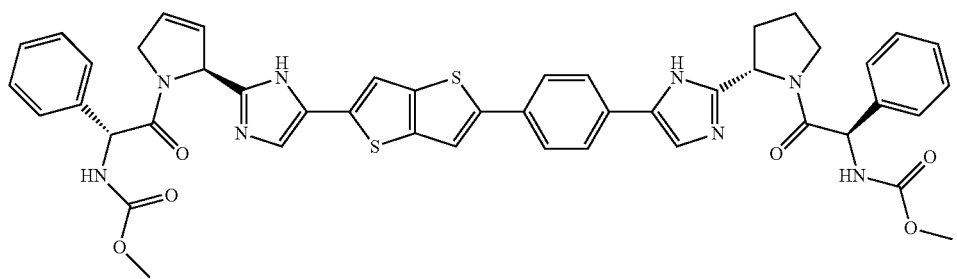
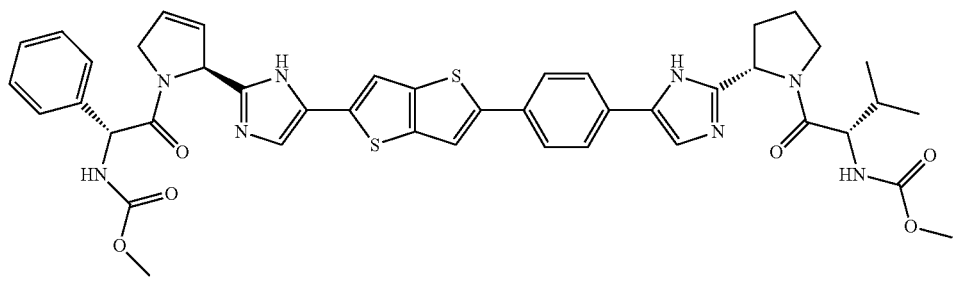
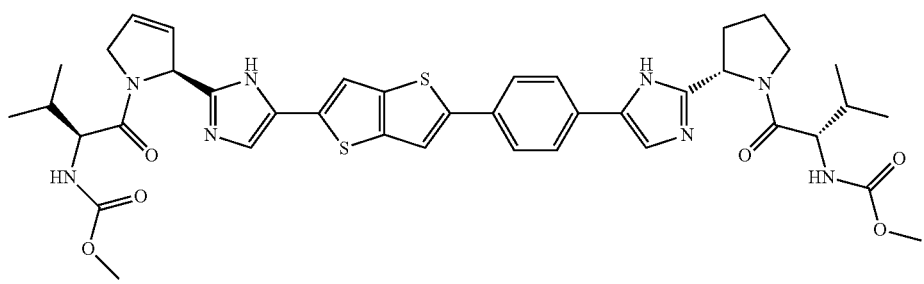
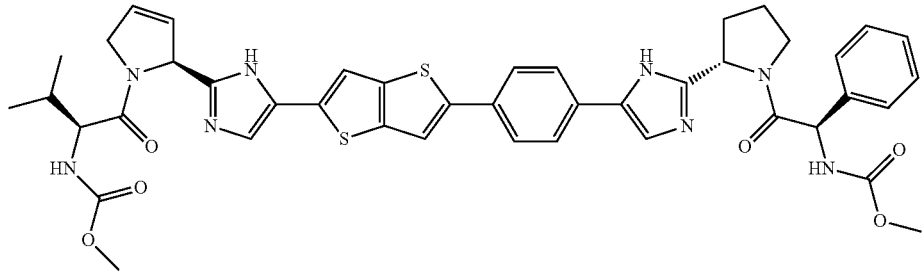
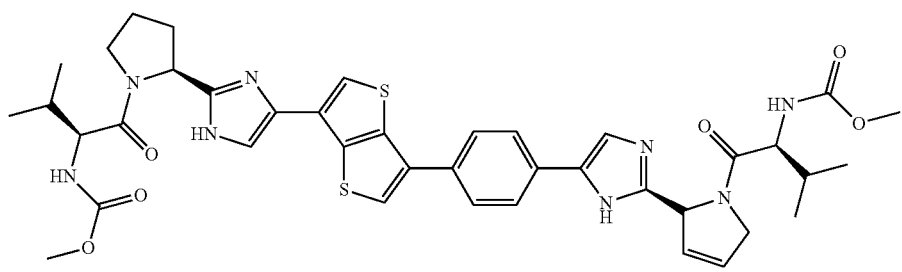
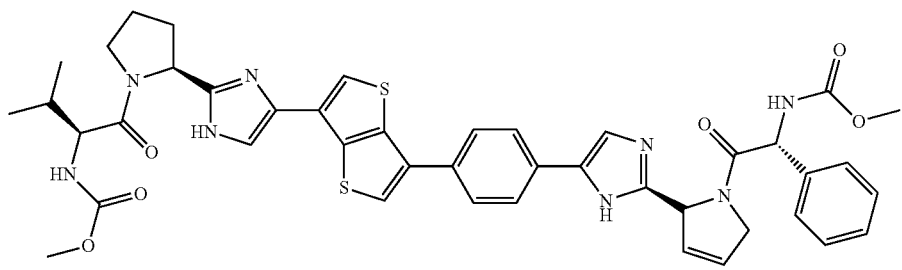

-continued
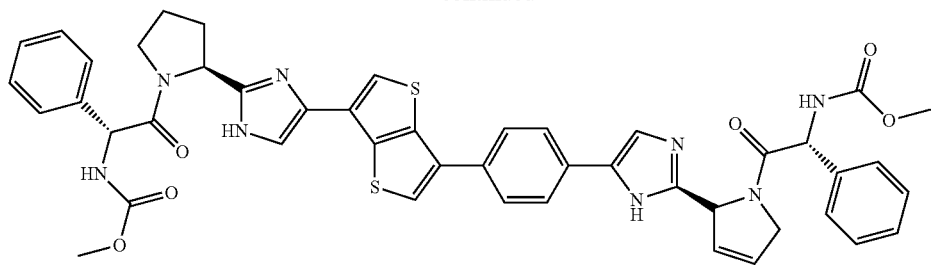
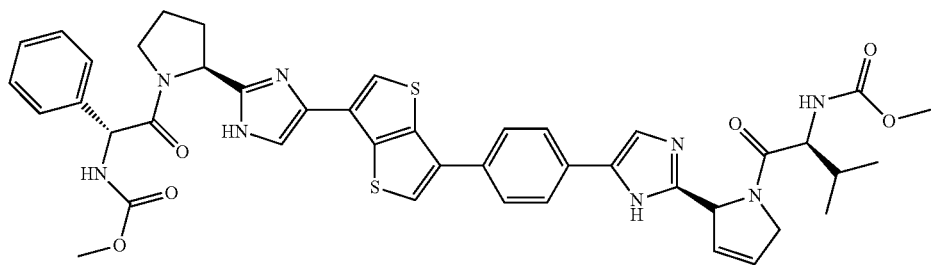
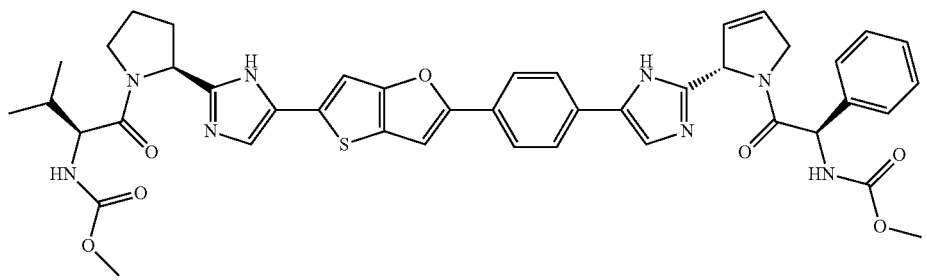 [SMILES: COC(=O)N[C@H](C(=O)N1CCC[C@H]1c1ncc(-c2cc3oc(-c4ccc(-c5cnc([C@@H]6C=CCN6C(=O)[C@H](NC(=O)OC)c6ccccc6)[nH]5)cc4)cc3s2)[nH]1)C(C)C]
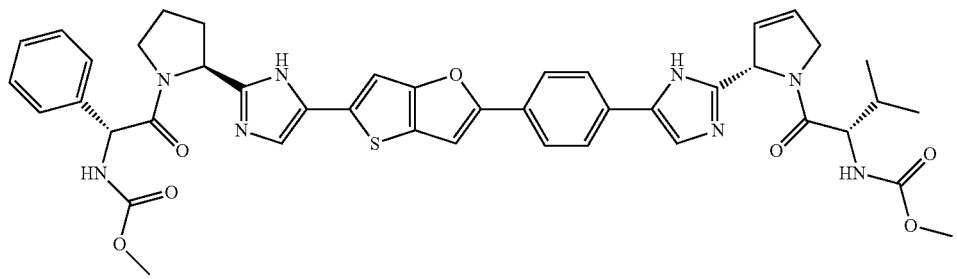 [SMILES: COC(=O)N[C@H](C(=O)N1CC=C[C@H]1c1ncc(-c2ccc(-c3cc4sc(-c5cnc([C@@H]6CCCN6C(=O)[C@H](NC(=O)OC)c6ccccc6)[nH]5)cc4o3)cc2)[nH]1)C(C)C]
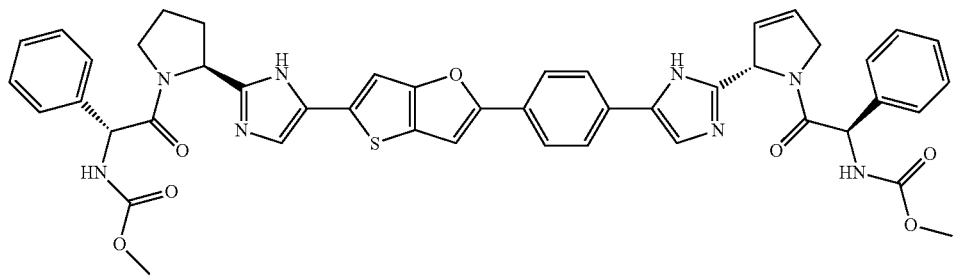
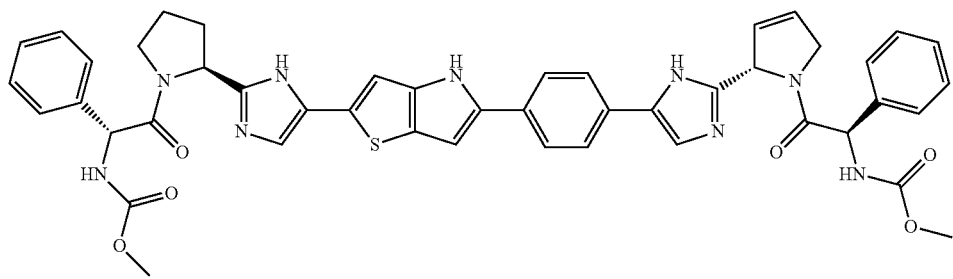

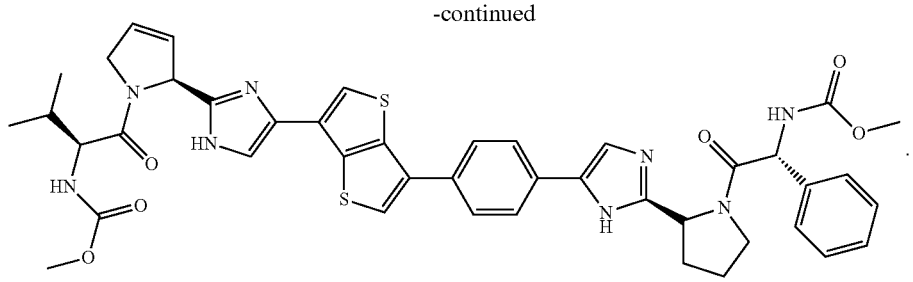

16. The compound according to claim 1, which is represented the following structure:

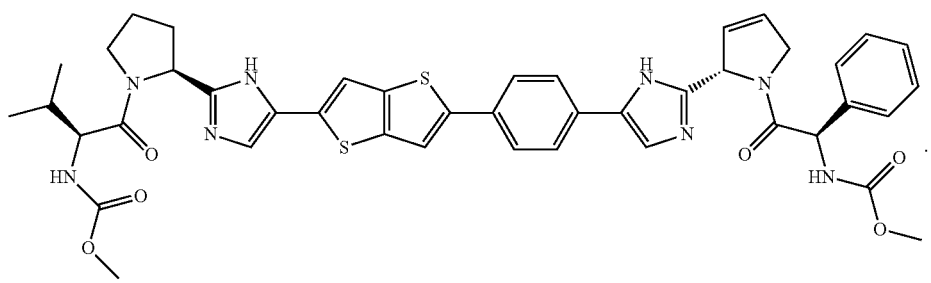 [SMILES: COC(=O)N[C@H](C(=O)N1CCC[C@H]1c1ncc(-c2cc3sc(-c4ccc(-c5cnc([C@@H]6C=CCN6C(=O)[C@H](NC(=O)OC)c6ccccc6)[nH]5)cc4)cc3s2)[nH]1)C(C)C]

17. The compound according to claim 1, wherein the dashed line connecting D to the adjacent carbon atom is a double bond.

18. The compound according to claim 1, wherein the dashed line connecting $D^1$ to the adjacent carbon atom is a double bond.

19. The compound according to claim 1, wherein the dashed line connecting D to the adjacent carbon atom is a double bond and the dashed line connecting $D^1$ to the adjacent carbon atom is a double bond.

20. The compound according to claim 1, wherein the dashed line connecting D to the adjacent carbon atom is a single bond and the dashed line connecting $D^1$ to the adjacent carbon atom is a double bond.

21. A pharmaceutical composition comprising the compound according to claim 1 and a pharmaceutically acceptable carrier.

22. A composition comprising at least one compound according to claim 1 and at least one compound selected from the group consisting of an HIV inhibitor and a hepatitis B virus (HBV) inhibitor.

23. A composition comprising at least one compound according to claim 1 and at least one compound selected from the group consisting of Lamivudine, Telbivudine, Adefovir, Entecavir, Tenofovir and Clevudine.

24. A composition comprising at least one compound according to claim 1 and at least one compound selected from the group consisting of (1) Immune modulators, (2) HCV protease inhibitors, (3) HCV polymerase inhibitors, (4) nucleosides and derivatives thereof, (5) Cyclophilin inhibitors, (6) Glucosidase I inhibitors, (7) IMPDH inhibitors, (8) Caspase inhibitors, (9) TLR agonists, (10) HIV inhibitors, (11) anti-inflammatory drugs, and (12) anti-cancer drugs.

25. A method of inhibiting Hepatitis C virus comprising contacting Hepatitis C virus with an effective amount of the compound according to claim 1.

26. A method of treating a subject infected with Hepatitis C virus comprising administering an effective amount of the compound according to claim 1 to the subject.

27. A method of treating a subject infected with Hepatitis C virus comprising administering an effective amount of the composition according to claim 21 to the subject.

28. A method of treating a subject infected with Hepatitis C virus comprising administering an effective amount of the composition according to claim 22 to the subject.

29. A method of treating a subject infected with Hepatitis C virus comprising administering an effective amount of the composition according to claim 23 to the subject.

30. A method of treating a subject infected with Hepatitis C virus comprising administering an effective amount of the composition according to claim 24 to the subject.

* * * * *